(12) United States Patent
Zimmerman et al.

(10) Patent No.: US 10,100,098 B2
(45) Date of Patent: Oct. 16, 2018

(54) INSULIN PRODUCTION METHODS AND PROINSULIN CONSTRUCTS

(71) Applicant: STELIS BIOPHARMA PRIVATE LIMITED, Bangalore (IN)

(72) Inventors: Ronald E. Zimmerman, Greenwood, IN (US); David John Stokell, Indianapolis, IN (US); Michael Patrick Akers, Indianapolis, IN (US)

(73) Assignee: Stelis Biopharma Private Limited, Bangalore (IN)

( * ) Notice: Subject to any disclaimer, the term of this patent is extended or adjusted under 35 U.S.C. 154(b) by 0 days.

(21) Appl. No.: 15/007,949

(22) Filed: Jan. 27, 2016

(65) Prior Publication Data

US 2016/0289291 A1    Oct. 6, 2016

Related U.S. Application Data

(63) Continuation-in-part of application No. 13/750,273, filed on Jan. 25, 2013, now abandoned, which is a continuation of application No. 12/658,852, filed on Feb. 16, 2010, now abandoned, which is a continuation of application No. 11/725,731, filed on Mar. 20, 2007, now Pat. No. 7,790,677, application No. 15/007,949, filed on Jan. 27, 2016, which is a continuation-in-part of application No. 13/032,806, filed on Feb. 23, 2011, now abandoned, and a continuation-in-part of application No. 14/725,039, filed on May 29, 2015, now abandoned, which is a continuation of application No. 13/740,794, filed on Jan. 14, 2013, now abandoned, which is a continuation of application No. 13/032,775, filed on Feb. 23, 2011, now abandoned, application No. 15/007,949, filed on Jan. 27, 2016, which is a continuation-in-part of application No. 14/673,146, filed on Mar. 30, 2015, now abandoned, which is a continuation of application No. 13/864,955, filed on Apr. 17, 2013, now abandoned, which is a continuation of application No. 13/032,814, filed on Feb. 23, 2011, now abandoned, application No. 15/007,949, filed on Jan. 27, 2016, which is a continuation-in-part of application No. 14/704,838, filed on May 5, 2015, now abandoned, which is a continuation of application No. 13/750,276, filed on Jan. 25, 2013, now abandoned, which is a continuation of application No. 13/032,797, filed on Feb. 23, 2011, now abandoned.

(60) Provisional application No. 60/874,655, filed on Dec. 13, 2006.

(51) Int. Cl.
| C07K 14/62 | (2006.01) |
| C12P 21/02 | (2006.01) |
| A61K 38/28 | (2006.01) |

(52) U.S. Cl.
CPC .............. *C07K 14/62* (2013.01); *A61K 38/28* (2013.01); *C12P 21/02* (2013.01)

(58) Field of Classification Search
None
See application file for complete search history.

(56) References Cited

U.S. PATENT DOCUMENTS

| 4,916,212 | A | 4/1990 | Markussen et al. |
| 5,395,822 | A | 3/1995 | Izumi et al. |
| 5,700,662 | A | 12/1997 | Chance et al. |
| 5,834,222 | A | 11/1998 | Friedman et al. |
| 5,962,267 | A | 10/1999 | Shin et al. |
| 6,777,207 | B2 | 8/2004 | Kjeldsen et al. |
| 7,790,677 | B2 | 9/2010 | Zimmerman et al. |
| 2001/0041787 | A1 | 11/2001 | Kjeldsen et al. |
| 2003/0044789 | A1* | 3/2003 | Burke ............... G01N 33/542 435/6.18 |
| 2003/0064052 | A1 | 4/2003 | Waters et al. |
| 2004/0132647 | A1 | 7/2004 | Dimarchi et al. |
| 2006/0222698 | A1 | 10/2006 | Lau et al. |
| 2008/0146492 | A1* | 6/2008 | Zimmerman ......... A61K 38/28 435/69.1 |
| 2009/0036353 | A1 | 2/2009 | Behrens et al. |
| 2009/0239785 | A1 | 9/2009 | Hubalek et al. |
| 2010/0183615 | A1* | 7/2010 | Kufer ................. C07K 16/2809 424/136.1 |

(Continued)

FOREIGN PATENT DOCUMENTS

| EP | 0 055 945 | 7/1982 |
| EP | 0214826 | 3/1987 |

(Continued)

OTHER PUBLICATIONS

Chan et al., "Biosynthesis and periplasmic segregation of human proinsulin in *Escherichia coli*," *Proc. Natl. Acad. Sci.*, 78:5401-5405 (1981).

(Continued)

*Primary Examiner* — Elizabeth Kemmerer
*Assistant Examiner* — Regina M Deberry
(74) *Attorney, Agent, or Firm* — Womble Bond Dickinson (US) LLP

(57) ABSTRACT

Novel proinsulins and glargine, aspart and Lis-Pro proinsulin analogs having specific amino acid and/or nucleic acid modifications suitable for improved methods of insulin production, as well as novel and highly efficient processes for preparing the same. The novel proinsulins and proinsulin analogs may be converted into human insulin and insulin analogs, respectively, that are useful in therapeutic preparations.

2 Claims, 30 Drawing Sheets

Specification includes a Sequence Listing.

(56) References Cited

U.S. PATENT DOCUMENTS

2010/0210815 A1    8/2010  Zimmerman et al.

FOREIGN PATENT DOCUMENTS

| UA | 76661 | 8/2006 |
|---|---|---|
| WO | WO 2009104199 | 8/2009 |
| WO | WO 2010002283 | 1/2010 |

OTHER PUBLICATIONS

Chance et al., "The Production of Human Insulin Using Recombination DNA Technology and a New Chain Combination Procedure," *Peptides: Proceedings of the 7th American Peptide Chemistry Symposium*, 721-728 (1981).

Chang et al., "Human insulin production from a novel mini-proinsulin which has high receptor-binding activity," *Biochem J.*, 329:631-635 (1998).

Forst et al., "Biological Activity of C-Peptide on the Skin Microcirculation in Patients with Insulin-dependent Diabetes Mellitus," *American Society for Clinical Investigation, Inc.*, vol. 101, 10:2036-2041 (1998).

Frank et al., "The Production of Human Proinsulin and its Transformation to Human Insulin and C-Peptide," *Peptides: Proceedings of the 7th American Peptide Chemistry Symposium*, 729-739 (1981).

Halban et al., "Mutant Proinsulan That Cannot Be Converted Is Secreted Efficiently from Primary Rat beta-Cells via the Regulated Pathway," *Molecular Biology of the Cell*, 14:1195-1203 (2003).

Ido et al., "Prevention of Vascular and Neural Dysfunction in Diabetic Rats by C-Peptide," *Science AAAS*, 83:6766-6770 (1997).

Johansson et al., "Effects of C-peptide on blood flow, capillary diffusion capacity and glucose utilization in the exercising forearm of Type 1 (insulin-dependent) diabetic patients," *Diabetologia*, 35:1151-1158 (1992).

Johansson et al., "The influence of human C-peptide on renal function and glucose utilization in Type 1 (insulin-dependent) diabetic patients," *Diabetologia*, 35:121-128 (1992).

Kitamura et al., "Proinsulin C-peptide rapidly stimulates mitogen-activated protein kinases in Swiss 3T3 fibroblasts: requirement of protein kinase C, phosphoinositide 3-kinase and pertussis toxin-sensitive G-protein," *Biochem J.*, 355:123-129 (2001).

Lipkind et al., "Predicted Structural Alterations in Proinsulin during Its Interactions with Prohormone Convertases," *Biochemistry*, 38:890-896 (1999).

Sjöquist et al., "Effects of C-peptide on renal function at the early stage of experimental diabetes," *Kidney International*, 54:758-764 (1998).

Steiner et al., "Processing Mechanisms in the Biosynthesis of Proteins," *Annals of the New York Academy of Sciences*, vol. 343:1-16 (1980).

Thim et al., "Secretion and processing of insulin precursors in yeast," *Proc. Natl. Acad. Sci.*, 83:6766-6770 (1986).

Wahren et al., "Role of C-peptide in human physiology," *Am. J. Physiol Endocrinol Metab*, 278:E759-E768 (2000).

Wiwanitkit et al., "Single amino acid substitution in important hemoglobinopathies does not disturb molecular function and biological process," *Int J. Nanomedicine*, Jun. 3(2):225-227 (2008).

Young-Jin Son et al., "Effects of citraconylation on enzymatic modification of human proinsulin using trypsin and carboxypeptidase," Biotechnology Progress, 25(4):1064-1070 (2009).

International Search Report of PCT/US2011/025934 dated Aug. 4, 2011.

Written Opinion of the International Searching Authority for of PCT/US2011/025934 dated Aug. 4, 2011.

\* cited by examiner

PRODUCTION BLOCK FLOW DIAGRAM FOR INSULIN GLARGINE    FIG. 10

PRODUCTION BLOCK FLOW DIAGRAM FOR INSULIN ASPART   *FIG. 11*

ALTERNATE PRODUCTION BLOCK FLOW DIAGRAM FOR INSULIN ASPART

PRODUCTION BLOCK FLOW DIAGRAM FOR INSULIN LISPRO

ALTERNATE PRODUCTION BLOCK FLOW DIAGRAM FOR INSULIN LISPRO

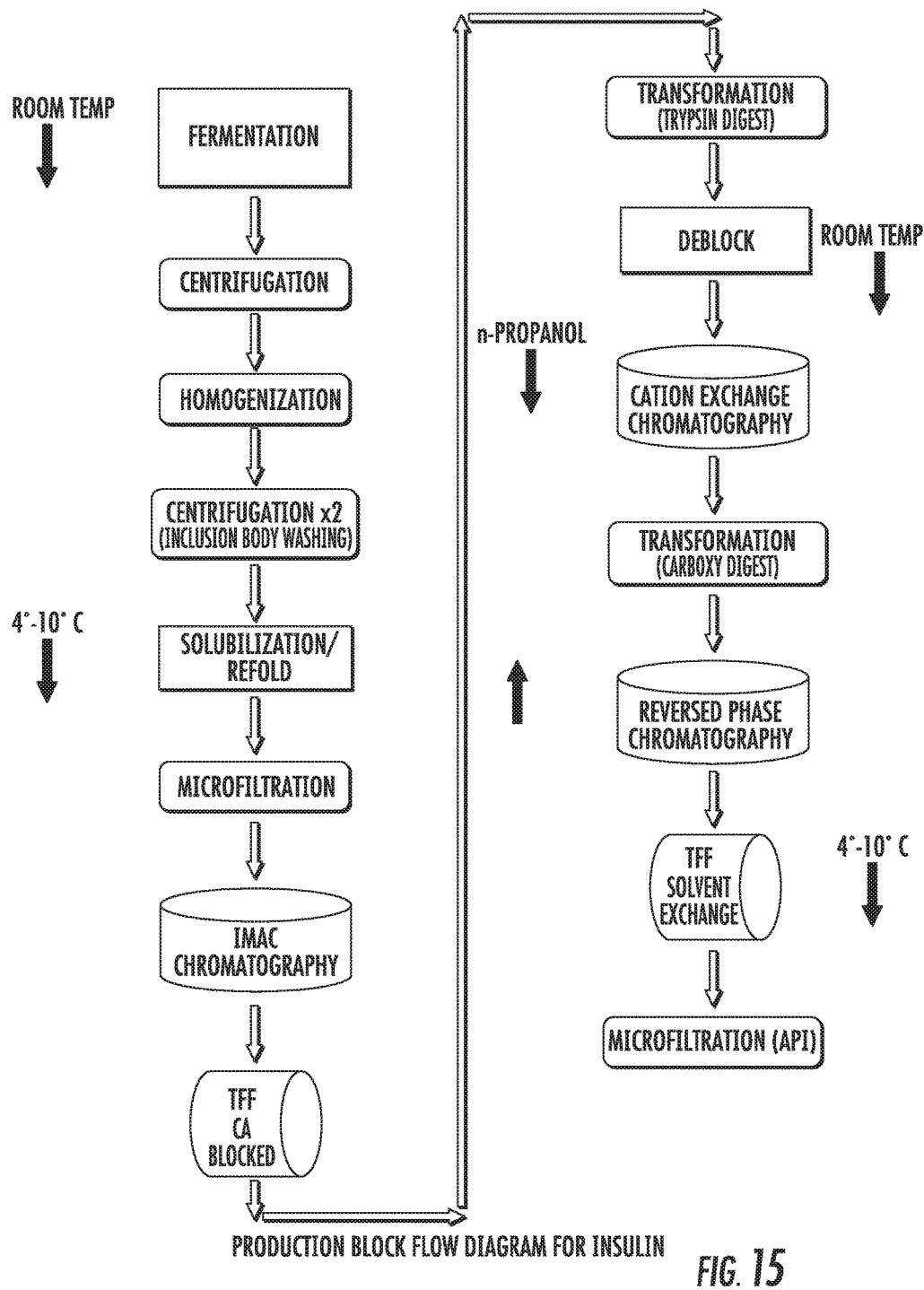
FIG. 15 — PRODUCTION BLOCK FLOW DIAGRAM FOR INSULIN

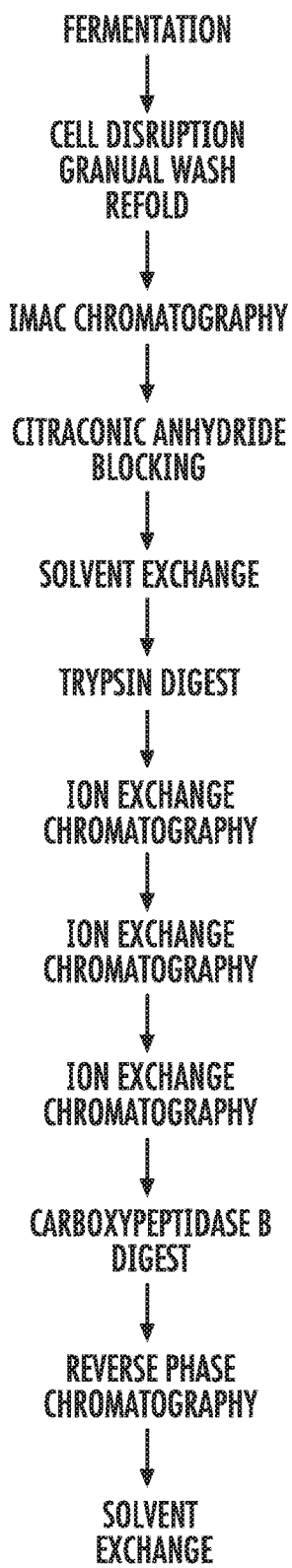
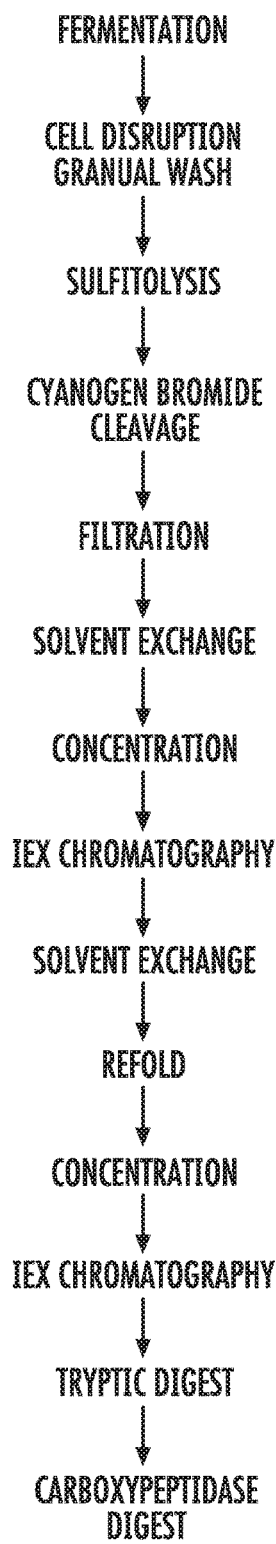
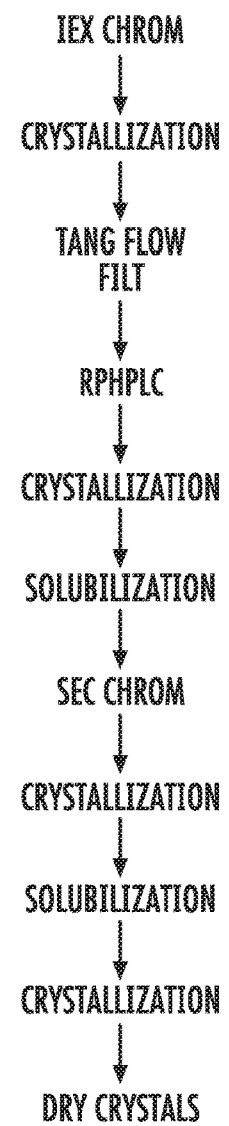
FIG. 16A
FIG. 16B

NON-REDUCED PEPTIDE MAP USING V8 PROTEASE

| PEPTIDE FRAGMENTS | | |
|---|---|---|
| FRAGMENT NUMBER | USP REFERENCE STANDARD | R & D INSULIN |
| I | ACHAIN gln-cys-cys-thr-ser-ile-cys-ser-leu-tyr-gln-leu-glu<br>BCHAIN phe-val-asn-gln-his-leu-cys-gly-ser-his-leu-val-glu | ACHAIN gln-cys-cys-thr-ser-ile-cys-ser-leu-tyr-gln-leu-glu<br>BCHAIN phe-val-asn-gln-his-leu-cys-gly-ser-his-leu-val-glu |
| II | ACHAIN asn-tyr-cys-asn<br>BCHAIN ala-leu-tyr-leu-val-cys-gly-glu | ACHAIN asn-tyr-cys-asn<br>BCHAIN ala-leu-tyr-leu-val-cys-gly-glu |
| III | Arg-gly-phe-phe-tyr-tyr-pro-lys-thr | Arg-gly-phe-phe-tyr-tyr-pro-lys-thr |
| IV | Gly-ile-val-glu | Gly-ile-val-glu |

*FIG. 18A*

REDUCED PEPTIDE MAP USING V8 PROTEASE

| PEPTIDE FRAGMENTS | | |
|---|---|---|
| FRAGMENT NUMBER | USP REFERENCE STANDARD | R & D INSULIN |
| I | Gly-ile-val-glu | Gly-ile-val-glu |
| II | Gln-cys-cys-thr-ser-ile-cys-ser-leu-tyr-gln-leu-glu | Gln-cys-cys-thr-ser-ile-cys-ser-leu-tyr-gln-leu-glu |
| III | Asn-tyr-cys-asn | Asn-tyr-cys-asn |
| IV | Phe-val-asn-gln-his-leu-cys-gly-ser-his-leu-val-glu | Phe-val-asn-gln-his-leu-cys-gly-ser-his-leu-val-glu |
| V | Ala-leu-tyr-leu-val-cys-gly-glu | Ala-leu-tyr-leu-val-cys-gly-glu |
| VI | Arg-gly-phe-phe-tyr-thr-pro-lys-thr | Arg-gly-phe-phe-tyr-thr-pro-lys-thr |

*FIG. 18B*

| RELATED SUBSTANCES | | | |
|---|---|---|---|
| R & D INSULIN DRUG SUBSTANCE | | | |
| IDENTITY | RETENTION TIME | PEAK AREA | RELATIVE AREA % |
| INSULIN | 21.19 | 884.701 | 99.11 |
| A5/B4 DESAMIDO | 22.96 | 0.842 | 0.11 |
|  | 26.3 | 0.508 | 0.07 |
| A21 DESAMIDO | 27.29 | 0.808 | 0.10 |
|  | 28.65 | 0.360 | 0.05 |
| MULTIMER | 46.23 | 2.575 | 0.29 |
| INSULIN HUMAN USP STANDARD | | | |
| IDENTITY | RETENTION TIME | PEAK AREA | RELATIVE AREA % |
| INSULIN | 21.06 | 1275.883 | 98.35 |
| A5/B4 DESAMIDO | 23.29 | 3.084 | 0.23 |
|  | 25.36 | 0.330 | 0.05 |
| A21 DESAMIDO | 27.26 | 5.746 | 0.49 |
|  | 31.93 | 0.350 | 0.05 |
|  | 37.87 | 0.330 | 0.05 |
| MULTIMER | 45.60 | 1.440 | 0.14 |
| MULTIMER | 46.21 | 1.086 | 0.11 |
| MULTIMER | 46.75 | 1.155 | 0.13 |
|  | 47.07 | 0.383 | 0.06 |
|  | 47.89 | 0.360 | 0.05 |

FIG. 23

STABILITY DATA OF INSULIN

INSULIN STABILITY*

|  | 5°C | | 25°C | | 40°C | |
|---|---|---|---|---|---|---|
|  | A | B | A | B | A | B |
| 14 DAY | 0 | 0 | 0.03 | 0.03 | 1.3 | 1.2 |
| 28 DAY | 0 | 0 | 0.04 | — | 3.6 | 3.5 |
| 60 DAY | 0 | 0 | — | 1.9 | 9.0 | 10.0 |
| 182 DAY | 0 | 0 | 4.0 | 3.3 | — | — |

FIG. 25

INSULIN PRODUCTION METHODS AND PROINSULIN CONSTRUCTS

CROSS-REFERENCE TO RELATED APPLICATIONS

The present application is a continuation-in-part of pending U.S. patent application Ser. No. 13/750,273, filed 25 Jan. 2013, which is a continuation of U.S. patent application Ser. No. 12/658,852, filed 16 Feb. 2010, now abandoned, which is a continuation of U.S. patent application Ser. No. 11/725,731, filed Mar. 20, 2007, which issued as U.S. Pat. No. 7,790,677 and which claims priority to U.S. Provisional Application No. 60/874,655, filed 13 Dec. 2006; a continuation-in-part of pending U.S. patent application Ser. No. 13/032,806, filed 23 Feb. 2011; a continuation-in-part of pending U.S. patent application Ser. No. 14/725,039, filed 29 May 2015, which is a continuation of U.S. patent application Ser. No. 13/740,794, filed 14 Jan. 2013, now abandoned, which is a continuation of U.S. patent application Ser. No. 13/032,775, filed 23 Feb. 2011, now abandoned; a continuation-in-part of pending U.S. patent application Ser. No. 14/673,146, filed 30 Mar. 2015, which is a continuation of U.S. patent application Ser. No. 13/864,955, filed 7 Apr. 2013, now abandoned, which is a continuation of U.S. patent application Ser. No. 13/032,814, filed 23 Feb. 2011, now abandoned; and a continuation-in-part of pending U.S. patent application Ser. No. 14/704,838, filed 5 May 2015, which is a continuation of U.S. patent application Ser. No. 13/750,276, filed 25 Jan. 2013, now abandoned, which is a continuation of U.S. patent application Ser. No. 13/032,797, filed 23 Feb. 2011, now abandoned. Each of the foregoing applications is hereby incorporated by reference in its entirety.

INCORPORATION BY REFERENCE TO SEQUENCE LISTING

A text file of the Sequence Listing named "SEQL.txt" is submitted herewith and incorporated by reference in its entirety. The Sequence Listing was created on X October 2015, is 81.7 kB in size, and discloses SEQ ID NOs: 1-93 described herein.

TECHNICAL FIELD OF THE INVENTION

The present invention in a general and overall sense relates to the field of recombinant proteins and peptides. The invention also relates to the field of molecular processes and methods for producing recombinant proteins particularly methods that employ *E. coli* as an expression vehicle. The invention also relates to compositions and methods for preparing proinsulin, insulin, and both of these alone or in combination with each other and with other compositions.

The invention also relates to compositions and preparations that comprise glargine proinsulin, in particular glargine proinsulin with modified C-peptide sequences. The invention also relates to methods of manufacture for manufacturing glargine insulin analogs from modified proinsulin sequences.

The invention also relates to compositions and preparations that comprise aspart proinsulin, in particular aspart proinsulin with modified C-peptide sequences. The invention also relates to methods of manufacture for manufacturing aspart insulin analogs from modified proinsulin sequences.

The invention also relates to compositions and preparations that comprise Lis-Pro proinsulin, and in particular Lis-Pro proinsulin with modified C-peptide sequences. The invention also relates to methods of manufacture for manufacturing Lis-Pro insulin analogs from modified proinsulin sequences.

The invention also relates to liquid insulin compositions and methods for preparing liquid insulin compositions.

BACKGROUND OF THE INVENTION

Insulin is a polypeptide hormone secreted by beta-cells of the pancreas. This hormone is made up of two polypeptide chains, an A-chain of 21 amino acids, and a B-chain of 30 amino acids. These two chains are linked to one another in the mature form of the hormone by two interchain disulfide bridges. The A-chain also features one intra-chain disulfide bridge.

Insulin is a hormone that is synthesized in the body in the form of a single-chain precursor molecule, proinsulin. Proinsulin is a molecule comprised of a prepeptide of 24 amino acids, followed by the B-chain peptide, a C-peptide of 35 amino acids, and an A-chain peptide. The C-peptide of this precursor insulin molecule contains the two amino acids, lysine-arginine (LR) at its carboxy end (where it attaches to the A-chain), and the two amino acids, arginine-arginine (RR) at its amino end (where it attaches to the B-chain). In the mature insulin molecule, the C-peptide is cleaved away from the peptide so as to leave the A-chain and the B-chain connected directly to one another in its active form.

Molecular biology techniques have been used to produce human proinsulin. In this regard, three major methods have been used for the production of this molecule. Two of these methods involve *Escherichia coli*, with either the expression of a large fusion protein in the cytoplasm (Chance et al. (1981), and Frank et al. (1981) in Peptides: Proceedings of the 7th American Peptide Chemistry Symposium (Rich, D. and Gross, E., eds.), pp. 721-728, 729-739, respectively, Pierce Chemical Company, Rockford, Ill.), or the use of a signal peptide to enable secretion into the periplasmic space (Chan et al. (1981) P.N.A.S., U.S.A., 78:5401-5404). A third method utilizes yeast, especially *Saccharomyces cerevisiae*, to secrete the insulin precursor into the medium (Thim, et al. (1986), P.N.A.S., U.S.A., 83: 6766-6770).

Chance et al. report a process for preparing insulin by producing each of the A and B chains of insulin in the form of a fusion protein by culturing *E. coli* that carries a vector compromising a DNA encoding the fusion protein, cleaving the fusion protein with cyanogen bromide to obtain the A and the B chains, sulfonating the A and B chains to obtain sulfonated chains, reacting the sulfonated B chain with an excess amount of the sulfonated A chain; and then purifying the resultant products to obtain insulin. Drawbacks associated with this process are that it requires two fermentation processes and the requirement of a reaction step for preparing the sulfonated A chain and the sulfonated B chain. This results in a low insulin yield.

Frank et al. described a process for preparing insulin in the form of a fusion protein in *E. coli*. In this process, proinsulin is produced in the form of a fusion protein by culturing *E. coli* which carries a vector comprising a nucleic acid sequence (DNA) encoding for the fusion protein, cutting the fusion protein with cyanogens bromide to obtain proinsulin, sulfonating the proinsulin and separation of the sulfonated proinsulin, refolding the sulfonated proinsulin to form correct disulfide bonds, treating the refolded proinsulin with trypsin and carboxypeptidase B, and then purifying the resultant product to obtain insulin. However, the yield of the refolded proinsulin having correctly-folded disulfide bonds is reported to sharply decrease as the concentration of the proinsulin increases. This is allegedly due to, at least among other reasons, misfolding of the protein, and some degree of polymerization being involved. Hence, the process entails the inconvenience of using laborious purification steps during the recovery of proinsulin and consequently any final insulin product.

Thim et al. report a process for producing insulin in yeast, *Saccharomyces cerevisiae*. This process has the steps of producing a single chain insulin analog having a certain amino acid sequence by culturing *Saccharomyces cerevisiae* cells, and isolating insulin therefrom through the steps of: purification, enzyme reaction, acid hydrolysis and a second purification. This process, however, results in an unacceptably low yield of insulin.

The role of the native C-peptide in the folding of proinsulin is not precisely known. The dibasic terminal amino acid sequence at both ends of the C-peptide sequence has been considered necessary to preserve the proper processing and/or folding of the proinsulin molecule to insulin. For example, U.S. Pat. No. 5,962,267 describes dibasic terminal amino acid sequences at both ends of the C-peptide. However, modification and/or deletion of other amino acids within the C-peptide sequence has been reported.

For example, Chang et al. (1998) (Biochem. J., 329:631-635) described a shortened C-peptide of a five (5) amino acid length, -YPGDV- (SEQ ID NO: 1), that includes a preserved terminal di-basic amino acid sequence, RR at one terminal end, and LR at the other terminal end, of the peptide. Preservation of the dibasic amino acid residues at the B-chain-C peptide (B-C) and C-peptide-A-chain junctures is taught as being a minimal requirement for retaining the capacity for converting the proinsulin molecule into a properly folded mature insulin protein. The production of the recombinant human insulin was described using *E. coli* with a shortened C-peptide having a dibasic amino acid terminal sequence.

U.S. Pat. No. 7,087,408 also describes insulin precursors and insulin precursor analogs having a mini C-peptide comprising at least one aromatic amino acid residue. However, cleavage of the mini C-peptide from the B chain may be enabled by cleavage at the natural $Lys(B_{29})$ amino acid residue in the B chain giving rise to a des-Thr($B_{30}$) insulin precursor or analogs thereof.

One of the difficulties and/or inefficiencies associated with the production of recombinant insulin employing a proinsulin construct having the conserved, terminal di-basic amino acid sequence in the C-peptide region is the presence of impurities, such as Arg-(A(0))-insulin, in the reaction mixture, once enzymatic cleavage to remove the C-peptide is performed. This occurs as a result of misdirected cleavage of the proinsulin molecule so as to cleave the C-peptide sequence away from the A-chain at this juncture, by the action of trypsin. Trypsin is a typical serine protease, and hydrolyses a protein or peptide at the carboxyl terminal of an arginine or lysine residue (Enzymes, pp. 261-262 (1979), ed. Dixon, M. & Webb, E. C. Longman Group Ltd., London). This unwanted hydrolysis results in the unwanted Arg(A (0))-insulin by-product, and typically constitutes about 10% of the reaction yield. Hence, an additional purification step is required. The necessity of an additional purification step makes the process much more time consuming, and thus expensive, to use. Moreover, an additional loss of yield may be expected from the necessity of this additional purification step.

Others have described the use of proinsulin constructs that do not have a conserved terminal dibasic amino acid sequence of the C-peptide region. For example, U.S. Pat. No. 6,777,207 (Kjeldsen et al.) relates to a novel proinsulin peptide construct containing a shortened C-peptide that includes the two terminal amino acids, glycine-arginine or glycine-lysine at the carboxyl terminal end that connects to the A-chain of the peptide. The B-chain of the proinsulin construct described therein has a length of 29 amino acids, in contrast to the native 30 amino acid length of the native B-chain in human insulin. The potential effects of this change to the native amino acid sequence of the B-chain in the human insulin produced are yet unknown. Methods of producing insulin using these proinsulin constructs in yeast are also described. Inefficiencies associated with correct folding of the mature insulin molecule when yeast utilized as the expression host, render this process, among other things, inefficient and more expensive and time consuming to use. In addition, yeast provides a relatively low insulin yield, due to the intrinsically low expression levels of a yeast system as compared to *E. coli*.

An ongoing difficulty with this conversion methodology has been and continues to be the presence of substantially large amounts of difficultly-removable by-products in the reaction mixture. Enzymatic modification of human proinsulin using trypsin and carboxypeptidase B results in accumulation of insulin derivatives, leading to more complicated purification processes. Specifically, in the conversion of human proinsulin to human insulin, a large amount (about 4-6%) of desthreonine (des-Thr(B30)) human insulin is formed. Des-Thr($B_{30}$) human insulin differs from human insulin by the absence of a single terminal amino acid and requires difficult and cumbersome purification methods to remove. U.S. Pat. No. 5,457,066 describes treating human insulin precursor with trypsin and carboxypeptidase B in an aqueous medium containing about 0.1 to about 2 moles of metal ions (specifically nickel ions), per mole of human insulin precursor. However, the use of metal ions as described in this patent may lead to potential production problems, among other concerns.

Son, et al., "Effects of citraconylation on enzymatic modification of human proinsulin using trypsin and carboxypeptidase B.," Biotechnol Prog. 25(4) (July-August 2009):1064-70, describes citraconylation and decitraconylation in the enzymatic modification process to reduce des-Thr($B_{30}$) human insulin formation.

Many of the foregoing technical problems are equally applicable to the production of insulin analogs. Insulin analogs are altered forms of native insulin that are available to the body for performing the same action as native insulin. One particular insulin analog known as glargine insulin has been described, e.g., in U.S. Pat. Nos. 5,547,930, 5,618,913, and 5,834,422. This analog is used in the treatment of diabetes. Glargine insulin is characterized as a slow release insulin analog that controls blood sugar when no food is being digested. Glargine insulin may form a hexamer when injected subcutaneously into the patient. This insulin analog has been available commercially as LANTUS® (SANOFI AVENTIS®). LANTUS® is an insulin analog wherein the molecule includes a $Gly(A_{21})$-$Arg(B_{31})$-$Arg(B_{32})$ amino acid sequence.

Another particular insulin analog known as aspart insulin has been described, e.g., in U.S. Pat. Nos. 5,618,913, 5,547, 930, and 5,834,422. This analog is also used in the treatment of diabetes. Aspart insulin analog has increased charge repulsion as compared with native insulin, which prevents the formation of hexamers and thus results in a faster acting insulin. This aspart insulin analog has been available commercially as NOVOLOG® (ELI LILLY®). NOVOLOG® is an insulin analog wherein the molecule includes a Asp($B_{28}$) amino acid sequence in place of the native insulin Pro($B_{28}$). NOVOLOG® is an injectable, fast-acting insulin. NOVOLOG® is also available as mix with insulin aspart protamine and commercially referred to as NOVOLOG® Mix 70/30, which contains 30% insulin aspart and 70% insulin aspart protamine. The insulin aspart protamine portion is a crystalline form of insulin aspart, which delays the action of the insulin, giving NOVOLOG® Mix 70/30 a prolonged absorption profile after injection.

Another particular insulin analog known as Lis-Pro insulin has been described, e.g., in U.S. Pat. Nos. 5,474,978 and 5,504,188. This analog is used in the treatment of diabetes. Lis-Pro insulin is characterized as a short acting insulin analog, which, when combined with an insulin pump, allows for better blood glucose stability without the risk of hyperglycemia. This Lis-Pro insulin analog has been available commercially as HUMALOG® (ELI LILLY®). HUMALOG® is an insulin analog wherein the molecule includes a Lys($B_{28}$)-Pro($B_{29}$) amino acid sequence in place of the native insulin Pro($B_{28}$)-Lys($B_{29}$). HUMALOG® is an injectable, fast-acting insulin.

Accordingly, a need exists for a more efficient process for production of human insulin that is efficient, eliminates currently necessary purification steps, and that at the same time improves and/or preserves acceptable production yield requirements of the pharmaceutical industry.

BRIEF SUMMARY OF THE INVENTION

The present invention relates to novel proinsulin compositions and insulin analogs and processes for producing the same.

In certain aspects, these compositions comprise a peptide, an amino acid sequence, or a nucleic acid sequence encoding a modified C-peptide, a modified proinsulin molecule, insulin analog, or a pharmaceutical preparation of these peptides in a pharmaceutically acceptable carrier solution and/or diluent.

In particular embodiments, the invention relates to proinsulin compositions that include a unique non-di-basic amino acid sequence at one or both of its C-peptide terminal ends. In some embodiments, the constructs are described as an N-terminal multiple His-tagged proinsulin construct. In particular embodiments, the N-terminal multiple His-tagged proinsulin construct comprises a 6-histidine N-terminal tag. In some embodiments, the construct comprises a structure as defined in Formula I or Formula II:

```
Formula I:
X1-C peptide-X2
                                 (SEQ ID NO: 2)
MHHHHHHGGR,
or Formula II:
X1-modified C peptide-X2
                                 (SEQ ID NO: 2)
MHHHHHHGGR
``` wherein $X_1$ comprises an insulin B Chain, and wherein $X_2$ comprises an insulin A chain. In the Formula II construct, the modified C peptide is defined as a sequence having a non-dibasic (such as AR) amino acid sequence at a terminal end of the modified C peptide component that is adjacent the $X_2$ component (insulin A chain) and/or a modification (such as RA) located adjacent the $X_1$ component (insulin B chain) in the construct as depicted in Formula II.

In particular embodiments, the modified proinsulin compositions have an amino acid or nucleic acid sequence that may be used to produce a glargine insulin analog. In these embodiments, the modified proinsulin composition has an amino acid sequence having the formula set forth as Formula III:

$$R_1\text{-}(B_1\text{-}B_{29})\text{-}B_{30}\text{-}R_2\text{-}R_3\text{-}X\text{-}R_4\text{-}R_5\text{-}(A_1\text{-}A_{20})\text{-}A_{21}\text{-}R_6 \quad \text{Formula III}$$

wherein $R_1$ is a tag sequence comprising one or more amino acids or $R_1$ is absent with an Arg or Lys present prior to the start of the B chain;

($B_1$-$B_{29}$) comprises residues 1-29 of a native human insulin B chain;

$B_{30}$ is Gly, Ala, Ser, Thr, Val, Leu, Ile, Asn, Gln, Cys, Met, Tyr, Phe, Pro, or Trp;

$R_2$, $R_3$ and $R_5$ are Arg;

X is a sequence that comprises one or more amino acids or is absent, provided that X does not comprise a C-terminal Gly, Lys, or Arg when $R_4$ is absent;

$R_4$ is any amino acid other than Gly, Lys or Arg or is absent;

($A_1$-$A_{20}$) comprises residues 1-20 of a native human insulin A chain;

$A_{21}$ is Gly, Ala, Val, Leu, Ile, Pro, Phe, Trp, Met, Ser, Thr, Tyr, Asp, or Glu; and $R_6$ is a tag sequence containing one or more amino acids or $R_6$ is absent.

In particular embodiments, the modified proinsulin compositions have an amino acid or nucleic acid sequence that may be used to produce an aspart insulin analog. In these embodiments, the modified proinsulin composition has an amino acid sequence having the formula set forth as Formula IV:

$$R_1\text{-}(B_1\text{-}B_{26})\text{-}B_{27}\text{-}B_{28}\text{-}B_{29}\text{-}B_{30}\text{-}R_2\text{-}R_3\text{-}X\text{-}R_4\text{-}R_5\text{-}(A_1\text{-}A_{20})\text{-}A_{21}\text{-}R_6 \quad \text{Formula IV:}$$

$R_1$ is a tag sequence comprising one or more amino acids or $R_1$ is absent with an Arg or Lys present prior to the start of the B chain;

($B_1$-$B_{26}$) comprises residues 1-26 of a native human insulin B chain;

$B_{27}$ is Thr, Asp, or Glu;

$B_{28}$ is Asp, Glu, or Pro;

$B_{29}$ is Lys, or Pro;

$B_{30}$ is Ala, Thr, or is absent;

$R_2$, $R_3$ and $R_5$ are Arg;

X comprises one or more amino acids or is absent, provided that X does not comprise a C-terminal Gly, Lys, or Arg when $R_4$ is absent;

$R_4$ is any amino acid other than Gly, Lys or Arg or is absent;

($A_1$-$A_{20}$) comprises residues 1-20 of a native human insulin A chain;

$A_{21}$ is Asn, Gly, Ala, Val, Leu, Ile, Pro, Phe, Trp, Met, Ser, Thr, Tyr, Asp, or Glu; and $R_6$ is a tag sequence comprising one or more amino acids or $R_6$ is absent.

In particular embodiments, the modified proinsulin compositions have an amino acid or nucleic acid sequence that may be used to produce a Lis-Pro insulin analog. In these embodiments, the modified proinsulin composition has an amino acid sequence having the formula set forth as Formula V:

$$R_1\text{-}(B_1\text{-}B_{27})\text{-}B_{28}\text{-}B_{29}\text{-}B_{30}\text{-}R_2\text{-}R_3\text{-}X\text{-}R_4\text{-}R_5\text{-}(A_1\text{-}A_{21})\text{-}R_6 \quad \text{Formula V}$$

wherein $R_1$ is a tag sequence containing one or more amino acids or $R_1$ is absent with an Arg or Lys present prior to the start of the B chain;

($B_1$-$B_{27}$) comprises residues 1-27 of a native human insulin B chain;

$B_{28}$ is any amino acid other than Pro;

$B_{29}$ is any amino acid other than Lys or Arg;

$B_{30}$ is Thr;

$R_2$, $R_3$ and $R_5$ are Arg;

X is a sequence comprises one or more amino acids or is absent, provided that X is not EAEALQVGQVELGGGP-GAGSLQPLALEGSLQ (SEQ ID NO: 3) and X does not comprise a C-terminal Gly, Lys, or Arg when $R_4$ is absent;

$R_4$ is any amino acid other than Gly, Lys or Arg or is absent;

($A_1$-$A_{21}$) comprises a native human insulin A chain;

$R_6$ is a tag sequence containing one or more amino acids or $R_6$ is absent.

In some embodiments, the modified proinsulin compositions comprise a pharmaceutically acceptable preparation comprising recombinant human insulin or insulin analog and are essentially free of proinsulin.

In other aspects, the invention relates to novel processes for producing highly purified insulin and insulin analogs that is more efficient than techniques described in the prior art. In particular aspects, these processes employ bacteria, such as E. coli.

These processes present many advantages, among them the advantage of reducing and/or eliminating the presence of unwanted and contaminating cleavage by-products characteristic of conventional manufacturing processes for producing recombinant human insulin in E. coli. Previously undesirable by-products evident in yield mixtures using conventional methods of producing recombinant human insulin included, by way of example, the production of an unwanted cleavage product, Arg(A(0))-insulin. A highly efficient process for the production of recombinant human insulin and related analogs is presented that reduces and/or eliminates the presence of this and other unwanted and undesirable cleavage by-products, and that further presents the advantages of eliminating several time consuming, expensive, purification steps. A process having fewer technician-assisted steps is thus devised, and illustrates the additional advantage of eliminating the degree of inconsistency and/or error associated with technician assisted steps in the manufacturing process.

In particular aspects, these processes are suitable for producing glargine insulin analogs. In general, such processes comprise the steps of (a) culturing a transformed E. coli comprising an expression vector comprising a nucleic acid sequence encoding a modified glargine proinsulin peptide having an amino acid sequence as set forth in Formula III; (b) disrupting the transformed E. coli, producing a composition comprising inclusion bodies containing the modified glargine proinsulin peptide; (c) solubilizing the composition comprising inclusion bodies, producing a solubilized composition thereby; and (d) recovering the modified glargine proinsulin peptide from the solubilized composition.

In related aspects, processes for producing glargine insulin analogs comprise the additional steps of: (e) folding the modified glargine proinsulin peptide, producing an glargine proinsulin derivative peptide thereby; (f) purifying the glargine proinsulin derivative peptide using a metal affinity chromatographic process; (g) enzymatically cleaving the glargine proinsulin derivative peptide to remove a connecting peptide (i.e., $R_2$-$R_3$-X-$R_4$-$R_5$), producing an intermediate solution comprising an glargine insulin analog thereby; and (h) purifying the intermediate solution using chromatography to produce the glargine insulin analog thereby.

In particular aspects, these processes are suitable for producing aspart insulin analogs. In general, such processes comprise the steps of (a) culturing a transformed E. coli comprising an expression vector comprising a nucleic acid sequence encoding a modified aspart proinsulin peptide having an amino acid sequence as set forth in Formula IV; (b) disrupting the transformed E. coli, producing a composition comprising inclusion bodies containing the modified aspart proinsulin peptide; (c) solubilizing the composition comprising inclusion bodies, producing a solubilized composition thereby; and (d) recovering the modified aspart proinsulin peptide from the solubilized composition.

In related aspects, processes for producing aspart insulin analogs comprise the additional steps of: (e) folding the modified aspart proinsulin peptide, producing an aspart proinsulin derivative peptide thereby; (f) purifying the aspart proinsulin derivative peptide using a metal affinity chromatographic process; (g) enzymatically cleaving the aspart proinsulin derivative peptide to remove a connecting peptide (i.e., $R_2$-$R_3$-X-$R_4$-$R_5$), producing an intermediate solution comprising an aspart insulin analog thereby; and (h) purifying the intermediate solution using chromatography to produce the aspart insulin analog thereby.

In particular aspects, these processes are suitable for producing Lis-Pro insulin analogs. In general, such processes comprise the steps of (a) culturing a transformed E. coli comprising an expression vector comprising a nucleic acid sequence encoding a modified Lis-Pro proinsulin peptide having an amino acid sequence as set forth in Formula V; (b) disrupting the transformed E. coli, producing a composition comprising inclusion bodies containing the modified Lis-Pro proinsulin peptide; (c) solubilizing the composition comprising inclusion bodies, producing a solubilized composition thereby; and (d) recovering the modified Lis-Pro proinsulin peptide from the solubilized composition.

In related aspects, processes for producing Lis-Pro insulin analogs comprise the additional steps of: (e) folding the modified Lis-Pro proinsulin peptide, producing an Lis-Pro proinsulin derivative peptide thereby; (f) purifying the Lis-Pro proinsulin derivative peptide using a metal affinity chromatographic process; (g) enzymatically cleaving the Lis-Pro proinsulin derivative peptide to remove a connecting peptide (i.e., $R_2$-$R_3$-X-$R_4$-$R_5$), producing an intermediate solution comprising an Lis-Pro insulin analog thereby; and (h) purifying the intermediate solution using chromatography to produce the Lis-Pro insulin analog thereby. In some embodiments, the composition comprising inclusion bodies is solubilized by adjusting the pH to at least 10.5. In some embodiments, the Lis-Pro insulin analog is eluted using a buffer comprising n-propanol.

The present invention also relates to processes for producing a highly purified liquid active pharmaceutical ingredient (API) comprising a recombinant human insulin having an amino acid sequence that is about 95% homologous with the amino acid sequence of native human insulin. These preparations have a greatly reduced amount of related contaminant substances. These related contaminant substances comprise, for example, high molecular weight substances such as non-monomeric forms of insulin (multimeric forms including dimeric forms, etc.), chemically modified insulin molecules (e.g., desamido insulin forms ($A_{21}$ desamino insulin products), carbamylated insulin forms, norvaline contaminants, and isopropyl phe products (e.g., isopropyl form of phenylalanine).

In some embodiments, compositions produced by these processes comprise 2% or less of a specific desamido form of insulin, $A_{21}$ desamino insulin, and 1% or less non-monomeric species of insulin (multimeric species of insulin). For purposes of the present invention, multimeric species generally refers to the insulin molecule that comprises multiple insulin monomers, e.g., dimers, trimers, tetramers, hexamer, etc. The multimeric species may be further described as high molecular weight insulin species.

In particular aspects, these processes are suitable for producing liquid insulin utilizing a modified proinsulin peptide having an amino acid sequence having the formula set forth as Formula VI:

Formula VI wherein:

$R_1$ is a tag sequence comprising one or more amino acids or $R_1$ is absent with an Arg or Lys present prior to the start of the B chain;

$(B_1\text{-}B_{30})$ comprises a native human insulin B chain;

$R_2$, $R_3$ and $R_5$ are Arg;

$R_4$ is any amino acid other than Gly, Lys or Arg or is absent;

X is a sequence comprises one or more amino acids or is absent, provided that X is not EAEALQVGQVELGGGP-GAGSLQPLALEGSLQ (SEQ ID NO: 3) and X does not comprise a C-terminal Gly, Lys, or Arg when $R_4$ is absent;

$R_4$ is any amino acid other than Gly, Lys or Arg or is absent;

$(A_1\text{-}A_{21})$ comprises a native human insulin A chain; and $R_6$ is a tag sequence containing one or more amino acids or $R_6$ is absent.

In general, such processes comprise the steps of a) culturing a transformed E. coli comprising an expression vector comprising a nucleic acid sequence encoding a modified proinsulin peptide having an amino acid sequence as set forth in Formula VI; (b) disrupting the transformed E. coli, producing a composition comprising inclusion bodies containing the modified proinsulin peptide; (c) solubilizing the composition comprising inclusion bodies, producing a solubilized composition thereby; (d) folding the modified proinsulin peptide, producing a proinsulin derivative peptide thereby; (e) purifying the proinsulin derivative peptide using a metal affinity chromatographic process; (f) protecting a Lys amino acid residue of the proinsulin derivative peptide with one or more protecting compounds, producing a blocked proinsulin derivative peptide thereby; (g) enzymatically cleaving the blocked proinsulin derivative peptide to remove a connecting peptide, producing an intermediate solution comprising an insulin intermediate thereby; (h) purifying the intermediate solution using a chromatographic process, producing a purified insulin intermediate thereby; (i) enzymatically cleaving arginine residues from the purified insulin intermediate, producing a partially purified insulin preparation thereby; and (j) purifying the partially purified insulin preparation using a chromatographic process, producing a highly purified liquid recombinant human insulin thereby.

An object of the invention is to solve at least the above problems and/or disadvantages and to provide at least the advantages described hereinafter.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF SUMMARY OF THE SEVERAL VIEWS OF THE DRAWINGS

The invention will be described in detail with reference to the following drawings in which like reference numerals refer to like elements wherein:

FIG. 15, according to one aspect of the invention, is a process flow scheme for the purification of insulin.

FIG. 16A, according to one aspect of the invention, is a process flow scheme for the purification of insulin. FIG. 16B is a conventional process flow scheme for the purification and crystallization of insulin.

FIG. 18A shows a map of peptide fragments of recombinant human insulin produced according to the methods of the invention. The peptide map is based on non-reducing conditions and the fragments were created with V8 protease. FIG. 18A discloses "USP Reference Standard" Fragment Numbers I-IV as SEQ ID NOs: 86-91, respectively, in order of appearance, and "R&D Insulin" Fragment Numbers I-IV as SEQ ID NOs: 86-91, respectively, in order of appearance.

FIG. 18B shows a map of peptide fragments of recombinant human insulin produced according to the methods of the invention. The peptide map is based on reducing conditions and the fragments were created with V8 protease. FIG. 18B discloses "USP Reference Standard" Fragment Numbers I-VI as SEQ ID NOs: 91, 86, 88, 87, 89 and 90, respectively, in order of appearance, and "R&D Insulin" Fragment Numbers I-VI as SEQ ID NOs: 91, 86, 88, 87, 89 and 90, respectively, in order of appearance.

FIG. 23 is a table showing the levels of contamination of related substances in recombinant human insulin (R&D insulin) versus wild-type human insulin (Insulin human USP standard) as determined by RP-HPLC.

FIG. 25 is table of stability data comparing liquid insulin, according to one aspect of the invention, with insulin prepared by ELI LILLY®.

DETAILED DESCRIPTION OF THE INVENTION

Figure 1:
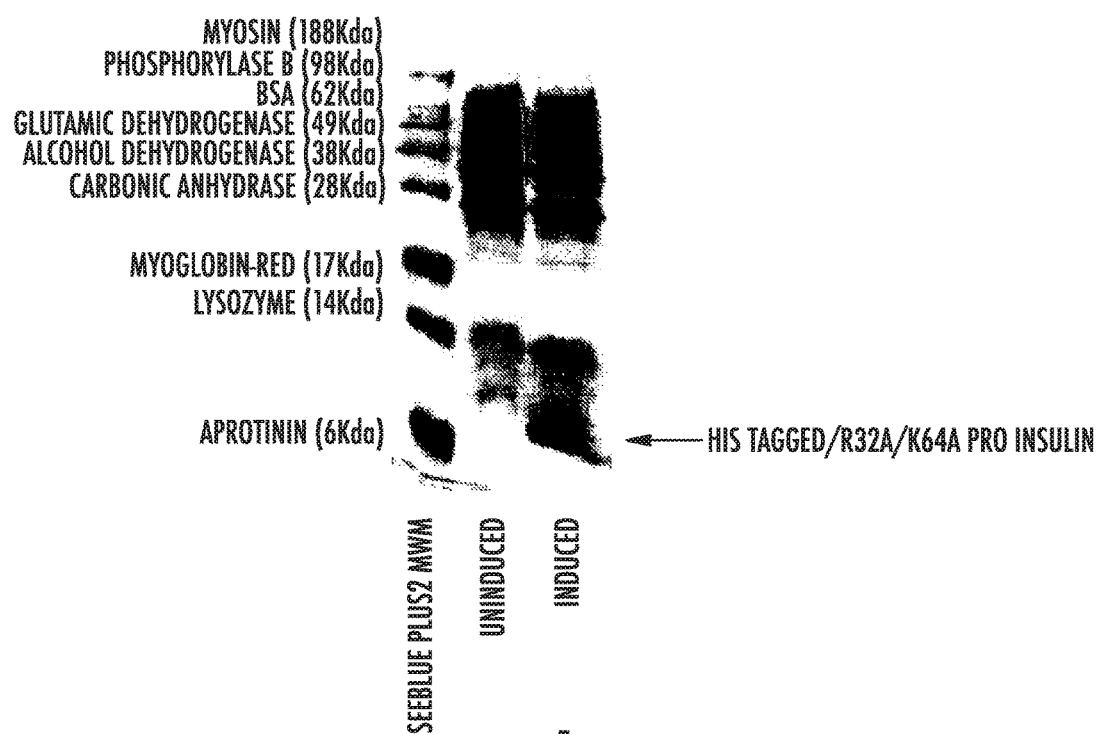
FIG. 1, according to one aspect of the invention, presents a gel showing expression of the full length His-tagged/K64A proinsulin (10.5 KDa) protein. The gel is from the expression product produced from the E. coli, BL21 strain, transformed with the above mentioned genes.

The present invention relates to novel proinsulin constructs, C-peptides, and methods for using these in a process to provide high yields of mature recombinant human insulin. The proinsulin constructs include a novel C-peptide that includes a non-dibasic terminal amino acid sequence at one end.

In particular embodiments, a non-dibasic alanine-arginine (AR) sequence is located at the carboxyl terminus of the C-chain. The C-terminus of the C-peptide connects to the A-chain of the proinsulin molecule. Advantageously, the positioning of these particular terminal amino acids in the C-peptide provides for an improved method for producing recombinant human insulin, having fewer steps, improved yields of the recombinant human insulin protein and less contaminating byproducts.

The present invention also relates to novel methods for manufacturing liquid insulin and novel compositions of liquid insulin.

The present invention also relates to a highly purified preparation of recombinant human insulin. In some aspects, the purified preparation of recombinant human insulin may be described as comprising an API (Active Pharmaceutical Ingredient) of recombinant human insulin having less than 2%, less than 1%, less than 0.5%, or even less than 0.11%, contaminant by weight of the total recombinant insulin protein preparation by total weight. In some aspects, the purified preparation of recombinant human insulin may be described as comprising an API of recombinant human insulin having less than 1%, less than 0.7%, less than 0.5%, or even less than 0.4%, multimeric species of insulin by weight of the total recombinant insulin protein preparation by total weight.

According to some embodiments of the invention, a preparation of recombinant insulin that is in a substantially liquid form and that has not been through a crystallization process is provided. In some embodiments, the preparation may be further described as a human recombinant insulin preparation in a substantially liquid form.

In other embodiments, insulin of the invention includes insulin analogs or variants, i.e., polypeptides having insulin activity and substantial amino acid sequence identity to wild-type insulin. For example, analog or variant insulin proteins, according to some embodiments of the invention include proteins having the biological activity of at least 10%, 20%, 50%, 70%, 80%, 90%, 95%, 99% or 100% in comparison to the biological activity of wild-type insulin. For example, analog or variant insulin proteins, according to some embodiments of the invention include proteins having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with wild-type insulin. To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=(# of identical positions/total/total # of positions)×100). The determination of homology between two sequences can be accomplished using a mathematical algorithm.

A non-limiting example of a mathematical algorithm utilized for the comparison of two sequences is the algorithm of Karlin and Altschul, (1990) Proc. Natl. Acad. Sci. USA. 87:2264-68, modified as in Karlin and Altschul, (1993) Proc. Natl. Acad. Sci. USA, 90:5873-77. Such an algorithm is incorporated into the NBLAST and XBLAST programs of Altschul et al., (1990) J. Mol. Biol., 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al., (1997) Nucleic Acids Research, 25(17):3389-3402. When utilizing BLAST and Gapped BLAST programs, the default parameters of the respective programs (e.g., XBLAST and NBLAST) can be used.

The present invention also relates to the preparation of insulin analogs from modified proinsulin sequences. Modified proinsulin sequences refer to a single-chain polypeptide that may be converted into human insulin or insulin analogs and comprise a connecting peptide (C-peptide) having at least one non-dibasic terminal amino acid sequence.

The present invention also provides modified proinsulin sequences having a modified C-peptide and methods for using these in a process to provide high yields of mature recombinant insulin analogs. In one embodiment, non-dibasic terminal amino acid sequences of an insulin analog may comprise (any amino acid except Lys or Arg-Arg ((any except R or K)R), and more preferably (any amino acid except Gly, Lys, or Arg-Arg ((any except G, R, or K)R). In one embodiment the terminal amino acid sequence may comprise Ala-Arg. Advantageously, the positioning of these particular terminal amino acids in the C-peptide may provide for an improved method for producing a recombinant insulin analog, having fewer steps, improved yields of the recombinant insulin analog and less contaminating byproducts.

The process for producing insulin analogs of the invention presents many advantages, among them the advantage of reducing and/or eliminating the presence of unwanted and contaminating cleavage by-products characteristic of conventional manufacturing processes for producing recombinant human insulin in *E. coli*. Previously undesirable by-products evident in yield mixtures using conventional methods of producing recombinant human insulin analogs included, by way of example, the production of an unwanted cleavage product, Arg(A(0)) insulin analogs. A highly efficient process for the production of recombinant human insulin analogs is presented that reduces and/or eliminates the presence of this and other unwanted and undesirable cleavage by-products, and that further presents the advantages of eliminating several time consuming, expensive, purification steps. A process having fewer technician-assisted steps is thus devised, and illustrates the additional advantage of eliminating the degree of inconsistency and/or error associated with technician assisted steps in the manufacturing process.

In certain embodiments, the process provides a second key advantage: the citraconylation of lysine at position 29 of the B chain using citraconic anhydride. The lysine in the proinsulin sequence PKTRR (SEQ ID NO: 4), is cleaved by trypsin during the transformation reaction at a rate of approximately 5-8%, which creates the desthreonine insulin contaminant. Citraconylation of the lysine prevents trypsin cleavage and in turn prevents desthreonine insulin. The citraconylation also decreases trypsin cleavage at the arginine at position $B_{31}$ of the C-peptide. Single Arg($B_{31}$)-insulin constitutes approximately 20-30% of the trypsin digest. However, when the lysine is blocked by citraconic anhydride, the level of Arg($B_{31}$)-insulin decreases to approximately 6-10% of the trypsin digest. Decreasing levels of desthreonine insulin and Arg($B_{31}$)-insulin provides for a simpler purification, as both these impurities are difficult to remove due to their high similarity to the end-product (e.g., glargine insulin).

Glargine insulin is an insulin analog that comprises a modified A-chain and B-chain having Gly($A_{21}$), Arg($B_{31}$), and Arg($B_{32}$). Glargine insulin analogs may be produced from modified proinsulin sequences or nucleic acids encoding the modified proinsulin sequences. In these embodiments, the modified proinsulin sequence has an amino acid sequence having the formula set forth as Formula III:

Formula III

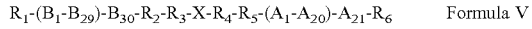

wherein $R_1$ is a tag sequence comprising one or more amino acids or $R_1$ is absent with an Arg or Lys present prior to the start of the B chain;

($B_1$-$B_{29}$) comprises residues 1-29 of a native human insulin B chain;

$B_{30}$ is Gly, Ala, Ser, Thr, Val, Leu, Ile, Asn, Gln, Cys, Met, Tyr, Phe, Pro, or Trp;

$R_2$, $R_3$ and $R_5$ are Arg;

X is a sequence that comprises one or more amino acids or is absent, provided that X does not comprise a C-terminal Gly, Lys, or Arg when $R_4$ is absent;

$R_4$ is any amino acid other than Gly, Lys or Arg or is absent;

($A_1$-$A_{20}$) comprises residues 1-20 of a native human insulin A chain;

$A_{21}$ is Gly, Ala, Val, Leu, Ile, Pro, Phe, Trp, Met, Ser, Thr, Tyr, Asp, or Glu; and $R_6$ is a tag sequence containing one or more amino acids or $R_6$ is absent.

Aspart insulin is an insulin analog that comprises a modified B-chain having Asp($B_{28}$). Aspart insulin analogs may be produced from modified proinsulin sequences or nucleic acids encoding the modified proinsulin sequences. In these embodiments, the modified proinsulin sequence has an amino acid sequence having the formula set forth as Formula IV:

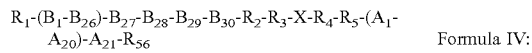

Formula IV:

$R_1$ is a tag sequence comprising one or more amino acids or $R_1$ is absent with an Arg or Lys present prior to the start of the B chain;

($B_1$-$B_{26}$) comprises residues 1-26 of a native human insulin B chain;

$B_{27}$ is Thr, Asp, or Glu;

$B_{28}$ is Asp, Glu, or Pro;

$B_{29}$ is Lys, or Pro;

$B_{30}$ is Ala, Thr, or is absent;

$R_2$, $R_3$ and $R_5$ are Arg;

X comprises one or more amino acids or is absent, provided that X does not comprise a C-terminal Gly, Lys, or Arg when $R_4$ is absent;

$R_4$ is any amino acid other than Gly, Lys or Arg or is absent;

($A_1$-$A_{20}$) comprises residues 1-20 of a native human insulin A chain;

$A_{21}$ is Asn, Gly, Ala, Val, Leu, Ile, Pro, Phe, Trp, Met, Ser, Thr, Tyr, Asp, or Glu; and $R_6$ is a tag sequence comprising one or more amino acids or $R_6$ is absent.

Lis-Pro insulin is an insulin analog in which the order of Pro($B_{28}$)-Lys($B_{29}$) is reversed. Lis-Pro insulin analogs may be produced from modified proinsulin sequences or nucleic acids encoding the modified proinsulin sequences. In these embodiments, the modified proinsulin sequence has an amino acid sequence having the formula set forth as Formula V:

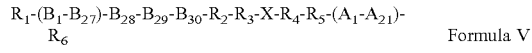

Formula V wherein $R_1$ is a tag sequence containing one or more amino acids or $R_1$ is absent with an Arg or Lys present prior to the start of the B chain;

($B_1$-$B_{27}$) comprises residues 1-27 of a native human insulin B chain;

$B_{28}$ is any amino acid other than Pro;

$B_{29}$ is any amino acid other than Lys or Arg;

$B_{30}$ is Thr;

$R_2$, $R_3$ and $R_5$ are Arg;

X is a sequence comprises one or more amino acids or is absent, provided that X is not EAEALQVGQVELGGGP- GAGSLQPLALEGSLQ (SEQ ID NO: 3) and X does not comprise a C-terminal Gly, Lys, or Arg when R$_4$ is absent;

R$_4$ is any amino acid other than Gly, Lys or Arg or is absent;

(A$_1$-A$_{21}$) comprises a native human insulin A chain;

R$_6$ is a tag sequence containing one or more amino acids or R$_6$ is absent.

Some embodiments of the invention relate to methods of producing insulin utilizing a modified or variant proinsulin having amino acid sequence having the formula set forth as Formula VI:

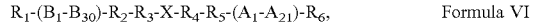  Formula VI wherein:

R$_1$ is a tag sequence comprising one or more amino acids or R$_1$ is absent with an Arg or Lys present prior to the start of the B chain;

(B$_1$-B$_{30}$) comprises a native human insulin B chain;

R$_2$, R$_3$ and R$_5$ are Arg;

R$_4$ is any amino acid other than Gly, Lys or Arg or is absent;

X is a sequence comprises one or more amino acids or is absent, provided that X is not EAEALQVGQVELGGGP-GAGSLQPLALEGSLQ (SEQ ID NO: 3) and X does not comprise a C-terminal Gly, Lys, or Arg when R$_4$ is absent;

R$_4$ is any amino acid other than Gly, Lys or Arg or is absent;

(A$_1$-A$_{21}$) comprises a native human insulin A chain; and

R$_6$ is a tag sequence containing one or more amino acids or R$_6$ is absent.

R$_1$ or R$_6$ in the modified proinsulin of Formula III, IV, V or VI comprises a pre or post-peptide that may be a native pre-peptide or an N-terminal multiple His-tag sequence, or any other commercially available tag utilized for protein purification, e.g. DSBC, Sumo, Thioredein, T7, S tag, Flag Tag, HA tag, V5 epitope, Pel B tag, Xpress epitope, GST, MBP, NusA, CBP, or GFP. In one embodiment at least one of R1 or R6 is present in Formula III. It is preferred that the terminal amino acid of the pre or post-peptide that connects to the B-chain or A-chain comprise Arg or Lys. Native pre-peptide has the sequence of MALWMRLLPLLALLAL-WGPDPAAA (SEQ ID NO: 5). In some embodiments, the N-terminal multiple His-tagged proinsulin construct comprises a 6-histidine N-terminal tag HHHHHH (SEQ ID NO: 6) and may have the sequence MHHHHHHGGR (SEQ ID NO: 2). The modified proinsulin sequence may replace the native 24 amino acid pre-peptide with the 6-histidine N-terminal tag sequence. In some embodiments, R$_1$ and/or R$_6$ may be a sequence of one or more amino acids, e.g., preferably from 1 to 30 and more preferably from 6 to 10.

Native insulin comprises an A-chain having the sequence GIVEQCCTSICSLYQLENYCN (SEQ ID NO: 7) and a B-chain having the sequence FVNQHLCGSHLVEALYL-VCGERGFFYTPKT (SEQ ID NO: 8). In accordance with the invention, the A-chain and B-chain of Formula III is modified from native insulin and contains at least one amino acid mutation, substitution, deletion, insertion, and/or addition. For glargine insulin analogs, preferably A$_{21}$ is modified and B$_{31}$ and B$_{32}$ of the B-chain are added. The asparagine (A$_{21}$) of native insulin is substituted with glycine and the two arginine amino acids are added to (B$_{30}$) of native insulin. In one embodiment, the two arginine amino acids may be amino acid residues from the C-peptide. In accordance with the invention, the B-chain of Formula IV is modified from native insulin and contains at least one amino acid mutation, substitution, deletion, insertion, and/or addition. For aspart insulin analogs, preferably B28 of the B-chain is modified. The proline B$_{28}$ of native insulin is substituted with aspartic acid. In addition B$_{27}$, B$_{29}$, and B$_{30}$ are preferably native amino acid residues. In accordance with the invention, the B-chain of Formula V is modified from native insulin and contains at least one amino acid mutation, substitution, deletion, insertion, and/or addition. For Lis-Pro insulin analogs, preferably B$_{28}$ and B$_{29}$ of the B-chain are modified. The lysine B$_{29}$ of native insulin is substituted with proline and the proline B$_{28}$ of native insulin is substituted with lysine.

In some embodiments, the A-chain and/or B-chain that is modified is a human insulin B-chain. In another embodiment, the A-chain and/or B-chain that is modified is porcine insulin B-chain.

As used in the description of the present invention, the term "connecting peptide" or "C-peptide" is meant the connecting moiety "C" of the B-C-A polypeptide sequence of a single chain proinsulin molecule. Specifically, in the native human insulin chain, the C-peptide connects to position 30 of the B-chain and position 1 of the A-chain. In some embodiments, the A-chain and the B-chain of the proinsulin constructs retain their native sequences and lengths. The C-peptide constructs disclosed have been modified so as to include different terminal amino acids relative to native C-peptide.

As in native human proinsulin, the C-peptide constructs of the present invention connect position 30 of the B-chain and position 1 of the A-chain. The single chain proinsulin molecules of the invention will include three (3) correctly positioned, disulfide bridges, as is characteristic of the native human proinsulin molecule. The amino acid sequence of the B-chain and the A-chain of the proinsulin constructs, as well as the human insulin products produced by the methods described herein, will have the native amino acid sequence characteristic of native human insulin.

In some embodiments, the C-peptide may comprise the sequence R$_2$-R$_3$-X-R$_4$-R$_5$, wherein R$_2$, R$_3$, R$_4$, R$_5$ and X are defined as in Formula III, Formula IV, Formula V, and/or Formula VI, depending on whether insulin or an insulin analog is being produced. In one embodiment, X may be a sequence having up to 40 amino acids, preferably up to 35 amino acids or more preferably up to 30 amino acids. Although X may be any amino acid sequence, in one embodiment, X is preferably not EAEALQVGQVELGGG-PGAGSLQPLALEGSLQ (SEQ ID NO: 3).

The C-peptide sequences of the present invention may include:

```
                                          (SEQ ID NO: 9)
RREAEDLQVGQVELGGGPGAGSLQPLALEGSLQAR;

(SEQ ID NO: 10)
RREAEDLQVGQVGLGGGPGAGSLQPLALEGSLQAR;

(SEQ ID NO: 11)
RREAEALQVGQVGLGGGPGAGSLQPLALEGSLQAR;

(SEQ ID NO: 12)
RREAEDLQVGQVELGGGPGAGSLQPLAIEGSLQAR;

(SEQ ID NO: 13)
RREAEDLQVGQVGLGGGPGAGSLQPLAIEGSLQAR;

(SEQ ID NO: 14)
RREAEALQVGQVGLGGGPGAGSLQPLAIEGSLQAR;
or (SEQ ID NO: 15)
RREAEALQVGQVELGGGPGAGSLQPLALEGSLQAR.
```

Preferred modified glargine proinsulin sequences of the present invention may include:

(SEQ ID NO: 16)
FVNQHLCGSHLVEALYLVCGERGFFYTPKTRREAEDLQVGQVELGGGPGA
GSLQPLALEGSLQARGIVEQCCTSICSLYQLENYCG;

(SEQ ID NO: 17)
MHHHHHHGGRFVNQHLCGSHLVEALYLVCGERGFFYTPKTRREAEDLQVG
QVELGGGPGAGSLQPLALEGSLQARGIVEQCCTSICSLYQLENYCG;

(SEQ ID NO: 18)
MALWMRLLPLLALLALWGPDPAAAFVNQHLCGSHLVEALYLVCGERGFFY
TPKTRREAEDLQVGQVELGGGPGAGSLQPLALEGSLQARGIVEQCCTSIC
SLYQLENYCG;

(SEQ ID NO: 19)
MHHHHHHGGRFVNQHLCGSHLVEALYLVCGERGFFYTPKTRREAEDLQVG
QVELGGGPGAGSLQPLALEGSLQARGIVEQCCTSICSLYQLENYCGRHHH
HHH;

(SEQ ID NO: 20)
MHHHHHHGGRFVNQHLCGSHILVEALYLVCGERGFFYTPKTRREAEDLQV
GQVELGGGPGAGSLQPLALEGSLQARGIVEQCCTSICSLYQLENYCGKHH
HHHH;

(SEQ ID NO: 21)
MRFVNQHLCGSHLVEALYLVCGERGFFYTPKTRREAEDLQVGQVELGGGP
GAGSLQPLALEGSLQARGIVEQCCTSICSLYQLENYCGRHHHHHH;
or (SEQ ID NO: 22)
MRFVNQHLCGSHLVEALYLVCGERGFFYTPKTRREAEDLQVGQVELGGGP
GAGSLQPLALEGSLQARGIVEQCCTSICSLYQLENYCGKHHHHHH.

The single chain glargine insulin analogs of the invention will include three (3) correctly positioned, disulfide bridges, as is characteristic of the native human insulin. In some embodiments, the folded modified glargine proinsulin, or glargine proinsulin derivative peptide, may include three (3) correctly positioned, disulfide bridges. In the production, the C-peptide of the glargine proinsulin derivative peptide is removed to produce the glargine insulin analog. Glargine insulin analogs of the invention have a sequence as shown below, wherein the disulfide bridges are represented as —S—S—. The A-chain (SEQ ID NO: 23) and B-chain (SEQ ID NO: 24) are also shown.

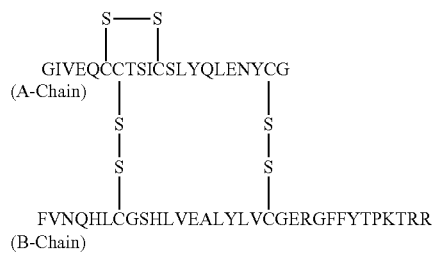

Preferred modified aspart proinsulin sequences of the present invention may include:

(SEQ ID NO: 25)
FVNQHLCGSHLVEALYLVCGERGFFYTDKTRREAEDLQVGQVELGGGPGA
GSLQPLALEGSLQARGIVEQCCTSICSLYQLENYCN;

(SEQ ID NO: 26)
MHHHHHHGGRFVNQHLCGSHLVEALYLVCGERGFFYTDKTRREAEDLQVG
QVELGGGPGAGSLQPLALEGSLQARGIVEQCCTSICSLYQLENYCN;

(SEQ ID NO: 27)
MALWMRLLPLLALLALWGPDPAAAFVNQHLCGSHLVEALYLVCGERGFFY
TDKTRREAEDLQVGQVELGGGPGAGSLQPLALEGSLQARGIVEQCCTSIC
SLYQLENYCN;

(SEQ ID NO: 28)
MHHHHHHGGRFVNQHLCGSHLVEALYLVCGERGFFYTDKTRREAEDLQVG
QVELGGGPGAGSLQPLALEGSLQARGIVEQCCTSICSLYQLENYCNRHHH
HHH;

(SEQ ID NO: 29)
MHHHHHHGGRFVNQHLCGSHILVEALYLVCGERGFFYTDKTRREAEDLQV
GQVELGGGPGAGSLQPLALEGSLQARGIVEQCCTSICSLYQLENYCNKHH
HHHH;

(SEQ ID NO: 30)
MRFVNQHLCGSHLVEALYLVCGERGFFYTDKTRREAEDLQVGQVELGGGP
GAGSLQPLALEGSLQARGIVEQCCTSICSLYQLENYCNRHHHHHH;
or (SEQ ID NO: 31)
MRFVNQHLCGSHLVEALYLVCGERGFFYTDKTRREAEDLQVGQVELGGGP
GAGSLQPLALEGSLQARGIVEQCCTSICSLYQLENYCNKHHHHHH.

The single chain aspart insulin analogs of the invention will include three (3) correctly positioned, disulfide bridges, as is characteristic of the native human insulin. In some embodiments, the folded modified aspart proinsulin, or aspart proinsulin derivative peptide, may include three (3) correctly positioned, disulfide bridges. In the production, the C-peptide of the aspart proinsulin derivative peptide is removed to produce the aspart insulin analog. Aspart insulin analogs of the invention have a sequence as shown below, wherein the disulfide bridges are represented as —S—S—. The A-chain (SEQ ID NO: 32) and B-chain (SEQ ID NO: 33) are also shown.

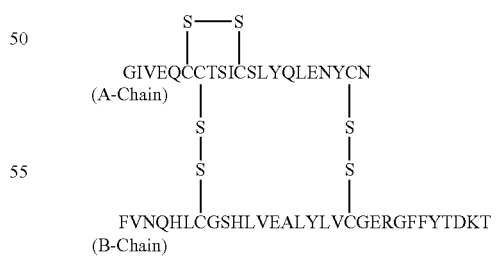

Preferred modified Lis-Pro proinsulin sequences of the present invention may include:

(SEQ ID NO: 34)
FVNQHLCGSHLVEALYLVCGERGFFYTKPTRREAEDLQVGQVELGGGPGA
GSLQPLALEGSLQARGIVEQCCTSICSLYQLENYCN;

(SEQ ID NO: 35)
MHHHHHHGGRFVNQHLCGSHLVEALYLVCGERGFFYTKPTRREAEDLQVG

QVELGGGPGAGSLQPLALEGSLQARGIVEQCCTSICSLYQLENYCN;

(SEQ ID NO: 36)
MALWMRLLPLLALLALWGPDPAAAFVNQHLCGSHLVEALYLVCGERGFFY

TKPTRREAEDLQVGQVELGGGPGAGSLQPLALEGSLQARGIVEQCCTSIC

SLYQLENYCN;

(SEQ ID NO: 37)
MHHHHHHGGRFVNQHLCGSHLVEALYLVCGERGFFYTKPTRREAEDLQVG

QVELGGGPGAGSLQPLALEGSLQARGIVEQCCTSICSLYQLENYCNRHHH

HHH;

(SEQ ID NO: 38)
MHHHHHHGGRFVNQHLCGSHILVEALYLVCGERGFFYTKPTRREAEDLQV

GQVELGGGPGAGSLQPLALEGSLQARGIVEQCCTSICSLYQLENYCNKHH

HHHH;

(SEQ ID NO: 39)
MRFVNQHLCGSHLVEALYLVCGERGFFYTKPTRREAEDLQVGQVELGGGP

GAGSLQPLALEGSLQARGIVEQCCTSICSLYQLENYCNRHHHHHH;
or (SEQ ID NO: 40)
MRFVNQHLCGSHLVEALYLVCGERGFFYTKPTRREAEDLQVGQVELGGGP

GAGSLQPLALEGSLQARGIVEQCCTSICSLYQLENYCNKHHHHHH.

The single chain Lis-Pro insulin analogs of the invention will include three (3) correctly positioned, disulfide bridges, as is characteristic of the native human insulin. In some embodiments, the folded modified Lis-Pro proinsulin, or Lis-Pro proinsulin derivative peptide, may include three (3) correctly positioned, disulfide bridges. In production, the C-peptide of the Lis-Pro proinsulin derivative peptide is removed to produce the Lis-Pro insulin analog. Lis-Pro insulin analogs of the invention have a sequence as shown below, wherein the disulfide bridges are represented as —S—S—. The A-chain (SEQ ID NO: 32) and B-chain (SEQ ID NO: 41) are also shown.

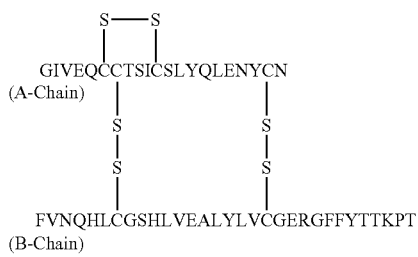

Preferred modified proinsulin sequences of the present invention may include:

(SEQ ID NO: 42)
FVNQHLCGSHLVEALYLVCGERGFFYTPKTRREAEDLQVGQVELGGGPGA

GSLQPLALEGSLQARGIVEQCCTSICSLYQLENYCN;

(SEQ ID NO: 43)
MHHHHHHGGRFVNQHLCGSHLVEALYLVCGERGFFYTPKTRREAEDLQVG

QVELGGGPGAGSLQPLALEGSLQARGIVEQCCTSICSLYQLENYCN;

(SEQ ID NO: 44)
MALWMRLLPLLALLALWGPDPAAAFVNQHLCGSHLVEALYLVCGERGFFY

TPKTRREAEDLQVGQVELGGGPGAGSLQPLALEGSLQARGIVEQCCTSIC

SLYQLENYCN;

(SEQ ID NO: 45)
MHHHHHHGGRFVNQHLCGSHLVEALYLVCGERGFFYTPKTRREAEDLQVG

QVELGGGPGAGSLQPLALEGSLQARGIVEQCCTSICSLYQLENYCNRHHH

HHH;

(SEQ ID NO: 46)
MHHHHHHGGRFVNQHLCGSHILVEALYLVCGERGFFYTPKTRREAEDLQV

GQVELGGGPGAGSLQPLALEGSLQARGIVEQCCTSICSLYQLENYCNKHH

HHHH;

(SEQ ID NO: 47)
MRFVNQHLCGSHLVEALYLVCGERGFFYTPKTRREAEDLQVGQVELGGGP

GAGSLQPLALEGSLQARGIVEQCCTSICSLYQLENYCNRHHHHHH;
or (SEQ ID NO: 48)
MRFVNQHLCGSHLVEALYLVCGERGFFYTPKTRREAEDLQVGQVELGGGP

GAGSLQPLALEGSLQARGIVEQCCTSICSLYQLENYCNKHHHHHH.

As used in the description of the present invention, the terms "insulin precursor" or "proinsulin" are described as a single-chain polypeptide in which, by one or more subsequent chemical and/or enzymatic processes, may be converted into human insulin.

As used in the description of the present invention, the term "proinsulin analog" is defined as a proinsulin molecule having one or more mutations, substitutions, deletions, and or additions, of the A, B and/or C chains relative to the native human proinsulin nucleic acid sequence. The proinsulin analogs are preferably such wherein one or more of the naturally occurring nucleic acids have been substituted with another nucleic acid within a triplet encoding for a particular amino acid.

The term "insulin analog" includes insulin molecules having one or more mutations, substitutions, deletions, additions, or modifications to one or more amino acids of a native insulin sequence. For example, in one embodiment, the native insulin sequence is porcine insulin, while in another embodiment, the native insulin sequence is human.

The term "a" as used in the description of the present invention is intended to mean "one or more", and is used to define both the singular and plural forms of the item or items to which it references, or to a feature or characteristic to which it refers. The use of the singular or plural in the claims or specification is not intended to be limiting in any way and also includes the alternative form.

The term "about" is intended to be inclusive of and to encompass both an exact amount as well as an approximate amount or range of values or levels of the item, ingredient, element, activity, or other feature or characteristic to which it references. Generally, and in some embodiment's, the term "about" is intended to reference a range of values relatively close to the specific numerical value specifically identified. For example, "about 3 grams to about 5 grams" is intended to encompass a measure of in or around a value of 3 grams, concentration values between 3 grams and 5 grams, concentration values in and around 5 grams, as well as concentration values that are exactly 3 grams and exactly 5 grams.

As used in the description of the present process, a high protein concentration of the proinsulin or insulin product is defined as a protein yield concentration of at least about 3 grams/liter, or between about 3 grams to about 5 grams per liter. The expression yield to be expected may be defined as a protein/peptide yield that is sufficient to detect via polyacrylamide gel electrophoresis (PAGE).

The invention in a general and overall sense relates to an improved process for preparing a heterologous recombinant protein in a prokaryotic host cell. This process is characterized in that it employs a unique recombinant protein that provides a useful and efficiently processed proinsulin peptide having a unique, modified C-peptide region, as well as a His tagged N-terminal sequence.

By heterologous protein is meant that said protein in said prokaryotic host cell is not native, i.e., it occurs as a protein in peculiar or foreign (i.e., not native to) the host prokaryotic cell.

"Recombinant" means produced or modified by molecular-biological methods.

(SEQ ID NO: 49)
FVNQHLCGSHLVEALYLVCGERGFFYTPKTGIVEQCCTSICSLYQLENYC
N

Table 1 provides the triplet codons corresponding to each of the various amino acids that are used in the description of the present invention. As will be understood by those of skill in the art, the amino acid that may be used in any particularly defined position as part of any of the peptide, protein, or constructs otherwise defined herein by reference to a particular nucleotide triplet base pair may be encoded by a number of different nucleotide triplets that function to encode the same amino acid. For example, where the amino acid of the sequence defined herein is alanine (Ala, or A), the triplet codon of nucleic acids that may encode for this amino acid are: GCT, GCC, GCA, or GCG. Table 1 illustrates this definition of variables at and substitutions as can be applied to all of the naturally occurring amino acids sequences of the disclosure.

TABLE 1

| | | Second Position | | | | |
|---|---|---|---|---|---|---|
| | | U | C | A | G | |
| First Position | U | UUU Phe | UCU Ser | UAU Tyr | UGU Cys | U Third Position |
| | | UUC | UCC | UAC | UGC | C |
| | | UUA Leu | UCA | UAA Stop | UGA Stop | A |
| | | UUG | UCG | UAG Stop | UGG Trp | G |
| | C | CUU Leu | CCU Pro | CAU His | CGU Arg | U |
| | | CUC | CCC | CAC | CGC | C |
| | | CUA | CCA | CAA Gln | CGA | A |
| | | CUG | CCG | CAG | CGG | G |
| | A | AUU Ile | ACU Thr | AAU Asn | AGU Ser | U |
| | | AUC | ACC | AAC | AGC | C |
| | | AUA | ACA | AAA Lys | AGA Arg | A |
| | | AUG Met | ACG | AAG | AGG | G |
| | G | GUU Val | GCU Ala | GAU Asp | GGU Gly | U |
| | | GUC | GCC | GAC | GGC | C |
| | | GUA | GCA | GAA Glu | GGA | A |
| | | GUG | GCG | GAG | GGG | G |

As used in the description of the present invention, the term "heterologous recombinant protein" is defined as any protein known to the skilled person in the molecular biological arts, such as, for example, insulin, proinsulin, C-peptide, and proteins containing these together with any other protein or peptide fragment.

Prokaryotic host cells may be any host cells known to the skilled artisan in the molecular biological arts, and by way of example, Escherichia coli. Such types of cells available form public collections and useful in the practice of the present invention include, by way of example, the Deutsche Sammlung von Mikrooganismen and Zellkulturen GmbH, Braunschweig, Germany, e.g., E. coli Strain K12 JM107 (DSM 3950).

Proteins and peptides are chains of amino acids linked by peptide bonds, which in the case of proteins give a defined structure that is typically required for activity. Peptides are chains of amino acids which may or may not have activity or a defined structure.

Human Insulin Amino Acid sequence: Sequence of amino acids which make up the native insulin A and B chains.

A glargine insulin analog prepared by the present invention may be formulated as liquid glargine insulin analog or crystalline glargine insulin analog. According to an embodiment of the invention, a preparation of recombinant liquid glargine insulin analog is in a substantially liquid form and that has not been through a crystallization process. Eliminating these steps has no negative impact on the purity of the liquid glargine insulin analog produced, but has the added advantage of reducing the amount of inactive insulin multimers in the liquid glargine insulin analog of the invention. Glargine insulin analog reconstituted from lyophilized and crystallized insulin may be contaminated with inactive insulin multimers and is less preferred.

Figure 10:
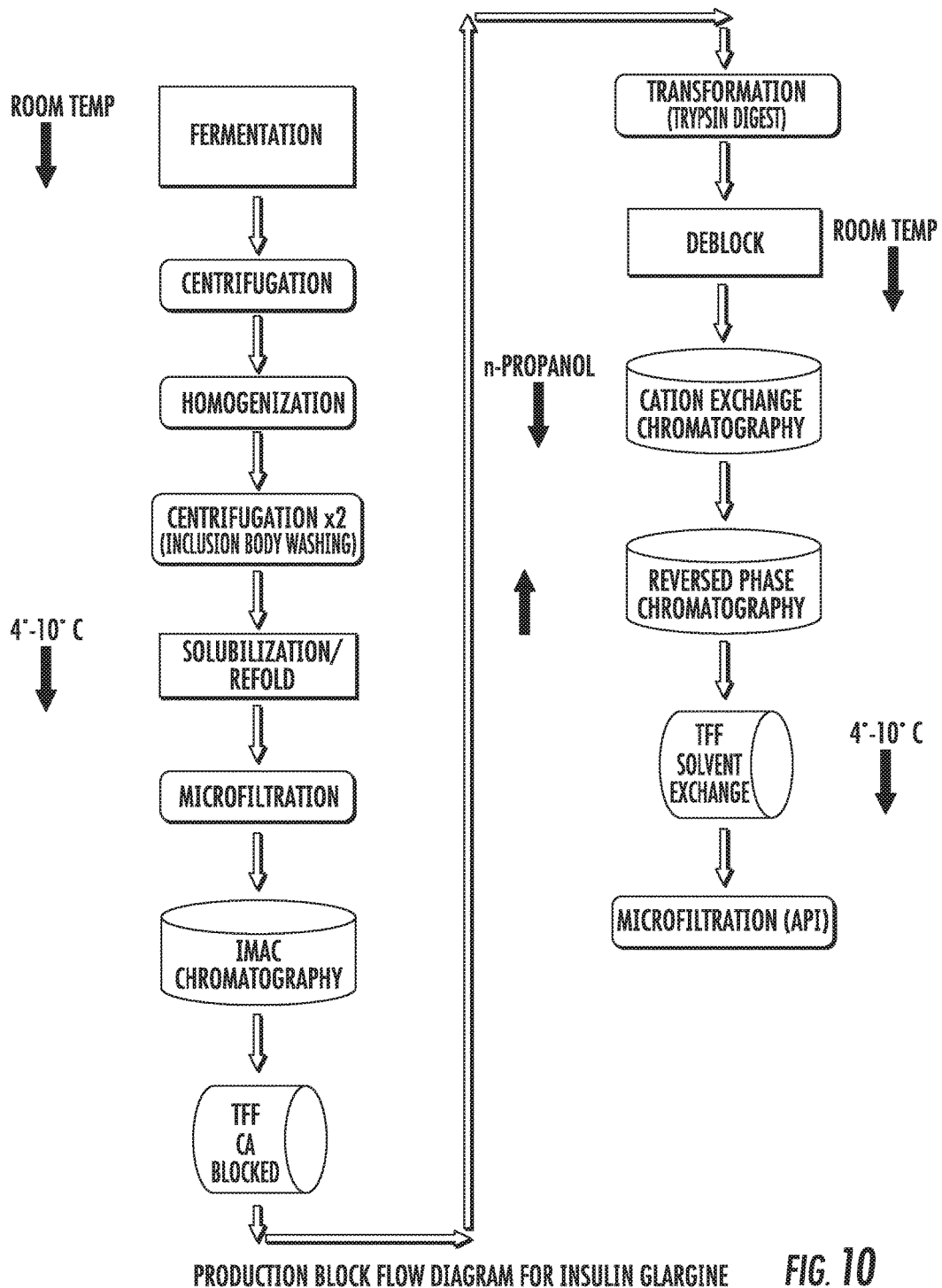
FIG. 10, according to one aspect of the invention, is a process flow scheme for the purification of glargine insulin analogs.

According to one embodiment, the methods of producing a glargine insulin analog described herein generally include the following steps: fermentation/expression, inclusion body isolation, solubilization of glargine proinsulin analog; refolding processing and transformation of glargine proinsulin analog to glargine insulin analog; and purification of glargine insulin analog. FIG. 10 illustrates a flow chart of preferred process steps in producing glargine insulin analog according to embodiments of the present invention.

Expression of glargine proinsulin analog may occur in a recombinant expression system. According to one embodiment, the recombinant expression system is a working cell bank (WCB) containing glargine proinsulin analog expressing vectors. For example, the cells of the WCB may be vertebrate or invertebrate cells, such as prokaryote or eukaryote cells, and most preferably the cells may be mammalian, bacterial, insect, or yeast cells. In one embodiment, the cell is a bacterial cell and in a further embodiment, the bacteria is *E. coli*. In another embodiment, the cell is a yeast cell and in a further embodiment, the yeast cell is *S. cerevisiae* or *S. pombe*.

In one embodiment, *E. coli* cells may be cultured and disrupted to provide a composition comprising inclusion bodies. The inclusion bodies contain the modified proinsulin sequence. The glargine proinsulin analogs expressed by cells of the WCB according to the method of the invention may be secreted from the cells and include a secretory sequence. In other embodiments, glargine proinsulin analogs expressed by cells of the WCB are not secreted from the cells, and thus do not include a secretory sequence.

The step of solubilizing the composition of inclusion bodies may Involve adjusting the pH to achieve complete solubilization of the modified glargine proinsulin sequences. In one embodiment, the inclusion bodies may be solubilized by adjusting the pH to at least 10.5, preferably from 10.5 to 12.5, preferably from 11.8-12. The pH may be adjusted by adding an alkali hydroxide such as NaOH or KOH to the composition of inclusion bodies.

In addition, the step of solubilization may use one or more reducing agents and/or chaotropic agent. Suitable reducing agents may include those selected from the group consisting of 2-mercaptoethanol, L-cysteine hydrochloride monohydrate, dithiothreitol, dithierythritol, and mixtures thereof. Suitable chaotropic agents include those selected from the group consisting of urea, thiourea, lithium perchlorate or guanidine hydrochloride, and mixtures thereof.

The solubilized inclusion bodies may be mixed in a refolding buffer, such as glycine or sodium carbonate, at a pH of 7-12, preferably from 10-11, preferably from 10.5-11, to refold the modified proinsulin sequences to a proinsulin derivative peptide, e.g., glargine proinsulin derivative peptide. The solution with refolded material should be pH adjusted to 7-9, preferably 7.8-8.2, with or without the addition of an alkaline salt, preferably sodium chloride to a final concentration of 100 mM to 1 M final concentration, preferably 500 mM to 1 M, preferably 700 mM, and may be filtered and loaded onto a column, such as an immobilized metal-ion affinity chromatography (IMAC) column. Commercially available resins suitable for embodiments of the present invention include Nickel SEPHAROSE® 6 Fast Flow (GE HEALTHCARE®), Nickel NTA Agarose (GE HEALTHCARE®), Chelating SEPHAROSE® Fast flow (GE HEALTHCARE®), IMAC Fast Flow (GE HEALTHCARE®).

During the step of processing of glargine proinsulin to glargine insulin analog one or more of the amino acids may be protected to prevent side reactions and impurities during the cleavage step. In a further embodiment, the addition of a protecting group to glargine insulin analog may be added prior to addition of trypsin. In particular, protecting groups may be used to protect the lysine residue of the B-chain. A preferred protecting group is citriconic anhydride.

In native human proinsulin, citriconic anhydride is preferably used to block $Lys(B_{29})$ in the proinsulin sequence PKTRR (SEQ ID NO: 4), thus reducing the formation of desthreonine insulin impurity. In glargine proinsulin analog of the present invention, citriconic anhydride may also be used to block $Lys(B_{29})$ in the proinsulin sequence PKTRR (SEQ ID NO: 4). The citriconic anhydride protecting group may reduce the formation of impurities such as desthreonine insulin and $Arg(B_{31})$-insulin.

In one embodiment, an excess molar ratio of citriconic anhydride to glargine proinsulin analog may be used. For example, about 10 fold molar excess or more of citriconic anhydride to glargine proinsulin analog may be suitable, and more preferably, about 20 fold molar excess or more. There is no upper limit on the excess molar ratio and the molar ratio may be as high as about 200 fold or about 300 fold.

After the citriconic anhydride blocking step, glargine proinsulin analog is subject to buffer exchange and concentration by tangential flow filtration or diafiltration. Proinsulin derivative peptide, with the blocking groups, may be enzymatically cleaved, preferably by subjecting the proinsulin derivative peptide to trypsin digestion. Although embodiments of the present invention may use commercially available rat, bovine, porcine or human trypsins or other isoenzymes or derivatives or variants thereof, it is also possible to use the following enzymes: trypsin from *Fusarium oxysporum* and from *Streptomyces* (*S. griseus, S. foliatus, S. erythraeus, S. fradiae* and *S. albidoflavus*), tryptase, mastin, acrosin, kallikrein, hepsin, prostasin I, lysyl endopeptidase (Lysin-C) and endoproteinase Arg-C (clostripain). In one embodiment, trypsin digestion occurs at pH from about 7 to 10, and more preferably from 8.8 to 9.2. In a further embodiment, the trypsin digest is quenched by adding glacial acetic acid. While it is contemplated that other additives may be employed, acetic acid appears to be most preferred and stable for this purpose.

Trypsin is an enzyme that has specific cleavage activity at the c-terminal side of arginine residues, and to a lesser extent, lysine residues, of the C-peptide. In the transformation reaction, it is required that the terminal arginine or lysine residues of the C-peptide be removed. In native human proinsulin, when trypsin cleaves at the lysine in position 64, it will be unable to remove the arginine at position 65, due to the fact that it requires at least one residue on both sides of a cleavage site. What results is the production of an unwanted by-product, Arg(A(0))-insulin. This by-product constitutes a small loss in yield and generates an undesired contaminant. By converting this lysine 64 into another uncharged amino acid, particularly alanine, the Arg(A(0))-insulin byproduct is preferentially not formed. When formed, less than 10%, and more preferably less than 0.3% of total byproducts from the trypsin transformation reaction may be Arg(A(0)). This is because the trypsin no longer acts to cleave at this particular site of the proinsulin derivative peptide.

The glargine insulin analog is subjected to deblocking after digestion with trypsin. Citriconic anhydride deblocking occurs by permitting the glargine insulin to be warmed to a temperature of 15° C. to 25° C., more preferably 18° C. to 20° C., and the pH is adjusted to 2.5 to 3.5, more preferably 2.8 to 3.0.

In one embodiment, after deblocking the glargine insulin is purified in a chromatography column, such as an ion exchange column. Following the ion exchange chromatography, the glargine insulin may be further purified using reverse phase chromatography. In one embodiment, the intermediate solution may be purified in a chromatography column by eluting the glargine insulin analog using a buffer comprising an alcohol or organic solvent, n-propanol or acetonitrile. The buffer may also further comprise an alkali metal salt, preferable sodium sulfate. The buffer may also further comprise an organic acid, preferable phosphoric acid.

According to the invention, insulin having two additional arginine residues at the carboxyl terminal end of the B chain, along with glycine substituted for asparagines at the carboxy terminal end of the A chain allows glargine insulin to form a precipitate (hexamer) when injected subcutaneously. Accordingly, upon administration of this glargine insulin analog to a patient, it can maintain a peakless level for up to 24 hours. In particular, this analog is particularly suitable for moderate control of serum glucose levels that more closely resemble typical basal insulin secretion. For example, if administered prior to sleep, insulin glargine can reduce the risk of nocturnal hypoglycaemia.

According to one embodiment of the invention, the insulin glargine analogue is provided to a patient in combination with a rapid acting insulin to provide optimal glycemic control. The manufacturing process described herein results in a preparation of glargine insulin analog in liquid active pharmaceutical ingredient (API) form.

According to one embodiment of the invention, the glargine insulin analog is provided to a patient in combination with human insulin or another insulin analog to provide optimal glycemic control.

In some embodiments, the preparations comprise a pharmaceutically acceptable preparation comprising recombinant glargine insulin analog and being essentially free of modified proinsulin sequences.

The aspart insulin analog prepared by the present invention may be formulated as liquid aspart insulin analog or crystalline aspart insulin analog. According to an embodiment of the invention, a preparation of recombinant liquid aspart insulin analog is in a substantially liquid form and that has not been through a crystallization process. Eliminating these steps has no negative impact on the purity of the liquid aspart insulin analog produced, but has the added advantage of reducing the amount of inactive insulin multimers in the liquid aspart insulin analog of the invention. Aspart insulin analog reconstituted from lyophilized and crystallized insulin may be contaminated with inactive insulin multimers and is less preferred.

Figure 11:
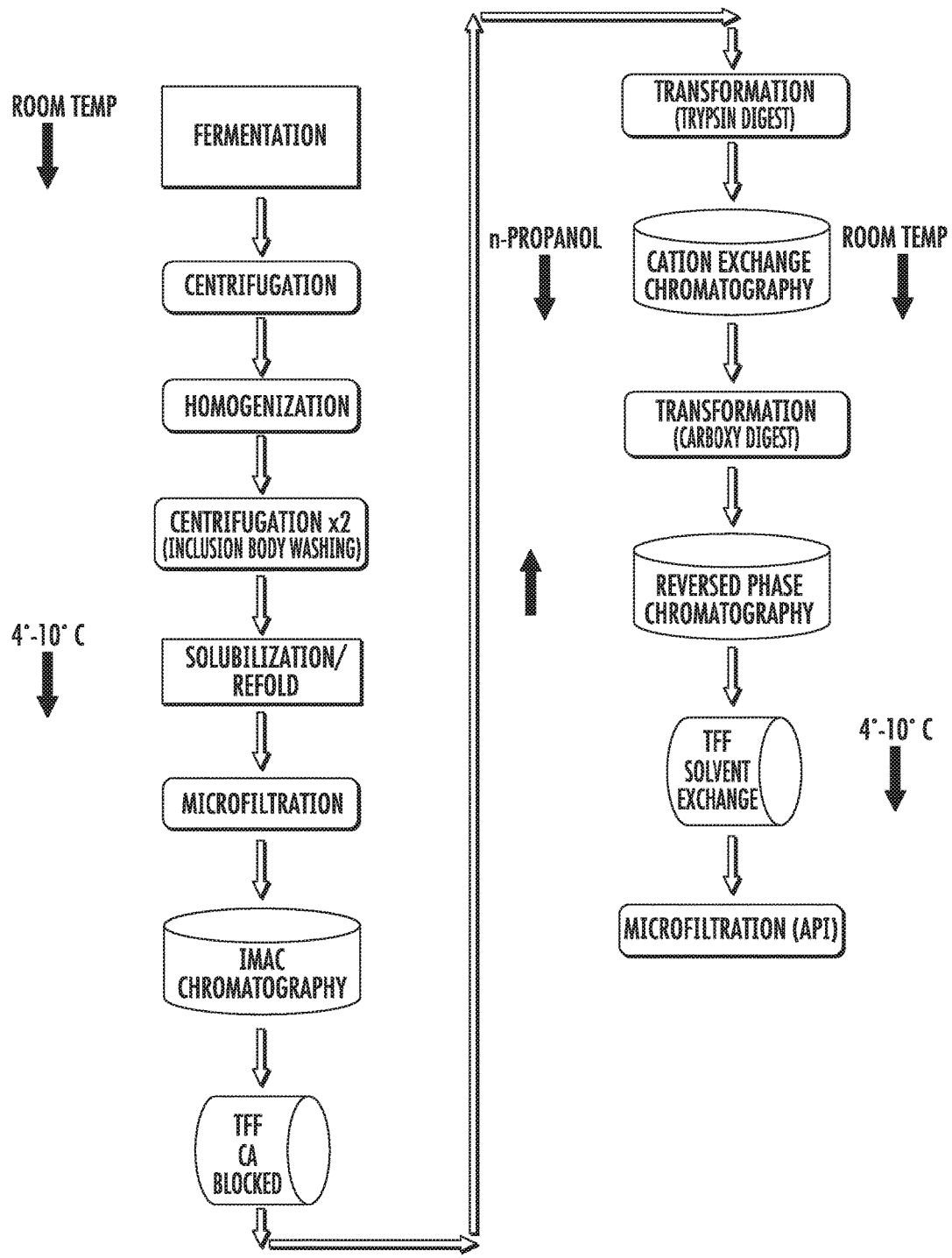
FIGS. 11 and 12, according to aspects to the invention, are process flow schemes for the purification of aspart insulin analogs.
Figure 12:
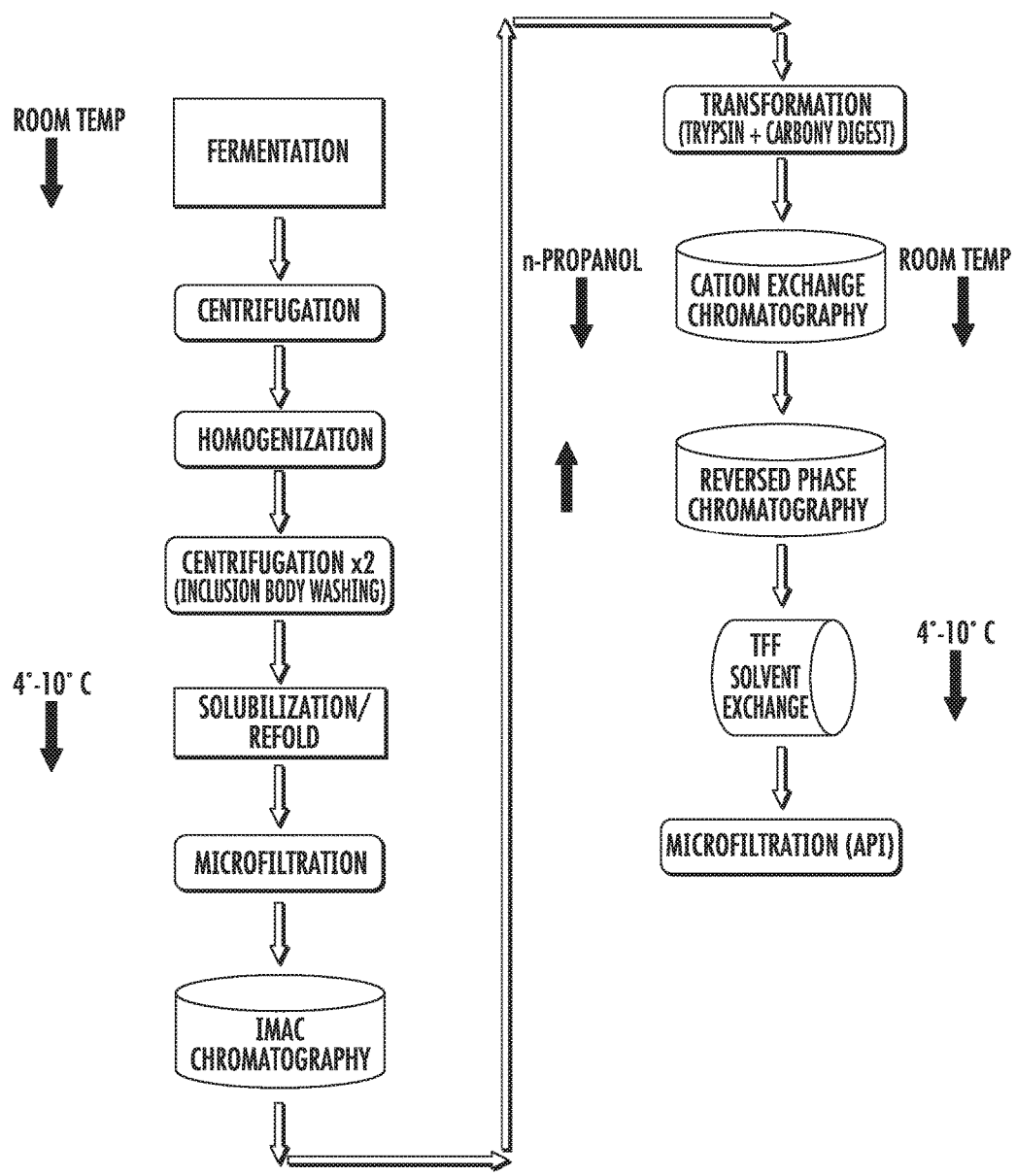

According to one embodiment, the methods of producing aspart insulin analog described herein generally include the following steps: fermentation/expression, inclusion body isolation, solubilization of aspart proinsulin analog; refolding processing and transformation of aspart proinsulin analog to aspart insulin analog; and purification of aspart insulin analog. FIGS. 11 and 12 illustrate flow charts of preferred processes steps in producing an aspart insulin analog according to embodiments of the present invention.

Expression of aspart proinsulin analog may occur in a recombinant expression system. According to one embodiment, the recombinant expression system is an *E. coli* expression system containing aspart proinsulin analog expressing vectors. A master cell bank (MCB) of *E. coli* is provided as an example herein. The cells of the MCB may be vertebrate or invertebrate cells, such as prokaryote or eukaryote cells, and most preferably the cells may be mammalian, bacterial, insect, or yeast cells. In one embodiment, the cell is a bacterial cell and in a further embodiment, the bacteria is *E. coli*. In another embodiment, the cell is a yeast cell and in a further embodiment, the yeast cell is *S. cerevisiae* or *S. pombe*.

In one embodiment, *E. coli* cells may be cultured and disrupted to provide a composition comprising inclusion bodies. The inclusion bodies contain the modified proinsulin sequence. The aspart proinsulin analogs expressed by cells of the MCB according to the method of the invention may be secreted from the cells and include a secretory sequence. In other embodiments, aspart proinsulin analogs expressed by cells of the MCB are not secreted from the cells, and thus do not include a secretory sequence.

The step of solubilizing of the composition of inclusion bodies may involve adjusting the pH to achieve complete solubilization of the modified aspart proinsulin sequences. In one embodiment, the inclusion bodies may be solubilized by adjusting the pH to at least 10.5, preferably from 10.5 to 12.5, and most preferably from 11.8-12. The pH may be adjusted by adding an alkali hydroxide such as NaOH or KOH to the composition of inclusion bodies. In addition, the step of solubilization may use one or more reducing agents and/or chaotropic agent. Suitable reducing agents may include those selected from the group consisting of 2-mercaptoethanol, L-cysteine hydrochloride monohydrate, dithiothreitol, dithierythritol, and mixtures thereof. Suitable chaotropic agents include those selected from the group consisting of urea, thiourea, lithium perchlorate or guanidine hydrochloride, and mixtures thereof.

The solubilized inclusion bodies may be mixed in a refolding buffer, such as glycine or sodium carbonate, at a pH of 7 to 12, preferably from 10 to 11, preferably from 10.5 to 11, to refold the modified aspart proinsulin sequences to a proinsulin derivative peptide, e.g., aspart proinsulin derivative peptide. The solution with refolded material should be pH adjusted to 7 to 9, preferably 7.8 to 8.2, with or without the addition of an alkaline salt, preferably sodium chloride to a final concentration of 100 mM to 1 M final concentration, preferably 500 mM to 1 M, preferably 700 mM, and may be filtered and loaded onto a column, such as an immobilized metal-ion affinity chromatography (IMAC) column. Commercially available resins suitable for embodiments of the present invention include Nickel SEPHAROSE® 6 Fast Flow (GE HEALTHCARE®), Nickel NTA Agarose (GE HEALTHCARE®), Chelating SEPHAROSE® Fast flow(GE HEALTHCARE®), IMAC Fast Flow (GE HEALTHCARE®).

The aspart proinsulin derivative peptide is subject to concentration by tangential flow filtration or diafiltration. Next, proinsulin derivative peptide is enzymatically cleaved, preferably by subjecting the proinsulin derivative peptide to trypsin digestion. Although embodiments of the present invention may use commercially available rat, bovine, porcine or human trypsins or other isoenzymes or derivatives or variants thereof, it is also possible to use the following enzymes: recombinant trypsin, trypzene, trypsin from *Fusarium oxysporum* and from *Streptomyces* (*S. griseus, S. exfoliatus, S. erythraeus, S. fradiae* and *S. albidoflavus*), tryptase, mastin, acrosin, kallikrein, hepsin, prostasin I, lysyl endopeptidase (Lysin-C) and endoproteinase Arg-C (clostripain). In one embodiment, trypsin digestion occurs at pH from about 7 to 10, and more preferably from 8.1 to 8.3. In a further embodiment, the trypsin digest is quenched by adding glacial acetic acid. While it is contemplated that other additives may be employed, acetic acid appears to be most preferred and stable for this purpose.

Trypsin is an enzyme that has specific cleavage activity at the terminal arginine residues, and to a lesser extent, lysine residues, of the C-peptide. In the transformation reaction, it is required that the terminal arginine or lysine residues of the C-peptide be removed. In native human proinsulin, when trypsin cleaves at the lysine in position 64, it will be unable to remove the arginine at position 65, due to the fact that it requires at least one residue on both sides of a cleavage site.

What results is the production of an unwanted by-product, Arg(A(0))-insulin. This by-product constitutes a small loss in yield and generates an undesired contaminant. By converting this lysine 64 into another uncharged amino acid, particularly alanine, the Arg(A(0))-insulin byproduct is preferentially not formed. When formed is less than 10%, and more preferably is less than 0.3% of total byproducts from the trypsin transformation reaction may be Arg(A(0)). This is because the trypsin no longer acts to cleave at this particular site of the proinsulin derivative peptide.

The proinsulin derivative peptide, may also be subjected to carboxypeptidase B digestion. In one embodiment, a trypsin inhibitor may be added to the insulin prior to addition of carboxypeptidase B. Trypsin inhibitor is added in an equal amount to the amount of trypsin added for the trypsin digest step. In another embodiment, a glycine solution is added to aspart proinsulin analog prior to addition of carboxypeptidase B. For example, in some embodiments, glycine is added to adjust the pH of the insulin solution to about 9.6±0.1. The target concentration of glycine is 50 mM using a 1 M glycine stock. In some embodiments, the carboxypeptidase B is permitted to digest for at least 1-16 hours, preferably at least 8 hours. A minimum of 10 hours is preferred, but overdigestion is rarely a significant issue so there is no maximum time limit.

After trypsin digestion the intermediate solution is preferably purified in a chromatography column, such as a ion exchange chromatography column or reverse phase chromatography. In one embodiment, the intermediate solution may be purified in a chromatography column by eluting the aspart insulin analog using a buffer comprising n-propanol or acetonitrile. The buffer may also further comprise sodium sulfate and phosphoric acid.

The manufacturing process described herein results in a preparation of aspart insulin analog in liquid active pharmaceutical ingredient (API) form. The process eliminates the need to prepare a crystallized insulin that is later reconstituted. As a result of eliminating the crystallization and drying steps, the amount of inactive insulin multimers present in the liquid formulation is reduced in comparison to the amounts otherwise present in crystallized forms of insulin and reconstituted crystallized insulin. Although crystallization is less preferred, in some embodiments, a crystallization step may be included to produce aspart insulin analog API crystals. The aspart insulin analog may be crystallized to allow for Increased shelf life to the API material. However, as mentioned the crystallization process will lead to increased levels of multimers and in turn an overall lower purity.

Aspart insulin analog may prevent the formation of non-monomeric insulin, such as dimers and hexamers. Accordingly, upon administration of the aspart insulin analog to a patient, larger amounts of active monomeric insulin are available to act in the patient. In particular, aspart insulin analog is particularly suitable for postprandial, i.e., after eating, injection as it is available immediately for use by the patient to control glucose levels. Accordingly, this analog has the advantage over native insulin in that its short delay of onset allows more flexibility with eating schedules for diabetic patients than regular insulin which requires a longer waiting period between injection and eating. According to one embodiment of the invention, the aspart insulin analog is provided to a patient in combination with a longer acting insulin to provide optimal glycemic control.

In some embodiments, the preparations comprise a pharmaceutically acceptable preparation comprising recombinant aspart insulin analog and being essentially free of modified proinsulin sequences.

The Lis-Pro insulin analog prepared by the present invention may be formulated as liquid Lis-Pro insulin analog or crystalline Lis-Pro insulin analog. According to an embodiment of the invention, a preparation of recombinant liquid Lis-Pro insulin analog is in a substantially liquid form and that has not been through a crystallization process. Eliminating these steps has no negative impact on the purity of the liquid Lis-Pro insulin analog produced, but has the added advantage of reducing the amount of inactive insulin multimers in the liquid Lis-Pro insulin analog of the invention. Lis-Pro insulin analog reconstituted from lyophilized and crystallized insulin may be contaminated with inactive insulin multimers and is less preferred.

Figure 13:
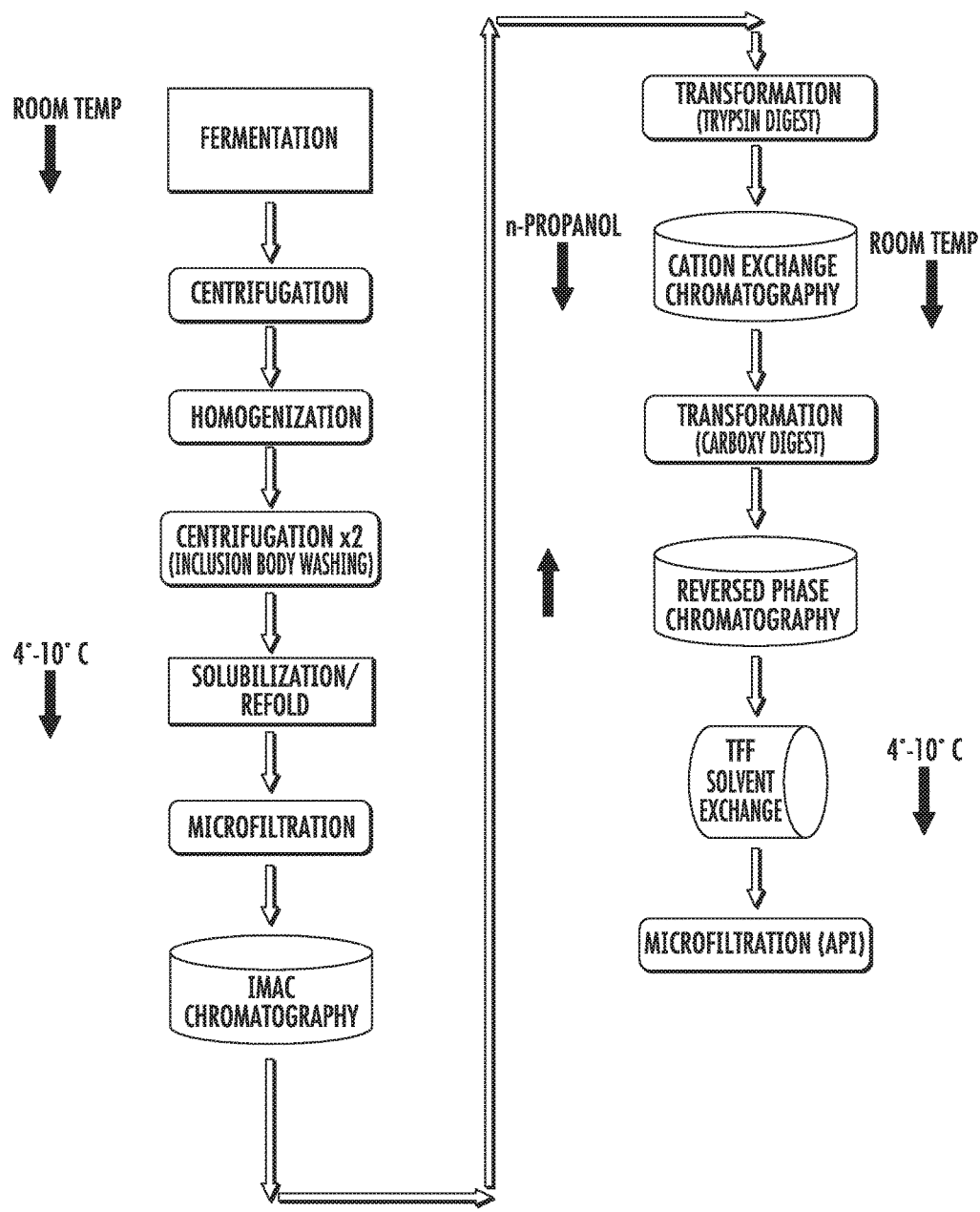
FIGS. 13 and 14, according to some aspects of the invention, present process flow schemes for the purification of Lis-Pro insulin analogs.
Figure 14:
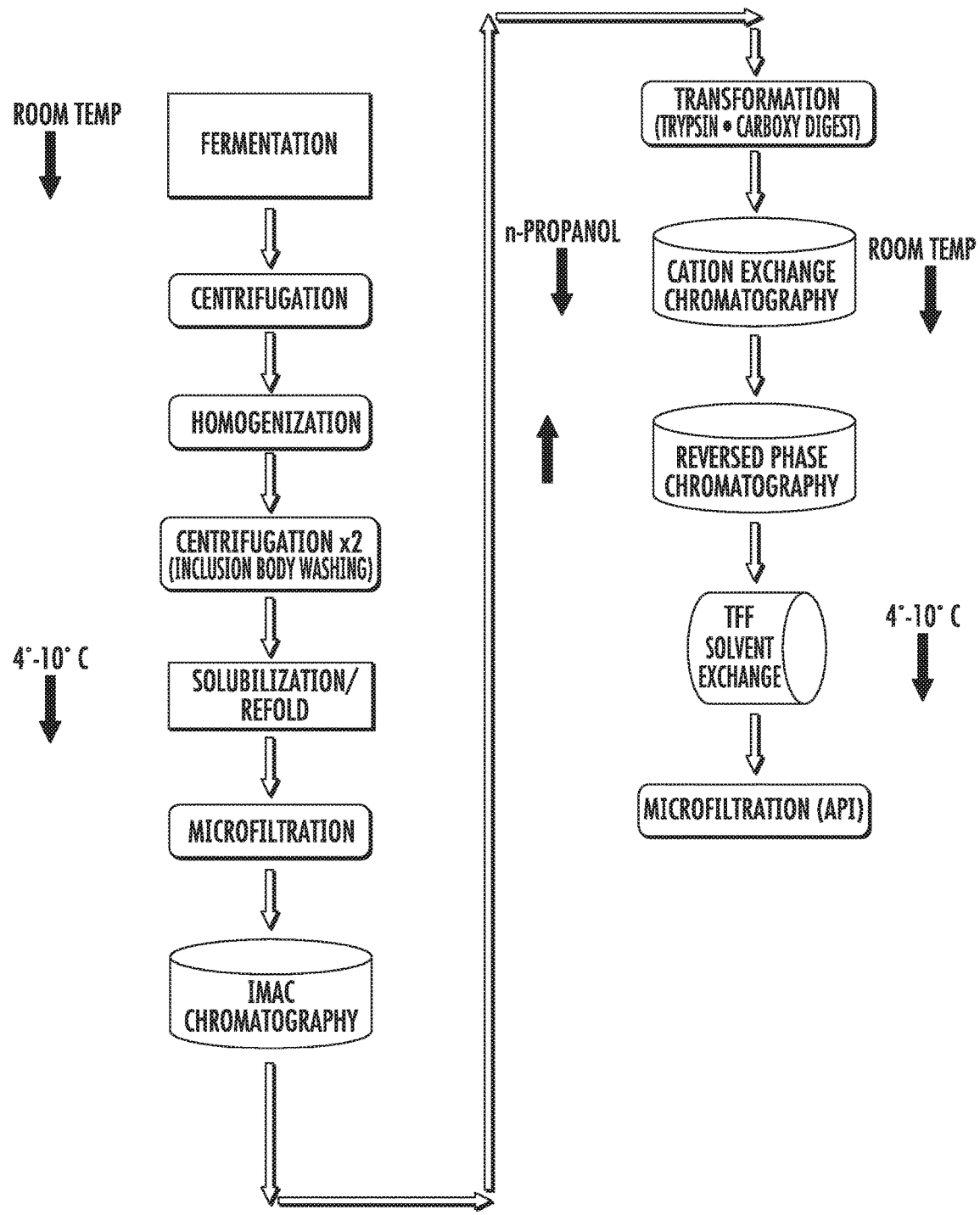

According to one embodiment, the methods of producing Lis-Pro insulin analog described herein generally include the following steps: fermentation/expression, inclusion body isolation, solubilization of Lis-Pro proinsulin analog; refolding, processing and transformation of Lis-Pro proinsulin analog to Lis-Pro insulin analog; and purification of Lis-Pro insulin analog. FIGS. 13 and 14 illustrate flow charts of preferred processes steps in producing an Lis-Pro insulin analog according to embodiments of the present invention.

Expression of aspart proinsulin analog may occur in a recombinant expression system. According to one embodiment, the recombinant expression system is an *E. coli* expression system containing aspart proinsulin analog expressing vectors. For example, the transformed cells may be vertebrate or invertebrate cells, such as prokaryote or eukaryote cells, and most preferably the cells may be mammalian, bacterial, insect, or yeast cells. In one embodiment, the cell is a bacterial cell and in a further embodiment, the bacteria is *E. coli*. In another embodiment, the cell is a yeast cell and in a further embodiment, the yeast cell is *S. cerevisiae* or *S. pombe*.

In one embodiment, *E. coli* cells may be cultured and disrupted to provide a composition comprising inclusion bodies. The inclusion bodies contain the modified proinsulin sequence. The Lis-Pro proinsulin analogs expressed by transformed *E. coli* cells according to the method of the invention may be secreted from the cells and include a secretory sequence. In other embodiments, Lis-Pro proinsulin analogs expressed by transformed *E. coli* cells are not secreted from the cells, and thus do not include a secretory sequence.

The step of solubilizing of the composition of inclusion bodies may involve adjusting the pH to achieve complete solubilization of the modified Lis-Pro proinsulin sequences. In one embodiment, the inclusion bodies may be solubilized by adjusting the pH to at least 10.5, preferably from 10.5 to 12.5, and most preferably from 11.8-12. The pH may be adjusted by adding an alkali hydroxide such as NaOH or KOH to the composition of inclusion bodies. In addition, the step of solubilization may use one or more reducing agents and/or chaotropic agent. Suitable reducing agents may include those selected from the group consisting of 2-mercaptoethanol, L-cysteine hydrochloride monohydrate, dithiothreitol, dithierythritol, and mixtures thereof. Suitable chaotropic agents include those selected from the group consisting of urea, thiourea, lithium perchlorate or guanidine hydrochloride, and mixtures thereof.

The solubilized inclusion bodies may be mixed in a refolding buffer, such as glycine or sodium carbonate, at a pH of 7 to 12, preferably from 10 to 11, preferably from 10.5 to 11, to refold the modified proinsulin sequences to a proinsulin derivative peptide, e.g., Lis-Pro proinsulin derivative peptide. The solution with refolded material should be pH adjusted to 7 to 9, preferably 7.8 to 8.2, with or without the addition of an alkaline salt, preferably sodium chloride to a final concentration of 100 mM to 1 M final concentration, preferably 500 mM to 1 M, preferably 700 mM, and may be filtered and loaded onto a column, such as an immobilized metal-ion affinity chromatography (IMAC) column. Commercially available resins suitable for embodiments of the present invention include Nickel SEPHAROSE® 6 Fast Flow (GE HEALTHCARE®), Nickel NTA Agarose (GE HEALTHCARE®), Chelating SEPHAROSE® Fast flow(GE HEALTHCARE®), IMAC Fast Flow (GE HEALTHCARE®).

The Lis-Pro proinsulin derivative peptide is subject to concentration by tangential flow filtration or diafiltration. Next, Lis-Pro proinsulin derivative peptide is enzymatically cleaved, preferably by subjecting the proinsulin derivative peptide to trypsin digestion. Although embodiments of the present invention may use commercially available rat, bovine, porcine or human trypsins or other isoenzymes or derivatives or variants thereof, it is also possible to use the following enzymes: recombinant trypsin, trypzene, trypsin from *Fusarium oxysporum* and from *Streptomyces* (*S. griseus, S. exfoliatus, S. erythraeus, S. fradiae* and *S. albidoflavus*), tryptase, mastin, acrosin, kallikrein, hepsin, prostasin I, lysyl endopeptidase (Lysin-C) and endoproteinase Arg-C (clostripain). In one embodiment, trypsin digestion occurs at pH from about 7 to 10, and more preferably from 8.1 to 8.3. In a further embodiment, the trypsin digest is quenched by adding glacial acetic acid. While it is contemplated that other additives may be employed, acetic acid appears to be most preferred and stable for this purpose.

Trypsin is an enzyme that has specific cleavage activity at the terminal arginine residues, and to a lesser extent, lysine residues, of the C-peptide. In the transformation reaction, it is required that the terminal arginine or lysine residues of the C-peptide be removed. In native human proinsulin, when trypsin cleaves at the lysine in position 64, it will be unable to remove the arginine at position 65, due to the fact that it requires at least one residue on both sides of a cleavage site. What results is the production of an unwanted by-product, Arg(A(0))-insulin. This by-product constitutes a small loss in yield and generates an undesired contaminant. By converting this lysine 64 into another uncharged amino acid, particularly alanine, the Arg(A(0))-insulin byproduct is preferentially not formed. When formed is less than 10%, and more preferably is less than 0.3% of total byproducts from the trypsin transformation reaction may be Arg(A(0)). This is because the trypsin no longer acts to cleave at this particular site of the proinsulin derivative peptide.

The proinsulin derivative peptide, may also be subjected to carboxypeptidase B digestion. In one embodiment, a trypsin inhibitor may be added to the insulin prior to addition of carboxypeptidase B. Trypsin inhibitor is added in an equal amount to the amount of trypsin added for the trypsin digest step. In another embodiment, a glycine solution is added to aspart proinsulin analog prior to addition of carboxypeptidase B. For example, in some embodiments, glycine is added to adjust the pH of the insulin solution to about 9.6±0.1. The target concentration of glycine is 50 mM using a 1 M glycine stock. In some embodiments, the carboxypeptidase B is permitted to digest for at least 1-16 hours, preferably at least 8 hours. A minimum of 10 hours is preferred, but overdigestion is rarely a significant issue so there is no maximum time limit.

In one embodiment, after typsin digest and pre-carboxy digestion, the intermediate DiR-Lis-Pro insulin is purified on a chromatography column, such as an ion exchange column or reverse phase chromatography column, prior to carboxypeptidase B digestion. Following carboxypeptidase B digestion, the Lis-Pro insulin material may be further purified using ion exchange or reverse phase chromatography. In another embodiment, after trypsin and carboxypeptidase B double digestion the Lis-Pro insulin solution is preferably purified in a chromatography column, such as an ion exchange chromatography column or reverse phase chromatography column. In one embodiment, the intermediate solution may be purified in a chromatography column by eluting the Lis-Pro insulin analog using a buffer comprising n-propanol or acetonitrile. The buffer may also further comprise sodium sulfate and phosphoric acid.

The manufacturing process described herein results in a preparation of Lis-Pro insulin analog in liquid active pharmaceutical ingredient (API) form. The process eliminates the need to prepare a crystallized insulin that is later reconstituted. As a result of eliminating the crystallization and drying steps, the amount of inactive insulin multimers present in the liquid formulation is reduced in comparison to the amounts otherwise present in crystallized forms of insulin and reconstituted crystallized insulin. Although crystallization is less preferred, in some embodiments, a crystallization step may be included to produce Lis-Pro insulin analog API crystals. The Lis-Pro insulin analog may be crystallized to allow for Increased shelf life to the API material. However, as mentioned the crystallization process will lead to increased levels of multimers and in turn an overall lower purity.

Lis-Pro insulin analog may prevent the formation of non-monomeric insulin, such as dimers and hexamers. Accordingly, upon administration of the Lis-Pro insulin analog to a patient, larger amounts of active monomeric insulin are available to act in the patient. In particular, Lis-Pro insulin analog is particularly suitable for postprandial, i.e., after eating, injection as it is available immediately for use by the patient to control glucose levels. Accordingly, this analog has the advantage over native insulin in that its short delay of onset allows more flexibility with eating schedules for diabetic patients than regular insulin which requires a longer waiting period between injection and eating. According to one embodiment of the invention, the Lis-Pro insulin analog is provided to a patient in combination with a longer acting insulin to provide optimal glycemic control.

In some embodiments, the preparations comprise a pharmaceutically acceptable preparation comprising recombinant Lis-Pro insulin analog and being essentially free of modified proinsulin sequences and/or non-monomeric Lis-Pro insulin molecules.

In another aspect, the invention is directed to formulations of liquid insulin that are not reconstituted from a lyophilized or crystallized preparation of recombinant insulin. For example, according to one embodiment, the liquid insulin composition is a human liquid insulin composition. According to some embodiments, the human liquid insulin is recombinantly produced. In certain embodiments, the liquid insulin composition of the invention includes zinc ions. For example, in some embodiments, zinc ions may be added to the liquid insulin preparation as a zinc chloride solution. Further, in some embodiments, the liquid insulin composition of the invention Includes HCl. In some embodiments, the formulation contains meta cresol at about 3.15 mg/ml and glycerol at about 16 mg/ml.

Liquid insulin preparations made according to the methods of the invention have several advantages. By way of example and not limitation, one such advantage is that they are essentially free of contaminants and/or byproducts associated with the processing of a recombinant human insulin preparation that has first been lyophilized and/or crystallized and then subsequently reconstituted into a liquid form. The lyophilization and/or crystallization of a recombinant human insulin liquid preparation has been associated with several disadvantages, including a host of impurities, decreased efficiency in product yield, changes in solubility and the presence of degradation products. The major impurities associated with the crystallization and drying is the formation of multimers which occurs during the crystallization process and end up in the final product, which in turn leads to a lower overall purity. The crystallization process decreases the yield, as the crystallization can never be taken to completion and therefore non-crystallized material is lost when the supernatant is discarded.

According to the invention, the methods of preparing insulin described herein eliminate the crystallization and drying steps that other manufacturers use to prepare recombinant insulin. Eliminating these steps has no negative impact on the purity of the insulin produced, but has the added advantage of reducing the amount of inactive insulin multimers in the liquid insulin product of the invention, whereas insulin reconstituted from lyophilized and crystallized insulin is contaminated with inactive insulin multimers.

According to one embodiment, the methods of producing Lis-Pro insulin analog described herein generally include the following steps: fermentation/expression, inclusion body isolation, solubilization of inclusion bodies; refolding, processing and transformation of proinsulin to insulin; and purification of insulin. FIG. 15 illustrates a flow chart of preferred processes steps in producing liquid insulin according to embodiments of the present invention. FIG. 16A compares processes steps in producing liquid insulin according to embodiments of the present invention in comparison with FIG. 16B which shows the current cumbersome process used to produce crystalline insulin.

Expression of aspart proinsulin analog may occur in a recombinant expression system. According to one embodiment, the recombinant expression system is a transformed *E. coli* culture. In some embodiments, the transformed *E. coli* has been prepared and qualified as a working cell bank (WCB) containing proinsulin expressing vectors. The cells of the WCB may be vertebrate or invertebrate cells, such as prokaryote or eukaryote cells, and most preferably the cells may be mammalian, bacterial, insect, or yeast cells. In one embodiment, the cell is a bacterial cell and in a further embodiment, the bacteria is *E. coli*. In another embodiment, the cell is a yeast cell and in a further embodiment, the yeast cell is *S. cerevisiae* or *S. pombe*.

In one embodiment, *E. coli* cells may be cultured and disrupted to provide a composition comprising inclusion bodies. The inclusion bodies contain the modified proinsulin sequence. The proinsulin expressed by cells of the WCB according to the method of the invention may be secreted from the cells and include a secretory sequence. In other embodiments, Lis-Pro proinsulin analogs expressed by transformed *E. coli* cells are not secreted from the cells, and thus do not include a secretory sequence.

The step of solubilizing of the composition of inclusion bodies may involve adjusting the pH to achieve complete solubilization of the modified proinsulin sequences. In one embodiment, the inclusion bodies may be solubilized by adjusting the pH to at least 10.5, preferably from 10.5 to 12.5, and most preferably from 11.8-12. The pH may be adjusted by adding an alkali hydroxide such as NaOH or KOH to the composition of inclusion bodies. In addition, the step of solubilization may use one or more reducing agents and/or chaotropic agent. Suitable reducing agents may include those selected from the group consisting of 2-mercaptoethanol, L-cysteine hydrochloride monohydrate, dithiothreitol, dithierythritol, and mixtures thereof. Suitable chaotropic agents include those selected from the group consisting of urea, thiourea, lithium perchlorate or guanidine hydrochloride, and mixtures thereof.

The solubilized inclusion bodies may be mixed in a refolding buffer, such as glycine or sodium carbonate, at a pH of 7 to 12, preferably from 10 to 11, preferably from 10.5 to 11, to refold the modified proinsulin sequences to a proinsulin derivative peptide. The solution with refolded material should be pH adjusted to 7 to 9, preferably 7.8 to 8.2, with or without the addition of an alkaline salt, preferably sodium chloride to a final concentration of 100 mM to 1 M final concentration, preferably 500 mM to 1 M, preferably 700 mM, and may be filtered and loaded onto a column, such as an immobilized metal-ion affinity chromatography (IMAC) column. Commercially available resins suitable for embodiments of the present invention include Nickel SEPHAROSE® 6 Fast Flow (GE HEALTHCARE®), Nickel NTA Agarose (GE HEALTHCARE®), Chelating SEPHAROSE® Fast flow(GE HEALTHCARE®), IMAC Fast Flow (GE HEALTHCARE®).

IMAC, or immobilized metal ion affinity chromatography (IMAC), is a technique based on the specific coordinate covalent bond of amino acids, particularly histidine, to metals. This technique works by allowing proteins with an affinity for metal ions to be retained in a column containing immobilized metal ions, such as cobalt, nickel, or copper for the purification of proteins or peptides containing 3 or more sequential histidine residues or peptides and, iron, zinc or gallium for the purification of phosphorylated proteins or peptides. Many naturally occurring proteins do not have an affinity for metal ions, therefore recombinant DNA technology can be used to introduce such a protein tag into the relevant gene. Methods used to elute the protein of interest include changing the pH, or adding a competitive molecule, such as imidazole.

During the processing step of enzymatically converting proinsulin to insulin, one or more of the amino acids may be protected to prevent side reactions and impurities. In a further embodiment, the addition of a protecting group to insulin may be added prior to addition of trypsin. In particular, protecting groups may be used to protect the lysine residue of the B-chain. A preferred protecting group is citriconic anhydride. In native human proinsulin, citriconic anhydride is preferably used to block Lys($B_{29}$) in the proinsulin sequence PKTRR (SEQ ID NO: 4), thus reducing the formation of desthreonine insulin impurity. The citriconic anhydride protecting group may reduce the formation of impurities such as desthreonine insulin and Arg($B_{31}$)-insulin.

In one embodiment, an excess molar ratio of citriconic anhydride to proinsulin may be used. For example, about 10-fold molar excess or more of citriconic anhydride to proinsulin may be suitable, and more preferably, about 20-fold molar excess or more. There is no upper limit on the excess molar ratio and the molar ratio may be as high as about 200-fold or about 300-fold.

After the citriconic anhydride blocking step, proinsulin is subject to concentration by tangential flow filtration or diafiltration. Proinsulin derivative peptide, with the blocking group may be enzymatically cleaved, preferably by subjecting the proinsulin derivative peptide to trypsin digestion. Although embodiments of the present invention may use commercially available rat, bovine, porcine or human trypsins or other isoenzymes or derivatives or variants thereof, it is also possible to use the following enzymes: recombinant trypsin, trypzene, trypsin from *Fusarium oxysporum* and from *Streptomyces* (*S. griseus, S. exfoliatus, S. erythraeus, S. fradiae* and *S. albidoflavus*), tryptase, mastin, acrosin, kallikrein, hepsin, prostasin I, lysyl endopeptidase (Lysin-C) and endoproteinase Arg-C (clostripain). In one embodiment, trypsin digestion occurs at pH from about 7 to 10, and more preferably from 8.0 to 8.2. In a further embodiment, the trypsin digest is quenched by adding glacial acetic acid. While it is contemplated that other additives may be employed, acetic acid appears to be most preferred and stable for this purpose.

Trypsin is an enzyme that has specific cleavage activity at the terminal arginine residues, and to a lesser extent, lysine residues, of the C-peptide. In the transformation reaction, it is required that the terminal arginine or lysine residues of the C-peptide be removed. In native human proinsulin, when trypsin cleaves at the lysine in position 64, it will be unable to remove the arginine at position 65, due to the fact that it requires at least one residue on both sides of a cleavage site. What results is the production of an unwanted by-product, Arg(A(0))-insulin. This by-product constitutes a small loss in yield and generates an undesired contaminant. By converting this lysine 64 into another uncharged amino acid, particularly alanine, the Arg(A(0))-insulin byproduct is preferentially not formed. When formed is less than 10%, and more preferably is less than 0.3% of total byproducts from the trypsin transformation reaction may be Arg(A(0)). This is because the trypsin no longer acts to cleave at this particular site of the proinsulin derivative peptide.

After trypsin digestion, the insulin intermediate is subjected to deblocking. Citriconic anhydride deblocking occurs by permitting the insulin intermediate to be warmed to a temperature of 15° C. to 25° C., more preferably 18° C. to 20° C., and the pH is adjusted to 2.5 to 3.5, more preferably 2.8 to 3.0

After deblocking the intermediate solution is preferably purified in a chromatography column, such as an ion exchange chromatography column or reverse phase chromatography column. In one embodiment, the intermediate solution may be purified in a chromatography column by eluting the insulin analog using a buffer comprising n-propanol or acetonitrile. The buffer may also further comprise sodium sulfate, sodium chloride, phosphoric acid or acetic acid.

In a further embodiment, the insulin intermediate is subjected to carboxypeptidase B digestion. In one embodiment, carboxypeptidase B digestion occurs after the insulin intermediate purification step. In a further embodiment, a trypsin inhibitor may be added to the insulin prior to addition of carboxypeptidase B. Trypsin inhibitor is added in an equal amount to the amount of trypsin added for the trypsin digest step. In another embodiment, a glycine solution is added to aspart proinsulin analog prior to addition of carboxypeptidase B. For example, in some embodiments, glycine is added to adjust the pH of the insulin solution to about 9.6±0.1. The target concentration of glycine is 50 mM using a 1 M glycine stock. In some embodiments, the carboxypeptidase B is permitted to digest for at least 1-16 hours, preferably at least 8 hours. A minimum of 10 hours is preferred, but overdigestion is rarely a significant issue so there is no maximum time limit.

In further embodiments, insulin is further purified after digestion by carboxypeptidase B. For example, in some embodiments, after carboxypeptidase digestion, insulin is subject to purification via reverse phase chromatography. In one embodiment, the intermediate solution may be purified in a chromatography column by eluting the insulin using a buffer comprising an alcohol or organic solvent, preferably n-propanol or acetonitrile. The buffer may also further comprise an alkali metal salt, preferable sodium sulfate. The buffer may also further comprise an organic acid, such as phosphoric acid.

In a further embodiment, insulin is concentrated and buffer exchanged using tangential flow filtration or diafiltration after reverse phase chromatography. This step has been modified, in some embodiments, to dilute the reverse phase material down with (4×) cold 100 mM phosphate buffer at pH 7-8 prior to tangential flow filtration or diafiltration. This is followed by tangential flow filtration or diafiltration/into cold purified water. The pH is maintained at 7.0-9.0, preferably 7.5-8 during the exchanges.

The manufacturing process described herein results in a preparation of insulin in liquid active pharmaceutical ingredient (API) form. The process eliminates the need to prepare a crystallized insulin that is later reconstituted. As a result of eliminating the crystallization and drying steps, the amount of inactive insulin multimers present in the liquid formulation is reduced in comparison to the amounts otherwise present in crystallized forms of insulin and reconstituted crystallized insulin.

In some embodiments, the preparations comprise a pharmaceutically acceptable preparation comprising recombinant insulin g and being essentially free of modified proinsulin sequences.

Formulations that are suitable for liquid insulin of the present invention may be used with a liquid API or by changing the API to one of the following:

1. Standard formulation—insulin plus zinc plus metacresol, sterile filtered into a vial at 100 Units/ml.

2. Insulin mixes—regular insulin mixed with isophane insulin at specific ratios such as 70/30 or 50/50. These are currently sold as NPH (Neutral Protamine Hagedorn) insulin, such as HUMULIN® N, NOVOLIN® N, NOVOLIN® NPH, and NPH LLETIN® II.

3. Lente formulations—The insulin API prepared for regular insulin is pH controlled to get solubility of the zinc-insulin complex. If the pH is not controlled a suspension of insulin crystals are formed. The size of these crystals is controlled to make either Lente or Ultra-lente formulations. These formulations are long acting and the Ultra-lente can act for longer than 24 hrs. Lente formulations are designed for single daily injections.

Inhaled insulins—The insulin is spray dried instead of crystallized to form very small particles which can be sprayed into the lungs. The large surface area sue to the small particles may allow for better absorption across the pulmonary cells into the blood stream. Oral insulin-Spray dried insulin is formulated into a tablet. The tablet would contain excipients that would allow it to hold together Insulin/insulin analog mixes—Mixing regular insulin with insulin analogs to create a fast acting to intermediate acting foul]. (reg. insulin and Lis-pro insulin) or mixing regular insulin with a long acting analog to produce a medium to long acting form (reg. insulin and LANTUS®).

It should be understood that process steps within the following description of the method may be modified, changed and/or eliminated, depending on the particular preferences of the processor and/or the particular mechanical apparatus available to the processor, as well as the specific reagents and/or materials available and/or convenience and/or economics of use.

EXAMPLES

Example 1

General Materials and Methods

The present example describes some of the general techniques used in the preparation and purification of the human proinsulin product and in the further processing of the proinsulin into a human insulin product.

A general outline of one method, by way of example and not exclusion, to isolate and/or enrich recombinant insulin from a composition that is not enriched for recombinant insulin and/or includes proinsulin can be described by the following series of steps:

1. Fermentation of *E. coli*, transformed with the vector containing the human proinsulin derivative-encoding amino acid sequence:

2. Lysis—Lyse the *E. coli* cells containing inclusion bodies enriched with the desired peptide, resuspended in a basic Tris/salt buffer, using a NIRO SOAVI® homogenizer.

3. Inclusion Body Washing—Contaminant protein removal is then accomplished via two sequential washes with a Tris/TRITON® X-100 buffer, followed by two sequential washes with a Tris/TWEEN®-20 buffer, and finally a single wash with a Tris/NaCl buffer.

4. Solubilization—Inclusion bodies are then solubilized in 8M urea containing reducing agents. Complete solubilization is achieved by adjusting the pH to 10.5 with NaOH.

5. Dilution refolding—The solubilized protein is then diluted into refolding buffer (5 mM CAPS, pH 10.5 at 4° C. to a final concentration of 0.5 mg/ml. Allow the sample to refold for ≥48 hours at 2-10° C. Add an equal amount of oxidized glutathione to the initial amount of reducing agent used in the solubilization buffer, followed by 5 M NaCl and 1 M phosphate additions, to final concentrations of 250 mM and 25 mM respectively. Adjust pH to 7.9 with 6 M HCl.

6. IMAC Chromatography—Load the dilute proinsulin derivative containing composition onto an IMAC column to a maximum capacity of ≤15 mg/ml of resin. Elute the proinsulin via a 15 CV gradient from 0-400 mM imidazole. Using RP-HPLC for analysis, pool the appropriate fractions containing the proinsulin peak of interest at the desired purity level.

7. Buffer exchange—To the pool, add EDTA to a final concentration of 10 mM. Exchange the buffer using a membrane with a suitable molecular weight cutoff (ex. 3000 Da). The final buffer should be at least 97% exchanged to a 20 mM Tris-Cl, pH 8.0 at 2-10° C. A protein concentration of approximately 10 mg/ml is desirable. Just prior to tryptic digest, 1 M glycine stock (pH 9.3-9.7 cold) is added to a final concentration of 100 mM and the sample pH is adjusted to 9.7 (cold).

8. Initial Trypsin Enzymatic Transformation/Proteolysis—The buffer exchanged sample is digested with a 2000:1 mass ratio of protein to trypsin. Once complete, based on HPLC, the digest is then quenched by the addition of acetic acid to ≥700 mM, to a pH of approximately 3.5. HPLC of the digest should show about 54% $R_{30}$ and DI-R($R_{30}$ & $R_{31}$) insulin analogs.

9. Reverse Phase Chromatography—The digested insulin is loaded onto a C18 column and eluted isocratically using a buffer of 23% acetonitrile, 200 mM sodium sulfate and 0.16% phosphoric acid. Alternatively, a C4 column may be used with a 22% acetonitrile, 200 mM sodium sulfate and 0.16% phosphoric acid buffer.

10. Buffer Exchange—Exchange the buffer using a membrane with a suitable molecular weight cutoff (3000 Da). The final buffer should be at least 97% exchanged to 5 mM acetic acid. 1M glycine stock (pH 9.3-9.7 cold) is then added to a final concentration of 100 mM, which shifts the pH of the sample to approximately 8.6. The pH is then adjusted to approximately 9.3 with NaOH, and the sample is concentrated to 8-12 mg/mL.

11. Carboxypeptidase B transformation—The buffer exchanged sample is digested with a 1:1000 ratio of protein to carboxypeptidase B. The digest is monitored by RP-HPLC to determine reaction completion.

12. Crystallization—To the carboxypeptidase B digested insulin, an equal volume of crystallization buffer (2.4 M NaCl, 0.1 M citric acid, 6 mM zinc chloride) is added, pH adjusted to ~6.3, and the sample is incubated at room temperature. Completion of crystallization is determined by UV analysis of the supernatant. Insulin crystals are harvested by centrifugation or filtration, washed with ethanol, and dried in vacuo. When ready for use, the recombinant product will be solubilized and portioned into appropriate sized individually packaged units. For example, the insulin prepared according to the present invention may be prepared in 100 units/mL vials.

Example 2

Process for Preparation of Human Proinsulin Derivative in a Modified ptrcHis 2A (Kan) Vector The present example demonstrates one of the expression vectors that may be used in the preparation of an appropriate vector that may be used to transform an appropriate cell capable of expressing the human proinsulin derivative. The specific vector described here is the ptrcHis2A vector. This ptrcHis2A vector was first modified before the human proinsulin derivative-encoding nucleic acid sequence was inserted into the vector.

The ptrcHis2A vector may be purchased from a commercial vendor (e.g., Invitrogen). Such a vector will then be modified to include a kanamycin resistance gene in the middle of the ampicillin resistance gene so as to negate the ampicillin resistance. Ampicillin resistance heightens the potential for allergic reactions to preparations made using vector constructs that include the ampicillin resistance gene. Therefore it is preferable to eliminate the ampicillin resistance in the constructs that are prepared and used.

Example 3

Construction of Purified Human Proinsulin Gene Segment for Insertion into Vector The present example is presented to demonstrate an example of the steps of a process that may be used in the present invention for preparing the human proinsulin derivative nucleic acid sequence, as well as for preparing the modified C-peptide construct disclosed herein. The nucleic acid segment isolated in the present example was used as the starting material for creating the various insertion nucleic acid sequences described in the following examples.

The nucleic acid sequence of ATCC® deposited clone, MCG-12292, was identified by the present inventors to include a nucleic acid sequence that encoded the native human proinsulin gene. The human proinsulin gene sequence was isolated from the nucleic acid sequence of the ATCC® deposited clone, MCG-12292, and employed as a starting material in the preparation of the various modified forms of human proinsulin and proinsulin derivatives having the mini-C-peptide sequence substitution as defined herein.

Human Proinsulin Gene in ATCC® Clone MGC-12292: (Nucleic acid sequence of interest=nucleic acid sequence at positions 132-392 (proinsulin) of the clone). The initial pDNR-LIB vector containing the nucleic acid sequence of interest was isolated/purified from the MCG-12292 clone using a QIAPREP® Spin Miniprep Kit.

The following nucleic acid sequence is a portion of the nucleic acid sequence of the ATCC® Clone MCC-12292 that was identified and selected by the present inventors, and does not represent the entire nucleic acid sequence of the deposited clone.

```
                                                          (SEQ ID NO: 50)
agccctccag gacaggctgc atcagaagag gccatcaagc agatcactgt ccttctgcca    60
tggccctgtg gatgcgcctc ctgcccctgc tggcgctgct ggccctctgg ggacctgacc   120
cagaggcagc ctttgtgaac caacacctgt gcggctcaca cctggtggaa gctctctacc   180
tagtgtgcgg ggaacgaggc ttcttctaca cacccaagac ccgccgggag gcagaggacc   240
tgcaggtggg gcaggtggag ctgggcgggg gccctggtgc aggcagcctg cagcccttgg   300
ccctggaggg gtccctgcag aagcgtggca ttgtggaaca atgctgtacc agcatctgct   360
ccctctacca gctggagaac tactgcaact agacgcagcc cgcaggcagc cccccacccg   420
ccgcctcctg caccgagaga gatggaataa agcccttgaa ccaacaaaaa aaaaaaaaaa   480
aaaaaaaaaa aaaaa                                                   495
```

The following nucleic acid sequence is a portion of the nucleic acid sequence of the ATCC® Clone MGC. The portion of the nucleic acid sequence that is bolded in the above sequence represents an amino acid fragment, which is not required in the final proinsulin molecule. The italicized nucleic acids represent the sequence fragment of interest (nucleic acids 132-392).

```
                                                          (SEQ ID NO: 51)
tttgtgaacc aacacctgtg cggctcacac ctggtggaag ctctctacct agtgtgcggg    60
gaacgaggct tcttctacac acccaagacc cgccsggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaact actgcaacta g                                            261
```

With the use of PCR, the above sequence of interest (nucleic acids 132-393) was amplified with an additional leader sequence
atgcatcatc atcatcatca tgaaggtggc cgc 33
(SEQ ID NO: 52)
which consists of a new start codon, a sequence encoding a histidine tag, and a sequence encoding a tryptic cleavage sequence) and purified using a QIAPREP® PCR purification kit.

Translation: The amino acids below, depicts the original native sequence coded in the ATCC® Clone MGC-12292.

```
                                                          (SEQ ID NO: 53)
MALWMRLLPL LALLALWGPD PAAAFVNQHL CGSHLVEALY LVCERGFFYT PKTRREAEDL    60

QVGQVELGGG PGAGSLQPLA LEGSLQKRGI VEQCCTSICS LYQLENYCN              109
```

The initial cloning step removed the bolded amino acid region above and replaced it with the new leader sequence in bold below. The "GGR" represents the tryptic cleavage site, which will be utilized in the tryptic transformation reaction to remove this new leader sequence. The italicized amino acids represent the C-peptide region of the native human pro-insulin molecule.

```
                                                          (SEQ ID NO: 54)
MHHHHHHGGR FVNQHLCGSH LVEALYLVCE RGFFYTPKTR REAEDLQVGQ VELGGGPGAG   60

SLQPLALEGS LQKRGIVEQC CTSICSLYQL ENYCN                             95
```

Cloning Procedure

The initial cloning step into the pTrcHis2A(Kan) vector utilized the EcoR1 site for the C-terminal ligation position, and the Ncol site, indirectly, for the N-terminal ligation. In order to use an Nco1 site directly for an N-terminal ligation, the gene of interest must contain an amino acid residue at position 2, which is encoded by a codon that starts with a guanine nucleotide. As the construct of interest does not have the required amino acid at position two, a "blunt end" ligation reaction was utilized instead of a direct Ncol "sticky end" ligation.

Sequence of the RBS site and the MCS of the ptrcHis2A (Kan) vector:

```
                                                          (SEQ ID NO: 55)
    RBS           Ncol          MCS          EcoR1
taaggaggaa taaaccatgg atccgagctc gagatctgca gctggtacca tatgggaatt   60
c                                                                  61
(3' to 5'orientation)
```

```
                                                          (SEQ ID NO: 56)
taaggaggaa taaaccatgg atccgagctc gagatctgca gctggtatat gggaattc    58
(3' to 5'orientation)
```

Primer Design:

Forward Primer:

The forward primer will introduce the new N-terminal histidine tag and tryptic cleavage site. The forward primer was ordered with a phosphorylated 5' end, which is required for the blunt end ligation reaction.

```
                                                          (SEQ ID NO: 57)
catcatcatc atcatcatgg tggccgcttt gtgaaccaac acctgtgcgg ctc         53
(5' to 3' orientation; phosphorylated)
```

Reverse Primer:

The reverse primer will introduce the EcoR1 site into the C-terminus of the sequence. The EcoR1 site will be used to accommodate the insertion of the proinsulin sequence into the vector.

```
                                    (SEQ ID NO: 58)
gatggtcgac ctcttgatga cgttgatcct taagg     35
(3' to 5'orientation)
```

New Generated PCR Product:

```
                                                          (SEQ ID NO: 59)
          His Tag              G G R
catcatcat catcatcatg gtggccgctt tgtgaaccaa cacctgtgcg gctcacacct   60
ggtggaagct ctctacctag tgtgcgggga acgggcttct tctacacacc caagacccgc  120
cgggaggcag aggacctgca ggtgggcagg tggagctggg cggggccct ggtgcaggca   180 gcctgcagcc cttggccctg gagggtccc tgcagaagcg tggcattgtg gaacaatgct  240
gtaccagcat ctgctccctc taccagctgg agaactactg caactagtcc ttaagg     296
(5' to 3' orientation, phosphorylated)            EcoR1
```

Following the PCR reaction, the insert DNA was purified using the QIAPREP® Spin Miniprep Kit from QIAGEN®. This purified insert DNA was used to create a pTrcHis2A (Kan) vector having this purified proinsulin gene sequence (See Example 4).

Example 4

Ligation Reaction for Cloning the N-Terminal Modified Proinsulin Gene into the Modified pTrcHis2A (Kan) Vector The present example demonstrates the process by which the proinsulin gene was ligated into the modified pTrcHis2A (Kan) vector.

A 5' blunt end and a 3' EcoR1 ligation reaction were utilized to insert the proinsulin gene into the pTrcHis2A (Kan) vector.

Sequence at the MCS site of the pTrcHis2A(Kan):

```
                                                   (SEQ ID NO: 60)
 RBS Site       NcoI                                   EcoR1
taaggaggaa taaaccatgg atccgagctc gagatctgca gctggtacca tatatgggaa   60
ttc                                                                 63
(5' to 3' orientation)
```

Initial Cut of the Vector with Nco1:

```
                                           (SEQ ID NO: 61)
taaggaggaa taaac                                        15
(5' to 3' orientation)
Nco1 cut leaves a "CATG" 5' overhang.

(SEQ ID NO: 62)
attcctcctt atttgctac                                    19
(3' to 5' orientation)

(SEQ ID NO: 63)
taaggaggaa taaaccatg                                    19
(5' to 3' orientation)
T4 DNA polymerase fills in the opposing strand (SEQ ID NO: 64)
attcctcctt atttggtac                                    19
(3' to 5' orientation)
leaving a blunt end.
```

Blunt End Reaction:

The DNA was digested with Nco1 for 1 hour at 37° C. using 2 μg of DNA and 10 units of Nco1. Following the hour digestion, 2 units of T4 DNA polymerase were added to the reaction and incubated at 12° C. for 15 minutes. The blunt end reaction was then stopped by addition of EDTA to a concentration of 10 mM and heating to 75° C. for 20 minutes. The vector DNA was then purified using the QIAPREP® Spin Miniprep Kit from QIAGEN®.

Following purification, the other end of the MCS was cut with EcoR1

```
                                      (SEQ ID NO: 65; bold)
    taaggaggaa taaaccatg aattc                        19
    (5' to 3' orientation)

(SEQ ID NO: 66; bold)
    attcctcctt atttggtact taa g                       23
    (3' to 5' orientation)
```

Now that the vector was prepared, the insert was digested with EcoR1, leaving a blunt ended phosphorylated N-terminus and an EcoR1 sticky end on the C-terminus. Following the EcoR1 digestions, the vector and insert DNA were both purified using the QIAPREP® Spin MiniPrep Kit from QIAGEN®.

Once purified, the insert was ligated into the vector using a 4 to 1 molar ratio of insert to vector DNA at 12° C. overnight.

Transformation

One microliter of the ligation reaction was used to transform competent BL21 *E. coli* cells, which were plated on LB-Kan agar plates and incubated overnight at 37° C. Several clones were picked and sent to IUPUI for DNA sequencing. Clones with the correct sequence were screened for expression. Good expression was verified in all clones.

Example 5

Site Directed Mutagenesis for the Conversion of Lysine 64 to Alanine in the C-Peptide Region of Human Proinsulin A site directed mutagenesis PCR reaction was employed to convert the lysine at position 64 to alanine. The constructed His-tagged-Gly-Gly-Arg proinsulin gene constructed in Example 4 was used as the template.

The creation of this amino acid mutation eliminates the possibility of generation Arg(A(0))-insulin during purification. Trypsin is an enzyme that has specific cleavage activity at the C-terminus of arginine residues, and to a lesser extent, towards the C-terminus of lysine residues. In the transformation reaction, it is required that the C-peptide, including the arginine at position 65, be removed along with the N-terminal sequence. If trypsin cleaves at the lysine in position 64, it will be unable to remove the arginine at position 65, due to the fact that it requires at least one residue on both sides of a cleavage site. What results is the production of an unwanted by-product, Arg(A(0))-insulin. This by-product constitutes a small loss in yield and generates an undesired contaminant.

By converting this lysine 65 into another uncharged amino acid, particularly alanine, the Arg(A(0))-insulin product is not formed. This is because the trypsin no longer acts to cleave at this particular site of the proinsulin sequence.

Site directed mutagenesis was used to convert the lysine at position 64 to alanine. The procedure was adapted from the protocol in the STRATAGENE™ QUIKCHANGE® Site Directed Mutagenesis kit. The PCR reaction utilized PFUTURBO® polymerase because of its high fidelity compared with Taq polymerase. Site directed mutagenesis involves the synthesis of the entire gene along with the vector (pTrcHis2A(Kan)). The insulin (Met-His-tagged-Gly-Gly-Arg)/)pTrcHis2A(Kan) clone synthesized above (Example 4) was used as the template for the PCR reaction.

PCR Primers Used:

```
Initial sequence K64
                                                    (SEQ ID NO: 67)
ccctggaggg gtccctgcag aagcgtggca ttgtggaaca atgctgtacc     50
(5' to 3' orientation)

Forward Primer
                                                    (SEQ ID NO: 68)
ggggtccctg caggcgcgtg gcattgtg                            28
(5' to 3' orientation)

Reverse Primer
                                                    (SEQ ID NO: 69)
ccccagggac gtccgcgcac cgtaacac                            28
(3' to 5' orientation)
```

The 50 µl PCR reaction was treated with 20 units of DpnI, and incubated at 37° C. for 1 hour to digest all methylated template DNA before transforming chemically competent BL21 cells.

Following transformation into BL21 cells, several clones were sequenced for gene verification. The clone that was isolated was: Met-His-tagged/Gly-Gly-Arg/proinsulin/K64A/pTrcHis2A(Kan).

The expression of this clone was very good. Final gene product (Met-His-tagged/Gly-Gly-Arg/proinsulin/K64A):

```
                                                    (SEQ ID NO: 70)
atgcatcatc atcatcatca tggtggccgc tttgtgaacc aacacctgtg cggctcacac    60
ctggtggaag ctctctacct agtgtgcggg gaacgaggct tcttctacac acccaagacc  120
cgccgggagg cagaggacct gcaggtgggg caggtggagc tgggcggggg ccctggtgca  180
ggcagcctgc agcccttggc cctggagggg tctctgcagg cgcgtggcat tgtggaacaa  240
tgctgtacca gcatctgctc cctctaccag ctggagaact actgcaacta g           291
(5' to 3' orientation)
```

Amino Acid Sequence of the his-Tagged/Gly-Gly-Arg/K64A Proinsulin:

```
                                                    (SEQ ID NO: 71)
MHHHHHHGGR FVNQHLCGSH LVEALYLVCG ERGFFYTPKT RREAEDLQVG QVELGGGPGA   60

GSLQPLALEG SLQARGIVEQ CCISICSLYQ LENYCN                             96
```

In the nucleic acid and amino acid sequences above, the bold and underlined portions identify the connecting C-peptide sequence.

Example 6

Full Length Substituted Proinsulin Construct and Uses Thereof in Production of Human Insulin With regards to the full length proinsulin substitution construct of His-Tagged/K64A, three unique modifications are present to the original gene that simplify purification and increase yield.

1) The N-terminal sequence was modified by the addition of a 6-Histidine tag, which could be used to simplify the purification via the use of a nickel chelating column as an initial purification step following refolding.

2) Following the 6-His tag sequence on the N-terminus, a well-documented tryptic cleavage site was introduced in order to provide a simple means of removing the N terminal tag following the metal chelating chromatography step. The sequence introduced was "Glycine, Glycine, Arginine", with cleavage after the arginine.

3) The third modification was the conversion of an amino acid located at position 64 (original proinsulin) of the native sequence, which is a lysine residue that is converted to an alanine. The modification prevents the formation of Arg(A(0))-insulin during the tryptic cleavage transformation step, which increases the theoretical yield.

All data thus far supports the modifications. The initial chelating column step yields a Tagged-proinsulin pool of approximately greater than or equal to about 92% purity. The tryptic transformation step yields a final insulin molecule with high digestion efficiency which demonstrates the effectiveness of the "gly, gly, arg" cleavage sequence for N-terminal removal and the lack of an Arg(A(0))-insulin at position 65 demonstrate the advantage of the replacement at position 64.

The individual transformation reactions, rather than a single transformation reaction, allows for the efficient removal of the desthreonine byproduct which is created by cleavage at the Lysine at position 29. This cleavage can be minimized in the native sequence by introducing nickel to the transformation reactions. However, the presence of the Histidine tag in the clone described herein, prevents this nickel protection of lysine 29. The separate transformation reactions allow for almost complete removal of the desthreonine byproduct, which is created when trypsin cleaves at the lysine at position 28, removing the threonine at position 29.

Figure 2A:
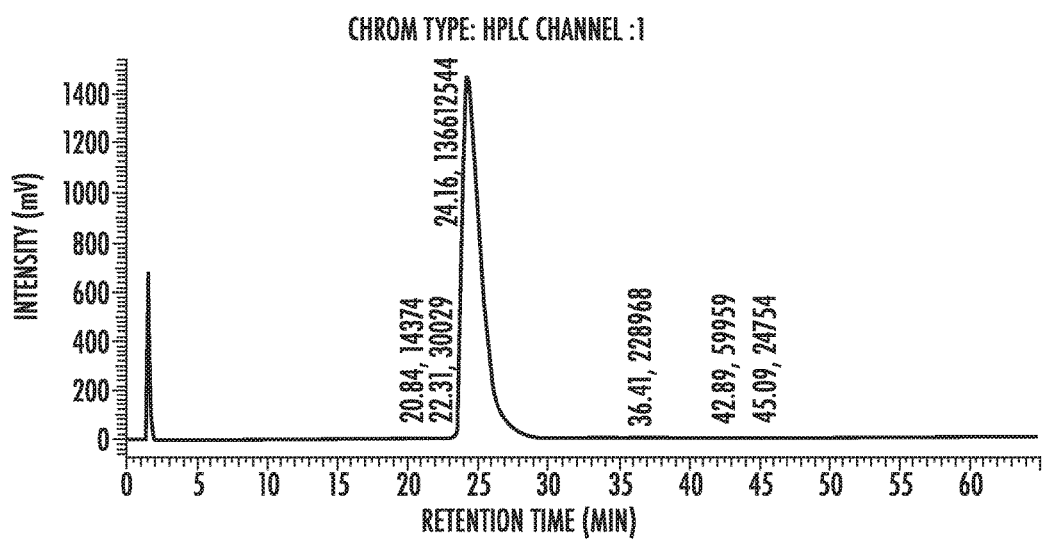
FIGS. 2A and 2B, according to one aspect of the invention, presents an HPLC of recombinant IPT human insulin. The chromatograph demonstrates that the preparation is high in purity with almost non-existent levels of proinsulin.
Figure 2B:
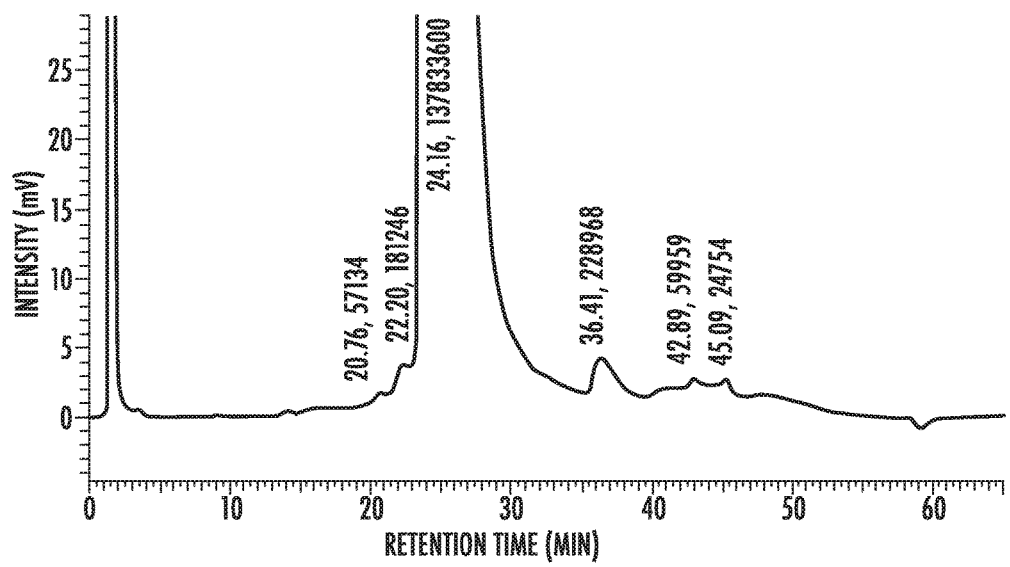

The final purification steps, including the reverse phase chromatography, carboxypeptidase B transformation reactions and crystallization, yields a highly pure insulin (99%) sample, which by HPLC reverse phase analysis shows essentially no proinsulin analogs or N-terminal fragments (see FIG. 2). As well, the desthreonine contaminant can essentially be completely removed.

Amino Acid Sequence: Natural Proinsulin Amino Acid Sequence:

(SEQ ID NO: 72)
MALWMRLLPL LALLALWGPD PAAAFVNQHL CGSHLVEALY LVCGERGFFY TPKTRREAED 60
LQVGQVELGG GPGAGSLQPL ALEGSLQKRG IVEQCCTSIC SLYQLENYCN 110

Replacement of Initial Sequence with Tag and Cleavage Site:

(SEQ ID NO: 73)
MHHHHHHGGR FVNQHLCGSH LVEALYLVCG ERGFFYTPKT RREAEDLQVG QVELGGGPGA 60
GSLQPLALEG SLQKRGIVEQ CCTSICSLYQ LENYCN 96

Conversion of Lysine 64 to Alanine:

(SEQ ID NO: 43)
MHHHHHHGGR FVNQHLCGSH LVEALYLVCG ERGFFYTPKT RREAEDLQVG QVELGGGPGA 60
GSLQPLALEG SLQARGIVEQ CCTSICSLYQ LENYCN 96

Example 7

Biopotency Study of the Full-Length Substituted Proinsulin Insulin Construct

The final purified insulin samples were tested in vivo on rabbits to compare the biopotency against HUMULIN® R. As analytical studies give a simple picture of a biological molecule's relative state compared with a standard, it is imperative that a bioassay be used to determine that the purified molecule of interest carries the required biological activity.

In Vivo Biological Method

The biological assay was on the current accepted procedure outlined in the United States Pharmacopeia. Testing was conducted by MPI Research.

Test subjects included 30 male rabbits which were given injections on two separate days of either the control (saline), positive control (HUMULIN® R), or test sample (IPT (ELONA BIOTECHNOLOGIES INC®) human insulin), through subcutaneous injection.

Dosing levels consisted of 0.35 or 0.7 international units (IU), administered at a dose volume of 0.35 ml/dose. The control group received saline on both days 1 and 3 at a dose volume of 0.35 ml/dose.

Figure 3A:
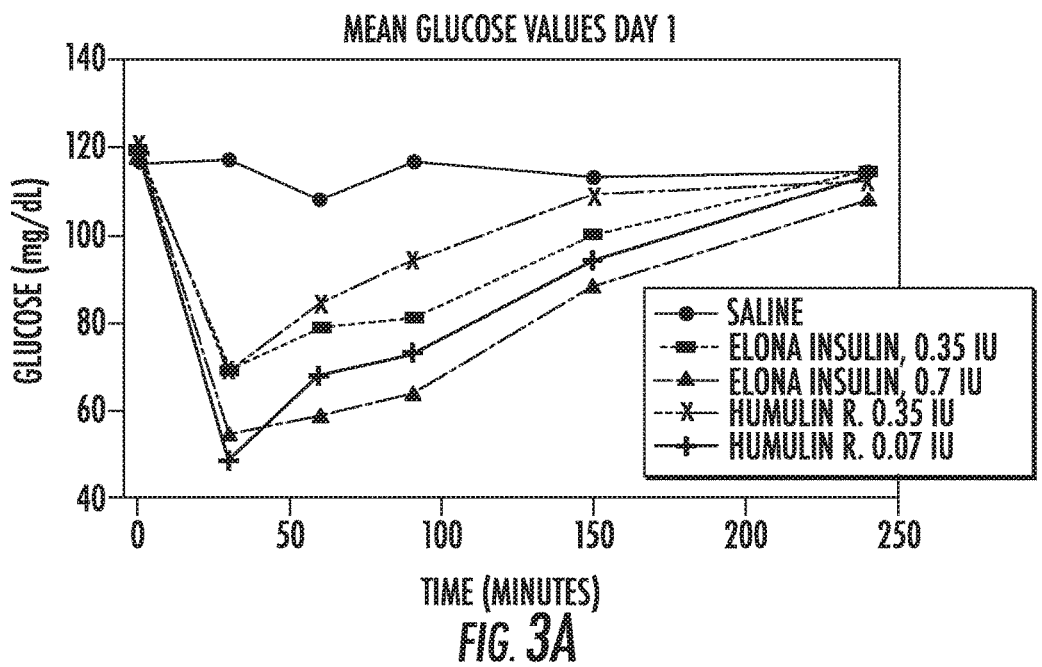
FIGS. 3A and 3B, according to some aspects of the invention, presents a biopotency study showing relative glucose curves for rabbits injected with saline (control), HUMULIN® R (positive control), and ELONA BIOTECH-NOLOGIES INC® human insulin (test sample).
Figure 3B:
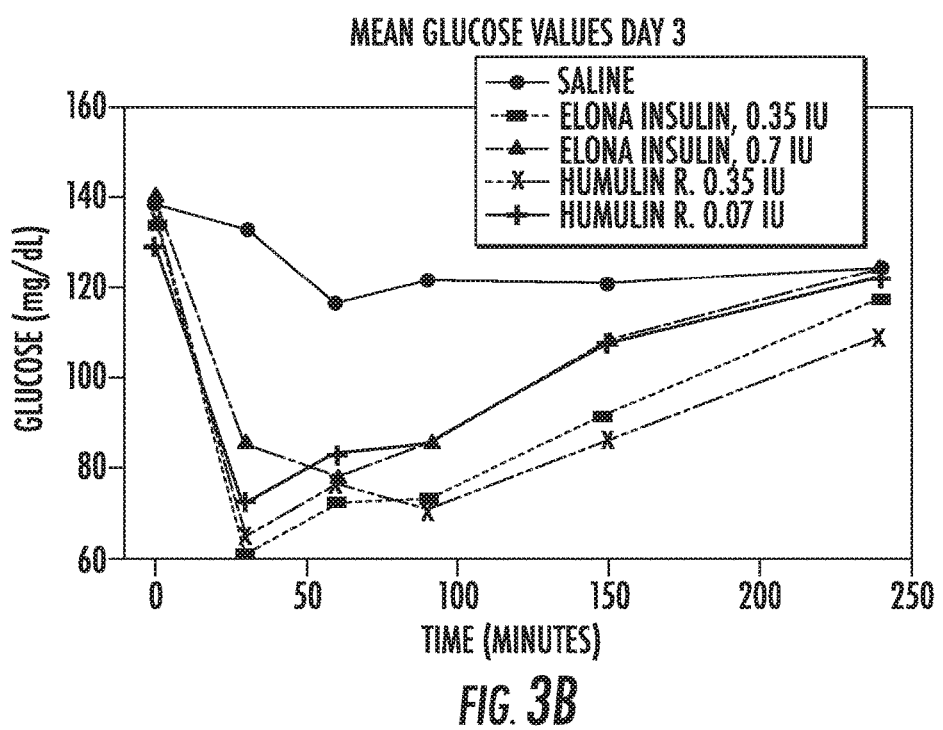

Glucose monitoring was conducted prior to dosing and at 30, 60, 90, 150, and 240 minutes following dosing on both days. Results showed comparable biopotency of IPT human insulin with HUMULIN® R (see FIG. 3).

Example 8

Proinsulin Constructs

The present example demonstrates the utility of the present invention for providing unique proinsulin constructs that are particularly useful and efficient in the methods of insulin production described herein.

Native Proinsulin Amino Acid sequence:

(SEQ ID NO: 74)
FVNQHLCGSH LVEALYLVCG ERGFFYTPKT RR*EAEDLQVG QVELGGGPGA GSLQPLALEG* 60
*SL*QKRGIVEQ CCTSICSLYQ LENYCN 86

N-Terminal 6-His tagged clone with tryptic cleavage sequence for removal: (Utilization of a nickel chelating column for high purity in a single step)

(SEQ ID NO: 73)
MHHHHHHGGR FVNQHLCGSH LVEALYLVCG ERGFFYTPKT RREAEDLQVG QVELGGGPGA 60
GSLQPLALEG SLQKRGIVEQ CCTSICSLYQ LENYCN 96

Site Directed Mutagenesis of Lysine 64 to Alanine:
Prevention of incorrect cleavage following the lysine. No Arg-insulin contaminant generated, resulting in an increased yield.

(SEQ ID NO: 43)
MHHHHHHGGR FVNQHLCGSH LVEALYLVCG ERGFFYTPKT RREAEDLQVG QVELGGGPGA 60
GSLQPLALEG SLQARGIVEQ CCTSICSLYQ LENYCN 96

Example 9

Preparation of an *E. coli* Clone Expressing Glargine Proinsulin

The preparation of transformed *E. coli* containing cells capable of expressing recombinant glargine proinsulin was carried out according to the following processes. In addition, a cell bank of the transformed *E. coli* is also described.

Step 1—Construction of a purified glargine proinsulin gene segment for insertion into the vector: The initial gene construct was synthesized in a basic cloning vector. The gene construct included the N-terminal histidine tag, MHHHHHHGGR (SEQ ID NO: 2), modified B-chain, and modified C-peptide with the alanine codon in place of the native lysine and having the amino acid sequence:

```
                                                     (SEQ ID NO: 17)
MHHHHHHGGR FVNQHLCGSH LVEALYLVCG ERGFFYTPKT RREAEDLQVG QVELGGGPGA   60

GSLQPLALEG SLQARGIVEQ CCTSICSLYQ LENYCG.                           96
```

Figure 4:
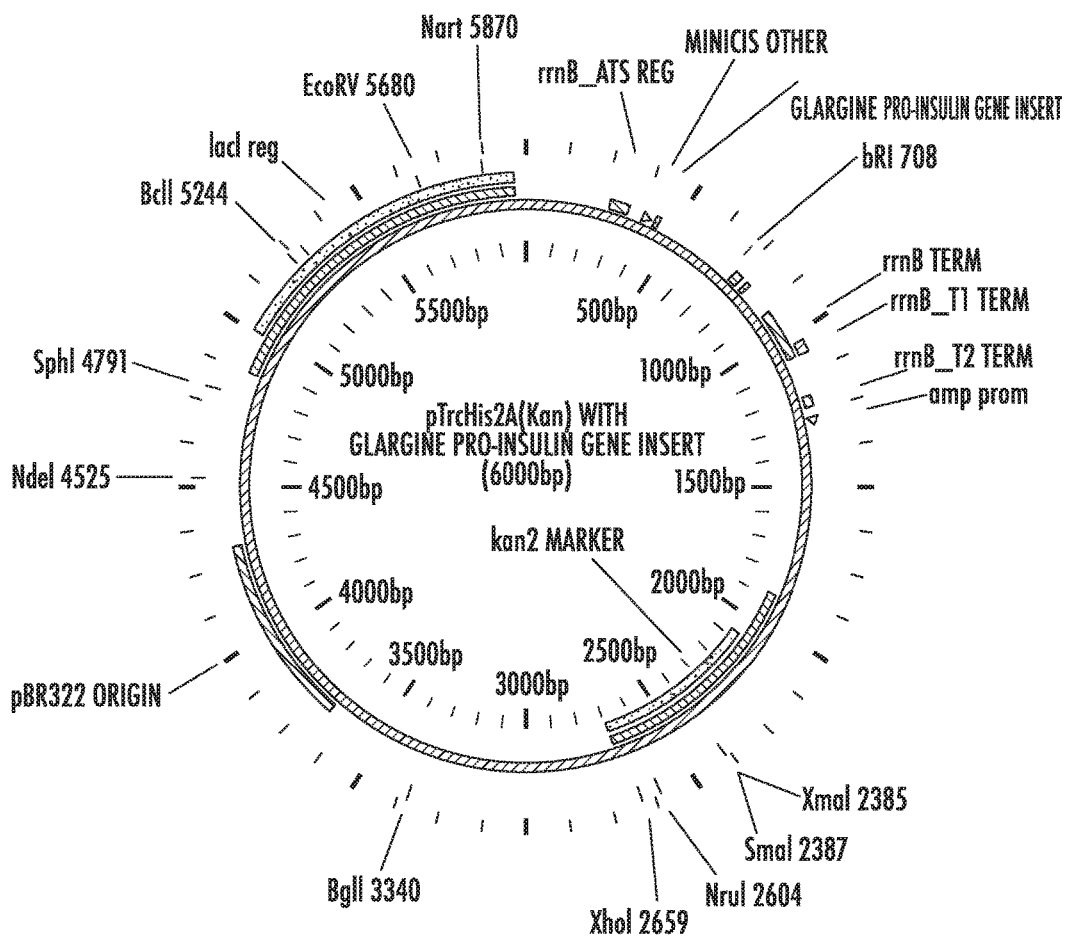
FIG. 4, according to one aspect of the invention, is a vector map of plasmid pTrcHis2A (Kan) with a glargine proinsulin gene insert.

The gene was flanked by NdeI and EcoRI restriction sites, for subsequent subcloning into the desired expression vector. The codons selected were optimized for expression in *E. coli*. The following sequence represents the pTrcHis2a(Kan) vector with glargine proinsulin insert (FIG. 4). The IPTG inducible promoter region which regulates the transcription rate is shown in italics, while the glargine proinsulin insert, adjacent the promoter region, is shown in bold. The sequence shown in bold and italics is the kanamycin gene, which provides the antibiotic selection marker for the vector.

```
                                                     (SEQ ID NO: 75)
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgatgca    420
tcatcatcat catcatggtg gccgctttgt gaaccaacac ctgtgcggct cacacctggt    480
ggaagctctc tacctagtgt gcggggaacg aggcttcttc tacacaccga cacccgccg     540 ggaggcagag gacctgcagg tggggcaggt ggagctgggc gggggccctg gtgcaggcag    600
cctgcagccc ttggccctgg agggtccct gcagaagcgt ggcattgtgg aacaatgctg     660
taccagcatc tgctccctct accagctgga gaactactgc ggctaggaat tcgaagcttg    720
ggcccgaaca aaaactcatc tcagaagagg atctgaatag cgccgtcgac catcatcatc    780
atcatcattg agtttaaacg gtctccagct tggctgtttt ggcggatgag agaagatttt    840
cagcctgata cagattaaat cagaacgcag aagcggtctg ataaaacaga atttgcctgg    900
cggcagtagc gcggtggtcc cacctgaccc catgccgaac tcagaagtga acgccgtag     960 cgccgatggt agtgtggggt ctccccatgc gagagtaggg aactgccagg catcaaataa   1020
aacgaaaggc tcagtcgaaa gactgggcct ttcgttttat ctgttgtttg tcggtgaacg   1080
ctctcctgag taggacaaat ccgccgggag cggatttgaa cgttgcgaag caacggcccg   1140
gagggtggcg ggcaggacgc ccgccataaa ctgccaggca tcaaattaag cagaaggcca   1200
tcctgacgga tggcctttt gcgtttctac aaactctttt tgtttatttt tctaaataca   1260
ttcaaatatg tatccgctca tgagacaata accctgataa atgcttcaat aatattgaaa   1320
aaggaagagt atgagtattc aacatttccg tgtcgccctt attcccttt ttgcggcatt    1380 ttgccttcct gtttttgctc acccagaaac gctggtgaaa gtaaaagatg ctgaagatca   1440
gttgggtgca cgagtgggtt acatcgaact ggatctcaac agcggtaaga tccttgagag   1500
```

-continued

```
ttttcgcccc gaagaacgtt ttccaatgat gagcactttt aaagttctgc tatgtggcgc    1560
ggtattatcc cgtgttgacg ccgggcaaga gcaactcggt cgccgcatac actattctca    1620
gaatgacttg gttgagtcct gaatcgcccc atcatccagc cagaaagtga gggagccacg    1680
gttgatgaga gctttgttgt aggtggacca gttggtgatt ttgaactttt gctttgccac    1740
ggaacggtct gcgttgtcgg gaagatgcgt gatctgatcc ttcaactcag caaaagttcg    1800
atttattcaa caaagccgcc gtcccgtcaa gtcagcgtaa tgctctgcca gtgttacaac    1860
caattaacca attctgatta gaaaaactca tcgagcatca aatgaaactg caatttattc    1920
atatcaggat tatcaatacc atattttga aaaagccgtt tctgtaatga aggagaaaac    1980
tcaccgaggc agttccatag gatggcaaga tcctggtatc ggtctgcgat tccgactcgt    2040
ccaacatcaa tacaacctat taatttcccc tcgtcaaaaa taaggttatc aagtgagaaa    2100
tcaccatgag tgacgactga atccggtgag aatggcaaaa gcttatgcat ttctttccag    2160
acttgttcaa caggccagcc attacgctcg tcatcaaaat cactgcatca accaaaccgt    2220
tattcattcg tgattgcgcc tgagcgagac gaaatacgcg atcgctgtta aaaggacaat    2280
tacaaacagg aatcgaatgc aaccggcgca ggaacactgc cagcgcatca acaatatttt    2340
cacctgaatc aggatattct tctaatacct ggaatgctgt tttcccgggg atcgcagtgg    2400
tgagtaacca tgcatcatca ggagtacgga taaaatgctt gatggtcgga agaggcataa    2460
attccgtcag ccagtttagt ctgaccatct catctgtaac atcattgca acgctacctt    2520 tgccatgttt cagaaacaac tctggcgcat cgggcttccc atacaatcga tagattgtcg    2580
cacctgattg cccgacatta tcgcgagccc atttataccc atataaatca gcatccatgt    2640
tggaatttaa tcgcggcctc gagcaagacg tttcccgttg aatatggctc ataacacccc    2700
ttgtattact gtttatgtaa gcagacagtt ttattgttca tgatgatata tttttatctt    2760
gtgcaatgta acatcagaga ttttgagaca caacgtggct ttgttgaata aatcgaactt    2820
ttgctgagtt gaaggatcag atcacgcatc ttcccgacaa cgcagaccgt tccgtggcaa    2880
agcaaaagtt caaaatcacc aactggtcca cctacaacaa agctctcatc aaccgtggct    2940
ccctcacttt ctggctggat gatggggcga ttcaggactc accagtcaca gaaaagcatc    3000
ttacggatgg catgacagta agagaattat gcagtgctgc cataaccatg agtgataaca    3060
ctgcggccaa cttacttctg acaacgatcg gaggaccgaa ggagctaacc gcttttttgc    3120
acaacatggg ggatcatgta actcgccttg atcgttggga accggagctg aatgaagcca    3180
taccaaacga cgagcgtgac accacgatgc ctgtagcaat ggcaacaacg ttgcgcaaac    3240
tattaactgg cgaactactt actctagctt cccggcaaca attaatagac tggatggagg    3300
cggataaagt tgcaggacca cttctgcgct cggcccttcc ggctggctgg tttattgctg    3360
ataaatctgg agccggtgag cgtgggtctc gcggtatcat tgcagcactg gggccagatg    3420
gtaagccctc ccgtatcgta gttatctaca cgacggggag tcaggcaact atggatgaac    3480
gaaatagaca gatcgctgag ataggtgcct cactgattaa gcattggtaa ctgtcagacc    3540
aagtttactc atatatactt tagattgatt taaaacttca ttttttaattt aaaaggatct    3600 aggtgaagat cctttttgat aatctcatga ccaaaatccc ttaacgtgag ttttcgttcc    3660
actgagcgtc agaccccgta gaaaagatca aaggatcttc ttgagatcct ttttttctgc    3720
gcgtaatctg ctgcttgcaa acaaaaaaac caccgctacc agcggtggtt tgtttgccgg    3780
atcaagagct accaactctt tttccgaagg taactggctt cagcagagcg cagataccaa    3840
atactgtcct tctagtgtag ccgtagttag gccaccactt caagaactct gtagcaccgc    3900
ctacatacct cgctctgcta atcctgttac cagtggctgc tgccagtggc gataagtcgt    3960
```

```
gtcttaccgg gttggactca agacgatagt taccggataa ggcgcagcgg tcgggctgaa    4020 cgggggttc gtgcacacag cccagcttgg agcgaacgac ctacaccgaa ctgagatacc     4080
tacagcgtga gctatgagaa agcgccacgc ttcccgaagg gagaaaggcg gacaggtatc    4140
cggtaagcgg cagggtcgga acaggagagc gcacgaggga gcttccaggg ggaaacgcct    4200
ggtatcttta tagtcctgtc gggtttcgcc acctctgact tgagcgtcga ttttttgtgat  4260 gctcgtcagg ggggcggagc ctatggaaaa acgccagcaa cgcggccttt ttacggttcc   4320
tggccttttg ctggcctttt gctcacatgt tctttcctgc gttatcccct gattctgtgg   4380
ataaccgtat taccgccttt gagtgagctg ataccgctcg ccgcagccga acgaccgagc   4440
gcagcgagtc agtgagcgag gaagcggaag agcgcctgat gcggtatttt ctccttacgc   4500
atctgtgcgg tatttcacac cgcatatggt gcactctcag tacaatctgc tctgatgccg   4560
catagttaag ccagtataca ctccgctatc gctacgtgac tgggtcatgg ctgcgccccg   4620
acacccgcca cacccgctg acgcgccctg acgggcttgt ctgctcccgg catccgctta    4680
cagacaagct gtgaccgtct ccgggagctg catgtgtcag aggttttcac cgtcatcacc   4740
gaaacgcgcg aggcagcaga tcaattcgcg cgcgaaggcg aagcggcatg catttacgtt   4800
gacaccatcg aatggtgcaa aacctttcgc ggtatggcat gatagcgccc ggaagagagt   4860
caattcaggg tggtgaatgt gaaaccagta acgttatacg atgtcgcaga gtatgccggt   4920
gtctcttatc agaccgtttc ccgcgtggtg aaccaggcca gccacgtttc tgcgaaaacg   4980
cgggaaaaag tggaagcggc gatggcggag ctgaattaca ttcccaaccg cgtggcacaa   5040
caactggcgg gcaaacagtc gttgctgatt ggcgttgcca cctccagtct ggccctgcac   5100
gcgccgtcgc aaattgtcgc ggcgattaaa tctcgcgccg atcaactggg tgccagcgtg   5160
gtggtgtcga tggtagaacg aagcggcgtc gaagcctgta aagcggcggt gcacaatctt   5220
ctcgcgcaac gcgtcagtgg gctgatcatt aactatccgc tggatgacca ggatgccatt   5280
gctgtggaag ctgcctgcac taatgttccg gcgttatttc ttgatgtctc tgaccagaca   5340
cccatcaaca gtattatttt ctcccatgaa gacggtacgc gactgggcgt ggagcatctg   5400
gtcgcattgg gtcaccagca aatcgcgctg ttagcgggcc cattaagttc tgtctcggcg   5460
cgtctgcgtc tggctggctg cataaatat ctcactcgca atcaaattca gccgatagcg    5520
gaacgggaag gcgactggag tgccatgtcc ggttttcaac aaaccatgca aatgctgaat   5580
gagggcatcg ttcccactgc gatgctggtt gccaacgatc agatggcgct gggcgcaatg   5640
cgcgccatta ccgagtccgg gctgcgcgtt ggtgcggata tctcggtagt gggatacgac   5700
gataccgaag acagctcatg ttatatcccg ccgtcaacca ccatcaaaca ggattttcgc   5760
ctgctggggc aaaccagcgt ggaccgcttg ctgcaactct ctcagggcca ggcggtgaag   5820
ggcaatcagc tgttgcccgt ctcactggtg aaaagaaaaa ccaccctggc gcccaatacg   5880
caaaccgcct ctccccgcgc gttggccgat tcattaatgc agctggcacg acaggtttcc   5940
cgactggaaa gcgggcagtg agcgcaacgc aattaatgtg agttagcgcg aattgatctg   6000
```

The modified proinsulin sequence without the tag is as follows:

```
                                                    (SEQ ID NO: 76)
tttgtgaacc aacacctgtg cggctcacac ctggtggaag ctctctacct agtgtgcggg   60
gaacgaggct tcttctacac accgaacacc cgccgggagg cagaggacct gcaggtgggg   120
caggtggagc tgggcggggg ccctggtgca ggcagcctgc agcccttggc cctggagggg   180
```

```
tccctgcaga agcgtggcat tgtggaacaa tgctgtacca gcatctgctc cctctaccag    240
ctggagaact actgcggcta g                                              261
```

Step 2—Generation of the pTrcHis2A(Kan) vector containing glargine proinsulin: Commercially available pTrcHis2A(Kan) vector was modified to include a kanamycin resistance gene in the middle of the ampicillin resistance gene to negate the ampicillin resistance prior to insertion of the proinsulin sequence into the vector. Ampicillin resistance heightens the potential for allergic reactions to preparations made using vector constructs that include the ampicillin resistance gene. Therefore it is preferable to eliminate the ampicillin resistance in the constructs that are prepared and used.

hepTrcHis2A(Kan) vector was modified at the start codon in the multiple cloning site by replacing the NcoI restriction site (ccatgg) with an NdeI site (catatg) to simplify subsequent subcloning work.

The proinsulin gene was isolated from the DNA 2.0 plasmid using MeI to cleave at the N-terminal side of the gene and EcoR1 to cleave at the C-terminal side of the gene. The Digested DNA was run over a 2% agarose gel to separate the plasmid DNA from the glargine proinsulin gene. A QIAQUICK® (QIAGEN®) gel purification kit was then used to purify the gene construct.

Accordingly, a sequential digest of the vector with NdeI and EcoRI, respectively, was performed. The vector DNA was also purified using a QIAQUICK® gel purification kit. Following purification of the vector and the gene, a 5' NdeI and a 3' EcoRl ligation reaction were utilized to insert the proinsulin gene into the pTreHis2A(Kan) vector.

Step 3—Transformation: One microliter of the ligation reaction was used to transform competent BL21 *E. coli* cells with the pTrcHis2A(Kan) plasmid containing the proinsulin gene. The transformed BL21 *E. coli* cells were plated on LB-Kan agar plates and incubated overnight at 37° C. Several clones were selected and sequenced. Clones with the correct sequence were then screened for expression. The resulting clone is referred to as the glargine proinsulin pTrcHis2A(Kan) vector.

Step 4: Preparation of the working cell bank (WCB). To establish the WCB, sterile growth medium was inoculated with the recombinant BL21 *E. coli* containing the glargine proinsulin Met-His-tagged/pTreHis2A(Kan) vector and incubated to allow cell growth. The cells were harvested in an IS05 (class 100) environment under a biosafety cabinet and then sterile filtered. Sterile medium and glycerol were added to the sterile filtered cells. 1 mL aliquots of the cells were then dispensed into sterile ampoules and stored at −80° C. Aseptic techniques were utilized to generate the WCB.

Example 10

Product Manufacture of Glargine Insulin Analog from Modified Proinsulin Sequence Step 1—Culturing of *E. coli* transformed with glargine modified proinsulin sequence from the WCB of Example 9: Seed an inoculum preparation of the WCB in a sterile growth medium that includes yeastolate (purchased from VWR®, Prod. #90004-426 or 488), select phytone, sodium chloride, purified water, sterile kanamycin solution, and incubate until growth to an Optical density ($OD_{600\ nm}$) of 2 to 4. Prepare a fermentation media (containing select phytone, yeastolate, glycerin, BIOSPUMEX® 153K (BASF®) in a disup. Add the following sterilized phosphate solutions to the fermentor. Prepare a Phosphate flask I—potassium phosphate monobasic and potassium phosphate dibasic containing kanamycin solution. Prepare a Phosphate flask 2—potassium phosphate monobasic and potassium phosphate dibasic. Add seed inoculate of *E. coli* to the fermentor—growth to O.D. (optical density) 600 nm of 8 to 10 (mid log phase). Add a dioxane free IPTG (purchased from PROMEGA®, Catalog No. #PA V3953)(VWR® Catalog #PAV3953) solution to the fermentor (to induce transcription of the K64A glargine proinsulin gene). Incubate for 4 hours. This results in the production of a concentrated cell suspension containing His-tagged glargine proinsulin inclusion bodies. The cell suspension is then centrifuged to provide a cell paste for the subsequent inclusion body isolation step.

Step 2—Disruption: Cells containing inclusion bodies expressing glargine modified proinsulin sequence are lysed in a basic Tris/salt buffer, using a NIRO SOAVI® homogenizer (1100-1200 bar).

Step 3—Inclusion Body Washing: Contaminant protein removal is accomplished via two sequential washes with a Tris/TRITON® X-100 buffer, followed by two sequential washes with a Tris/TWEEN®-20 buffer, and finally a single wash with a Tris/NaCl buffer.

Step 4—Solubilization: Inclusion bodies enriched with the modified glargine proinsulin peptide are solubilized in 4-8 M urea, preferably 6-8 M urea, containing reducing agents (2-mercaptoethanol, L-cysteine hydrochloride monohydrate). Complete solubilization is achieved by adjusting the pli to 10.5-12, preferably 11.8-12 with NaOH.

Step 5—Dilution refolding: The solubilized glargine insulin analog protein is then diluted into refolding buffer (20 mM glycine, pH 10-11 at 6–10° C.) to a final concentration of 1.5 mg/ml and permitted to refold for 24 to 72 hours, preferentially about 48 hours, at 6–10° C. Higher protein concentration may be used in the refold if desired, however, overall refold efficiency will decrease. Sodium chloride and phosphate are then added to final concentrations of 700 mM and 25 mM respectively, followed by pH adjustment to 7.0 to 9.0, preferably 7.9-8.0 with 6M HCl.

Step 6—IMAC Chromatography: The dilute proinsulin derivative is loaded onto an IMAC column to a maximum capacity of ≤26.5 mg main peak protein per ml of resin. A 75 mM imidizole buffer is used to isocratically strip the majority of impurities from the column. Tagged glargine proinsulin is then eluted isocratically using 300 mM imidizole.

Step 7—Citriconic anhydride (CA) Blocking: To the IMAC pool, add citriconic anhydride at a molar ratio of 20:1 (CA to glargine-tagged proinsulin), while stirring at 4-10° C. Allow the sample to stir for not less than 3 hour at 4-10° C.

Step 8—Buffer exchange: To the blocked material, add EDTA to a final concentration of 20 mM. Exchange the buffer using a membrane with a suitable molecular weight cutoff (e.g. 3000 Da). The final buffer should be at least 97% exchanged to a 20 mM Tris-Cl, pH 7.0-10.0, preferably 8.8 to 9.2 at 8-10° C. A protein concentration of approximately 5 mg/ml is desirable.

Step 9—Trypsin Enzymatic Transformation/Proteolysis: The buffer exchanged sample is digested with a 1000:1 mass ratio of main peak protein to trypsin, in the presence of 5 mM CaCl. The ratio of trypsin may be increased or decreased depending on the desired length of time for the reaction. Once complete, based on HPLC, the digest is then quenched by the addition of acetic acid to ≥700 mM.

Step 10—Citriconic anhydride Deblocking: The trypsin digest solution is then warmed to 18 to 20° C. and the pH is adjusted to 2.8 to 3.0. The digest is stored at room temperature for not less than 10 hours to permit release of the citriconic anhydride.

Example 11

Final Purification

Step 11—Ion Exchange Chromatography: The digested material is loaded onto a cation exchange column and eluted with a NaCl gradient, in the presence of 20% n-propanol or acetonitrile at pH 2-5, preferably 4.0. RP-HPLC is used to pool the appropriate fractions containing the glargine insulin peak of interest at the desired purity level.

Step 12—Reverse Phase Chromatography The S-column pool containing the glargine insulin is loaded onto an RPC30 or C18 reverse phase column and eluted using an n-propanol or acetonitrile gradient in the presence of 200 mM sodium sulfate and 0.136% phosphoric acid. Fractions are immediately diluted 1:4 with water if n-propanol is used for elution; or 1:2 with water if acetonitrile is used for elution, or no dilution if acetonitrile is used for elution. RP-HPLC is used to pool the appropriate fractions containing the glargine insulin peak of interest at the desired purity level.

Step 13—Buffer Exchange: Exchange the sample into WFI (water for injection) using a membrane with a suitable molecular weight cutoff (e.g. 3000 Da). The pH of the solution should be monitored and maintained at 2-5, preferably 3.5 to 4.0. The final sample is concentrated to 5-8 mg/ml, with an adjusted pH of 2-5, preferably 3.8 to 4.2, chilled to 6-10° C. This material represents the liquid API form of the presently disclosed preparations of glargine insulin analog. The API should be stored in the dark at 6-10° C.

Example 12

API Formulation

The glargine insulin analog purified by Example 3 is formulated by diluting the API material with cold WFI to a final concentration of 4.54725 mg/ml. A concentrated formulation buffer stock containing 85 mg/ml glycerol, 13.5 mg/ml meta cresol, 0.150 mg/ml zinc chloride and 0.1 mg/ml polysorbate (20) is added to the API material in a 1/5 ratio of formulation buffer stock to API. The solution is mixed, followed by sterile filtration into appropriate vials in 10 mL aliquots.

Example 13

Working Cell Bank

The preparation of a WCB (working cell bank) for research and development containing cells capable of expressing recombinant glargine proinsulin is carried out according to the following processes:

The cloning procedure outlined in Example 9 is utilized to create the initial vector. Purified His-tagged glargine proinsulin pTrcHis2A(Kan) vector is transformed into competent BL21 E. coli cells and plated on sterile LB-Kan plates. From the plates, an isolated colony is used to inoculate sterile LB-Kan media (~100 ml). The cells are grown at 37° C. to mid log phase (~4-5 hours) $OD_{600\ nm}$ of ~1.5-2.0. Culture media containing cells is then aliquoted into sterile cryovials, combined with glycerol at a 20% final concentration. The vials are then stored at −80° C.

Example 14

Comparative Analysis

Figure 17:
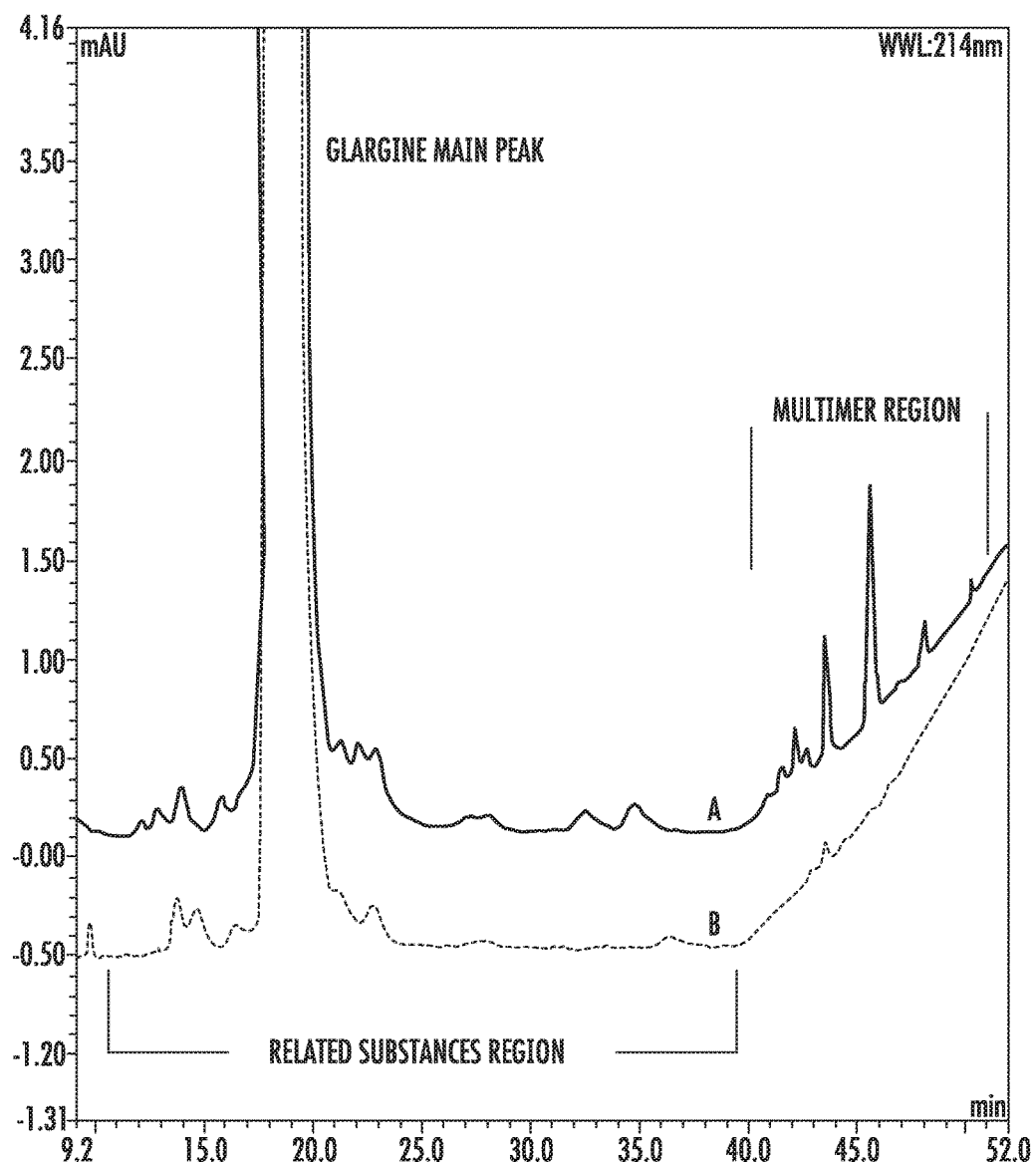
FIG. 17 is an analytical HPLC overlay of glargine product by the method (B) according to one aspect of the invention, compared with LANTUS®, manufactured by SANOFI AVENTIS®.

The present example demonstrates the enhanced purity of the glargine analog product according to Example 12. FIG. 17 depicts an analytical HPLC overlay of LANTUS® (A) and the glargine analog (B). The glargine analog demonstrates increased purity with respect to related substances and multimeric species over LANTUS®. In the related substance region, the glarine analog shows noticeably lower levels of contaminants in both the related substance region and the multimeric region. Most notably the number of multimeric species is much lower in the glargine analog. Overall purity for the LANTUS® material (A) in the current profile was 98.8%, while the glargine product produced by the herein described method (B) was 99.6%.

Example 15

Preparation of an E. coli Clone Expressing Aspart Proinsulin

The preparation of an E. coli containing cells capable of expressing recombinant aspart proinsulin is carried out according to the following processes.

Step 1: Construction of a purified aspart proinsulin gene segment for insertion into the vector. The initial gene construct was synthesized in a basic cloning vector. The gene construct included the N-terminal histidine tag, MHHHHHHGGR (SEQ ID NO: 2), modified B-chain, and modified C-peptide with the alanine codon in place of the native lysine and having the amino acid sequence:

```
                                                           (SEQ ID NO: 26)
         MHHHHHHGGR FVNQHLCGSH LVEALYLVCG ERGFFYTDKT RREAEDLQVG QVELGGGPGA    60

GSLQPLALEG SLQARGIVEQ CCTSICSLYQ LENYCN                              96
```

Figure 5:
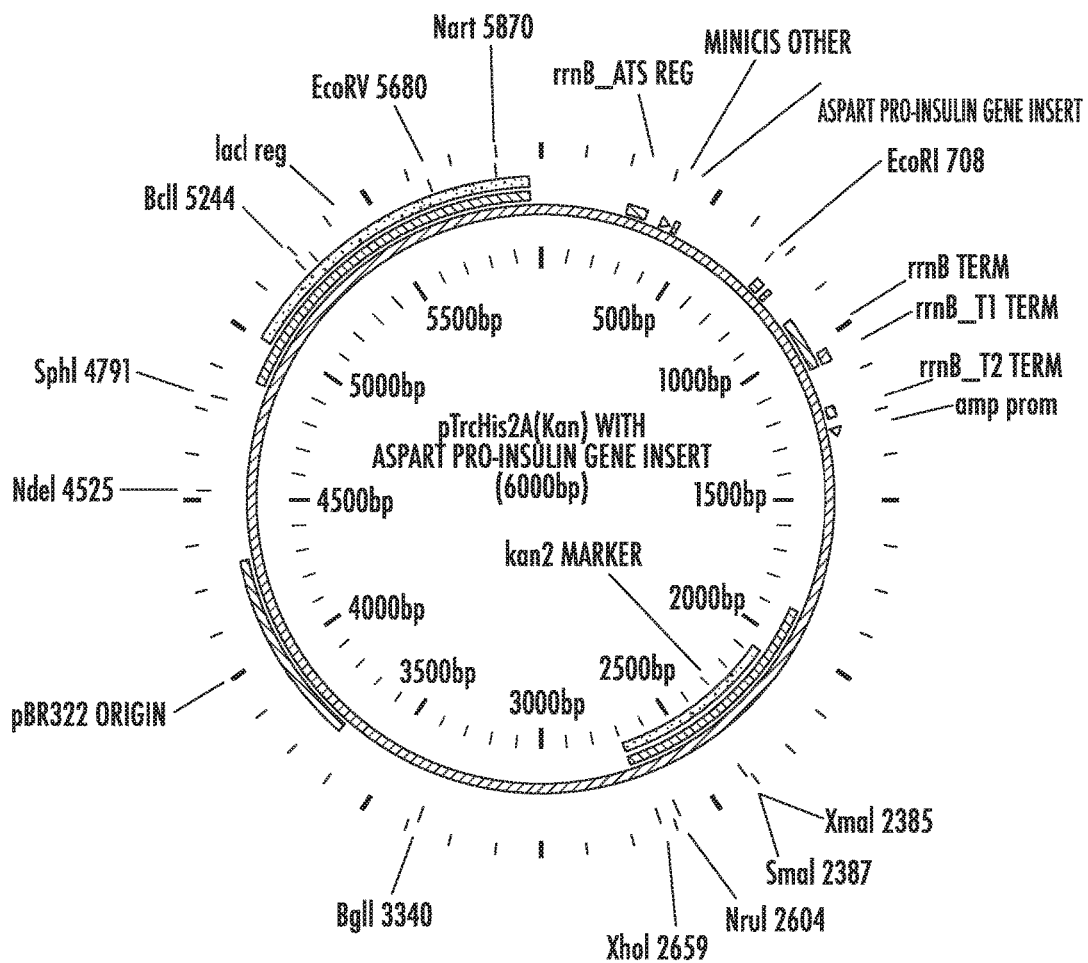
FIG. 5, according to one aspect of the invention, is a vector map of plasmid pTrcHis2A (Kan) with an aspart proinsulin gene insert.

The gene was flanked by Nde 1 and EcoRl restriction sites, for subsequent subcloning into the desire expression vector. The codons selected were optimized for expression in E. coli. The following sequence represents the pTrcHis2a(Kan) vector with aspart proinsulin insert (FIG. 5). The IPTG inducible promoter region which regulates the transcription rate is shown by a dotted underlined, while the aspart proinsulin insert, adjacent the promoter region, is shown by a solid underlined. The sequence indicated as bolded and italicized is the kanamycin gene, which provides the antibiotic selection marker for the vector.

(SEQ ID NO: 77)

```
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatgatgca   420
tcatcatcat catcatggtg gccgctttgt gaaccaacac ctgtgcggct cacacctggt   480
ggaagctctc tacctagtgt gcggggaacg aggcttcttc tacacagaca agacccgccg   540
ggaggcagag gacctgcagg tggggcaggt ggagctgggc gggggccctg gtgcaggcag   600
cctgcagccc ttggccctgg aggggtccct gcagaagcgt ggcattgtgg aacaatgctg   660
taccagcatc tgctccctct accagctgga gaactactgc ggctaggaat tcgaagcttg   720
ggcccgaaca aaaactcatc tcagaagagg atctgaatag cgccgtcgac catcatcatc   780
atcatcattg agtttaaacg gtctccagct tggctgtttt ggcggatgag agaagatttt   840
cagcctgata cagattaaat cagaacgcag aagcggtctg ataaaacaga atttgcctgg   900
cggcagtagc gcggtggtcc cacctgaccc catgccgaac tcagaagtga acgccgtag    960 cgccgatggt agtgtggggt ctccccatgc gagagtaggg aactgccagg catcaaataa  1020
aacgaaaggc tcagtcgaaa gactgggcct ttcgttttat ctgttgtttg tcggtgaacg  1080
ctctcctgag taggacaaat ccgccgggag cggatttgaa cgttgcgaag caacggcccg  1140
gagggtggcg gcaggacgc ccgccataaa ctgccaggca tcaaattaag cagaaggcca  1200
tcctgacgga tggccttttt gcgtttctac aaactctttt tgtttatttt tctaaataca  1260
ttcaaatatg tatccgctca tgagacaata accctgataa atgcttcaat aatattgaaa  1320
aaggaagagt atgagtattc aacatttccg tgtcgccctt attcccttt ttgcggcatt  1380 ttgccttcct gttttgctc acccagaaac gctggtgaaa gtaaaagatg ctgaagatca  1440
gttgggtgca cgagtgggtt acatcgaact ggatctcaac agcggtaaga tccttgagag  1500
ttttcgcccc gaagaacgtt ttccaatgat gagcactttt aaagttctgc tatgtggcgc  1560
ggtattatcc cgtgttgacg ccgggcaaga gcaactcggt cgccgcatac actattctca  1620
gaatgacttg gttgagtcct gaatcgcccc atcatccagc cagaaagtga gggagccacg  1680
gttgatgaga gctttgttgt aggtggacca gttggtgatt ttgaactttt gctttgccac  1740
ggaacggtct gcgttgtcgg aagatgcgt gatctgatcc ttcaactcag caaaagttcg  1800
atttattcaa caaagccgcc gtcccgtcaa gtcagcgtaa tgctctgcca gtgttacaac  1860
caattaacca attctgatta gaaaaactca tcgagcatca aatgaaactg caatttattc  1920
atatcaggat tatcaatacc atattttga aaaagccgtt tctgtaatga aggagaaaac  1980
tcaccgaggc agttccatag gatggcaaga tcctggtatc ggtctgcgat tccgactcgt  2040
ccaacatcaa taacctat taatttcccc tcgtcaaaaa taaggttatc aagtgagaaa  2100
tcaccatgag tgacgactga atccggtgag aatggcaaaa gcttatgcat ttctttccag  2160
acttgttcaa caggccagcc attacgctcg tcatcaaaat cactgcatca accaaaccgt  2220
tattcattcg tgattgcgcc tgagcgagac gaaatacgcg atcgctgtta aaaggacaat  2280
tacaaacagg aatcgaatgc aaccggcgca ggaacactgc cagcgcatca acaatatttt  2340
cacctgaatc aggatattct tctaatacct ggaatgctgt tttcccgggg atcgcagtgg  2400
```

-continued

```
tgagtaacca tgcatcatca ggagtacgga taaaatgctt gatggtcgga agaggcataa    2460
attccgtcag ccagtttagt ctgaccatct catctgtaac atcattggca acgctacctt    2520
tgccatgttt cagaaacaac tctggcgcat cgggcttccc atacaatcga tagattgtcg    2580
cacctgattg cccgacatta tcgcgagccc atttataccc atataaatca gcatccatgt    2640
tggaatttaa tcgcggcctc gagcaagacg tttcccgttg aatatggctc ataacacccc    2700
ttgtattact gtttatgtaa gcagacagtt ttattgttca tgatgatata ttttttatctt    2760 gtgcaatgta acatcagaga ttttgagaca caacgtggct tgttgaata aatcgaactt     2820 ttgctgagtt gaaggatcag atcacgcatc ttcccgacaa cgcagaccgt tccgtggcaa    2880
agcaaaagtt caaaatcacc aactggtcca cctacaacaa agctctcatc aaccgtggct    2940
ccctcacttt ctggctggat gatggggcga ttcaggactc accagtcaca gaaaagcatc    3000
ttacggatgg catgacagta agagaattat gcagtgctgc cataaccatg agtgataaca    3060
ctgcggccaa cttacttctg acaacgatcg gaggaccgaa ggagctaacc gcttttttgc    3120
acaacatggg ggatcatgta actcgccttg atcgttggga accggagctg aatgaagcca    3180
taccaaacga cgagcgtgac accacgatgc ctgtagcaat ggcaacaacg ttgcgcaaac    3240
tattaactgg cgaactactt actctagctt cccggcaaca attaatagac tggatggagg    3300
cggataaagt tgcaggacca cttctgcgct cggcccttcc ggctggctgg tttattgctg    3360
ataaatctgg agccggtgag cgtgggtctc gcggtatcat tgcagcactg ggccagatg    3420 gtaagccctc ccgtatcgta gttatctaca cgacggggag tcaggcaact atggatgaac    3480
gaaatagaca gatcgctgag ataggtgcct cactgattaa gcattggtaa ctgtcagacc    3540
aagtttactc atatatactt tagattgatt taaaacttca tttttaattt aaaaggatct    3600
aggtgaagat ccttttttgat aatctcatga ccaaaatccc ttaacgtgag ttttcgttcc    3660
actgagcgtc agacccccgta gaaaagatca aaggatcttc ttgagatcct ttttttctgc    3720
gcgtaatctg ctgcttgcaa acaaaaaaac caccgctacc agcggtggtt tgtttgccgg    3780
atcaagagct accaactctt tttccgaagg taactggctt cagcagagcg cagataccaa    3840
atactgtcct tctagtgtag ccgtagttag gccaccactt caagaactct gtagcaccgc    3900
ctacatacct cgctctgcta atcctgttac cagtggctgc tgccagtggc gataagtcgt    3960
gtcttaccgg gttggactca agacgatagt taccggataa ggcgcagcgg tcgggctgaa    4020
cggggggttc gtgcacacag cccagcttgg agcgaacgac ctacaccgaa ctgagatacc    4080
tacagcgtga gctatgagaa agcgccacgc ttcccgaagg gagaaaggcg gacaggtatc    4140
cggtaagcgg cagggtcgga acaggagagc gcacgaggga gcttccaggg ggaaacgcct    4200
ggtatcttta tagtcctgtc gggtttcgcc acctctgact tgagcgtcga ttttttgtgat   4260 gctcgtcagg ggggcggagc ctatggaaaa acgccagcaa cgcggccttt ttacggttcc    4320
tggccttttg ctggcctttt gctcacatgt tctttcctgc gttatcccct gattctgtgg    4380
ataaccgtat taccgccttt gagtgagctg ataccgctcg ccgcagccga acgaccgagc    4440
gcagcgagtc agtgagcgag gaagcggaag agcgcctgat gcggtatttt ctccttacgc    4500
atctgtgcgg tatttcacac cgcatatggt gcactctcag tacaatctgc tctgatgccg    4560
catagttaag ccagtataca ctccgctatc gctacgtgac tgggtcatgg ctgcgccccg    4620
acacccgcca cacccgctg acgcgccctg acgggcttgt ctgctcccgg catccgctta    4680
cagacaagct gtgaccgtct ccgggagctg catgtgtcag aggttttcac cgtcatcacc    4740
gaaacgcgcg aggcagcaga tcaattcgcg cgcgaaggcg aagcggcatg catttacgtt    4800
gacaccatcg aatggtgcaa aacctttcgc ggtatggcat gatagcgccc ggaagagagt    4860
```

```
caattcaggg tggtgaatgt gaaaccagta acgttatacg atgtcgcaga gtatgccggt   4920
gtctcttatc agaccgtttc ccgcgtggtg aaccaggcca gccacgtttc tgcgaaaacg   4980
cgggaaaaag tggaagcggc gatggcggag ctgaattaca ttcccaaccg cgtggcacaa   5040
caactggcgg gcaaacagtc gttgctgatt ggcgttgcca cctccagtct ggccctgcac   5100
gcgccgtcgc aaattgtcgc ggcgattaaa tctcgcgccg atcaactggg tgccagcgtg   5160
gtggtgtcga tggtagaacg aagcggcgtc gaagcctgta aagcggcggt gcacaatctt   5220
ctcgcgcaac gcgtcagtgg gctgatcatt aactatccgc tggatgacca ggatgccatt   5280
gctgtggaag ctgcctgcac taatgttccg gcgttatttc ttgatgtctc tgaccagaca   5340
cccatcaaca gtattatttt ctcccatgaa gacggtacgc gactgggcgt ggagcatctg   5400
gtcgcattgg gtcaccagca aatcgcgctg ttagcgggcc cattaagttc tgtctcggcg   5460
cgtctgcgtc tggctggctg gcataaatat ctcactcgca atcaaattca gccgatagcg   5520
gaacgggaag gcgactggag tgccatgtcc ggttttcaac aaaccatgca aatgctgaat   5580
gagggcatcg ttcccactgc gatgctggtt gccaacgatc agatggcgct gggcgcaatg   5640
cgcgccatta ccgagtccgg gctgcgcgtt ggtgcggata tctcggtagt gggatacgac   5700
gataccgaag acagctcatg ttatatcccg ccgtcaacca ccatcaaaca ggattttcgc   5760 ctgctgggc aaaccagcgt ggaccgcttg ctgcaactct ctcagggcca ggcggtgaag   5820
ggcaatcagc tgttgcccgt ctcactggtg aaaagaaaaa ccaccctggc gcccaatacg   5880
caaaccgcct ctccccgcgc gttggccgat tcattaatgc agctggcacg acaggtttcc   5940
cgactggaaa gcgggcagtg agcgcaacgc aattaatgtg agttagcgcg aattgatctg   6000
```

The modified proinsulin sequence without the tag is as follows:

```
                                                      (SEQ ID NO: 78)
tttgtgaacc aacacctgtg cggctcacac ctggtggaag ctctctacct agtgtgcggg   60
gaacgaggct tcttctacac agacaagacc cgccgggagg cagaggacct gcaggtgggg   120
caggtggagc tgggcggggg ccctggtgca ggcagcctgc agcccttggc cctgagggg   180 tccctgcaga agcgtggcat tgtggaacaa tgctgtacca gcatctgctc cctctaccag   240
ctggagaact actgcggcta g
```

Step 2—Generation of the pTrcHis2A(Kan) vector containing aspart proinsulin: Commercially available pTrcHis2A(Kan) vector was modified to Include a kanamycin resistance gene in the middle of the ampicillin resistance gene to negate the ampicillin resistance prior to insertion of the proinsulin sequence into the vector. Ampicillin resistance heightens the potential for allergic reactions to preparations made using vector constructs that include the ampicillin resistance gene. Therefore it is preferable to eliminate the ampicillin resistance in the constructs that are prepared and used.

The pTrcHis2A(Kan) vector was modified at the start codon in the multiple cloning site by replacing the NcoI restriction site (ccatgg) with an NdeI site (catatg) to simplify subsequent subcloning work.

The proinsulin gene was isolated from the DNA 2.0 plasmid using NdeI to cleave at the N-terminal side of the gene and EcoR1 to cleave at the C-terminal side of the gene. The digested DNA was run over a 2% agarose gel to separate the plasmid DNA from the aspart proinsulin gene. A QIAQUICK® (QIAGEN®) gel purification kit was then used to purify the gene construct.

Accordingly, a sequential digest of the vector with NdeI and EcoR1, respectively, was performed. The vector DNA was also purified using a QIAQUICK® gel purification kit. Following purification of the vector and the gene, a 5' Nde 1 and a 3' EcoR1 ligation reaction was utilized to insert the proinsulin gene into the pTrcHis2A(Kan) vector.

Step 3—Transformation: One microliter of the ligation reaction was used to transform competent BL21 E. coli cells with the pTrcHis2A(Kan) plasmid containing the proinsulin gene. The transformed BL21 E. coli cells were plated on LB-Kan agar plates and incubated overnight at 37° C. Several clones were selected and sequenced. Clones with the correct sequence were then screened for expression. The resulting clone is referred to as the aspart His Tagged proinsulin pTrcHis2A(Kan) vector.

Step 4—Preparation of the working cell bank (WCB): To establish the WCB, sterile growth medium was inoculated with the recombinant BL21 *E. coli* containing the His-tagged aspart proinsulin/pTrcHis2A(Kan) vector and incubated to allow cell growth. The cells were harvested in an IS05 (class 100) environment under a biosafety cabinet via centrifugation. Sterile medium and glycerol were added to the cells. 1 mL aliquots of the cells were then dispensed into sterile ampoules and stored at −80° C. Aseptic techniques were utilized to generate the MCB.

Example 16

Product Manufacture of Aspart Insulin Analog from Modified Proinsulin Sequence

Step 1—Culturing of *E. coli* transformed with aspart modified proinsulin sequence from the WCB of Example 15: Seed an inoculum preparation of the WCB in a sterile growth medium that includes yeastolate (purchased from VWR®, Prod. #90004-426 or -488), select phytone, sodium chloride, purified water, sterile kanamycin solution), and incubate until growth to an optical density ($OD_{600\ nm}$) of 2 to 4. Prepare a fermentation media (containing select phytone, yeastolate, glycerin, BIOSPUMEX® 153K (BASF®) in a fermentor. Add the following sterilized phosphate solutions to the fermentor. Prepare a Phosphate flask 1—potassium phosphate monobasic and potassium phosphate dibasic containing kanamycin solution. Prepare a Phosphate flask 2—potassium phosphate monobasic and potassium phosphate dibasic. Add seed inoculate of *E. coli* to the fermentor—growth to $O.D._{600\ nm}$ of 8 to 10 (mid log phase). Add a dioxane free IPTG (purchased from PROMEGA®, Catalog No. #PA V3953 (VWR® Catalog #PAV3953) solution to the fermentor (to induce transcription of the K64A aspart proinsulin gene). Incubate for 4 hours. This results in the production of a concentrated cell suspension containing His-tagged aspart proinsulin inclusion bodies. The cell suspension is then centrifuged to provide a cell paste for the subsequent inclusion body isolation step.

Step 2—Disruption: Cells containing inclusion bodies expressing aspart modified proinsulin sequence are lysed in a basic Tris/salt buffer, using a NIRO SOAVI® homogenizer (1100-1200 bar).

Step 3—Inclusion Body Washing: Contaminant protein removal is accomplished via two sequential washes with a Tris/TRITON® X-100 buffer, followed by two sequential washes with a Tris/TWEEN®-20 buffer, and finally a single wash with a Tris/NaCl buffer.

Step 4—Solubilization: Inclusion bodies enriched with the modified proinsulin peptide are solubilized in 4-8M urea, preferably about 6-urea, containing reducing agents (2-mercaptoethanol, L-cysteine hydrochloride monohydrate). Complete solubilization is achieved by adjusting the pH to 10.5-12, preferably 11.8-12 with NaOH.

Step 5—Dilution refolding: The solubilized protein is then diluted into refolding buffer (20 mM glycine, pH 10-11 at 6-10° C.) to a final concentration of 1 mg/ml and permitted to refold for 24 to 72 hours, preferentially about 48 hours, at 6-10° C. Higher protein concentration may be used in the refold if desired, however, overall refold efficiency will decrease. Sodium chloride and phosphate are then added to final concentrations of 700 mM and 25 mM respectively, followed by pH adjustment to 7.9-9.0, preferably 7.9 to 8.0, with 6M HCl.

Step 6—IMAC Chromatography: The dilute proinsulin derivative is loaded onto an IMAC column to a maximum capacity of ≤26.5 mg main peak protein per ml of resin. A 75 mM imidizole buffer is used to isocratically strip the majority of impurities from the column. Aspart proinsulin is eluted isocratically using ≤300 mM imidizole.

Step 7—Buffer exchange: To the IMAC main peak pool material, add EDTA to a final concentration of 20 mM. Exchange the buffer using a membrane with a suitable molecular weight cutoff (e.g. 3000 Da). The final buffer should be at least 97% exchanged to a 20 mM Tris-HCl, pH 7 to 10, preferably 8.1, at 8-10° C. A protein concentration of approximately 5 mg/ml is desirable.

Step 8—Trypsin/Carboxypeptidase B Enzymatic Transformation and Proteolysis: Buffer exchanged sample is digested with a 1500:1 mass ratio of main peak protein to trypsin and 1000:1 mass ratio of main peak protein to carboxypeptidase B, in the presence of 5 mM CaCl. The ratios of trypsin and carboxypeptidase may be increased or decreased depending on the desired length of time for the reaction. Once complete, based on HPLC, the digest is then quenched by the addition of acetic acid to ≥700 mM, to a pH of approximately 3-3.5.

Example 17

Final Purification

After step 8 in Example 16, the final purification may proceed using the following process or the process described in the Example 18.

Step 9a—Ion Exchange Chromatography: The digested material is loaded onto a cation exchange column and eluted with a NaCl gradient, in the presence of 20% n-propanol or at pH 4.0. RP-HPLC is used to pool the appropriate fractions containing the aspart insulin peak of interest at the desired purity level.

Step 10a—Reverse Phase Chromatography: The S-column pool containing the aspart insulin is loaded onto an RPC30 or C18 reverse phase column and eluted using an n-propanol or acetonitrile gradient in the presence of 200 mM sodium sulfate and 0.136% phosphoric acid. Fractions are immediately diluted 1:4 with 100 mM phosphate at pH 7.0-9.0, preferably 7.5-8.0 as they are collected. RP-HPLC is used to pool the appropriate fractions containing the Insulin peak of interest at the desired purity level.

Step 11a—Buffer Exchange: Exchange the sample into WFI (water for injection) using a membrane with a suitable molecular weight cutoff (e.g. 3000 Da). The pH of the solution should be monitored and maintained at 7.0-9.0, preferably 7.5-8.0. The final sample is concentrated to 5.5-8 mg/ml, with an adjusted pH of 7.0-9.0, preferably 7.5-8.0 at 6-10° C. This material represents the liquid API form of the presently disclosed preparations of aspart insulin analog. The API should be stored in the dark at 6-10° C.

Example 18

Final Purification (Alternate Method)

Step 10b—Reverse Phase Chromatography: The digested material containing the aspart insulin is loaded onto a RPC30 or C18 reverse phase column and eluted using a n-propanol or acetonitrile gradient in the presence of 200 mM sodium sulfate and 0.136% phosphoric acid. Fractions are immediately diluted 1:4 with 100 mM phosphate buffer at pH 7.0-9.0 preferably, 7.5-8.0 as they are collected. RP-HPLC is used to pool the appropriate fractions containing the aspart insulin peak of interest at the desired purity level.

Step 11b—Buffer Exchange: Exchange the sample into WEI using a membrane with a suitable molecular weight cutoff (e.g. 3000 Da). The pH of the solution should be monitored and maintained at 7.0-9.0, preferably 7.5-8.0. The final sample is concentrated to 5.5-8 mg/ml, with an adjusted pH of 7.0-9.0, preferably 7.5-8.0 at 6-10° C. This material represents the liquid API form of the presently disclosed preparations and formulations of aspart insulin analog.

Example 19

API Formulation

The purified aspart insulin analog is formulated by diluting the API material with cold WFI to a final concentration of 4.3375 mg/ml. A concentrated formulation buffer stock containing 80 mg/ml glycerol, 15.75 mg/ml meta cresol, 0.0985 mg/ml zinc chloride at pH 7.5±0.1 is added to the API material in a 1/5 ratio of formulation buffer stock to API. The solution is mixed, followed by sterile filtration into appropriate vials in 10 ml aliquots.

Example 20

Working Cell Bank

The preparation of a WCB (working cell bank) for research and development containing cells capable of expressing recombinant aspart proinsulin is carried out according to the following processes:

The cloning procedure outlined in Example 15 is utilized to create the initial vector. Purified His-tagged aspart proinsulin pTrcHis2A(Kan) vector is transformed into competent BL21 cells and plated on sterile LB-Kan plates. From the plates, an isolated colony is used to inoculate sterile LB-Kan media (~100 mls). The cells are grown at 37° C. to mid log phase (about 4-5 hours) $OD_{600\ nm}$ of about 1.5-2.0. Culture media containing cells is then aliquoted into sterile cryovials, combined with glycerol at a 20% final concentration. The vials are then stored at 80° C.

Example 21

Preparation of an *E. coli* Clone Expressing Lis-Pro Proinsulin

The preparation of transformed *E. coli* containing cells capable of expressing recombinant Lis-Pro proinsulin is carried out according to the following processes.

Step 1: Construction of a purified Lis-Pro proinsulin gene segment for insertion into the vector. The initial gene construct was synthesized in a basic cloning vector (ptrcKis2a(Kan)). The gene construct included the N-terminal histidine tag, MHHHHHHGGR (SEQ ID NO: 2), modified B-chain, and modified C-peptide with the alanine codon in place of the native lysine and having the amino acid sequence:

```
                                                       (SEQ ID NO: 35)
MHHHHHHGGR FVNQHLCGSH LVEALYLVCG ERGFFYTKPT RREAEDLQVG QVELGGGPGA    60

GSLQPLALEG SLQARGIVEQ CCTSICSLYQ LENYCN.                            96
```

Figure 6:
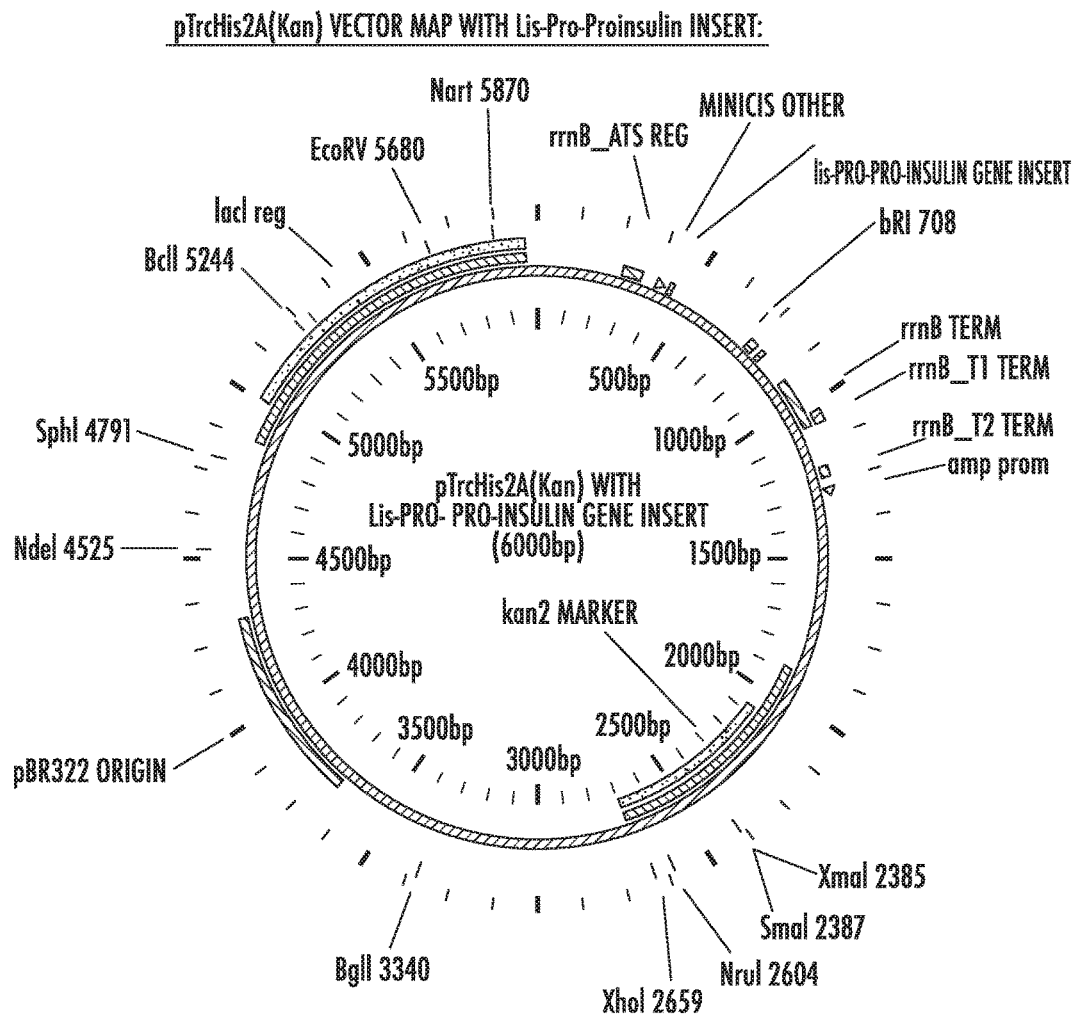
FIG. 6, according to one aspect of the invention, is a vector map of plasmid pTrcHis2A (Kan) with a Lis-Pro proinsulin gene insert.

The gene was flanked by Nde 1 and EcoR1 restriction sites, for subsequent subcloning into the desired expression vector. The codons selected were optimized for expression in *E. coli*. The following sequence represents the pTrcHis2a(Kan) vector with a Lis-Pro proinsulin insert (FIG. 6). The IPTG inducible promoter region which regulates the transcription rate is shown by the dotted underline, while the Lis-Pro proinsulin insert, adjacent the promoter region, is shown by the solid underlined. The sequence shown by the bold and italicized is the kanamycin gene, which provides the antibiotic selection marker for the vector.

```
                                                          (SEQ ID NO: 79)
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatgatgca   420
tcatcatcat catcatggtg gccgctttgt gaaccaacac ctgtgcggct cacacctggt   480
ggaagctctc tacctagtgt gcggggaacg aggcttcttc tacacaaagc cgacccgccg   540
ggaggcagag gacctgcagg tggggcaggt ggagctgggc gggggccctg gtgcaggcag   600
cctgcagccc ttggccctgg agggtccct gcagaagcgt ggcattgtgg aacaatgctg   660
taccagcatc tgctccctct accagctgga gaactactgc ggctaggaat tcgaagcttg   720
ggcccgaaca aaaactcatc tcagaagagg atctgaatag cgccgtcgac catcatcatc   780
```

```
                                  -continued
atcatcattg agtttaaacg gtctccagct tggctgtttt ggcggatgag agaagatttt    840
cagcctgata cagattaaat cagaacgcag aagcggtctg ataaaacaga atttgcctgg    900
cggcagtagc gcggtggtcc cacctgaccc catgccgaac tcagaagtga acgccgtag    960 cgccgatggt agtgtggggt ctccccatgc gagagtaggg aactgccagg catcaaataa   1020
aacgaaaggc tcagtcgaaa gactgggcct ttcgttttat ctgttgtttg tcggtgaacg   1080
ctctcctgag taggacaaat ccgccggag cggatttgaa cgttgcgaag caacggcccg    1140
gagggtggcg ggcaggacgc ccgccataaa ctgccaggca tcaaattaag cagaaggcca   1200
tcctgacgga tggccttttt gcgtttctac aaactctttt tgtttatttt tctaaataca   1260
ttcaaatatg tatccgctca tgagacaata accctgataa atgcttcaat aatattgaaa   1320
aaggaagagt atgagtattc aacatttccg tgtcgccctt attcccttt ttgcggcatt    1380 ttgccttcct gttttgctc acccagaaac gctggtgaaa gtaaagatg ctgaagatca     1440 gttgggtgca cgagtgggtt acatcgaact ggatctcaac agcggtaaga tccttgagag   1500
ttttcgcccc gaagaacgtt ttccaatgat gagcactttt aaagttctgc tatgtggcgc   1560
ggtattatcc cgtgttgacg ccgggcaaga gcaactcggt cgccgcatac actattctca   1620
gaatgacttg gttgagtcct gaatcgcccc atcatccagc cagaaagtga gggagccacg   1680
gttgatgaga gctttgttgt aggtggacca gttggtgatt ttgaacttt gctttgccac    1740 ggaacggtct gcgttgtcgg gaagatgcgt gatctgatcc ttcaactcag caaaagttcg   1800
atttattcaa caaagccgcc gtcccgtcaa gtcagcgtaa tgctctgcca gtgttacaac   1860
caattaacca attctgatta gaaaaactca tcgagcatca aatgaaactg caatttattc   1920
atatcaggat tatcaatacc atattttga aaaagccgtt tctgtaatga aggagaaaac    1980
tcaccgaggc agttccatag gatggcaaga tcctggtatc ggtctgcgat tccgactcgt   2040
ccaacatcaa tacaacctat taattttcccc tcgtcaaaaa taaggttatc aagtgagaaa   2100
tcaccatgag tgacgactga atccggtgag aatggcaaaa gcttatgcat ttctttccag   2160
acttgttcaa caggccagcc attacgctcg tcatcaaaat cactgcatca accaaaccgt   2220
tattcattcg tgattgcgcc tgagcgagac gaaatacgcg atcgctgtta aaaggacaat   2280
tacaaacagg aatcgaatgc aaccggcgca ggaacactgc cagcgcatca acaatatttt   2340
cacctgaatc aggatattct tctaatacct ggaatgctgt tttcccgggg atcgcagtgg   2400
tgagtaacca tgcatcatca ggagtacgga taaaatgctt gatggtcgga agaggcataa   2460
attccgtcag ccagtttagt ctgaccatct catctgtaac atcattggca acgctacctt   2520
tgccatgttt cagaaacaac tctggcgcat cgggcttccc atacaatcga tagattgtcg   2580
cacctgattg cccgacatta tcgcgagccc atttatacc atataaatca gcatccatgt    2640
tggaatttaa tcgcggcctc gagcaagacg tttcccgttg aatatggctc ataacacccc   2700
ttgtattact gtttatgtaa gcagacagtt ttattgttca tgatgatata ttttatctt    2760 gtgcaatgta acatcagaga ttttgagaca caacgtggct ttgttgaata atcgaactt    2820 ttgctgagtt gaaggatcag atcacgcatc ttcccgacaa cgcagaccgt tccgtggcaa   2880
agcaaaagtt caaaatcacc aactggtcca cctacaacaa agctctcatc aaccgtggct   2940
ccctcacttt ctggctggat gatggggcga ttcaggactc accagtcaca gaaaagcatc   3000
ttacggatgg catgacagta agagaattat gcagtgctgc cataaccatg agtgataaca   3060
ctgcggccaa cttacttctg acaacgatcg gaggaccgaa ggagctaacc gcttttttgc   3120
acaacatggg ggatcatgta actcgccttg atcgttggga accggagctg aatgaagcca   3180
taccaaacga cgagcgtgac accacgatgc ctgtagcaat ggcaacaacg ttgcgcaaac   3240
```

-continued

```
tattaactgg cgaactactt actctagctt cccggcaaca attaatagac tggatggagg   3300
cggataaagt tgcaggacca cttctgcgct cggcccttcc ggctggctgg tttattgctg   3360
ataaatctgg agccggtgag cgtgggtctc gcggtatcat tgcagcactg gggccagatg   3420
gtaagccctc ccgtatcgta gttatctaca cgacggggag tcaggcaact atggatgaac   3480
gaaatagaca gatcgctgag ataggtgcct cactgattaa gcattggtaa ctgtcagacc   3540
aagtttactc atatatactt tagattgatt taaaacttca tttttaattt aaaaggatct   3600
aggtgaagat cctttttgat aatctcatga ccaaaatccc ttaacgtgag ttttcgttcc   3660
actgagcgtc agaccccgta gaaaagatca aaggatcttc ttgagatcct tttttctgc    3720
gcgtaatctg ctgcttgcaa acaaaaaaac caccgctacc agcggtggtt tgtttgccgg   3780
atcaagagct accaactctt tttccgaagg taactggctt cagcagagcg cagataccaa   3840
atactgtcct tctagtgtag ccgtagttag gccaccactt caagaactct gtagcaccgc   3900
ctacatacct cgctctgcta atcctgttac cagtggctgc tgccagtggc gataagtcgt   3960
gtcttaccgg gttggactca agacgatagt taccggataa ggcgcagcgg tcgggctgaa   4020
cggggggttc gtgcacacag cccagcttgg agcgaacgac ctacaccgaa ctgagatacc   4080
tacagcgtga gctatgagaa agcgccacgc ttcccgaagg gagaaaggcg gacaggtatc   4140
cggtaagcgg cagggtcgga acaggagagc gcacgaggga gcttccaggg ggaaacgcct   4200
ggtatcttta tagtcctgtc gggtttcgcc acctctgact tgagcgtcga ttttgtgat    4260
gctcgtcagg ggggcggagc ctatggaaaa acgccagcaa cgcggccttt ttacggttcc   4320
tggccttttg ctggcctttt gctcacatgt tctttcctgc gttatcccct gattctgtgg   4380
ataaccgtat taccgccttt gagtgagctg ataccgctcg ccgcagccga acgaccgagc   4440
gcagcgagtc agtgagcgag gaagcggaag agcgcctgat gcggtatttt ctccttacgc   4500
atctgtgcgg tatttcacac cgcatatggt gcactctcag tacaatctgc tctgatgccg   4560
catagttaag ccagtataca ctccgctatc gctacgtgac tgggtcatgg ctgcgccccg   4620
acacccgcca cacccgctg acgcgccctg acgggcttgt ctgctcccgg catccgctta    4680
cagacaagct gtgaccgtct ccgggagctg catgtgtcag aggttttcac cgtcatcacc   4740
gaaacgcgcg aggcagcaga tcaattcgcg cgcgaaggcg aagcggcatg catttacgtt   4800
gacaccatcg aatggtgcaa aacctttcgc ggtatggcat gatagcgccc ggaagagagt   4860
caattcaggg tggtgaatgt gaaaccagta acgttatacg atgtcgcaga gtatgccggt   4920
gtctcttatc agaccgtttc ccgcgtggtg aaccaggcca ccacgtttc tgcgaaaacg    4980
cgggaaaaag tggaagcggc gatggcggag ctgaattaca ttcccaaccg cgtggcacaa   5040
caactggcgg gcaaacagtc gttgctgatt ggcgttgcca cctccagtct ggccctgcac   5100
gcgccgtcgc aaattgtcgc ggcgattaaa tctcgcgccg atcaactggg tgccagcgtg   5160
gtggtgtcga tggtagaacg aagcggcgtc gaagcctgta aagcggcggt gcacaatctt   5220
ctcgcgcaac gcgtcagtgg gctgatcatt aactatccgc tggatgacca ggatgccatt   5280
gctgtggaag ctgcctgcac taatgttccg gcgttatttc ttgatgtctc tgaccagaca   5340
cccatcaaca gtattatttt ctcccatgaa gacggtacgc gactgggcgt ggagcatctg   5400
gtcgcattgg gtcaccagca aatcgcgctg ttagcgggcc cattaagttc tgtctcggcg   5460
cgtctgcgtc tggctggctg gcataaatat ctcactcgca atcaaattca gccgatagcg   5520
gaacgggaag gcgactggag tgccatgtcc ggttttcaac aaaccatgca aatgctgaat   5580
gagggcatcg ttcccactgc gatgctggtt gccaacgatc agatggcgct gggcgcaatg   5640
```

```
                                                          -continued
cgcgccatta  ccgagtccgg  gctgcgcgtt  ggtgcggata  tctcggtagt  gggatacgac    5700
gataccgaag  acagctcatg  ttatatcccg  ccgtcaacca  ccatcaaaca  ggattttcgc    5760
ctgctggggc  aaaccagcgt  ggaccgcttg  ctgcaactct  ctcagggcca  ggcggtgaag    5820
ggcaatcagc  tgttgcccgt  ctcactggtg  aaaagaaaaa  ccaccctggc  gcccaatacg    5880
caaaccgcct  ctccccgcgc  gttggccgat  tcattaatgc  agctggcacg  acaggtttcc    5940
cgactggaaa  gcgggcagtg  agcgcaacgc  aattaatgtg  agttagcgcg  aattgatctg    6000
```

The modified proinsulin sequence without the tag is as follows:

```
                                                          (SEQ ID NO: 80)
tttgtgaacc  aacacctgtg  cggctcacac  ctggtggaag  ctctctacct  agtgtgcggg      60
gaacgaggct  tcttctacac  aaagccgacc  cgccgggagg  cagaggacct  gcaggtgggg     120
caggtggagc  tgggcggggg  ccctggtgca  ggcagcctgc  agcccttggc  cctggagggg     180
tccctgcaga  agcgtggcat  tgtggaacaa  tgctgtacca  gcatctgctc  cctctaccag     240
ctggagaact  actgcggcta  g                                                  261
```

Step 2—Generation of the pTrcHis2A(Kan) vector containing Lis-Pro proinsulin: Commercially available pTrcHis2A(Kan) vector was modified to include a kanamycin resistance gene in the middle of the ampicillin resistance gene to negate the ampicillin resistance prior to insertion of the proinsulin sequence into the vector. Ampicillin resistance heightens the potential for allergic reactions to preparations made using vector constructs that include the ampicillin resistance gene. Therefore it is preferable to eliminate the ampicillin resistance in the constructs that are prepared and used.

The pTrcHis2A(Kan) vector was modified at the start codon in the multiple cloning site by replacing the Nco1 restriction site (ccatgg) with an NdeI site (catatg) to simplify subsequent subcloning work The proinsulin gene was isolated from the DNA 2.0 plasmid using Nde1 to cleave at the N-terminal side of the gene and EcoR1 to cleave at the C-terminal side of the gene. The Digested DNA was run over a 2% agarose gel to separate the plasmid DNA from the Lis-Pro proinsulin gene. A QIAQUICK® (QIAGEN®) gel purification kit was then used to purify the gene construct.

Accordingly, a sequential digest of the vector with NdeI and EcoR1, respectively, was performed. The vector DNA was also purified using a QIAQUICK® gel purification kit. Following purification of the vector and the gene, a 5' NdeI and a 3' EcoR1 ligation reaction was utilized to insert the proinsulin gene into the pTrcHis2A(Kan) vector.

Step 3—Transformation: One microliter of the ligation reaction was used to transform competent BL21 E. coli cells with the pTrcHis2A(Kan) plasmid containing the proinsulin gene. The transformed BL21 E. coli cells were plated on LB-Kan agar plates and incubated overnight at 37° C. Several clones were selected and sequenced. Clones with the correct sequence were then screened for expression.

The resulting clone is referred to as the His Tagged Lis-Pro proinsulin pTrcHis2A(Kan) vector.

Step 4—Preparation of the working cell bank (WCB): To establish the MCB, sterile growth medium was inoculated with the recombinant BL21 E. coli containing the His-tagged Lis-Pro proinsulin pTrcHis2A(Kan) vector and incubated to allow cell growth. The cells were harvested in an ISO5 (class 100) environment under a biosafety cabinet via centrifugation. Sterile medium and glycerol were added to the cells. 1 mL aliquots of the cells were then dispensed into sterile ampoules and stored at −80° C. Aseptic techniques were utilized to generate the WCB.

Example 22

Product Manufacture of Lis-Pro Insulin Analog from Modified Proinsulin Sequence Carrying Transformed E. coli.

Step 1—Culturing of E. coli transformed with Lis-Pro modified proinsulin sequence as described in Example 20: Seed an inoculum preparation of the transformed E. coli in a sterile growth medium that includes yeastolate (purchased from VWR®, Prod. #90004-426 or -488), select phytone, sodium chloride, purified water, sterile kanamycin solution), and incubate until growth to an optical density ($OD_{600\ nm}$) of 2 to 4. Prepare a fermentation media (containing select phytone, yeastolate, glycerin, BIOSPUMEX® 153K (BASF®) in a fermentor. Add the following sterilized phosphate solutions to the fermentor. Prepare a Phosphate flask 1—potassium phosphate monobasic and potassium phosphate dibasic containing kanamycin solution. Prepare a Phosphate flask 2—potassium phosphate monobasic and potassium phosphate dibasic. Add seed inoculate of E. coli to the germentor and grow to $OD_{600\ nm}$ of 8 to 10 (mid log phase). Add a dioxane free IPTG (purchased from PROMEGA®, Catalog No. #PA V3953 (VWR® Catalog #PAV3953) solution to the fermentor (to induce transcription of the K64A Lis-Pro proinsulin gene). Incubate for 4 hours. This results in the production of a concentrated cell suspension containing His-tagged Lis-Pro proinsulin inclusion bodies. The cell suspension is then centrifuged to provide a cell paste for the subsequent inclusion body isolation step.

Step 2—Disruption: Cells containing inclusion bodies expressing Lis-Pro modified proinsulin sequence are lysed in a basic Tris/salt buffer, using a NIRO SOAVI® homogenizer (1100-1200 bar).

Step 3—Inclusion Body Washing: Contaminant protein removal is accomplished via two sequential washes with a Tris/TRITON® X-100 buffer, followed by two sequential washes with a Tris/TWEEN®-20 buffer, and finally a single wash with a Tris/NaCl buffer.

Step 4—Solubilization: Inclusion bodies enriched with the modified proinsulin peptide are solubilized in 4-8M urea, preferably 6-8M urea, containing reducing agents (2-mercaptoethanol, L-cysteine hydrochloride monohydrate). Complete solubilization is achieved by adjusting the pH to 10.5-12, preferably 11.8-12 with NaOH.

Step 5—Dilution refolding: The solubilized protein is then diluted into refolding buffer (20 mM glycine, pH 10-11 at 6–10° C.) to a final concentration of 1 mg/ml and permitted to refold for 24 to 72 hours, preferentially about 48 hours, at 6-10° C. Higher protein concentration may be used in the refold if desired. However, overall refold efficiency will decrease. Sodium chloride and phosphate are then added to final concentrations of 700 mM and 25 mM respectively, followed by pH adjustment to 7.0 to 9.0, preferably 7.9-8.0 with 6M HCl.

Step 6—IMAC Chromatography: The dilute proinsulin derivative is loaded onto an IMAC column to a maximum capacity of ≤26.5 mg main peak protein per ml of resin. A 75 mM imidizole buffer is used to isocratically strip the majority of impurities from the column Lis-Pro proinsulin is eluted isocratically using ≤300 mM imidizole.

Step 7—Buffer exchange—To the IMAC main peak pool material, add EDTA to final concentration of 20 mM. Exchange the buffer using a membrane with a suitable molecular weight cutoff (e.g. 3000 Da). The final buffer should be at least 97% exchanged to a 20 mM Tris-HCl, pH 7.0-10.0, preferably 8.1 at 8-10° C. A protein concentration of approximately 5 mg/ml is desirable.

Step 8—Trypsin/Carboxypeptidase B Enzymatic Transformation and Proteolysis: The buffer exchanged sample is digested with a 1500:1 mass ratio of main peak protein to trypsin and 1000:1 mass ratio of main peak protein to carboxypeptidase B, in the presence of 5 mM CaCl. The ratios of trypsin and carboxypeptidase may be increased or decreased depending on the desired length of time for the reaction. Once complete, based on HPLC, the digest is then quenched by the addition of acetic acid to 700 mM, to a pH of approximately 3-3.5.

Example 23

Final Purification

After step 8 in Example 22, the final purification may proceed using the following process or the process described in the Example 24.

Step 9a—Ion Exchange Chromatography: The digested material is loaded onto a cation exchange column and eluted with a NaCl gradient, in the presence of 20% n-propanol or acetonitrile at pH 2-5, preferably 4.0. Fractions are diluted 1:4 if n-propanol is used for elution or 1:2 with cold purified water if acetonitrile is used for elution, or no dilution if acetonitrile is used for elution. RP-HPLC is used to pool the appropriate fractions containing the Lis-Pro insulin peak of interest at the desired purity level.

Step 10a—Reverse Phase Chromatography: The S-column pool containing the Lis-Pro insulin is loaded onto an RPC30 or C18 reverse phase column and eluted using an n-propanol or acetonitrile gradient in the presence of 200 mM sodium sulfate and 0.136% phosphoric acid. Fractions are immediately diluted 1:4 with 100 mM phosphate buffer at pH 7.0-9.0, preferably 7.5-8, as they are collected. RP-HPLC is used to pool the appropriate fractions containing the Lis-Pro Insulin peak of interest at the desired purity level.

Step 11a—Buffer Exchange: Exchange the sample into WFI (water for injection) using a membrane with a suitable molecular weight cutoff (e.g. 3000 Da). The pH of the solution should be monitored and maintained at 7.0-9.0, preferably 7.5-8.0. The final sample is concentrated to 5.5-8 mg/ml, with an adjusted pH of 7.0-9.0, preferably 7.5-8.0 at 6-10° C. This material represents the liquid API form of the presently disclosed preparations of Lis-Pro insulin analog. The API should be stored in the dark at 6-10° C.

Example 24

Final Purification (Alternate Method)

Step 10b—Reverse Phase Chromatography: The digested material containing the Lis-Pro insulin is loaded onto an RPC30 or C18 reverse phase column and eluted using a n-propanol or acetonitrile gradient in the presence of 200 mM sodium sulfate and 0.136% phosphoric acid. Fractions are immediately diluted 1:4 with 100 mM phosphate buffer at pH 7.0-9.0, preferably 7.5-8 as they are collected. RP-HPLC is used to pool the appropriate fractions containing the Lis-Pro insulin peak of interest at the desired purity level.

Step 11b—Buffer Exchange: Exchange the sample into WFI using a membrane with a suitable molecular weight cutoff (e.g. 3000 Da). The pH of the solution should be monitored and maintained at 7.0-9.0, preferably 7.5-8.0. The final sample is concentrated to 5.5-5.8 mg/ml, with an adjusted pH of 7.5-8.0 at 6-10° C. This material represents the liquid API form of the presently disclosed preparations and formulations of Lis-Pro insulin analog.

Example 25

API Formulation

The Lis-Pro insulin analog purified in accordance with Examples 22 and 23 is formulated by diluting the API material with cold WFI to a final concentration of 4.3375 mg/ml. A concentrated formulation buffer stock containing 80 mg/ml glycerol, 15.75 mg/ml meta cresol, and 0.0985 mg/ml zinc chloride at pH 7.5±0.1 is added to the API material in a 1/5 ratio of formulation buffer stock to API. The solution is mixed, followed by sterile filtration into appropriate vials in 10 ml aliquots.

Example 26

Working Cell Bank

The preparation of a WCB (working cell bank) for research and development containing cells capable of expressing recombinant Lis-Pro proinsulin is carried out according to the following processes.

The cloning procedure outlined in Example 20 is utilized to create the initial vector (transfection vector). Purified His-tagged Lis-Pro proinsulin pTrcHis2A(Kan) vector is transformed into competent BL21 cells and plated on sterile LB-Kan plates. From the plates, an isolated colony is used to inoculate sterile LB-Kan media (~100 mls). The cells are grown at 37° C. to mid log phase (about 4-5 hours) $OD_{600\ nm}$ of about 1.5-2.0. Culture media containing cells is then aliquoted into sterile cryovials, combined with glycerol at a 20% final concentration. The vials are then stored at 80° C.

Example 27

Purification Method for Production of Lis-Pro Insulin

The present example demonstrates the utility of the present invention for providing a unique construct and purification scheme that significantly improves the purification method for the production of Lis-Pro insulin.

Lis-Pro insulin is characterized as a short acting insulin analog, which, when combined with an insulin pump, allows for better blood glucose stability without the risk of hyperglycemia.

Amino acid sequence of the unique construct as defined in Example 8.

```
                                                  (SEQ ID NO: 43)
MHHHHHHGGR FVNQHLCGSH LVEALYLVCG ERGFFYTPKT RREAEDLQVG QVELGGGPGA   60

GSLQPLALEG SLQARGIVEQ CCTSICSLYQ LENYCN                            96
```

Lis-Pro insulin modification with residues 28 and 29 reversed in their order:

```
                                                  (SEQ ID NO: 35)
MHHHHHHGGR FVNQHLCGSH LVEALYLVCG ERGFFYTKPT RREAEDLQVG QVELGGGPGA   60

GSLQPLALEG SLQARGIVEQ CCTSICSLYQ LENYCN                            96
```

A general outline of one method, by way of example and not exclusion, to isolate and/or enrich recombinant Lis-Pro insulin from a composition that is not enriched for recombinant Lis-Pro insulin and/or includes proinsulin can be described by the following series of steps:

1. Fermentation of *E. coli* transformed with the vector containing the human proinsulin derivative-encoding amino acid sequence:

2. Lysis—Lyse the *E. coli* cells containing inclusion bodies enriched with the desired peptide, resuspended in a basic Tris/salt buffer, using a NIRO SOAVI® homogenizer.

3. Inclusion Body Washing—Contaminant protein removal is then accomplished via two sequential washes with a Tris/TRITON® X-100 buffer, followed by two sequential washes with a Tris/TWEEN®-20 buffer, and finally a single wash with a Tris/NaCl buffer.

4. Solubilization—Inclusion bodies are then solubilized in 8M urea containing reducing agents. Complete solubilization is achieved by adjusting the pH to 10.5 with NaOH.

5. Dilution refolding—The solubilized protein is then diluted into refolding buffer (5 mM CAPS, pH 10.5 at 4° C.) to a final concentration of 0.5 mg/ml. Allow the sample to refold for ≥48 hours at 2-10° C. Add an equal amount of oxidized glutathione to the initial amount of reducing agent used in the solubilization buffer, followed by 5 M NaCl and 1M Phosphate additions, to final concentrations of 250 mM and 25 mM respectively. Adjust pH to 7.9 with 6 M HCl.

6. IMAC Chromatography—Load the dilute proinsulin derivative containing composition onto an IMAC column to a maximum capacity of ≥15 mg/ml of resin. Elute the proinsulin via a 15 CV gradient from 0-400 mM imidazole. Using RP-HPLC for analysis, pool the appropriate fractions containing the proinsulin peak of interest at the desired purity level.

7. Buffer exchange—To the pool, add EDTA to a final concentration of 10 mM. Exchange the buffer using a membrane with a suitable molecular weight cutoff (ex. 3000 Da). The final buffer should be at least 97% exchanged to a 20 mM Tris-Cl, pH 8.0 at 2-10° C. A protein concentration of approximately 20-25 mg/ml is desirable.

8. Trypsin and Carboxypeptidase Enzymatic Transformation—The buffer exchanged sample is digested with a 2000:1 and 1000:1 mass ratio of protein to trypsin and protein to carboxypeptidase B respectively. Once complete, based on HPLC, the digest is then quenched by the addition of acetic acid to ≥700 mM, to a pH of approximately 3.5. HPLC of the digest should show about 54% HUMALOG® (Lis-Pro insulin).

9. Reverse Phase Chromatography—The digested Lis-Pro insulin is loaded onto a C18 column and eluted isocratically using a buffer of 23% acetonitrile, 200 mM sodium sulfate and 0.16% phosphoric acid. Alternatively, a C4 column may be used with a 22% acetonitrile, 200 mM sodium sulfate and 0.16% phosphoric acid buffer.

10. Buffer Exchange—Exchange the buffer using a membrane with a suitable molecular weight cutoff (3000 Da). The final buffer should be at least 97% exchanged to 0.01 N acid, and the sample is concentrated to 8-12 mg/ml.

11. Crystallization—To the Lis-Pro insulin, an equal volume of crystallization buffer (2.4M NaCl, 0.1 M citric acid, 6 mM zinc chloride) is added, pH adjusted to ~6.3, and the sample is incubated at room temperature. Completion of crystallization is determined by UV analysis of the supernatant. Insulin crystals are harvested by centrifugation or filtration, washed with ethanol, and dried in vaccuo. When ready for use, the recombinant product will be solubilized and portioned into appropriate sized individually packaged units. For example, the insulin prepared according to the present invention may be prepared in 100 unit/ml vials.

The present example demonstrates several advantages that utilization of the Lis-Pro insulin construct has over the original insulin sequence used in the purification scheme seen Example 1:

a. Step 7 does not require the glycine addition and pH adjustment to 9.7, which decreases the chances of desamino formation, typically seen in the high or low pH ranges.

b. The separate digestion reaction found in steps 8 and 11 of Example 1 are combined into a single digestion reaction in Step 8 above, which is carried out at pH 8.0, which decreases the possibility of desamino formation.

c. The Lis-Pro insulin construct prevents the formation of desthreonine-insulin, which is created in the trypsin transformation reaction. It represents approximately a 6-10% yield loss, and can only be separated from the Arg and di-Arg insulin species on the reverse phase step.

Example 28

Preparation of an *E. coli* Clone Expressing Proinsulin

The present example is provided to demonstrate the utility of the present invention for providing stable transformed *E. coli* that are capable of expressing recombinant human proinsulin protein. In addition, the present example provides a description of the process to be followed to create a stable working cell bank (WCB) containing recombinant *E. coli* cells capable of expressing recombinant human proinsulin.

Figure 8:
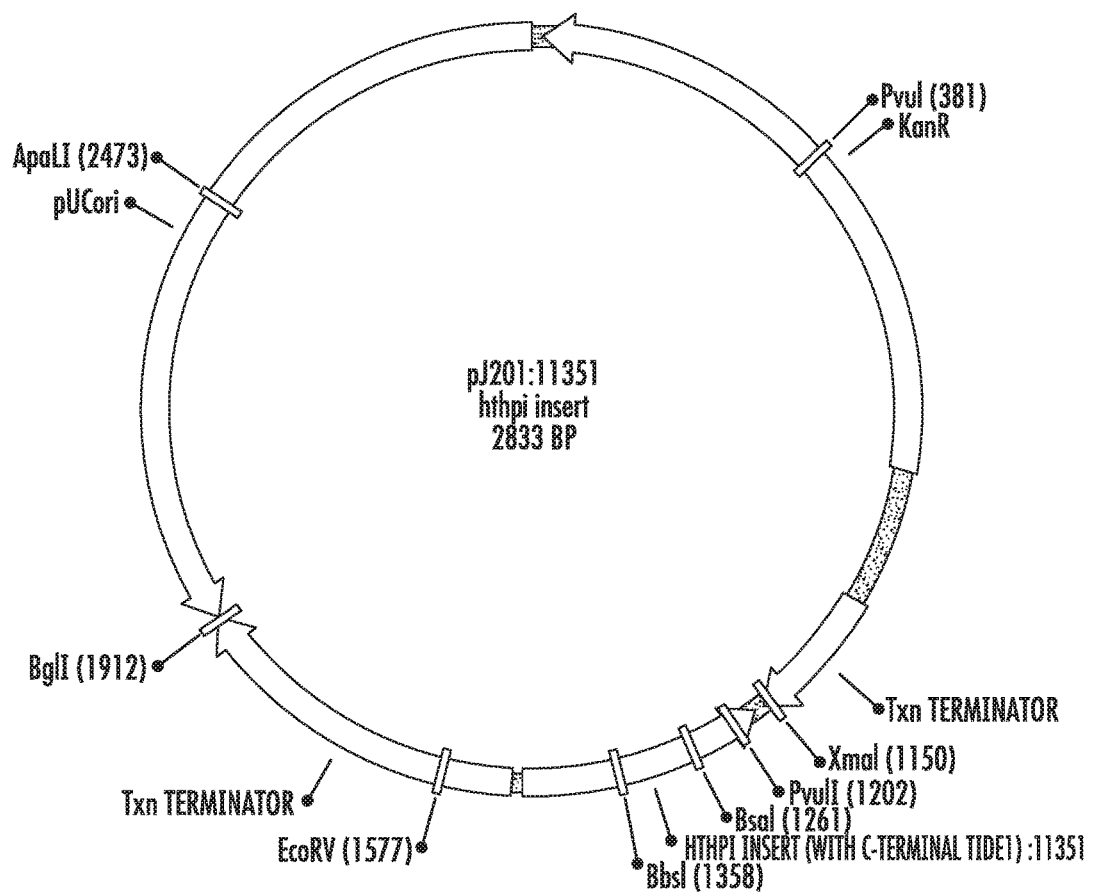
FIG. 8, according to one aspect of the invention, is a vector map of plasmid pJ201:11351 with a HTHPI insert.
Figure 9:
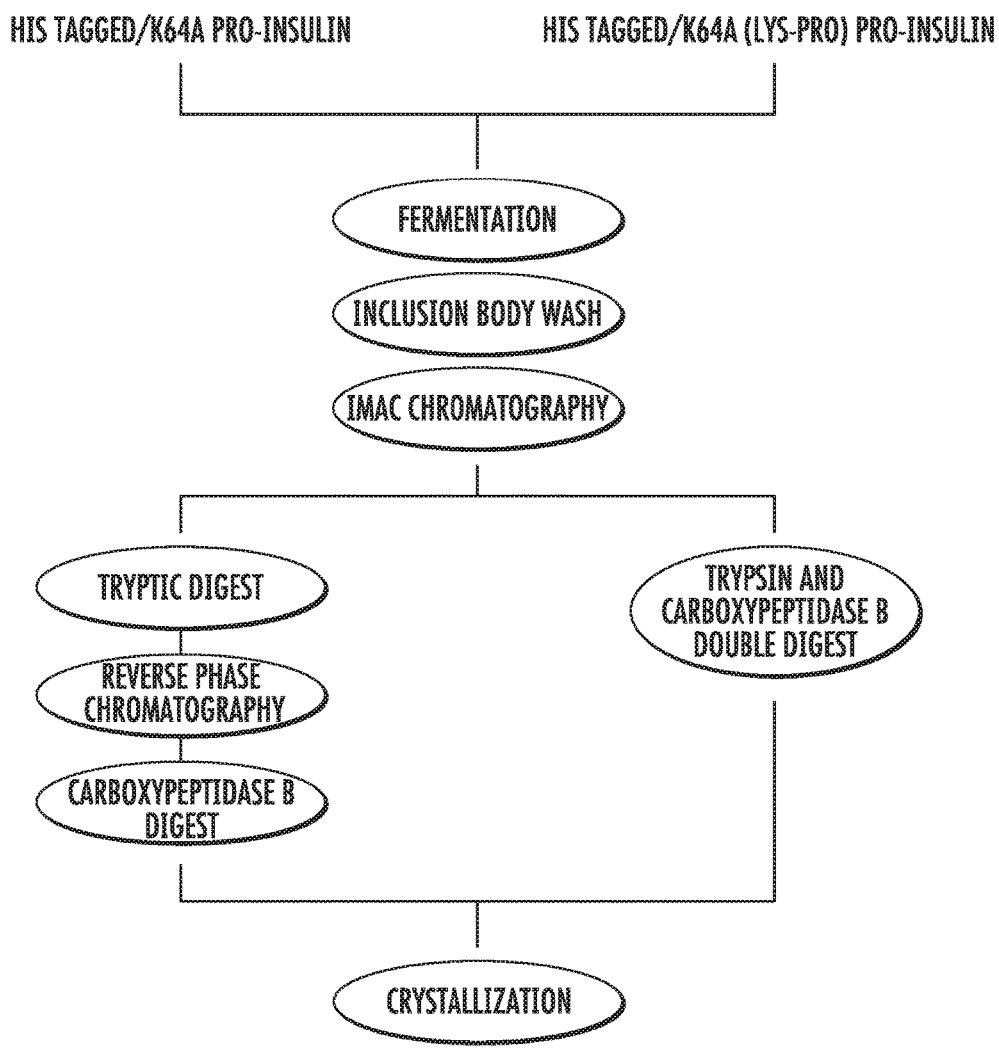
FIG. 9, according to some aspects to the invention, presents a flow scheme for the purification of insulin and Lys-Pro insulin, using the purification methods described in Examples 1 and 9.

Step 1—Construction of a purified proinsulin gene segment for insertion into the vector: The initial gene construct was synthesized in a basic cloning vector, 0201:11351 vector (FIG. 8; See also SEQ ID NO: 82 below) The gene construct included the N-terminal histidine tag, MHHHH-HHGGR (SEQ ID NO: 2), modified B-chain, and modified C-peptide with the alanine codon in place of the native lysine and having the amino acid sequence:

```
                                                           (SEQ ID NO: 71)
         MHHHHHHGGR FVNQHLCGSH LVEALYLVCG ERGFFYTPKT RREAEDLQVG QVELGGGPGA    60

GSLQPLALEG SLQARGIVEQ CCTSICSLYQ LENYCG                              96
```

Figure 7:
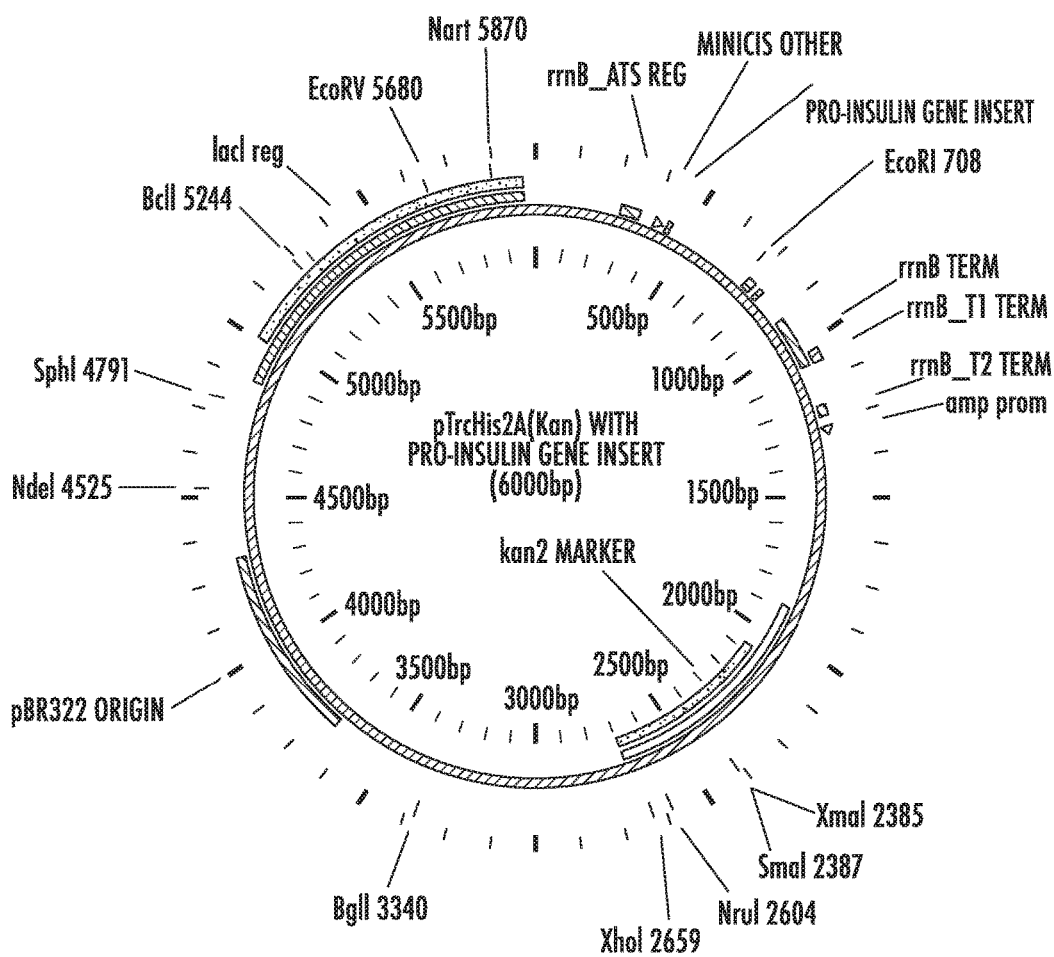
FIG. 7 according to one aspect of the invention, is a vector map of plasmid pTrcHis2A (Kan) with a proinsulin gene insert.

The gene was flanked by NdeI and EcoR1 restriction sites, for subsequent subcloning into the desired expression vector. The codons selected were optimized for expression in *E. coli*. The following sequence represents the pTrcHis2a(Kan) vector with proinsulin insert (FIG. 7). The IPTG inducible promoter region which regulates the transcription rate is shown by the dotted underline, while the proinsulin insert, adjacent the promoter region is shown by the solid underlined. The sequence shown in bold and italicized is the kanamycin gene, which provides the antibiotic selection marker for the vector.

```
                                                           (SEQ ID NO: 81)
         gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatgatgca   420
tcatcatcat catcatggtg gccgctttgt gaaccaacac ctgtgcggct cacacctggt   480
ggaagctctc tacctagtgt gcggggaacg aggcttcttc tacacaccga agacccgccg   540
ggaggcagag gacctgcagg tggggcaggt ggagctgggc gggggccctg gtgcaggcag   600
cctgcagccc ttggccctgg aggggtccct gcagaagcgt ggcattgtgg aacaatgctg   660
taccagcatc tgctccctct accagctgga gaactactgc ggctaggaat tcgaagcttg   720
ggcccgaaca aaaactcatc tcagaagagg atctgaatag cgccgtcgac catcatcatc   780
atcatcattg agtttaaacg gtctccagct tggctgtttt ggcggatgag agaagatttt   840
cagcctgata cagattaaat cagaacgcag aagcggtctg ataaaacaga atttgcctgg   900
cggcagtagc gcggtggtcc cacctgaccc catgccgaac tcagaagtga acgccgtag   960 cgccgatggt agtgtggggt ctccccatgc gagagtaggg aactgccagg catcaaataa  1020
aacgaaaggc tcagtcgaaa gactgggcct ttcgttttat ctgttgtttg tcggtgaacg  1080
ctctcctgag taggacaaat ccgccgggag cggatttgaa cgttgcgaag caacggcccg  1140
gagggtggcg ggcaggacgc ccgccataaa ctgccaggca tcaaattaag cagaaggcca  1200
tcctgacgga tggcctttttt gcgtttctac aaactctttt tgtttatttt tctaaataca  1260
ttcaaatatg tatccgctca tgagacaata accctgataa atgcttcaat aatattgaaa  1320
aaggaagagt atgagtattc aacatttccg tgtcgccctt attcccttttt ttgcggcatt  1380 ttgccttcct gtttttgctc acccagaaac gctggtgaaa gtaaaagatg ctgaagatca  1440
gttgggtgca cgagtgggtt acatcgaact ggatctcaac agcggtaaga tccttgagag  1500
ttttcgcccc gaagaacgtt ttccaatgat gagcactttt aaagttctgc tatgtggcgc  1560
ggtattatcc cgtgttgacg ccgggcaaga gcaactcggt cgccgcatac actattctca  1620
```

-continued

```
gaatgacttg gttgagtcct gaatcgcccc atcatccagc cagaaagtga gggagccacg    1680
gttgatgaga gctttgttgt aggtggacca gttggtgatt ttgaactttt gctttgccac    1740
ggaacggtct gcgttgtcgg aagatgcgt gatctgatcc ttcaactcag caaaagttcg     1800
atttattcaa caaagccgcc gtcccgtcaa gtcagcgtaa tgctctgcca gtgttacaac    1860
caattaacca attctgatta gaaaaactca tcgagcatca aatgaaactg caatttattc    1920
atatcaggat tatcaatacc atattttga aaaagccgtt tctgtaatga aggagaaaac     1980
tcaccgaggc agttccatag gatggcaaga tcctggtatc ggtctgcgat tccgactcgt    2040
ccaacatcaa tacaacctat taatttcccc tcgtcaaaaa taaggttatc aagtgagaaa    2100
tcaccatgag tgacgactga atccggtgag aatggcaaaa gcttatgcat ttctttccag    2160
acttgttcaa caggccagcc attacgctcg tcatcaaaat cactgcatca accaaaccgt    2220
tattcattcg tgattgcgcc tgagcgagac gaaatacgcg atcgctgtta aaaggacaat    2280
tacaaacagg aatcgaatgc aaccggcgca ggaacactgc cagcgcatca acaatatttt    2340
cacctgaatc aggatattct tctaatacct ggaatgctgt tttcccgggg atcgcagtgg    2400
tgagtaacca tgcatcatca ggagtacgga taaaatgctt gatggtcgga agaggcataa    2460
attccgtcag ccagtttagt ctgaccatct catctgtaac atcattggca acgctacctt    2520
tgccatgttt cagaaacaac tctggcgcat cgggcttccc atacaatcga tagattgtcg    2580
cacctgattg cccgacatta tcgcgagccc atttataccc atataaatca gcatccatgt    2640
tggaatttaa tcgcggcctc gagcaagacg tttcccgttg aatatggctc ataacacccc    2700
ttgtattact gtttatgtaa gcagacagtt ttattgttca tgatgatata tttttatctt    2760
gtgcaatgta acatcagaga ttttgagaca caacgtggct ttgttgaata aatcgaactt    2820
ttgctgagtt gaaggatcag atcacgcatc ttcccgacaa cgcagaccgt tccgtggcaa    2880
agcaaaagtt caaaatcacc aactggtcca cctacaacaa agctctcatc aaccgtggct    2940
ccctcacttt ctggctggat gatggggcga ttcaggactc accagtcaca gaaaagcatc    3000
ttacggatgg catgacagta agagaattat gcagtgctgc cataaccatg agtgataaca    3060
ctgcggccaa cttacttctg acaacgatcg gaggaccgaa ggagctaacc gcttttttgc    3120
acaacatggg ggatcatgta actcgccttg atcgttggga accggagctg aatgaagcca    3180
taccaaacga cgagcgtgac accacgatgc ctgtagcaat ggcaacaacg ttgcgcaaac    3240
tattaactgg cgaactactt actctagctt cccggcaaca attaatagac tggatggagg    3300
cggataaagt tgcaggacca cttctgcgct cggcccttcc ggctggctgg tttattgctg    3360
ataaatctgg agccggtgag cgtgggtctc gcggtatcat tgcagcactg gggccagatg    3420
gtaagccctc ccgtatcgta gttatctaca cgacggggag tcaggcaact atggatgaac    3480
gaaatagaca gatcgctgag ataggtgcct cactgattaa gcattggtaa ctgtcagacc    3540
aagtttactc atatatactt tagattgatt taaaacttca ttttaattt aaaaggatct    3600 aggtgaagat ccttttgat aatctcatga ccaaaatccc ttaacgtgag ttttcgttcc    3660
actgagcgtc agaccccgta gaaaagatca aaggatcttc ttgagatcct ttttttctgc    3720
gcgtaatctg ctgcttgcaa acaaaaaaac caccgctacc agcggtggtt tgtttgccgg    3780
atcaagagct accaactctt tttccgaagg taactggctt cagcagagcg cagataccaa    3840
atactgtcct tctagtgtag ccgtagttag gccaccactt caagaactct gtagcaccgc    3900
ctacatacct cgctctgcta atcctgttac cagtggctgc tgccagtggc gataagtcgt    3960
gtcttaccgg gttggactca agacgatagt taccggataa ggcgcagcgg tcgggctgaa    4020
cggggggttc gtgcacacag cccagcttgg agcgaacgac ctacaccgaa ctgagatacc    4080
```

-continued

```
tacagcgtga gctatgagaa agcgccacgc ttcccgaagg gagaaaggcg gacaggtatc    4140
cggtaagcgg cagggtcgga acaggagagc gcacgaggga gcttccaggg ggaaacgcct    4200
ggtatcttta tagtcctgtc gggtttcgcc acctctgact tgagcgtcga ttttgtgat     4260 gctcgtcagg ggggcggagc ctatggaaaa acgccagcaa cgcggccttt ttacggttcc    4320
tggccttttg ctggcctttt gctcacatgt tctttcctgc gttatcccct gattctgtgg    4380
ataaccgtat taccgccttt gagtgagctg ataccgctcg ccgcagccga acgaccgagc    4440
gcagcgagtc agtgagcgag gaagcggaag agcgcctgat gcggtatttt ctccttacgc    4500
atctgtgcgg tatttcacac cgcatatggt gcactctcag tacaatctgc tctgatgccg    4560
catagttaag ccagtataca ctccgctatc gctacgtgac tgggtcatgg ctgcgccccg    4620
acacccgcca cacccgctg acgcgccctg acgggcttgt ctgctcccgg catccgctta    4680
cagacaagct gtgaccgtct ccgggagctg catgtgtcag aggttttcac cgtcatcacc    4740
gaaacgcgcg aggcagcaga tcaattcgcg cgcgaaggcg aagcggcatg catttacgtt    4800
gacaccatcg aatggtgcaa aacctttcgc ggtatggcat gatagcgccc ggaagagagt    4860
caattcaggg tggtgaatgt gaaaccagta acgttatacg atgtcgcaga gtatgccggt    4920
gtctcttatc agaccgtttc ccgcgtggtg aaccaggcca gccacgtttc tgcgaaaacg    4980
cgggaaaaag tggaagcggc gatggcggag ctgaattaca ttcccaaccg cgtggcacaa    5040
caactggcgg gcaaacagtc gttgctgatt ggcgttgcca cctccagtct ggccctgcac    5100
gcgccgtcgc aaattgtcgc ggcgattaaa tctcgcgccg atcaactggg tgccagcgtg    5160
gtggtgtcga tggtagaacg aagcggcgtc gaagcctgta aagcggcggt gcacaatctt    5220
ctcgcgcaac gcgtcagtgg gctgatcatt aactatccgc tggatgacca ggatgccatt    5280
gctgtggaag ctgcctgcac taatgttccg gcgttatttc ttgatgtctc tgaccagaca    5340
cccatcaaca gtattatttt ctcccatgaa gacggtacgc gactgggcgt ggagcatctg    5400
gtcgcattgg gtcaccagca aatcgcgctg ttagcgggcc cattaagttc tgtctcggcg    5460
cgtctgcgtc tggctggctg cataaatat ctcactcgca atcaaattca gccgatagcg    5520
gaacgggaag gcgactggag tgccatgtcc ggttttcaac aaaccatgca aatgctgaat    5580
gagggcatcg ttcccactgc gatgctggtt gccaacgatc agatggcgct gggcgcaatg    5640
cgcgccatta ccgagtccgg gctgcgcgtt ggtgcggata tctcggtagt gggatacgac    5700
gataccgaag acagctcatg ttatatcccg ccgtcaacca ccatcaaaca ggattttcgc    5760
ctgctggggc aaaccagcgt ggaccgcttg ctgcaactct ctcagggcca ggcggtgaag    5820
ggcaatcagc tgttgcccgt ctcactggtg aaaagaaaaa ccaccctggc gcccaatacg    5880
caaaccgcct ctccccgcgc gttggccgat tcattaatgc agctggcacg acaggtttcc    5940
cgactggaaa gcgggcagtg agcgcaacgc aattaatgtg agttagcgcg aattgatctg    6000
```

Human his-Tagged Proinsulin

```
                                                  (SEQ ID NO: 82)
atgatgcatc atcatcatca tcatggtggc cgctttgtga accaacacct gtgcggctca    60
cacctggtgt aagctctcta cctagtgtgc ggggaacgag gcttcttcta cacaccgaag    120
acccgccggg aggcagagga cctgcaggtg ggcaggtgg agctgggcgg gggccctggt    180
gcaggcagcc tgcagccctt ggccctggag gggtccctgc agaagcgtgg cattgtggaa    240
caatgctgta ccagcatctg ctccctctac cagctggaga actactgcgg ctag           294
```

The modified proinsulin sequence without the tag is as follows:

(SEQ ID NO: 83)

```
tttgtgaacc aacacctgtg cggctcacac ctggtggaag ctctctacct agtgtgcggg  60
gaacgaggct tcttctacac accgaagacc cgccggagg cagaggacct gcaggtgggg  120 caggtgggagc tgggcggggg ccctggtgca ggcagcctgc agcccttggc cctggagggg  180
tccctgcaga agcgtggcat tgtggaacaa tgctgtacca gcatctgctc cctctaccag  240
ctggagaact actgcggcta g                                            261
```

Step 2—Generation of the pTrcHis2A(Kan) vector containing proinsulin: Commercially available pTrcHis2A (Kan) vector was modified to include a kanamycin resistance gene in the middle of the ampicillin resistance gene to negate the ampicillin resistance prior to insertion of the proinsulin sequence into the vector. Ampicillin resistance heightens the potential for allergic reactions to preparations made using vector constructs that include the ampicillin resistance gene. Therefore it is preferable to eliminate the ampicillin resistance in the constructs that are prepared and used.

The pTrcHis2A(Kan) vector was modified at the start codon in the multiple cloning site by replacing the NcoI restriction site (ccatgg) with an NdeI site (catatg) to simplify subsequent subcloning work.

The proinsulin gene was isolated from the DNA 2.0 plasmid using NdeI to cleave at the N-terminal side of the gene and EcoR1 to cleave at the C-terminal side of the gene. The Digested DNA was run over a 2% agarose gel to separate the plasmid DNA from the proinsulin gene. A QIAQUICK® (QIAGEN®) gel purification kit was then used to purify the gene construct.

Accordingly, a sequential digest of the vector with Nde 1 and EcoR I, respectively, was performed. The vector DNA was also purified using a QIAQUICK® gel purification kit. Following purification of the vector and the gene, a 5' NdeI and a 3' EcoR1 ligation reaction were utilized to insert the proinsulin gene into the pTrcHis2A(Kan) vector.

Step 3—Transformation: One microliter of the ligation reaction was used to transform competent BL21 *E. coli* cells with the pTrcHis2A(Kan) plasmid containing the proinsulin gene. The transformed BL21 *E. coli* cells were plated on LB-Kan agar plates and incubated overnight at 37° C. Several clones were selected and sequenced. Clones with the correct sequence were then screened for expression. The resulting clone is referred to as the His-tagged proinsulin pTrcHis2A(Kan) vector.

Step 4—Preparation of the working cell bank (WCB): To establish the WCB, sterile growth medium was inoculated with the recombinant BL21 *E. coli* containing the His-tagged proinsulin/pTrcHis2A(Kan) vector and incubated to allow cell growth. The cells were harvested in an IS05 (Class 100) environment under a biosafety cabinet and via centrifugation. Sterile medium and glycerol were added to cells. 1 mL aliquots of the cells were then dispensed into sterile ampoules and stored at −80° C. Aseptic techniques were utilized to generate the WCB.

Example 29

Product Manufacture of Insulin from Modified Proinsulin Sequence

The present example demonstrates the utility of the present invention as a method of providing a high yield, highly purified (reduced contaminant insulin related compounds) recombinant human insulin preparation from the proinsulin expressing transformed *E. coli* (WCB) described in Example 28.

Step 1—Culturing of *E. coli* transformed with modified proinsulin sequence from the WCB of Example 28: Seed an inoculum preparation of the WCB in a sterile growth medium that includes yeastolate (purchased from VWR®, Prod. #90004-426 or -488), select phytone, sodium chloride, purified water, sterile kanamycin solution), and incubate until growth to an optical density ($OD_{600\ nm}$) of 2 to 4. Prepare a fermentation media (containing select phytone, yeastolate, glycerin, BIOSPUMEX® 153K (BASF®) in a fermentor. Add the following sterilized phosphate solutions to the fermentor. Prepare a Phosphate flask 1—potassium phosphate monobasic and potassium phosphate dibasic containing kanamycin solution. Prepare a Phosphate flask 2—potassium phosphate monobasic and potassium phosphate dibasic. Add seed inoculate of *E. coli* to the fermentor—growth to an optical density ($OD_{600\ nm}$) of 8 to 10 (mid log phase). Add a dioxane free IPTG (purchased from PROMEGA®, Catalog No. #PA V3953 (VWR® Catalog #PAV3953) solution to the fermentor (to induce transcription of the K64A proinsulin gene). Incubate for 4 hours. This results in the production of a concentrated cell suspension containing His-tagged proinsulin inclusion bodies. The cell suspension is then centrifuged to provide a cell paste for the subsequent inclusion body isolation step.

Step 2—Disruption: Cells containing inclusion bodies expressing modified proinsulin are lysed in a basic Tris/salt buffer, using a NIRO SOAVI® homogenizer (1100-1200 bar).

Step 3—Inclusion Body Washing: Contaminant protein removal is accomplished via two sequential washes with a Tris/TRITON® X-100 buffer, followed by two sequential washes with a Tris/TWEEN®-20 buffer, and finally a single wash with a Tris/NaCl buffer.

Step 4—Solubilization: Inclusion bodies enriched with the modified proinsulin peptide are solubilized in 4-8 M urea, preferably 6-8 M urea containing reducing agents (mercaptoethanol, L-cysteine hydrochloride monohydrate). Complete solubilization is achieved by adjusting the pH to 10.5-12, preferably 11.8-12 with NaOH.

Step 5—Dilution refolding: The solubilized protein is then diluted into refolding buffer (20 mM glycine, pH 10-11 at 6-10° C.) to a final concentration of 1 mg/ml and permitted to refold for 24 to 72 hours, preferentially about 48 hours, at 6-10° C. Higher protein concentration may be used in the refold if desired, however, overall refold efficiency will Sodium chloride and phosphate are then added to final concentrations of 700 mM and 25 mM respectively, followed by pH adjustment to 7.0 to 9.0, preferably 7.9-8.0 with 6M HCl.

Step 6—IMAC Chromatography: The dilute proinsulin derivative is loaded onto an IMAC column to a maximum capacity of 26.5 mg main peak protein per ml of resin. A 75 mM imidizole buffer is used to isocratically strip the majority of impurities from the column. The tagged proinsulin is then eluted isocratically using 300 mM imidizole.

Step 7—Citriconic anhydride (CA) Blocking: To the IMAC pool, add citriconic anhydride at a molar ratio of 20:1 (CA to proinsulin), while stirring at 4-10° C. Allow the sample to stir for not less than 3 hour at 4-10° C.

Step 8—Buffer exchange: To the IMAC main peak pool material, add EDTA to a final concentration of 20 mM. Exchange the buffer using a membrane with a suitable molecular weight cutoff (e.g. 3000 Da). The final buffer should be at least 97% exchanged to a 20 mM Tris-HCl, pH 7.0-10.0, preferably 8.1 at 8-10° C. A protein concentration of approximately 5 mg/ml is desirable.

Step 9—Trypsin Enzymatic Transformation/Proteolysis: The buffer exchanged sample is digested with a 1500:1 mass ratio of main peak protein to trypsin, in the presence of 5 mM CaCl. The ratio of trypsin may be increased or decreased depending on the desired length of time for the reaction. Once complete, based on HPLC, the digest is then quenched by the addition of acetic acid to ≥700 mM.

Step 10—Citriconic anhydride Deblocking: The trypsin digest solution is then warmed to 18 to 20° C. and the pH is adjusted to 2.8 to 3.0. The digest was stored at room temperature for not less than 10 hours to permit release of the citriconic anhydride.

The resulting preparation from Step 10 includes the di-Arg recombinant human insulin and other products resulting from the trypsin enzymatic digestion of the proinsulin sequence. This preparation is then subjected to the purification steps provided in Example 30 to provide a purified preparation of the recombinant human insulin product. The C-peptide and tag (His-tag) have been dissociated from the recombinant human insulin sequence.

Example 30

Manufacturing Purification Process

Step 11—Ion Exchange Chromatography: The digested material is loaded onto a cation exchange column and eluted with a NaCl gradient, in the presence of 20% n-propanol or acetonitrile at pH 2-5, preferably 4.0. RP-HPLC is used to pool the appropriate fractions containing the di-Arg recombinant human insulin peak of interest at the desired purity level.

Step 12-Reverse Phase Chromatography—The S-column pool containing the insulin is loaded onto an RPC30 or C18 reverse phase column and eluted using an n-propanol or acetonitrile gradient in the presence of 200 mM sodium sulfate and 0.136% phosphoric acid. Fractions are immediately diluted 1:4 with 100 mM Phosphate, pH 7-9, preferably 7.5-8 if n-propanol is used for elution; or 1:2 with 100 mM phosphate, pH 7-9, preferably 7.5-8 if acetonitrile is use for elution or no dilution if acetonitrile is used for elution. RP-HPLC is used to pool the appropriate fractions containing the insulin peak of interest at the desired purity level.

Step 13—Buffer Exchange: Exchange the sample into WFI (water for injection) using a membrane with a suitable molecular weight cutoff (e.g. 3000 Da). The pH of the solution should be monitored and maintained at 7.0-9.0, preferably 7.5-8.0. The final sample is concentrated to 5-8 mg/ml, preferably 5-5.8 mg/ml, with an adjusted pH of 7.0-9.0, preferably 7.5-8.0 at 6-10° C. This material represents the liquid API form of the presently disclosed preparations of insulin.

Example 31

Recombinant Human Insulin Liquid API Formulation

The insulin purified in Example 30 is formulated by diluting the API material with cold WFI to a final concentration of 4.3375 mg/ml. A concentrated formulation buffer stock containing 80 mg/ml glycerol, 15.75 mg/ml meta cresol, 0.0985 mg/ml zinc chloride at pH 7.5±0.1 is added to the API material in a 1/5 ratio of formulation buffer stock to API. The solution is mixed, followed by sterile filtration into appropriate vials in 10 ml aliquots.

Example 32

Mass Spectrometry Analysis of Liquid Recombinant Human Insulin Product

Recombinant human insulin produced according to the methods described herein was tested and verified to be equivalent to wild-type (native) human insulin by amino acid sequencing, peptide mapping, molecular weight, isoform pattern, electrophorectic patterns, and liquid chromatography.

Figure 19:
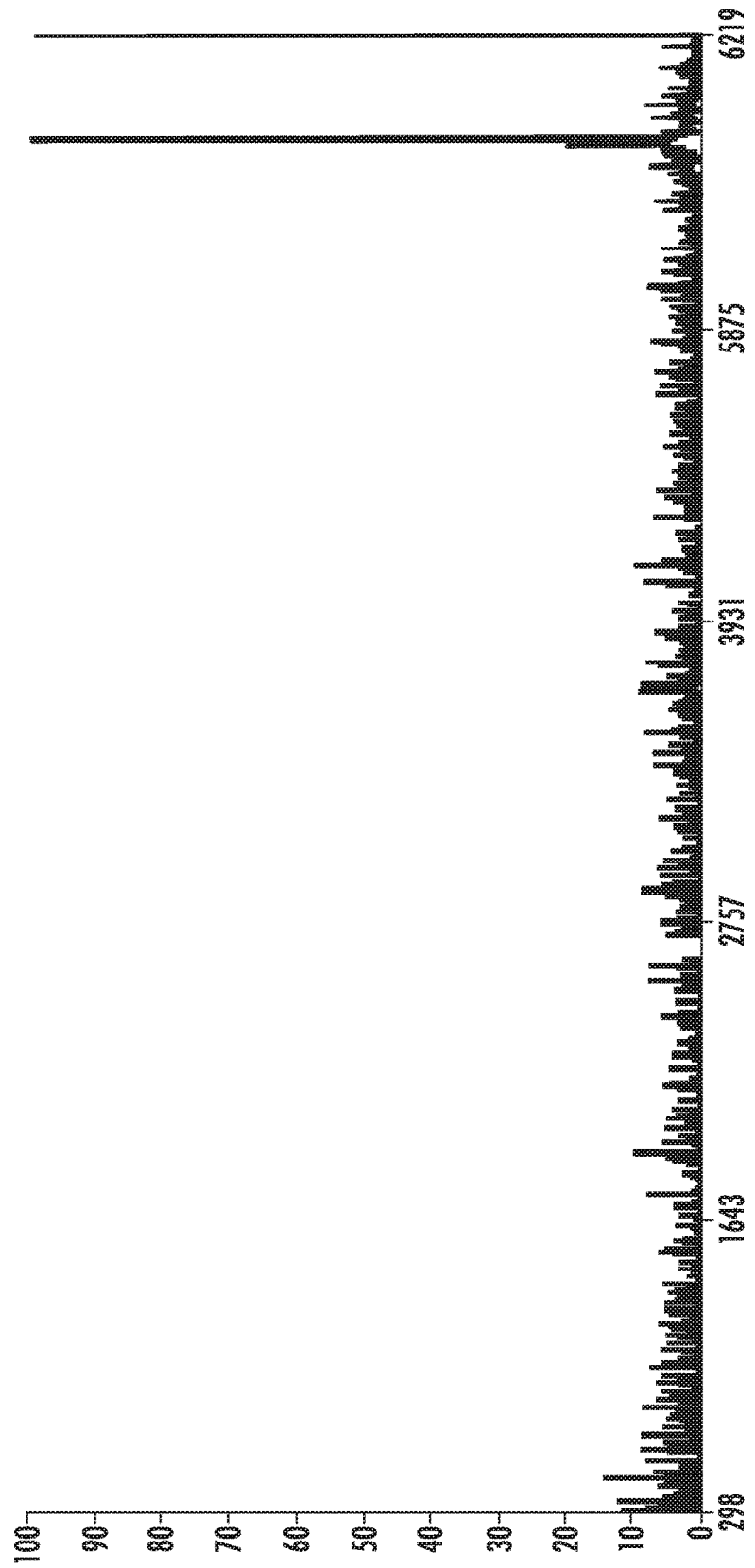
FIG. 19 shows mass spectrometry data for recombinant human insulin.

Mass spectrometry was performed to determine the amino acid sequence, peptide map and disulfide bonds of the recombinant human insulin protein. The reduced and non-reduced peptide mapping performed using Staph Aureus V8 protease showed the expected cleavages. These cleavages are shown in FIGS. 18 and 19. There are 4 cleavages in the non-reduced peptide map and 6 cleavages in the reduced peptide map. All of the recombinant human insulin protein fragments are identical to wild-type human insulin.

Figure 20:
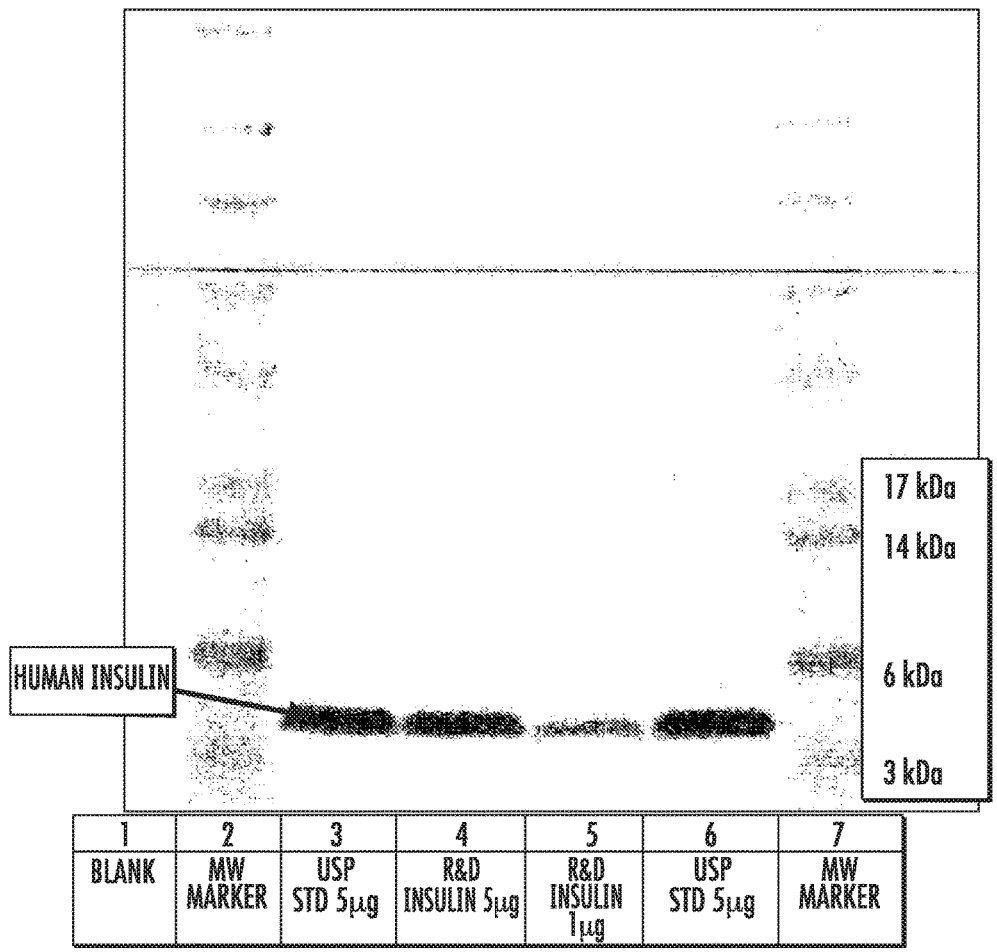
FIG. 20 shows an SDS PAGE reduced gel comparing electrophoretic patterns of wild-type human insulin and recombinant human insulin.

The molecular weight of recombinant human insulin was determined to be 5806 Da by mass spectrometry. This is within 2 Daltons of the theoretical mass of wild-type human insulin of 5807.58 Da. The mass spectrographic data is shown in FIG. 20.

Figure 21:
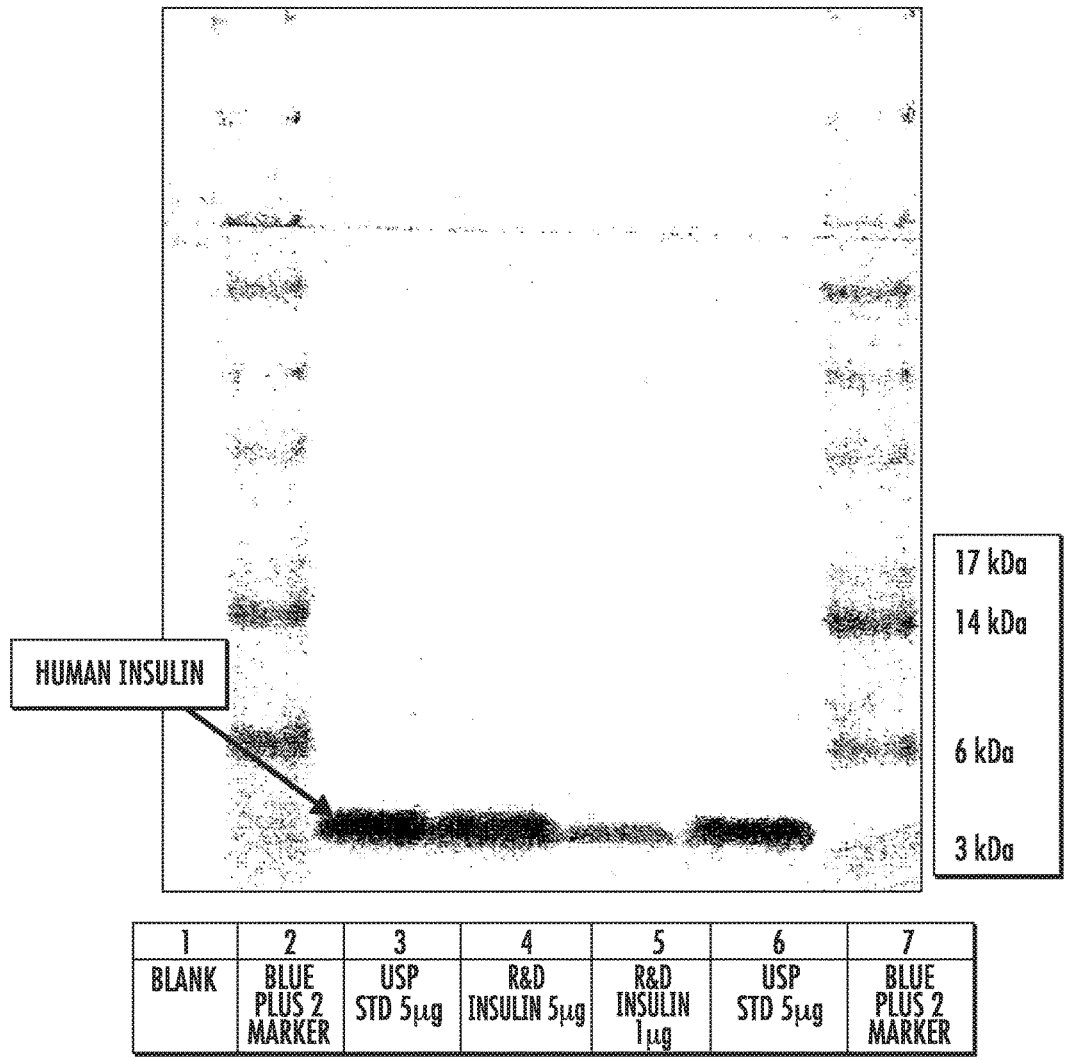
FIG. 21 shows an SDS PAGE non-reduced gel comparing electrophoretic patterns of wild-type human insulin and recombinant human insulin.
Figure 22:
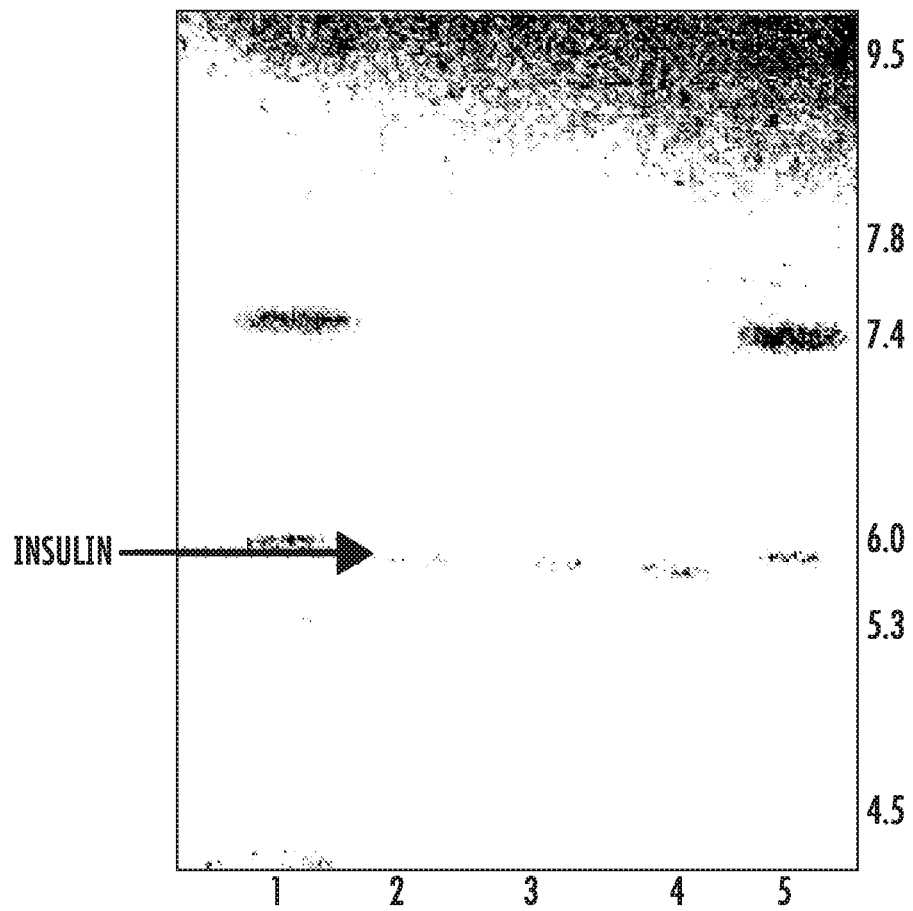
FIG. 22 shows an electrophoretic gel where recombinant (R&D Insulin) and wild-type insulin (Insulin Human, USP) have been subject to isoelectric focusing. Lanes 1 and 5 show isoelectric point markers (pI 3-10), lane 2 shows wild-type human insulin, and lanes 3 and 4 show recombinant human insulin from two different lots.

The eletrophoretic patterns of recombinant insulin and wild-type insulin were determined by polyacrylamide gel electrophoresis (PAGE) under non-reduced and reduced conditions. The results of these assays are shown in FIGS. 21 (reduced) and 22 (non reduced). In both cases, the electrophoretic patterns of recombinant human insulin and wild-type human insulin were identical. In each case, the proteins were run on NuPage 4-12% Bis-Tris gels with a MES SDS running buffer.

The isoelectric point of recombinant human insulin was determined by isoelectric focusing (IEF) gel electrophoresis. The isoelectric point was identical to that of wild-type human insulin. The gel can be seen in FIG. 23.

Example 33

Purity Analysis of Liquid Recombinant Human Insulin

Figure 24:
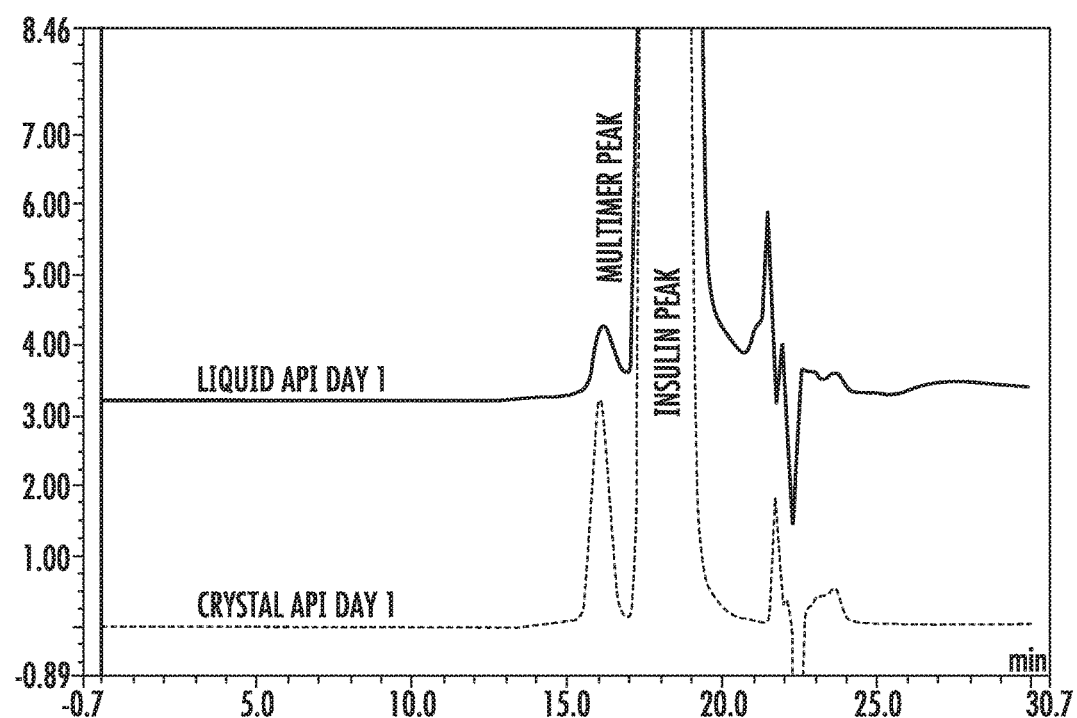
FIG. 24 shows an analytical HPLC overlay of liquid insulin product by the method according to one aspect of, the invention, with crystal insulin product.

The recombinant human insulin prepared according to the methods provided herein was assessed using high performance liquid chromatography (HPLC) to determine the presence of any impurities, including related substances of human insulin, as compared to wild-type human insulin (Insulin Human USP Standard). FIG. 24 is a summary of the identity of substances identified via HPLC which include insulin, A5/B4 desamido, A21 desamido, and insulin multimers. As shown in FIG. 24, the overall amount of related substances in the recombinant human insulin is lower than that of the insulin standard, indicating that the method of production described herein produces a lower amount of contaminants than found in insulin produced by other methods. For example, according to the data, the method described herein produces recombinant human insulin of greater than 99% purity, while as shown in FIG. 16B, the standard had only 98.35% insulin. Further, recombinant insulin produced according to the method of the invention is shown in FIG. 24*to* have 0.11% $A_5/B_4$ desamido, while the standard has 0.23%, which is more than twice the contaminant level of the recombinant insulin made according to a method of the invention. Further, recombinant insulin produced according to the method of the invention is shown in FIG. 24 to have 0.10% $A_{21}$ desamido, while the standard has 0.49%, which is almost 5 times the level of contamination found in the recombinant insulin made according to the methods described herein.

Example 34

Comparison/Analysis of Liquid and Crystalline Recombinant Human Insulin

The present example is provided to demonstrate the utility of the present compositions and methods for providing a liquid insulin product and method for manufacturing a liquid insulin product having a higher purity level than crystalline preparations of recombinant insulin.

The crystalline API insulin product employed in the present example was prepared by incubating a ~5 mg/ml (insulin) sample at 18-21° C. overnight in the presence of 1.2 M sodium chloride, 0.05 M citric acid and 3 mM zinc chloride at pH 6.3. Crystals formed overnight and were harvested the following day via centrifugations, followed by drying in a vacuum dessicator to a final moisture content of 6-15%. For analytical analysis, crystals were reconstituted in 10 mM hydrochloric acid.

FIG. 25 shows a comparison of liquid recombinant human insulin API prepared according to the methods provided herein and a crystalline recombinant human insulin API. As demonstrated in FIG. 25, the liquid API is shown to contain 0.09% high molecular weight impurities compared with the crystal API which contains 0.34% high molecular weight impurities.

Example 35

Stability Data

Figure 26:
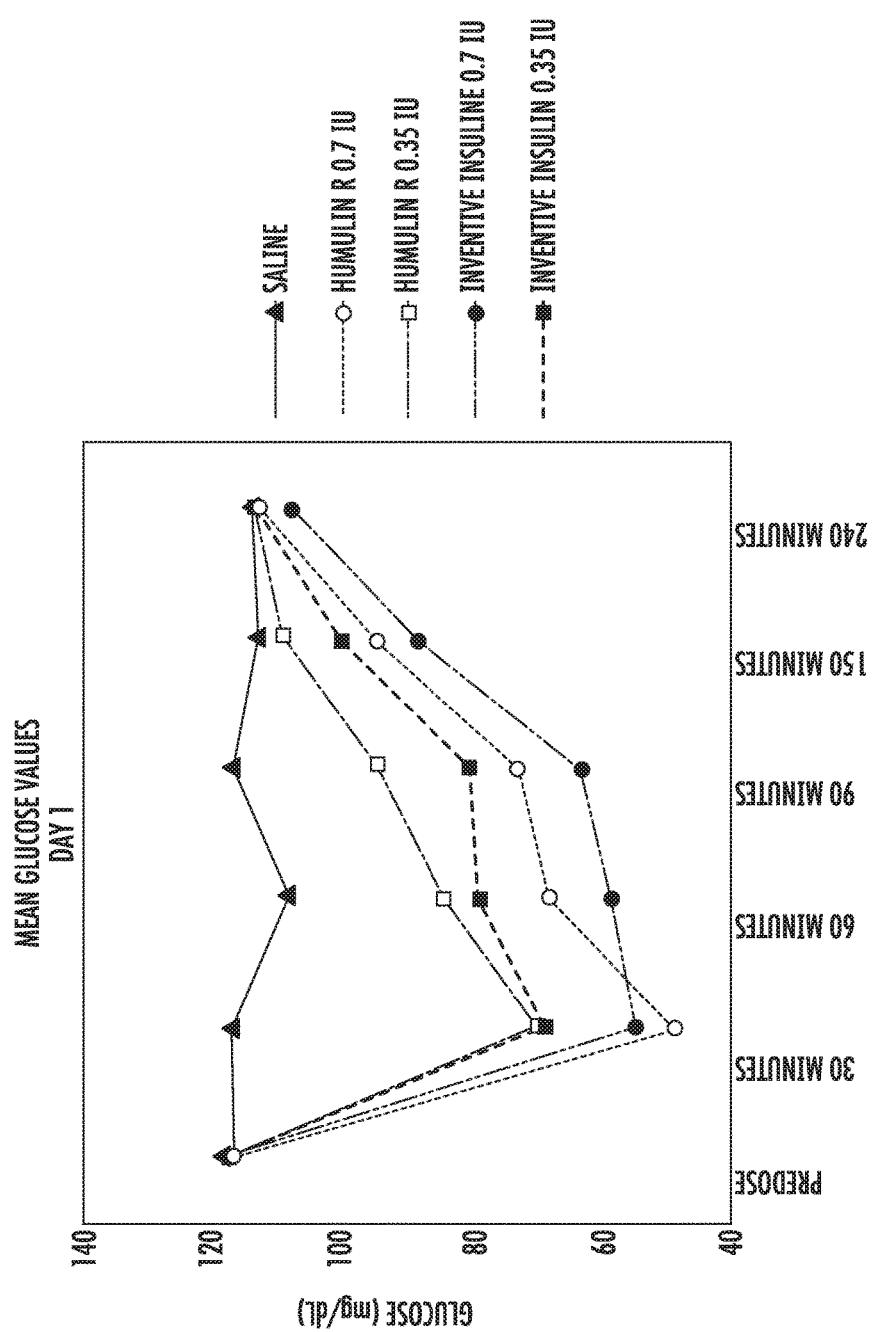
FIG. 26 is a graph of United States Pharmacopeia (USP) insulin assay on day 1.

FIG. 26 shows stability data time points at 5° C., 25° C., and 40° C., over a 182 day period. The values are given in percent loss of main peak. The data demonstrates that the insulin produced by the herein described method (A) degrades at an equivalent rate to that of the currently marketed material (B), at all three temperatures.

Example 36

In Vivo Study with Liquid Recombinant Human Insulin-Glucose Values

The present example is provided to demonstrate the utility of the present invention for providing a product that provides an effective preparation for maintaining glucose levels in vivo. A rabbit model was employed in the present study, and demonstrates the effectiveness of the present preparations for regulating glucose levels in all animals and in humans.

Figure 27:
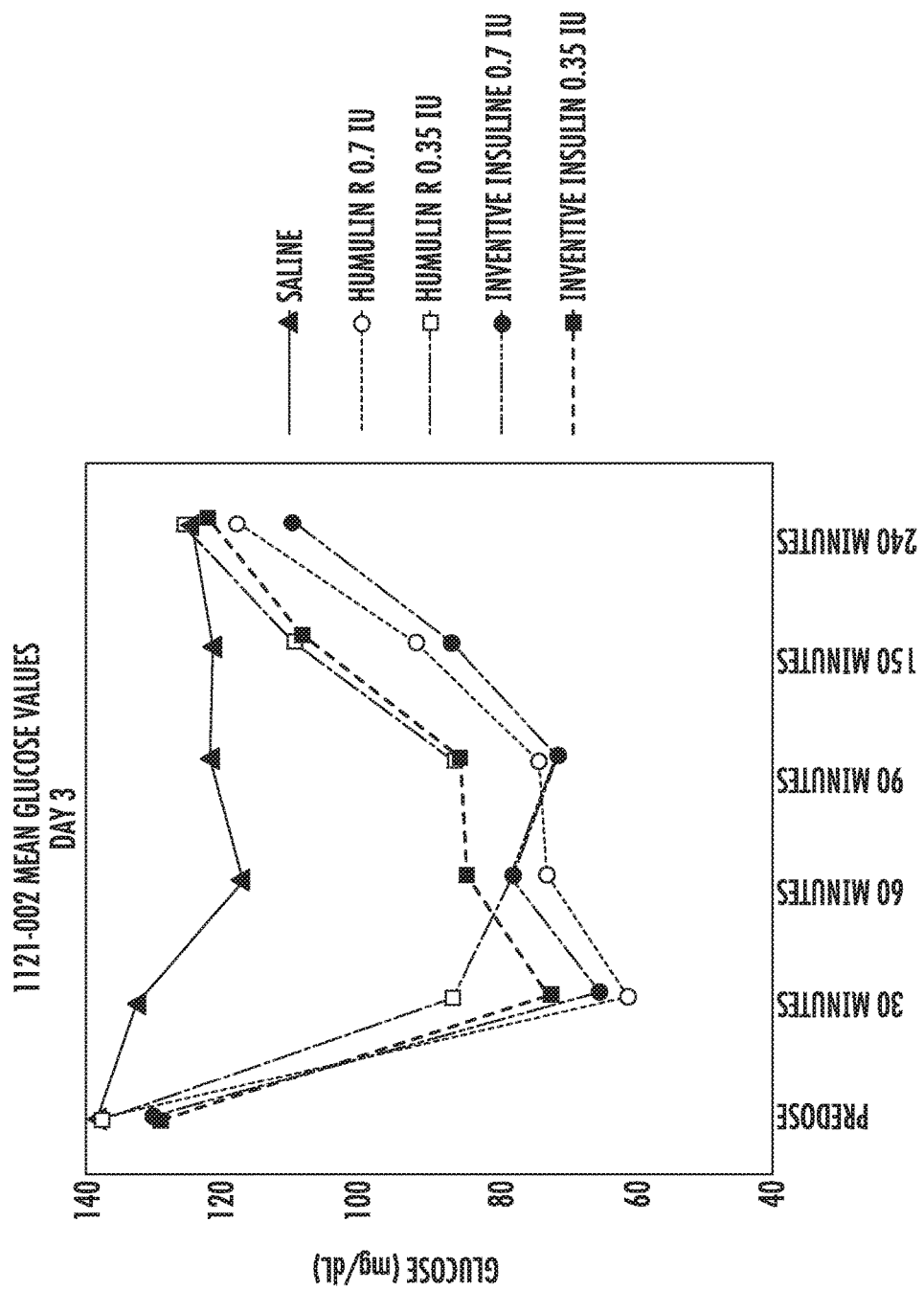
FIG. 27 is a graph of USP insulin assay on day 3.
Figure 28:
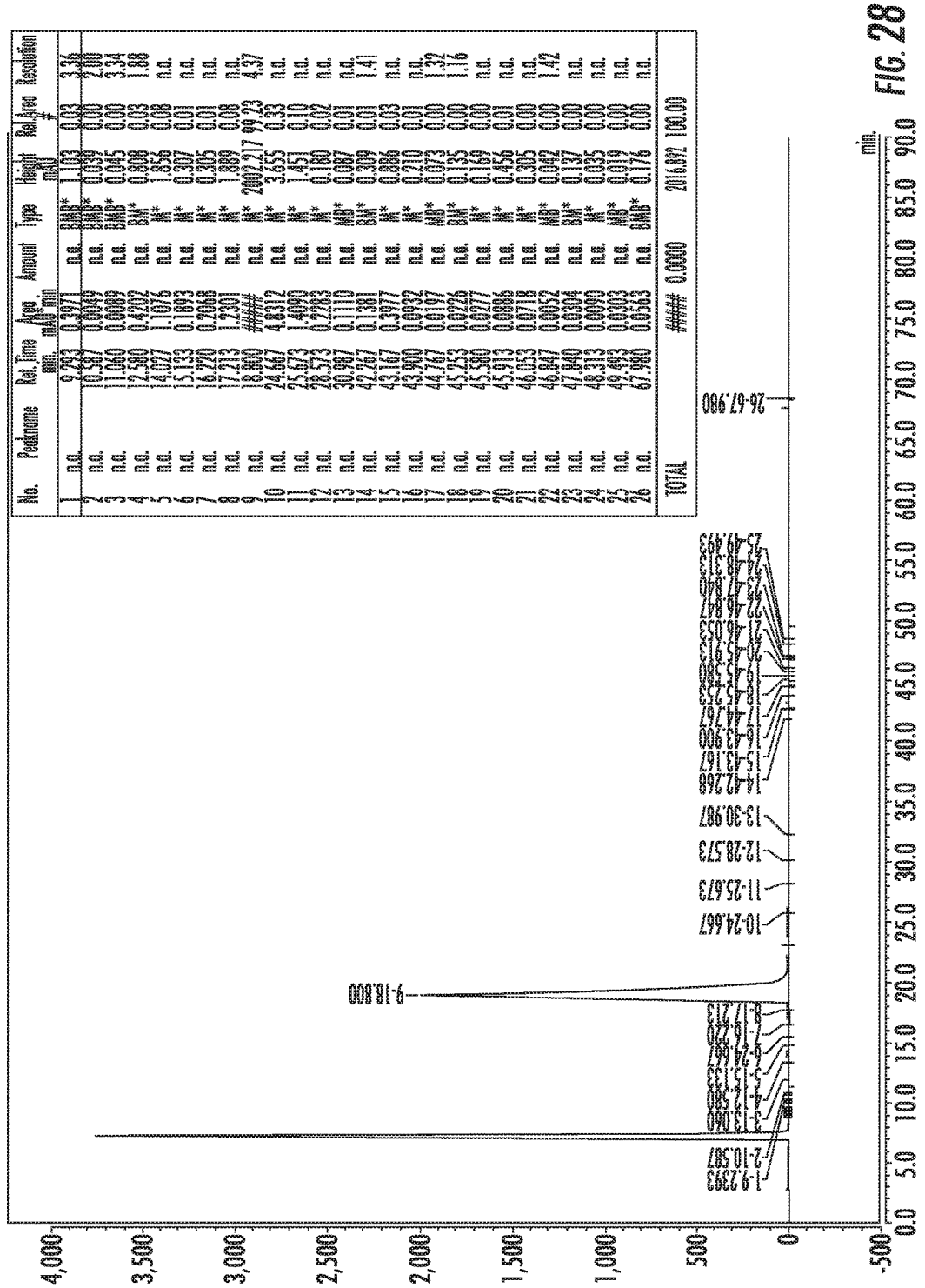
FIG. 28 is the resulting data from an analytical HPLC run of material produced by the herein described method, using the USP, standardized related substance method.

FIGS. 27 and 28 show the results of an in vivo animal (rabbit) study, looking at blood glucose levels pre and post subcutaneous injection of insulin produced by the herein described method compared with currently marketed insulin at days 1 and days 3. The method was based on the current International Conference on Harmonisation (ICH) Harmonised Tripartite Guidelines, the United States Pharmacopeia guidelines for insulin assay. Assay controls, vehicles and test articles and preparations information are summarized in Table 2.

TABLE 2

| Group Assignments | | |
|---|---|---|
| Group Number | Dose Level (IU/animal) First Treatment/Second Treatment | Number of Male Animals |
| 1 | Control (saline) | 6 |
| 2 | 0.35 IU Insulin/0.7 IU Humulin R | 6 |
| 3 | 0.7 IU Insulin/0.35 IU Humulin R | 6 |
| 4 | 0.35 IU Insulin/0.7 IU Humulin R | 6 |
| 5 | 0.7 IU Insulin/0.35 IU Humulin R | 6 |

IU—International Units
The first treatment was administered on Day 1, and the second treatment was administered on Day 3.

The control(saline), positive control (HUMULIN® R), and liquid recombinant human insulin (a.k.a. inventive insulin) prepared according to the methods provided herein were administered once on day 1 and/or 3 during the study via subcutaneous injection. The groups received a dose of positive control or test material on day 1, followed by a dose of positive control or test material on day 3. The dose levels for treated groups were 0.35 or 0.7 international units (IU) of inventive insulin and HUMULIN® R, with combinations described in the above table. The dose volume was maintained at 0.35 mL/dose of test material, while the control group received 0.35 mL of saline. TABLES 3 and 4 summarize the average of six animals glucose values for test and control groups, which is show in FIGS. 27 and 28.

TABLE 3

| Interval of Study | N | Control (saline) | | 0.35 IU Insulin/ 0.7 IU Humulin R | | 0.7 IU Insulin/ 0.35 IU Humulin R | | 0.35 IU Humulin R/ 0.7 IU Insulin | | 0.7 IU Humulin R/ 0.35 IU Insulin | |
|---|---|---|---|---|---|---|---|---|---|---|---|
| | | SD | Mean | Mean | SD | Mean | SD | Mean | SD | Mean | SD |
| Day 1 Pre | 6 | 10.03 | 116.2 | 117.7 | 6.35 | 118.0 | 11.24 | 11.24 | 4.710 | 121.2 | 5.91 |
| Day 1 30 min | 6 | 4.13 | 117.3 | 69.5 | 5.79 | 55.2 | 9.33 | 70.0 | 10.97 | 119.8 | 5.91 |
| Day1 60 min | 6 | 22.24 | 108.7 | 79.2 | 6.11 | 59.0 | 11.21 | 84.5 | 8.50 | 49.3 | 5.50 |

TABLE 3-continued

| Interval of Study | N | Control (saline) SD | Control (saline) Mean | 0.35 IU Insulin/ 0.7 IU Humulin R Mean | 0.35 IU Insulin/ 0.7 IU Humulin R SD | 0.7 IU Insulin/ 0.35 IU Humulin R Mean | 0.7 IU Insulin/ 0.35 IU Humulin R SD | 0.35 IU Humulin R/ 0.7 IU Insulin Mean | 0.35 IU Humulin R/ 0.7 IU Insulin SD | 0.7 IU Humulin R/ 0.35 IU Insulin Mean | 0.7 IU Humulin R/ 0.35 IU Insulin SD |
|---|---|---|---|---|---|---|---|---|---|---|---|
| Day1 90 min | 6 | 2.48 | 117.2 | 81.2 | 11.63 | 64.2 | 10.57 | 95.0 | 12.85 | 68.5 | 6.95 |
| Day1 150 min | 6 | 6.19 | 113.3 | 100.7 | 12.39 | 89.5 | 16.23 | 109.7 | 13.63 | 73.7 | 8.80 |
| Day1 240 min | 6 | 7.67 | 114.0 | 114.8 | 5.88 | 109.0 | 15.09 | 113.0 | 4.77 | 94.7 | 14.88 |

All values reported are in mg/dL
N—number of measures used to calculate mean
SD—Standard Deviation
Pre—Predose
min—minutes
IU—International Units

TABLE 4

| Interval of Study | N | Control (saline) SD | Control (saline) Mean | 0.35 IU Insulin/ 0.7 IU Humulin R Mean | 0.35 IU Insulin/ 0.7 IU Humulin R SD | 0.7 IU Insulin/ 0.35 IU Humulin R Mean | 0.7 IU Insulin/ 0.35 IU Humulin R SD | 0.35 IU Humulin R/ 0.7 IU Insulin Mean | 0.35 IU Humulin R/ 0.7 IU Insulin SD | 0.7 IU Humulin R/ 0.35 IU Insulin Mean | 0.7 IU Humulin R/ 0.35 IU Insulin SD |
|---|---|---|---|---|---|---|---|---|---|---|---|
| Day 1 Pre | 6 | 5.57 | 138.5 | 141.3 | 2.14 | 139.7 | 7.74 | 135.2 | 3.13 | 129.8 | 6.37 |
| Day 1 30 min | 6 | 6.57 | 133.0 | 60.8 | 7.73 | 86.3 | 19.79 | 64.8 | 10.25 | 72.0 | 12.79 |
| Day1 60 min | 6 | 6.02 | 117.3 | 73.0 | 8.63 | 77.8 | 11.92 | 76.5 | 5.89 | 83.3 | 10.37 |
| Day1 90 min | 6 | 7.57 | 121.8 | 73.5 | 5.54 | 86.0 | 12.15 | 70.8 | 7.76 | 85.7 | 9.73 |
| Day1 150 min | 6 | 6.31 | 121.7 | 91.6 | 12.76 | 109.2 | 9.47 | 86.5 | 13.78 | 108.3 | 10.13 |
| Day1 240 min | 6 | 3.78 | 124.7 | 118.3 | 11.25 | 125.5 | 3.45 | 109.8 | 13.96 | 122.8 | 7.57 |

All values reported are in mg/dL
N—number of measures used to calculate mean
SD—Standard Deviation
Pre—Predose
min—minutes
IU—International Units The results of the study indicate that the glucose values in the test group subjected to insulin produced by the herein method and test group dosed with HUMULIN® R followed very similar patterns of initial glucose decrease and subsequent increases over time. An anticipated difference between the low and high does groups for both compounds was observed. The low dose group showed a lower initial glucose decrease then the high does group, with both groups returning to predose levels during the study.

Example 37

His-Tagged Proinsulin E. coli Working Cell Bank Characterization

The present example demonstrates the utility of the present invention for providing a stable transformed E. coli working cell bank suitable for the commercial manufacture of high grade recombinant human insulin. The analysis was performed to establish the qualification of the cell bank as a cGMP quality cell bank stock suitable for producing clinical grade human recombinant insulin. Plasmid copy number analysis was performed by qPCR using BECKMAN COULTER® Genomic assays ECOAPH v 1.0 (detects the kanamycin resistance gene from transposon.

The working cell bank was further analyzed to identify specific characteristics that define the stably transformed E. coli cells that carry the recombinant human insulin sequence containing plasmids. Some of the characteristics that may be used to define the transformed E. coli cells include plasmid copy number, DNA sequence analysis of isolated plasmids, genetic stability testing assessment, marker retention, cell viability count, and restriction mapping characterization. Plasmid DNA sequencing, plasmid copy number determination, and genetic stability testing assessment was conducted on transformed E. coli prepared according to these procedures described herein. The test results are summarized in Table 5.

TABLE 5

| Test | Results |
|---|---|
| Detection of Non-Host Organisms in Microbial Phage Testing | Negative Negative |
| Confirmation of Host System Identity - E. coli | Identity: E. coli (99.9%) |

TABLE 5-continued

| Test | Results |
|---|---|
| Plasmid Retention by Selective Marker Sensitivity | 100% Plasmid Retained |
| DNA sequencing | 291 bp sequence identical to reference sequence |
| Copy Plasmid number | 34.77 +/− 4.12 |
| Restriction Endonuclease Mapping | Restriction digestions of test article and reference plasmid yield identical patterns |
| Viable Cell Count determination | $1.3 \times 10^{14}$ CFU/mL |

Eight (8) vials of the plasmid material from transformed E. coli cells were analyzed. These test articles were as identified in the study as noted in Table 6:

TABLE 6

| Type | Identity | Test Designation | Storage Condition |
|---|---|---|---|
| Cells | E03-INhis (pTrcHis2AKan) Lot# 09-001 - Vial 05 | ZZ191088 | −80° C. |
| Cells | E03-INhis (pTrcHis2AKan) Lot# 09-001 - Vial 14 | ZZ191085 | −80° C. |
| Cells | E03-INhis (pTrcHis2AKan) Lot# 09-001 - Vial 37 | ZZ191086 | −80° C. |
| Cells | E03-INhis (pTrcHis2AKan) Lot# 09-001 - Vial 54 | ZZ191087 | −80° C. |
| Cells | E03-INhis (pTrcHis2AKan) Lot# 09-001 - Vial 75 | ZZ191090 | −80° C. |
| Cells | E03-INhis (pTrcHis2AKan) Lot# 09-001 - Vial 91 | ZZ203666 | −80° C. |
| Cells | E03-INhis (pTrcHis2AKan) Lot# 09-001 - Vial 97 | ZZ191089 | −80° C. |
| Cells | E03-INhis (pTrcHis2AKan) Lot# 09-001 - Vial 99 | ZZ203665 | −80° C. |

The control articles used in the analysis were as noted in Table 7.

TABLE 7

| Type | Identity | Test Designation | Storage Condition |
|---|---|---|---|
| Host | BL21 Competent Cells - Novagen | ZZ191097 | −80° C. |
| Host | BL21 Competent Cells - Novagen | ZZ191098 | −80° C. |
| Plasmid | pTrcHis2Akan reference plasmid | ZZ191099 | −80° C. |
| Plasmid | pTrcHis2Akan reference plasmid | ZZ191100 | −80° C. |

Regulatory commission grade double strand DNA sequence (2-fold coverage for each strand) was generated for the 291 bp plasmid insert of working cell bank E03-INhis. Plasmid DNA was isolated from an LB broth plus kanamycin culture grown from an aliquote of each test article. Plasmid DNA was prepared from each culture using a QIAGEN® QIAAMP® DNA Mini-kit, then assesed by agarose gel electropooresis and quantitated by spectrophotometry. The plasmid DNA was used as the template for DNA sequencing. The plasmid DNA was used as the template for DNA sequencing. The sequencing primers used are shown in Table 8.

TABLE 8

| Primer Name | Primer Sequence |
|---|---|
| Inhis F1_836-001F | gaggaataaatcgaccggaat (SEQ ID NO: 84) |
| Inhis F1_836-001F | aaaacagccaagctggagac (SEQ ID NO: 85) |

DNA sequencing was performed via the BIGDYE® Terminator Cycle Sequencing Kit (APPLIED BIOSYSTEMS®). Sequencing reactions were purified then analyzed on an ABI PRISM® 3730×1 DNA Analyzer. The raw data was analyzed using Sequencing Analysis software (APPLIED BIOSYSTEMS®). Sequence data was assembled and analyzed using the Sequencher® software (GENE CODES CORP.®).

PCR amplification of the test articles produced amplicons of the expected sizes for each primer set. No differences were observed in the derived consensus sequences generated for either test article and the reference sequences employed in this analysis. Copy number analysis was performed by qPCR using the BECKMAN COULTER® Genomics assays ECOAPH v1.0 (detects the kanamycin resistance gene from transposon Tn903) and ECODNAP v1.1. (detects the E. coli DNA polymerase gene). The ECODNAP v1.1 assay was used as an endogenous control to normalize for the number of cells assayed. A series of dilutions of the pTrcHis2A(Kan) plasmid were used to generate a standard curve to calibrate the ECOAPH v1.0 target assay. Total DNA extracted from the host E. coli cells was used to generate a standard curve to calibrate the ECODNAP v1.1 assay. The assumptions were made that there is a single DNA polymerase gene.

Total DNA was extracted from each working cell bank ("WCB") using the PROMEGA® MAXWELL® 16 robot. One target assay (ECOAPH v1.0 detecting the plasmid) and one normalizing assay (ECODNAP v1.1, detecting the E. roll genomic DNA) were performed on the extracted DNA from each WCB. Six independent dilutions of DNA from each WCB were prepared and analyzed in duplicate. Each of the qPCR reactions was assembled based upon the TAQMAN Universal PCR Master Mix protocol (APPLIED BIOSYSTEMS®). The reactions were run in duplicate. The reactions were thermal cycled using the following conditions: 50° C. for 2 minutes, 95° C. for 10 minutes, followed by 40 cycles of 95° C. for 15 seconds and 60° C. for 1 minute. Data was collected by the ABI Prism 7900 Sequence Detection System software (APPLIED BIOSYSTEMS®). Copy number was calculated as the number of copies (target gene) per cell (normalizing gene) as shown in Table 9.

TABLE 9

Results: Plasmid Copy Number Determination by qPCR

| Test Article | Copy Number |
|---|---|
| E03-INhis | 34.77 ± 4.12 |

Method—Bacterial Species Characterization: The working cell bank samples were streaked on agar plates for colony isolation and incubated at 37 C for approximately 16 hours. BL21 E. coli cells were processed in parallel to serve as a control. A single colony from each plate was transferred to a 0.85% solution, and the suspension used to inoculate API 20E kit test strips (BIOMERIEUX®) which are composed of 23 microtubes to perform 23 biochemical tests for the identification of glucose-fermenting Gram negative rods. The strips were incubated for 18-24 hours at 37° C. then scored to identify the genus and species of the bacterium. Gram staining was performed from colonies representing both test articles and the control cells then fixed to glass slides. Each group of cells was Gram stained and viewed under 100× magnification. E. coli cells were identified as rod shaped bacteria. Confirmation of the host control cells validated the assay and thus no repeat was necessary.

Results—Bacterial Species Characterization: Gram stain results indicated the presence of gram negative cells. E03-INhis was identified to be E. coli (99.9%1D). Gram stain results indicated the presence of gram negative cells.

Method—Cell Purity Assessment: Three vials were selected from the working cell bank (E03-NhGH vials 44, 57, and 66). Six 100 mm Tryptic Soy Agar plates were inoculated from each vial with 100 uL. Two additional plates were inoculated with PBS to serve as controls. Plates were incubated at 25° C. or 37° C. for 7 days and monitored daily for heterogeneous growth.

Results—Cell Purity Assessment: E03INhis displayed completely homogeneous lawn growth. Not growth was detectable on either negative control plate inoculated with PBS.

Results—Phage Contamination Assessment: Supernatants were collected from both chloroform treated and non-treated WCB samples. The supernatants were plated with JM109 cells to test for plaque formation. Supernatants from K-12 and lambda phage were used as positive controls, and supernatant from phage-free XL 1-Blue and lambda suspension medium were used as negative controls. Plates were all observed after 16 hours for plaque formation, and the number of plaques recorded.

Results—Phage Contamination Assessment: E031Nhis displayed zero pfu/mL, indicated lack of detectable phage contamination.

Method—Viable Cell Count Determination: Viable cell counting was performed by preparing a series of dilutions from WCB E03INhis samples and plating three aliquots of each dilution on separate 100 mm LB agar plus kanamycin plates. As a negative control, 100 µL of PBS was spread onto a 100 mm LB agar plus kanamycin plate. The plates were incubated at 37° C. for approximately 16 hours. After incubation, the number of colonies was counted on the plates where individual colonies were observed. The viable cell count per milliliter of sample was calculated.

TABLE 10

|  | $10^{-11}$ Dilution | $10^{-12}$ Dilution | $10^{-13}$ Dilution |
| --- | --- | --- | --- |
| Replica 1 | 132 | 90 | 76 |
| Replica 2 | 127 | 95 | 64 |
| Replica 3 | 143 | 98 | 72 |
| Average | 134 | 94.3 | 70.6 |
| Vol Plated | 100 | 100 | 100 |
| CFU/mL of Dilution | 1340 | 943 | 706 |

Method—Marker Retention: 320 colonies from each WCB were tested for the presence or absence of the selective marker (the kanamycin resistance gene on the plasmid). The sample and positive (kanamycin resistance) and negative (kanamycin sensitive) cells were plated onto LB agar to obtain isolated colonies. For each WCB, four master plates each containing 80 sample colonies, 8 positive controls, and 8 negative controls—were created. Colonies from the master plates were then transferred to selective (LB agar plus kanamycin) and non-selective media (LB agar). Results are reported on Table 11 as the percentage of colonies retaining the kanamycin marker (those that grew on the selective medium).

TABLE 11

| Test Article | # Colonies on Selective Media | # Colonies on Non-Selective Media | % Marker Retention |
| --- | --- | --- | --- |
| E03-INhis | 320 | 320 | 100% |

Method—Restriction Mapping: Plasmid DNA isolated from an LB broth plus kanamycin culture grown from aliquots of each test article was restriction enzyme digested using the restriction enzymes listed in Table 12.

TABLE 12

| Restriction Enzyme | Expected Fragments (kb) | Observed Fragments (kb) |
| --- | --- | --- |
| Nde I | ~5.9 | 5.875 |
| Pst I | ~5.9 | 5.875 |
| Sma I | ~5.9 | 5.968 |
| Xho I | ~5.9 | 6.062 |
| Nde I. EcoR I | ~4.9, ~1.0 | 4.867, 1.019 |

Example 38

Analytical HPLC Analysis

Figure 29:
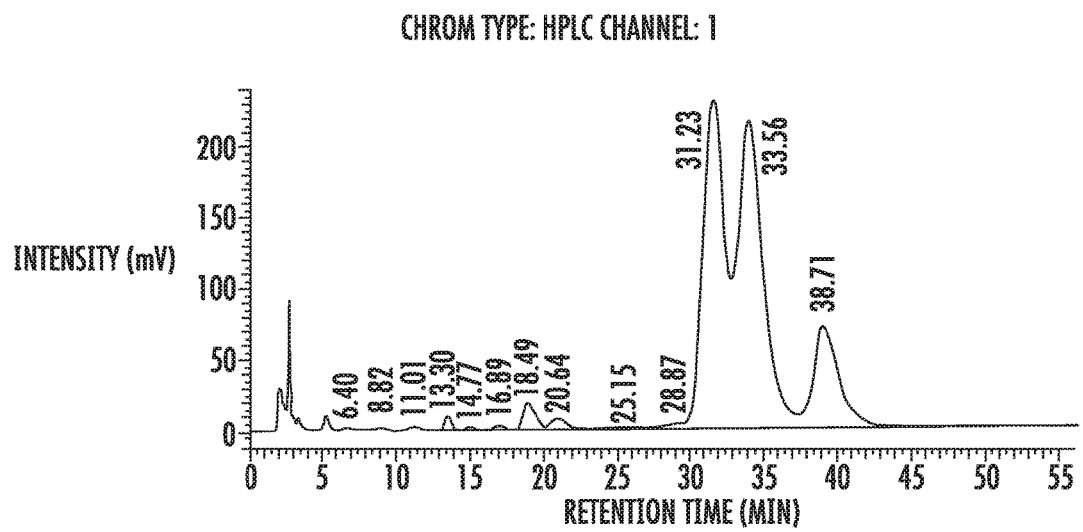
FIGS. 29 and 30, according to some aspects of the invention, presents a reverse phase chromatography analysis of chromatogram with and without sodium sulfate.

FIG. 29 shows material produced by the current method analyzed using the related substances standardized United States Pharmacoeial (USP) method. The results show that the liquid recombinant human insulin prepared according to the methods described herein provided an insulin main peak overall purity of 99.23%. Of the overall impurities present (0.77%), only 0.06% are contributed by multimeric species (peaks after 40 minutes in the chromatography).

Example 39

Sodium Sulfate in Recovery Process for Insulin

The reverse phase chromatography step for purification of di-Arg and single-Arg insulin species following tryptic digestion and prior to carboxypeptidase B digestion involves one of two methods:

1. A shallow gradient elution from 23.5% to 25% acetonitrile in the presence of 200 mM sodium sulfate and 0.16% phosphate, over 15 column volumes. 2. An isocratic elution of 23.5% acetonitrile in the presence of 200 mM sodium sulfate and 0.16 phosphate, over approximately 15 column volumes.

The above methods are specific to a C18 reverse phase system with a 15 µM particle size and 200-300 Å pore, but may be adapted to a C4 or C8 system by adjusting the acetonitrile concentrations. As well, the particle size may be varied to decrease back pressure.

Figure 30:
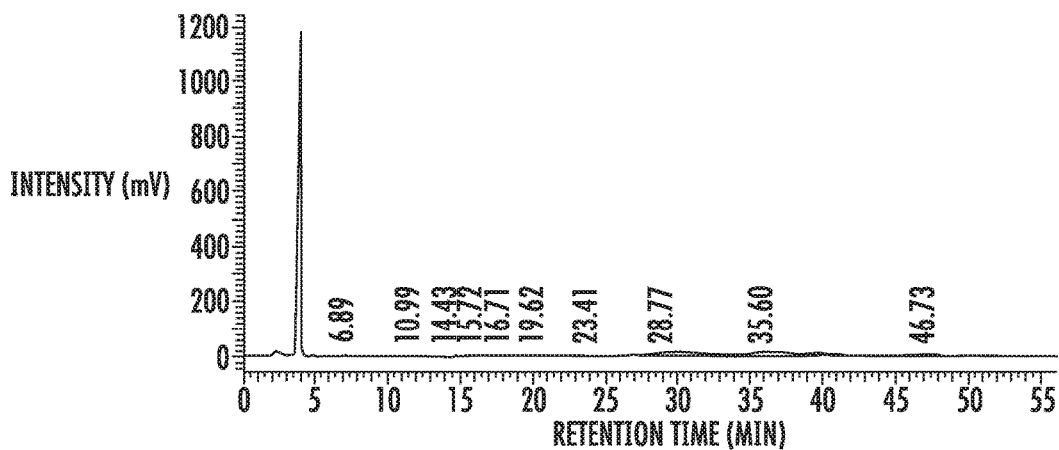

A study of the above methods was conducted to look at the effects of sodium sulfate on the chromatography. It was found that the sodium sulfate when removed from the buffers resulted in a high yield loss. The material did not seem to stick to the column effectively, leading to some material crashing off at the column void volume. Sodium sulfate is required to increase mass transfer within the column. See FIGS. 30 and 31.

This study demonstrates the requirement of sodium sulfate in the reverse phase buffers. Although a more detailed study has not been conducted to determine the minimum required concentration, it is also understood that the flow rate during loading is a crucial parameter, since the slower the load, the better chance that there will be binding to the column before the void volume is through.

All of the compositions and methods disclosed and claimed herein can be made and expressed without undue experimentation in light of the present disclosure. While the compositions and methods of this invention have been described in terms of preferred embodiments, it will be apparent to those of skill in the art that variations may be applied to the compositions, the methods, and in the steps and in the sequence of steps of the methods and processes described herein without departing from the concept, spirit and scope of the invention. More specifically, it will be apparent that certain agents which are both chemically and physiologically related may be substituted for the agents described herein while the same or similar results would be achieved. All such similar substitutions and modifications apparent to those skilled in the art are deemed to be within the spirit, scope and concept of the inventions disclosed herein by the appended claims. Accordingly, the exclusive rights sought to be patented are as described in the claims below.

BIBLIOGRAPHY

The following references are specifically incorporated in their entirety.
1. U.S. Pat. No. 6,777,207 B2—Kjeldsen et al. (2004).
2. U.S. Pat. No. 4,916,212—Markussen et al. (1990).
3. U.S. Pat. No. 5,962,267—Shin et al. (1999).
4. EP Patent No. 0 055 945—Goeddel et al. (1981).
5. Chance et al. (1981), Peptides: Proceedings of the 7th American Peptide Chemistry Symposium, pp. 721-728 (Rich, D. and Gross, E. eds.).
6. Chan et al. (1981), P.N.A.S., U.S.A., 78:5401-5404.
7. Thim et al. (1986), P.N.A.S., U.S.A., 83: 6766-6770.
8. Frank et al. (1981), Peptides: Proceedings of the 7th American Peptide Chemistry Symposium, pp. 729-739 (Rich, D. and Gross, E. eds.).
9. Chang et al. (1998), Biochem. J. 329: 63 1-635.

What is claimed is:

1. A composition comprising a modified proinsulin sequence having the formula $R_1$-($B_1$-$B_{29}$)-$B_{30}$-$R_2$-$R_3$-X-$R_4$-$R_5$-($A_1$-$A_{20}$)-$A_{21}$-$R_6$, wherein:
   $R_1$ is a tag sequence comprising one or more amino acids or $R_1$ is absent with an Arg or Lys present prior to the start of the B chain;
   ($B_1$-$B_{29}$) comprises residues 1-29 of a native human insulin B chain;
   $B_{30}$ is Gly, Ala, Ser, Thr, Val, Leu, Ile, Asn, Gln, Cys, Met, Tyr, Phe, Pro, or Trp;
   $R_2$, $R_3$ and $R_5$ are Arg;
   X is a sequence that comprises one or more amino acids or is absent, provided that X does not comprise a C-terminal Gly, Lys, or Arg when $R_4$ is absent;
   $R_4$ is any amino acid other than Gly, Lys or Arg or is absent;
   ($A_1$-$A_{20}$) comprises residues 1-20 of a native human insulin A chain;
   $A_{21}$ is Gly, Ala, Val, Leu, Ile, Pro, Phe, Trp, Met, Ser, Thr, Tyr, Asp, or Glu; and
   $R_6$ is a tag sequence containing one or more amino acids or $R_6$ is absent, wherein the modified proinsulin sequence is MRFVNQHLCGSHLVEALYL-VCGERGFFYTPKTRREAEDLQVGQVELGGGP-GAGSLQPL ALEGSLQARGIVEQCCTSICSLY-QLENYCGRHHHHHH (SEQ ID NO: 21).

2. A composition comprising a modified proinsulin sequence having the formula $R_1$-($B_1$-$B_{29}$)-$B_{30}$-$R_2$-$R_3$-X-$R_4$-$R_5$-($A_1$-$A_{20}$)-$A_{21}$-$R_6$, wherein:
   $R_1$ is a tag sequence comprising one or more amino acids or $R_1$ is absent with an Arg or Lys present prior to the start of the B chain;
   ($B_1$-$B_{29}$) comprises residues 1-29 of a native human insulin B chain;

$B_{30}$ is Gly, Ala, Ser, Thr, Val, Leu, Ile, Asn, Gln, Cys, Met, Tyr, Phe, Pro, or Trp;

$R_2$, $R_3$ and $R_5$ are Arg;

X is a sequence that comprises one or more amino acids or is absent, provided that X does not comprise a C-terminal Gly, Lys, or Arg when $R_4$ is absent;

$R_4$ is any amino acid other than Gly, Lys or Arg or is absent;

$(A_1-A_{20})$ comprises residues 1-20 of a native human insulin A chain;

$A_{21}$ is Gly, Ala, Val, Leu, Ile, Pro, Phe, Trp, Met, Ser, Thr, Tyr, Asp, or Glu; and $R_6$ is a tag sequence containing one or more amino acids or $R_6$ is absent, wherein the modified proinsulin sequence is

```
                                         (SEQ ID NO: 22)
MRFVNQHLCGSHLVEALYLVCGERGFFYTPKTRREAEDLQVGQVELGGGP
GAGSLQPLALEGSLQARGIVEQCCTSICSLYQLENYCGKHHHHHH.
```

\* \* \* \* \*

SEQUENCE LISTING

```
<160> NUMBER OF SEQ ID NOS: 93

<210> SEQ ID NO 1
<211> LENGTH: 5
<212> TYPE: PRT
<213> ORGANISM: Artificial Sequence
<220> FEATURE:
<223> OTHER INFORMATION: C-peptide

<400> SEQUENCE: 1

Tyr Pro Gly Asp Val
1               5

<210> SEQ ID NO 2
<211> LENGTH: 10
<212> TYPE: PRT
<213> ORGANISM: Artificial Sequence
<220> FEATURE:
<223> OTHER INFORMATION: N-terminal tag

<400> SEQUENCE: 2

Met His His His His His His Gly Gly Arg
1               5                   10

<210> SEQ ID NO 3
<211> LENGTH: 31
<212> TYPE: PRT
<213> ORGANISM: Artificial Sequence
<220> FEATURE:
<223> OTHER INFORMATION: C-peptide

<400> SEQUENCE: 3

Glu Ala Glu Ala Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 4
<211> LENGTH: 5
<212> TYPE: PRT
<213> ORGANISM: Homo sapiens

<400> SEQUENCE: 4
```

```
Pro Lys Thr Arg Arg
1               5

<210> SEQ ID NO 5
<211> LENGTH: 24
<212> TYPE: PRT
<213> ORGANISM: Homo sapiens

<400> SEQUENCE: 5

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 6
<211> LENGTH: 6
<212> TYPE: PRT
<213> ORGANISM: Artificial Sequence
<220> FEATURE:
<223> OTHER INFORMATION: N-terminal His-tag

<400> SEQUENCE: 6

His His His His His His
1               5

<210> SEQ ID NO 7
<211> LENGTH: 21
<212> TYPE: PRT
<213> ORGANISM: Homo sapiens

<400> SEQUENCE: 7

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 8
<211> LENGTH: 30
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 9
<211> LENGTH: 35
<212> TYPE: PRT
<213> ORGANISM: Artificial Sequence
<220> FEATURE:
<223> OTHER INFORMATION: C-peptide

<400> SEQUENCE: 9

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 10
```

```
<211> LENGTH: 35
<212> TYPE: PRT
<213> ORGANISM: Artificial Sequence
<220> FEATURE:
<223> OTHER INFORMATION: C-peptide

<400> SEQUENCE: 10

Arg Arg Glu Ala Glu Asp Leu Gln Val Gly Gln Val Gly Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 11
<211> LENGTH: 35
<212> TYPE: PRT
<213> ORGANISM: Artificial Sequence
<220> FEATURE:
<223> OTHER INFORMATION: C-peptide

<400> SEQUENCE: 11

Arg Arg Glu Ala Glu Ala Leu Gln Val Gly Gln Val Gly Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 12
<211> LENGTH: 35
<212> TYPE: PRT
<213> ORGANISM: Artificial Sequence
<220> FEATURE:
<223> OTHER INFORMATION: C-peptide

<400> SEQUENCE: 12

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Ile Glu Gly Ser Leu
            20                  25                  30

Gln Ala Arg
        35

<210> SEQ ID NO 13
<211> LENGTH: 35
<212> TYPE: PRT
<213> ORGANISM: Artificial Sequence
<220> FEATURE:
<223> OTHER INFORMATION: C-peptide

<400> SEQUENCE: 13

Arg Arg Glu Ala Glu Asp Leu Gln Val Gly Gln Val Gly Leu Gly Gly
1               5                   10                  15

Gly Pro Gly Ala Gly Ser Leu Gln Pro Leu Ala Ile Glu Gly Ser Leu
            20                  25                  30

Gln Ala Arg
        35

<210> SEQ ID NO 14
<211> LENGTH: 35
<212> TYPE: PRT
<213> ORGANISM: Artificial Sequence
```

<220> FEATURE:
<223> OTHER INFORMATION: C-peptide

<400> SEQUENCE: 14

Arg Arg Glu Ala Glu Ala Leu Gln Val Gly Gln Val Gly Leu Gly Gly
1               5                   10                  15

Gly Pro Gly Ala Gly Ser Leu Gln Pro Leu Ala Ile Glu Gly Ser Leu
            20                  25                  30

Gln Ala Arg
        35

<210> SEQ ID NO 15
<211> LENGTH: 35
<212> TYPE: PRT
<213> ORGANISM: Artificial Sequence
<220> FEATURE:
<223> OTHER INFORMATION: C-peptide

<400> SEQUENCE: 15

Arg Arg Glu Ala Glu Ala Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 16
<211> LENGTH: 86
<212> TYPE: PRT
<213> ORGANISM: Artificial Sequence
<220> FEATURE:
<223> OTHER INFORMATION: Glargine-proinsulin

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Leu Gly Gly Gly Pro
        35                  40                  45

Gly Ala Gly Ser Leu Gln Pro Leu Ala Leu Glu Gly Ser Leu Gln Ala
    50                  55                  60

Arg Gly Ile Val Glu Gln Cys Cys Thr Ser Ile Cys Ser Leu Tyr Gln
65                  70                  75                  80

Leu Glu Asn Tyr Cys Gly
                85

<210> SEQ ID NO 17
<211> LENGTH: 96
<212> TYPE: PRT
<213> ORGANISM: Artificial Sequence
<220> FEATURE:
<223> OTHER INFORMATION: Glargine-proinsulin

<400> SEQUENCE: 17

Met His His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

```
Val Gly Gln Val Glu Leu Gly Gly Pro Gly Ala Gly Ser Leu Gln
    50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Gly
                85                  90                  95

<210> SEQ ID NO 18
<211> LENGTH: 110
<212> TYPE: PRT
<213> ORGANISM: Artificial Sequence
<220> FEATURE:
<223> OTHER INFORMATION: Glargine-proinsulin

<400> SEQUENCE: 18

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Pro Gly Ala Gly Ser Leu Gln Pro Leu
65                  70                  75                  80

Ala Leu Glu Gly Ser Leu Gln Ala Arg Gly Ile Val Glu Gln Cys Cys
                85                  90                  95

Thr Ser Ile Cys Ser Leu Tyr Gln Leu Glu Asn Tyr Cys Gly
            100                 105                 110

<210> SEQ ID NO 19
<211> LENGTH: 103
<212> TYPE: PRT
<213> ORGANISM: Artificial Sequence
<220> FEATURE:
<223> OTHER INFORMATION: Glargine-proinsulin

<400> SEQUENCE: 19

Met His His His His His Gly Gly Arg Phe Val Asn Gln His Leu
1               5                   10                  15

Cys Gly Ser His Leu Val Glu Ala Leu Tyr Leu Val Cys Gly Glu Arg
                20                  25                  30

Gly Phe Phe Tyr Thr Pro Lys Thr Arg Arg Glu Ala Glu Asp Leu Gln
            35                  40                  45

Val Gly Gln Val Glu Leu Gly Gly Gly Pro Gly Ala Gly Ser Leu Gln
        50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Gly
                85                  90                  95

Arg His His His His His His
            100

<210> SEQ ID NO 20
<211> LENGTH: 104
<212> TYPE: PRT
<213> ORGANISM: Artificial Sequence
<220> FEATURE:
<223> OTHER INFORMATION: Glargine-proinsulin
```

<400> SEQUENCE: 20

Met His His His His His Gly Gly Arg Phe Val Asn Gln His Leu
1               5                   10                  15

Cys Gly Ser His Ile Leu Val Glu Ala Leu Tyr Leu Val Cys Gly Glu
            20                  25                  30

Arg Gly Phe Phe Tyr Thr Pro Lys Thr Arg Glu Ala Glu Asp Leu
        35                  40                  45

Gln Val Gly Gln Val Glu Leu Gly Gly Pro Gly Ala Gly Ser Leu
50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys
                85                  90                  95

Gly Lys His His His His His His
            100

<210> SEQ ID NO 21
<211> LENGTH: 95
<212> TYPE: PRT
<213> ORGANISM: Artificial Sequence
<220> FEATURE:
<223> OTHER INFORMATION: Glargine-proinsulin

<400> SEQUENCE: 21

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Pro Lys Thr
            20                  25                  30

Arg Arg Glu Ala Glu Asp Leu Gln Val Gly Gln Val Glu Leu Gly Gly
        35                  40                  45

Gly Pro Gly Ala Gly Ser Leu Gln Pro Leu Ala Leu Glu Gly Ser Leu
50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Gly Arg His His His His His
                85                  90                  95

<210> SEQ ID NO 22
<211> LENGTH: 94
<212> TYPE: PRT
<213> ORGANISM: Artificial Sequence
<220> FEATURE:
<223> OTHER INFORMATION: Glargine-proinsulin

<400> SEQUENCE: 22

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Pro Lys Thr
            20                  25                  30

Arg Arg Glu Ala Glu Asp Leu Gln Val Gly Gln Val Glu Leu Gly Gly
        35                  40                  45

Gly Pro Gly Ala Gly Ser Leu Gln Pro Leu Ala Leu Glu Gly Ser Leu
50                  55                  60

Gln Ala Arg Gly Ile Val Glu Gln Cys Cys Thr Ser Cys Ser Leu Tyr
65                  70                  75                  80

Gln Leu Glu Asn Tyr Cys Gly Lys His His His His His
                85                  90

```
<210> SEQ ID NO 23
<211> LENGTH: 21
<212> TYPE: PRT
<213> ORGANISM: Artificial Sequence
<220> FEATURE:
<223> OTHER INFORMATION: Glargine-insulin A-chain

<400> SEQUENCE: 23

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 24
<211> LENGTH: 32
<212> TYPE: PRT
<213> ORGANISM: Artificial Sequence
<220> FEATURE:
<223> OTHER INFORMATION: Glargine-insulin B-chain

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 25
<211> LENGTH: 86
<212> TYPE: PRT
<213> ORGANISM: Artificial Sequence
<220> FEATURE:
<223> OTHER INFORMATION: Aspart proinsulin

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Ala
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 26
<211> LENGTH: 96
<212> TYPE: PRT
<213> ORGANISM: Artificial Sequence
<220> FEATURE:
<223> OTHER INFORMATION: Aspart-proinsulin

<400> SEQUENCE: 26

Met His His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Asp Lys Thr Arg Arg Glu Ala Glu Asp Leu Gln
        35                  40                  45
```

Val Gly Gln Val Glu Leu Gly Gly Pro Gly Ala Gly Ser Leu Gln
 50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 27
<211> LENGTH: 110
<212> TYPE: PRT
<213> ORGANISM: Artificial Sequence
<220> FEATURE:
<223> OTHER INFORMATION: Aspart-proinsulin

<400> SEQUENCE: 27

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Asp Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
65                  70                  75                  80

Ala Leu Glu Gly Ser Leu Gln Ala Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 28
<211> LENGTH: 103
<212> TYPE: PRT
<213> ORGANISM: Artificial Sequence
<220> FEATURE:
<223> OTHER INFORMATION: Aspart-proinsulin

<400> SEQUENCE: 28

Met His His His His His Gly Gly Arg Phe Val Asn Gln His Leu
1               5                   10                  15

Cys Gly Ser His Leu Val Glu Ala Leu Tyr Leu Val Cys Gly Glu Arg
                20                  25                  30

Gly Phe Phe Tyr Thr Asp Lys Thr Arg Arg Glu Ala Glu Asp Leu Gln
            35                  40                  45

Val Gly Gln Val Glu Leu Gly Gly Gly Pro Gly Ala Gly Ser Leu Gln
 50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Asn
                85                  90                  95

Arg His His His His His His
            100

<210> SEQ ID NO 29
<211> LENGTH: 104
<212> TYPE: PRT
<213> ORGANISM: Artificial Sequence
<220> FEATURE:
<223> OTHER INFORMATION: Aspart-proinsulin

<400> SEQUENCE: 29

Met His His His His His Gly Gly Arg Phe Val Asn Gln His Leu
1               5                   10                  15

Cys Gly Ser His Ile Leu Val Glu Ala Leu Tyr Leu Val Cys Gly Glu
                20                  25                  30

Arg Gly Phe Phe Tyr Thr Asp Lys Thr Arg Glu Ala Glu Asp Leu
            35                  40                  45

Gln Val Gly Gln Val Glu Leu Gly Gly Pro Gly Ala Gly Ser Leu
50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys
                85                  90                  95

Asn Lys His His His His His His
            100

<210> SEQ ID NO 30
<211> LENGTH: 95
<212> TYPE: PRT
<213> ORGANISM: Artificial Sequence
<220> FEATURE:
<223> OTHER INFORMATION: Aspart-proinsulin

<400> SEQUENCE: 30

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Asp Lys Thr
                20                  25                  30

Arg Arg Glu Ala Glu Asp Leu Gln Val Gly Gln Val Glu Leu Gly Gly
            35                  40                  45

Gly Pro Gly Ala Gly Ser Leu Gln Pro Leu Ala Leu Glu Gly Ser Leu
50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Arg His His His His His
                85                  90                  95

<210> SEQ ID NO 31
<211> LENGTH: 95
<212> TYPE: PRT
<213> ORGANISM: Artificial Sequence
<220> FEATURE:
<223> OTHER INFORMATION: Aspart-proinsulin

<400> SEQUENCE: 31

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Asp Lys Thr
                20                  25                  30

Arg Arg Glu Ala Glu Asp Leu Gln Val Gly Gln Val Glu Leu Gly Gly
            35                  40                  45

Gly Pro Gly Ala Gly Ser Leu Gln Pro Leu Ala Leu Glu Gly Ser Leu
50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Lys His His His His His
                85                  90                  95

<210> SEQ ID NO 32
<211> LENGTH: 21
<212> TYPE: PRT
<213> ORGANISM: Artificial Sequence
<220> FEATURE:
<223> OTHER INFORMATION: Aspart-insulin/Lis-Pro-insulin A chain

<400> SEQUENCE: 32

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 33
<211> LENGTH: 30
<212> TYPE: PRT
<213> ORGANISM: Artificial Sequence
<220> FEATURE:
<223> OTHER INFORMATION: Aspart-insulin B-chain

<400> SEQUENCE: 33

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 34
<211> LENGTH: 86
<212> TYPE: PRT
<213> ORGANISM: Artificial Sequence
<220> FEATURE:
<223> OTHER INFORMATION: Lis-Pro-proinsulin

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Ala
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 35
<211> LENGTH: 96
<212> TYPE: PRT
<213> ORGANISM: Artificial Sequence
<220> FEATURE:
<223> OTHER INFORMATION: Lis-Pro-proinsulin

<400> SEQUENCE: 35

Met His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Lys Pro Thr Arg Arg Glu Ala Glu Asp Leu Gln
        35                  40                  45

```
Val Gly Gln Val Glu Leu Gly Gly Pro Gly Ala Gly Ser Leu Gln
 50                  55                  60

Pro Leu Ala Leu Glu Gly Ser Leu Gln Ala Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95
```

<210> SEQ ID NO 36
<211> LENGTH: 110
<212> TYPE: PRT
<213> ORGANISM: Artificial Sequence
<220> FEATURE:
<223> OTHER INFORMATION: Lis-Pro-proinsulin

<400> SEQUENCE: 36

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                 20                  25                  30

Ser His Leu Val Glu Ala Leu Tyr Leu Val Cys Gly Glu Arg Gly Phe
             35                  40                  45

Phe Tyr Thr Lys Pro Thr Arg Arg Glu Ala Glu Asp Leu Gln Val Gly
 50                  55                  60

Gln Val Glu Leu Gly Gly Pro Gly Ala Gly Ser Leu Gln Pro Leu
 65                  70                  75                  80

Ala Leu Glu Gly Ser Leu Gln Ala Arg Gly Ile Val Glu Gln Cys Cys
                 85                  90                  95

Thr Ser Ile Cys Ser Leu Tyr Gln Leu Glu Asn Tyr Cys Asn
            100                 105                 110
```

<210> SEQ ID NO 37
<211> LENGTH: 103
<212> TYPE: PRT
<213> ORGANISM: Artificial Sequence
<220> FEATURE:
<223> OTHER INFORMATION: Lis-Pro-proinsulin

<400> SEQUENCE: 37

```
Met His His His His His His Gly Gly Arg Phe Val Asn Gln His Leu
 1               5                  10                  15

Cys Gly Ser His Leu Val Glu Ala Leu Tyr Leu Val Cys Gly Glu Arg
                 20                  25                  30

Gly Phe Phe Tyr Thr Lys Pro Thr Arg Arg Glu Ala Glu Asp Leu Gln
             35                  40                  45

Val Gly Gln Val Glu Leu Gly Gly Pro Gly Ala Gly Ser Leu Gln
 50                  55                  60

Pro Leu Ala Leu Glu Gly Ser Leu Gln Ala Arg Gly Ile Val Glu Gln
 65                  70                  75                  80

Cys Cys Thr Ser Ile Cys Ser Leu Tyr Gln Leu Glu Asn Tyr Cys Asn
                 85                  90                  95

Arg His His His His His His
            100
```

<210> SEQ ID NO 38
<211> LENGTH: 104
<212> TYPE: PRT
<213> ORGANISM: Artificial Sequence
<220> FEATURE:
<223> OTHER INFORMATION: Lis-Pro-proinsulin

<400> SEQUENCE: 38

Met His His His His His Gly Gly Arg Phe Val Asn Gln His Leu
1               5                   10                  15

Cys Gly Ser His Ile Leu Val Glu Ala Leu Tyr Leu Val Cys Gly Glu
            20                  25                  30

Arg Gly Phe Phe Tyr Thr Lys Pro Thr Arg Glu Ala Glu Asp Leu
            35                  40                  45

Gln Val Gly Gln Val Glu Leu Gly Gly Pro Gly Ala Gly Ser Leu
50                  55                  60

Gln Pro Leu Ala Leu Glu Gly Ser Leu Gln Ala Arg Gly Ile Val Glu
65                  70                  75                  80

Gln Cys Cys Thr Ser Ile Cys Ser Leu Tyr Gln Leu Glu Asn Tyr Cys
                85                  90                  95

Asn Lys His His His His His His
            100

<210> SEQ ID NO 39
<211> LENGTH: 95
<212> TYPE: PRT
<213> ORGANISM: Artificial Sequence
<220> FEATURE:
<223> OTHER INFORMATION: Lis-Pro-proinsulin

<400> SEQUENCE: 39

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Lys Pro Thr
            20                  25                  30

Arg Arg Glu Ala Glu Asp Leu Gln Val Gly Gln Val Glu Leu Gly Gly
            35                  40                  45

Gly Pro Gly Ala Gly Ser Leu Gln Pro Leu Ala Leu Glu Gly Ser Leu
        50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Arg His His His His His
                85                  90                  95

<210> SEQ ID NO 40
<211> LENGTH: 95
<212> TYPE: PRT
<213> ORGANISM: Artificial Sequence
<220> FEATURE:
<223> OTHER INFORMATION: Lis-Pro-proinsulin

<400> SEQUENCE: 40

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Lys Pro Thr
            20                  25                  30

Arg Arg Glu Ala Glu Asp Leu Gln Val Gly Gln Val Glu Leu Gly Gly
            35                  40                  45

Gly Pro Gly Ala Gly Ser Leu Gln Pro Leu Ala Leu Glu Gly Ser Leu
        50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Lys His His His His His
                85                  90                  95

```
<210> SEQ ID NO 41
<211> LENGTH: 30
<212> TYPE: PRT
<213> ORGANISM: Artificial Sequence
<220> FEATURE:
<223> OTHER INFORMATION: Lis-Pro-insulin B-chain

<400> SEQUENCE: 41

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 42
<211> LENGTH: 86
<212> TYPE: PRT
<213> ORGANISM: Artificial Sequence
<220> FEATURE:
<223> OTHER INFORMATION: Modified proinsulin

<400> SEQUENCE: 42

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Ala
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 43
<211> LENGTH: 96
<212> TYPE: PRT
<213> ORGANISM: Artificial Sequence
<220> FEATURE:
<223> OTHER INFORMATION: Modified proinsulin

<400> SEQUENCE: 43

Met His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
            35                  40                  45

Val Gly Gln Val Glu Leu Gly Gly Gly Pro Gly Ala Gly Ser Leu Gln
        50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Asn
                85                  90                  95

<210> SEQ ID NO 44
<211> LENGTH: 110
<212> TYPE: PRT
<213> ORGANISM: Artificial Sequence
<220> FEATURE:
```

<223> OTHER INFORMATION: Modified proinsulin

<400> SEQUENCE: 44

Met Ala Leu Trp Met Arg Leu Leu Pro Leu Leu Ala Leu Leu Ala Leu
1               5                   10                  15

Trp Gly Pro Asp Pro Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Ala Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 45
<211> LENGTH: 103
<212> TYPE: PRT
<213> ORGANISM: Artificial Sequence
<220> FEATURE:
<223> OTHER INFORMATION: Modified proinsulin

<400> SEQUENCE: 45

Met His His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

Val Gly Gln Val Glu Leu Gly Gly Gly Pro Gly Ala Gly Ser Leu Gln
    50                  55                  60

Pro Leu Ala Leu Glu Gly Ser Leu Gln Ala Arg Gly Ile Val Glu Gln
65                  70                  75                  80

Cys Cys Thr Ser Ile Cys Ser Leu Tyr Gln Leu Glu Asn Tyr Cys Asn
                85                  90                  95

Arg His His His His His His
            100

<210> SEQ ID NO 46
<211> LENGTH: 104
<212> TYPE: PRT
<213> ORGANISM: Artificial Sequence
<220> FEATURE:
<223> OTHER INFORMATION: Modified proinsulin

<400> SEQUENCE: 46

Met His His His His His His Gly Gly Arg Phe Val Asn Gln His Leu
1               5                   10                  15

Cys Gly Ser His Ile Leu Val Glu Ala Leu Tyr Leu Val Cys Gly Glu
            20                  25                  30

Arg Gly Phe Phe Tyr Thr Pro Lys Thr Arg Arg Glu Ala Glu Asp Leu
        35                  40                  45

Gln Val Gly Gln Val Glu Leu Gly Gly Gly Pro Gly Ala Gly Ser Leu
    50                  55                  60

Gln Pro Leu Ala Leu Glu Gly Ser Leu Gln Ala Arg Gly Ile Val Glu

|  | 65 |  |  | 70 |  |  | 75 |  |  | 80 |
| --- | --- | --- | --- | --- | --- | --- | --- | --- | --- | --- |

Gln Cys Cys Thr Ser Ile Cys Ser Leu Tyr Gln Leu Glu Asn Tyr Cys
                85                  90                  95

Asn Lys His His His His His His
            100

<210> SEQ ID NO 47
<211> LENGTH: 95
<212> TYPE: PRT
<213> ORGANISM: Artificial Sequence
<220> FEATURE:
<223> OTHER INFORMATION: Modified proinsulin

<400> SEQUENCE: 47

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Pro Lys Thr
            20                  25                  30

Arg Arg Glu Ala Glu Asp Leu Gln Val Gly Gln Val Glu Leu Gly Gly
        35                  40                  45

Gly Pro Gly Ala Gly Ser Leu Gln Pro Leu Ala Leu Glu Gly Ser Leu
    50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Arg His His His His His
                85                  90                  95

<210> SEQ ID NO 48
<211> LENGTH: 95
<212> TYPE: PRT
<213> ORGANISM: Artificial Sequence
<220> FEATURE:
<223> OTHER INFORMATION: Modified proinsulin

<400> SEQUENCE: 48

Met Arg Phe Val Asn Gln His Leu Cys Gly Ser His Leu Val Glu Ala
1               5                   10                  15

Leu Tyr Leu Val Cys Gly Glu Arg Gly Phe Phe Tyr Thr Pro Lys Thr
            20                  25                  30

Arg Arg Glu Ala Glu Asp Leu Gln Val Gly Gln Val Glu Leu Gly Gly
        35                  40                  45

Gly Pro Gly Ala Gly Ser Leu Gln Pro Leu Ala Leu Glu Gly Ser Leu
    50                  55                  60

Gln Ala Arg Gly Ile Val Glu Gln Cys Cys Thr Ser Ile Cys Ser Leu
65                  70                  75                  80

Tyr Gln Leu Glu Asn Tyr Cys Asn Lys His His His His His
                85                  90                  95

<210> SEQ ID NO 49
<211> LENGTH: 51
<212> TYPE: PRT
<213> ORGANISM: Homo sapiens

<400> SEQUENCE: 49

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn

Tyr Cys Asn
    50

<210> SEQ ID NO 50
<211> LENGTH: 495
<212> TYPE: DNA
<213> ORGANISM: Homo sapiens

<400> SEQUENCE: 50
agccctccag gacaggctgc atcagaagag gccatcaagc agatcactgt ccttctgcca     60
tggccctgtg gatgcgcctc ctgcccctgc tggcgctgct ggccctctgg ggacctgacc    120
cagaggcagc ctttgtgaac aacacctgt gcggctcaca cctggtggaa gctctctacc     180
tagtgtgcgg ggaacgaggc ttcttctaca cacccaagac ccgccgggag cagaggacc     240 tgcaggtggg gcaggtggag ctgggcgggg ccctggtgc aggcagcctg cagcccttgg     300
ccctggaggg gtccctgcag aagcgtggca ttgtggaaca atgctgtacc agcatctgct    360
ccctctacca gctggagaac tactgcaact agacgcagcc cgcaggcagc ccccacccg     420 ccgcctcctg caccgagaga gatggaataa agcccttgaa ccaacaaaaa aaaaaaaaa     480 aaaaaaaaaa aaaaa                                                    495

<210> SEQ ID NO 51
<211> LENGTH: 261
<212> TYPE: DNA
<213> ORGANISM: Homo sapiens

<400> SEQUENCE: 51
tttgtgaacc aacacctgtg cggctcacac ctggtggaag ctctctacct agtgtgcggg     60
gaacgaggct tcttctacac acccaagacc cgccsggagg cagaggacct gcaggtgggg    120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
ctggagaact actgcaacta g                                              261

<210> SEQ ID NO 52
<211> LENGTH: 33
<212> TYPE: DNA
<213> ORGANISM: Artificial Sequence
<220> FEATURE:
<223> OTHER INFORMATION: Leader sequence

<400> SEQUENCE: 52
atgcatcatc atcatcatca tgaaggtggc cgc                                  33

<210> SEQ ID NO 53
<211> LENGTH: 109
<212> TYPE: PRT
<213> ORGANISM: Homo sapiens

<400> SEQUENCE: 53

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Glu Arg Gly Phe Phe
        35                  40                  45

Tyr Thr Pro Lys Thr Arg Arg Glu Ala Glu Asp Leu Gln Val Gly Gln

```
                50                  55                  60
Val Glu Leu Gly Gly Gly Pro Gly Ala Gly Ser Leu Gln Pro Leu Ala
 65                  70                  75                  80

Leu Glu Gly Ser Leu Gln Lys Arg Gly Ile Val Glu Gln Cys Cys Thr
                 85                  90                  95

Ser Ile Cys Ser Leu Tyr Gln Leu Glu Asn Tyr Cys Asn
                100                 105

<210> SEQ ID NO 54
<211> LENGTH: 95
<212> TYPE: PRT
<213> ORGANISM: Artificial Sequence
<220> FEATURE:
<223> OTHER INFORMATION: Artificial pro-insulin sequence

<400> SEQUENCE: 54

Met His His His His His Gly Gly Arg Phe Val Asn Gln His Leu
 1               5                  10                  15

Cys Gly Ser His Leu Val Glu Ala Leu Tyr Leu Val Cys Glu Arg Gly
                20                  25                  30

Phe Phe Tyr Thr Pro Lys Thr Arg Arg Glu Ala Glu Asp Leu Gln Val
             35                  40                  45

Gly Gln Val Glu Leu Gly Gly Gly Pro Gly Ala Gly Ser Leu Gln Pro
         50                  55                  60

Leu Ala Leu Glu Gly Ser Leu Gln Lys Arg Gly Ile Val Glu Gln Cys
 65                  70                  75                  80

Cys Thr Ser Ile Cys Ser Leu Tyr Gln Leu Glu Asn Tyr Cys Asn
                 85                  90                  95

<210> SEQ ID NO 55
<211> LENGTH: 61
<212> TYPE: DNA
<213> ORGANISM: Artificial Sequence
<220> FEATURE:
<223> OTHER INFORMATION: ptrcHis2A(Kan) vector sequence

<400> SEQUENCE: 55
taaggaggaa taaaccatgg atccgagctc gagatctgca gctggtacca tatgggaatt      60
c                                                                     61

<210> SEQ ID NO 56
<211> LENGTH: 58
<212> TYPE: DNA
<213> ORGANISM: Artificial Sequence
<220> FEATURE:
<223> OTHER INFORMATION: ptrcHis2A(Kan) vector sequence

<400> SEQUENCE: 56
taaggaggaa taaaccatgg atccgagctc gagatctgca gctggtatat gggaattc        58

<210> SEQ ID NO 57
<211> LENGTH: 53
<212> TYPE: DNA
<213> ORGANISM: Artificial Sequence
<220> FEATURE:
<223> OTHER INFORMATION: Forward primer

<400> SEQUENCE: 57
catcatcatc atcatcatgg tggccgcttt gtgaaccaac acctgtgcgg ctc             53

<210> SEQ ID NO 58
```

<211> LENGTH: 35
<212> TYPE: DNA
<213> ORGANISM: Artificial Sequence
<220> FEATURE:
<223> OTHER INFORMATION: Reverse primer

<400> SEQUENCE: 58
gatggtcgac ctcttgatga cgttgatcct taagg                            35

<210> SEQ ID NO 59
<211> LENGTH: 295
<212> TYPE: DNA
<213> ORGANISM: Artificial Sequence
<220> FEATURE:
<223> OTHER INFORMATION: PCR product

<400> SEQUENCE: 59
catcatcatc atcatcatgg tggccgcttt gtgaaccaac acctgtgcgg ctcacacctg    60
gtggaagctc tctacctagt gtgcggggaa cgggcttctt ctacacaccc aagacccgcc   120
gggaggcaga ggacctgcag gtgggcaggt ggagctgggc ggggccctg gtgcaggcag    180 cctgcagccc ttggccctgg agggtcccct gcagaagcgt ggcattgtgg aacaatgctg   240
taccagcatc tgctccctct accagctgga gaactactgc aactagtcct taagg        295

<210> SEQ ID NO 60
<211> LENGTH: 63
<212> TYPE: DNA
<213> ORGANISM: Artificial Sequence
<220> FEATURE:
<223> OTHER INFORMATION: pTrcHis2A(Kan) sequence

<400> SEQUENCE: 60
taaggaggaa taaaccatgg atccgagctc gagatctgca gctggtacca tatatgggaa    60
ttc                                                                 63

<210> SEQ ID NO 61
<211> LENGTH: 15
<212> TYPE: DNA
<213> ORGANISM: Artificial Sequence
<220> FEATURE:
<223> OTHER INFORMATION: pTrcHis2A(Kan) sequence

<400> SEQUENCE: 61
taaggaggaa taaac                                                    15

<210> SEQ ID NO 62
<211> LENGTH: 19
<212> TYPE: DNA
<213> ORGANISM: Artificial Sequence
<220> FEATURE:
<223> OTHER INFORMATION: pTrcHis2A(Kan) sequence

<400> SEQUENCE: 62
attcctcctt atttgctac                                                19

<210> SEQ ID NO 63
<211> LENGTH: 19
<212> TYPE: DNA
<213> ORGANISM: Artificial Sequence
<220> FEATURE:
<223> OTHER INFORMATION: pTrcHis2A(Kan) sequence

<400> SEQUENCE: 63
taaggaggaa taaccatg                                                 19

<210> SEQ ID NO 64
<211> LENGTH: 19
<212> TYPE: DNA
<213> ORGANISM: Artificial Sequence
<220> FEATURE:
<223> OTHER INFORMATION: pTrcHis2A(Kan) sequence

<400> SEQUENCE: 64
attcctcctt atttggtac                                                19

<210> SEQ ID NO 65
<211> LENGTH: 19
<212> TYPE: DNA
<213> ORGANISM: Artificial Sequence
<220> FEATURE:
<223> OTHER INFORMATION: pTrcHis2A(Kan) vector sequence

<400> SEQUENCE: 65
taaggaggaa taaaccatg                                                19

<210> SEQ ID NO 66
<211> LENGTH: 23
<212> TYPE: DNA
<213> ORGANISM: Artificial Sequence
<220> FEATURE:
<223> OTHER INFORMATION: pTrcHis2A(Kan) vector sequence

<400> SEQUENCE: 66
attcctcctt atttggtact taa                                           23

<210> SEQ ID NO 67
<211> LENGTH: 50
<212> TYPE: DNA
<213> ORGANISM: Artificial Sequence
<220> FEATURE:
<223> OTHER INFORMATION: (Met-His-tagged-Gly-Gly-Arg)/)pTrcHis2A(Kan)
      vector sequence

<400> SEQUENCE: 67
ccctggaggg gtccctgcag aagcgtggca ttgtggaaca atgctgtacc              50

<210> SEQ ID NO 68
<211> LENGTH: 28
<212> TYPE: DNA
<213> ORGANISM: Artificial Sequence
<220> FEATURE:
<223> OTHER INFORMATION: Forward primer

<400> SEQUENCE: 68
ggggtccctg caggcgcgtg gcattgtg                                      28

<210> SEQ ID NO 69
<211> LENGTH: 28
<212> TYPE: DNA
<213> ORGANISM: Artificial Sequence
<220> FEATURE:
<223> OTHER INFORMATION: Reverse primer

<400> SEQUENCE: 69
ccccagggac gtccgcgcac cgtaacac                                      28

<210> SEQ ID NO 70
<211> LENGTH: 291
<212> TYPE: DNA
<213> ORGANISM: Artificial Sequence
<220> FEATURE:
<223> OTHER INFORMATION: Met-His-tagged/Gly-Gly-Arg/pro-insulin/K64A
    sequence

<400> SEQUENCE: 70
atgcatcatc atcatcatca tggtggccgc tttgtgaacc aacacctgtg cggctcacac    60
ctggtggaag ctctctacct agtgtgcggg gaacgaggct tcttctacac acccaagacc   120
cgccgggagg cagaggacct gcaggtgggg caggtggagc tgggcggggg ccctggtgca   180
ggcagcctgc agcccttggc cctggagggg tctctgcagg cgcgtggcat tgtggaacaa   240
tgctgtacca gcatctgctc cctctaccag ctggagaact actgcaacta g            291

<210> SEQ ID NO 71
<211> LENGTH: 96
<212> TYPE: PRT
<213> ORGANISM: Artificial Sequence
<220> FEATURE:
<223> OTHER INFORMATION: His-tagged/Gly-Gly-Arg/K64A pro-insulin

<400> SEQUENCE: 71

Met His His His His His His Gly Gly Arg Phe Val Asn Gln His Leu
1               5                   10                  15

Cys Gly Ser His Leu Val Glu Ala Leu Tyr Leu Val Cys Gly Glu Arg
            20                  25                  30

Gly Phe Phe Tyr Thr Pro Lys Thr Arg Arg Glu Ala Glu Asp Leu Gln
        35                  40                  45

Val Gly Gln Val Glu Leu Gly Gly Gly Pro Gly Ala Gly Ser Leu Gln
    50                  55                  60

Pro Leu Ala Leu Glu Gly Ser Leu Gln Ala Arg Gly Ile Val Glu Gln
65                  70                  75                  80

Cys Cys Ile Ser Ile Cys Ser Leu Tyr Gln Leu Glu Asn Tyr Cys Asn
                85                  90                  95

<210> SEQ ID NO 72
<211> LENGTH: 110
<212> TYPE: PRT
<213> ORGANISM: Homo sapiens

<400> SEQUENCE: 72

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 73
<211> LENGTH: 96
<212> TYPE: PRT
<213> ORGANISM: Artificial Sequence
<220> FEATURE:

<223> OTHER INFORMATION: Modified proinsulin

<400> SEQUENCE: 73

```
Met His His His His His Gly Gly Arg Phe Val Asn Gln His Leu
1               5                   10                  15
Cys Gly Ser His Leu Val Glu Ala Leu Tyr Leu Val Cys Gly Glu Arg
                20                  25                  30
Gly Phe Phe Tyr Thr Pro Lys Thr Arg Arg Glu Ala Glu Asp Leu Gln
            35                  40                  45
Val Gly Gln Val Glu Leu Gly Gly Pro Gly Ala Gly Ser Leu Gln
        50                  55                  60
Pro Leu Ala Leu Glu Gly Ser Leu Gln Lys Arg Gly Ile Val Glu Gln
65                  70                  75                  80
Cys Cys Thr Ser Ile Cys Ser Leu Tyr Gln Leu Glu Asn Tyr Cys Asn
                85                  90                  95
```

<210> SEQ ID NO 74
<211> LENGTH: 86
<212> TYPE: PRT
<213> ORGANISM: Homo sapiens

<400> SEQUENCE: 74

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr Arg Arg
                20                  25                  30
Glu Ala Glu Asp Leu Gln Val Gly Gln Val Glu Leu Gly Gly Pro
            35                  40                  45
Gly Ala Gly Ser Leu Gln Pro Leu Ala Leu Glu Gly Ser Leu Gln Lys
        50                  55                  60
Arg Gly Ile Val Glu Gln Cys Cys Thr Ser Ile Cys Ser Leu Tyr Gln
65                  70                  75                  80
Leu Glu Asn Tyr Cys Asn
                85
```

<210> SEQ ID NO 75
<211> LENGTH: 6000
<212> TYPE: DNA
<213> ORGANISM: Artificial Sequence
<220> FEATURE:
<223> OTHER INFORMATION: pTrcHis2A(Kan) Vector with Glargine-proinsulin insert

<400> SEQUENCE: 75

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgatgca     420
tcatcatcat catcatggtg gccgctttgt gaaccaacac ctgtgcggct cacacctggt     480
ggaagctctc tacctagtgt gcggggaacg aggcttcttc tacacaccga acacccgccg     540
ggaggcagag gacctgcagg tggggcaggt ggagctgggc gggggccctg gtgcaggcag     600
```

```
cctgcagccc ttggccctgg aggggtccct gcagaagcgt ggcattgtgg aacaatgctg    660
taccagcatc tgctccctct accagctgga gaactactgc ggctaggaat tcgaagcttg    720
ggcccgaaca aaaactcatc tcagaagagg atctgaatag cgccgtcgac catcatcatc    780
atcatcattg agtttaaacg gtctccagct tggctgtttt ggcggatgag agaagatttt    840
cagcctgata cagattaaat cagaacgcag aagcggtctg ataaaacaga atttgcctgg    900
cggcagtagc gcggtggtcc cacctgaccc catgccgaac tcagaagtga acgccgtag    960 cgccgatggt agtgtggggt ctccccatgc gagagtaggg aactgccagg catcaaataa   1020
aacgaaaggc tcagtcgaaa gactgggcct ttcgttttat ctgttgtttg tcggtgaacg   1080
ctctcctgag taggacaaat ccgccgggag cggatttgaa cgttgcgaag caacggcccg   1140
gagggtggcg gcaggacgc ccgccataaa ctgccaggca tcaaattaag cagaaggcca   1200
tcctgacgga tggccttttt gcgtttctac aaactctttt tgtttatttt tctaaataca   1260
ttcaaatatg tatccgctca tgagacaata accctgataa atgcttcaat aatattgaaa   1320
aaggaagagt atgagtattc aacatttccg tgtcgccctt attccctttt ttgcggcatt   1380
ttgccttcct gttttgctc acccagaaac gctggtgaaa gtaaaagatg ctgaagatca   1440
gttgggtgca cgagtgggtt acatcgaact ggatctcaac agcggtaaga tccttgagag   1500
ttttcgcccc gaagaacgtt ttccaatgat gagcactttt aaagttctgc tatgtggcgc   1560
ggtattatcc cgtgttgacg ccgggcaaga gcaactcggt cgccgcatac actattctca   1620
gaatgacttg gttgagtcct gaatcgcccc atcatccagc cagaaagtga gggagccacg   1680
gttgatgaga gctttgttgt aggtggacca gttggtgatt ttgaactttt gctttgccac   1740
ggaacggtct gcgttgtcgg aagatgcgt gatctgatcc ttcaactcag caaaagttcg   1800
atttattcaa caaagccgcc gtcccgtcaa gtcagcgtaa tgctctgcca gtgttacaac   1860
caattaacca attctgatta gaaaaactca tcgagcatca aatgaaactg caatttattc   1920
atatcaggat tatcaatacc atattttga aaaagccgtt tctgtaatga aggagaaaac   1980
tcaccgaggc agttccatag gatggcaaga tcctggtatc ggtctgcgat tccgactcgt   2040
ccaacatcaa tacaacctat taatttcccc tcgtcaaaaa taaggttatc aagtgagaaa   2100
tcaccatgag tgacgactga atccggtgag aatggcaaaa gcttatgcat ttcttccag   2160 acttgttcaa caggccagcc attacgctcg tcatcaaaat cactgcatca accaaaccgt   2220
tattcattcg tgattgcgcc tgagcgagac gaaatacgcg atcgctgtta aaaggacaat   2280
tacaaacagg aatcgaatgc aaccggcgca ggaacactgc cagcgcatca acaatatttt   2340
cacctgaatc aggatattct tctaatacct ggaatgctgt tttcccgggg atcgcagtgg   2400
tgagtaacca tgcatcatca ggagtacgga taaaatgctt gatggtcgga agaggcataa   2460
attccgtcag ccagtttagt ctgaccatct catctgtaac atcattggca acgctacctt   2520
tgccatgttt cagaaacaac tctgcgcat cgggcttccc atacaatcga tagattgtcg   2580
cacctgattg cccgacatta tcgcgagccc atttataccc atataaatca gcatccatgt   2640
tggaatttaa tcgcggcctc gagcaagacg tttcccgttg aatatggctc ataacacccc   2700
ttgtattact gtttatgtaa gcagacagtt ttattgttca tgatgatata ttttatctt   2760 gtgcaatgta acatcagaga ttttgagaca acgtggct ttgttaata atcgaactt   2820 ttgctgagtt gaaggatcag atcacgcatc ttcccgacaa cgcagaccgt tccgtggcaa   2880
agcaaaagtt caaaatcacc aactggtcca cctacaacaa agctctcatc aaccgtggct   2940
ccctcacttt ctggctggat gatggggcga ttcaggactc accagtcaca gaaaagcatc   3000
```

```
ttacggatgg catgacagta agagaattat gcagtgctgc cataaccatg agtgataaca   3060
ctgcggccaa cttacttctg acaacgatcg gaggaccgaa ggagctaacc gcttttttgc   3120
acaacatggg ggatcatgta actcgccttg atcgttggga accggagctg aatgaagcca   3180
taccaaacga cgagcgtgac accacgatgc ctgtagcaat ggcaacaacg ttgcgcaaac   3240
tattaactgg cgaactactt actctagctt cccggcaaca attaatagac tggatggagg   3300
cggataaagt tgcaggacca cttctgcgct cggcccttcc ggctggctgg tttattgctg   3360
ataaatctgg agccggtgag cgtgggtctc gcggtatcat tgcagcactg gggccagatg   3420
gtaagccctc ccgtatcgta gttatctaca cgacggggag tcaggcaact atggatgaac   3480
gaaatagaca gatcgctgag ataggtgcct cactgattaa gcattggtaa ctgtcagacc   3540
aagtttactc atatatactt tagattgatt taaaacttca ttttttaattt aaaaggatct   3600
aggtgaagat cctttttgat aatctcatga ccaaaatccc ttaacgtgag ttttcgttcc   3660
actgagcgtc agaccccgta gaaaagatca aaggatcttc ttgagatcct ttttttctgc   3720
gcgtaatctg ctgcttgcaa acaaaaaaac caccgctacc agcggtggtt tgtttgccgg   3780
atcaagagct accaactctt tttccgaagg taactggctt cagcagagcg cagataccaa   3840
atactgtcct tctagtgtag ccgtagttag gccaccactt caagaactct gtagcaccgc   3900
ctacatacct cgctctgcta atcctgttac cagtggctgc tgccagtggc gataagtcgt   3960
gtcttaccgg gttggactca agacgatagt taccggataa ggcgcagcgg tcgggctgaa   4020
cggggggttc gtgcacacag cccagcttgg agcgaacgac ctacaccgaa ctgagatacc   4080
tacagcgtga gctatgagaa agcgccacgc ttcccgaagg gagaaaggcg gacaggtatc   4140
cggtaagcgg cagggtcgga acaggagagc gcacgaggga gcttccaggg ggaaacgcct   4200
ggtatcttta tagtcctgtc gggtttcgcc acctctgact tgagcgtcga ttttttgtgat   4260
gctcgtcagg gggcggagc ctatggaaaa acgccagcaa cgcggccttt ttacggttcc   4320
tggccttttg ctggcctttt gctcacatgt tctttcctgc gttatcccct gattctgtgg   4380
ataaccgtat taccgccttt gagtgagctg ataccgctcg ccgcagccga acgaccgagc   4440
gcagcgagtc agtgagcgag gaagcggaag agcgcctgat gcggtatttt ctccttacgc   4500
atctgtgcgg tatttcacac cgcatatggt gcactctcag tacaatctgc tctgatgccg   4560
catagttaag ccagtataca ctccgctatc gctacgtgac tgggtcatgg ctgcgccccg   4620
acacccgcca cacccgctg acgcgccctg acgggcttgt ctgctcccgg catccgctta   4680
cagacaagct gtgaccgtct ccgggagctg catgtgtcag aggttttcac cgtcatcacc   4740
gaaacgcgcg aggcagcaga tcaattcgcg cgcgaaggcg aagcggcatg catttacgtt   4800
gacaccatcg aatggtgcaa aacctttcgc ggtatggcat gatagcgccc ggaagagagt   4860
caattcaggg tggtgaatgt gaaaccagta acgttatacg atgtcgcaga gtatgccggt   4920
gtctcttatc agaccgtttc ccgcgtggtg aaccaggcca gccacgtttc tgcgaaaacg   4980
cgggaaaaag tggaagcggc gatggcggag ctgaattaca ttcccaaccg cgtggcacaa   5040
caactggcgg gcaaacagtc gttgctgatt ggcgttgcca cctccagtct ggccctgcac   5100
gcgccgtcgc aaattgtcgc ggcgattaaa tctcgcgccg atcaactggg tgccagcgtg   5160
gtggtgtcga tggtagaacg aagcggcgtc gaagcctgta aagcggcggt gcacaatctt   5220
ctcgcgcaac gcgtcagtgg gctgatcatt aactatccgc tggatgacca ggatgccatt   5280
gctgtggaag ctgcctgcac taatgttccg gcgttatttc ttgatgtctc tgaccagaca   5340
```

```
cccatcaaca gtattatttt ctcccatgaa gacggtacgc gactgggcgt ggagcatctg    5400
gtcgcattgg gtcaccagca aatcgcgctg ttagcgggcc cattaagttc tgtctcggcg    5460
cgtctgcgtc tggctggctg gcataaatat ctcactcgca atcaaattca gccgatagcg    5520
gaacgggaag gcgactggag tgccatgtcc ggttttcaac aaaccatgca aatgctgaat    5580
gagggcatcg ttcccactgc gatgctggtt gccaacgatc agatggcgct gggcgcaatg    5640
cgcgccatta ccgagtccgg gctgcgcgtt ggtgcggata tctcggtagt gggatacgac    5700
gataccgaag acagctcatg ttatatcccg ccgtcaacca ccatcaaaca ggattttcgc    5760 ctgctgggc aaaccagcgt ggaccgcttg ctgcaactct ctcagggcca ggcggtgaag    5820
ggcaatcagc tgttgcccgt ctcactggtg aaaagaaaaa ccaccctggc gcccaatacg    5880
caaaccgcct ctccccgcgc gttggccgat tcattaatgc agctggcacg acaggtttcc    5940
cgactggaaa gcgggcagtg agcgcaacgc aattaatgtg agttagcgcg aattgatctg    6000
```

<210> SEQ ID NO 76
<211> LENGTH: 261
<212> TYPE: DNA
<213> ORGANISM: Artificial Sequence
<220> FEATURE:
<223> OTHER INFORMATION: Glargine-proinsulin

<400> SEQUENCE: 76

```
tttgtgaacc aacacctgtg cggctcacac ctggtggaag ctctctacct agtgtgcggg     60
gaacgaggct tcttctacac accgaacacc cgccgggagg cagaggacct gcaggtgggg    120
caggtggagc tgggcggggg ccctggtgca ggcagcctgc agcccttggc cctggagggg    180
tccctgcaga gcgtggcat tgtggaacaa tgctgtacca gcatctgctc cctctaccag    240
ctggagaact actgcggcta g                                              261
```

<210> SEQ ID NO 77
<211> LENGTH: 6000
<212> TYPE: DNA
<213> ORGANISM: Artificial Sequence
<220> FEATURE:
<223> OTHER INFORMATION: pTrcHis2A(Kan) Vector with Aspart-proinsulin
      insert

<400> SEQUENCE: 77

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgatgca    420
tcatcatcat catcatggtg ccgctttgt gaaccaacac ctgtgcggct cacacctggt    480
ggaagctctc tacctagtgt gcggggaacg aggcttcttc tacacagaca agacccgccg    540
ggaggcagag gacctgcagg tggggcaggt ggagctgggc ggggccctg gtgcaggcag    600 cctgcagccc ttggccctgg aggggtccct gcagaagcgt ggcattgtgg aacaatgctg    660
taccagcatc tgctccctct accagctgga gaactactgc ggctaggaat tcgaagcttg    720
ggcccgaaca aaaactcatc tcagaagagg atctgaatag cgccgtcgac catcatcatc    780
```

```
atcatcattg agtttaaacg gtctccagct tggctgtttt ggcggatgag agaagatttt    840
cagcctgata cagattaaat cagaacgcag aagcggtctg ataaaacaga atttgcctgg    900
cggcagtagc gcggtggtcc cacctgaccc catgccgaac tcagaagtga acgccgtag     960
cgccgatggt agtgtggggt ctccccatgc gagagtaggg aactgccagg catcaaataa   1020
aacgaaaggc tcagtcgaaa gactgggcct ttcgttttat ctgttgtttg tcggtgaacg   1080
ctctcctgag taggacaaat ccgccggag cggatttgaa cgttgcgaag caacggcccg    1140
gagggtggcg ggcaggacgc ccgccataaa ctgccaggca tcaaattaag cagaaggcca   1200
tcctgacgga tggcctttt gcgtttctac aaactctttt tgtttatttt tctaaataca    1260
ttcaaatatg tatccgctca tgagacaata accctgataa atgcttcaat atattgaaa    1320
aaggaagagt atgagtattc aacatttccg tgtcgccctt attccctttt ttgcggcatt   1380
ttgccttcct gtttttgctc acccagaaac gctggtgaaa gtaaagatg ctgaagatca    1440
gttgggtgca cgagtgggtt acatcgaact ggatctcaac agcggtaaga tccttgagag   1500
ttttcgcccc gaagaacgtt ttccaatgat gagcactttt aaagttctgc tatgtggcgc   1560
ggtattatcc cgtgttgacg ccgggcaaga gcaactcggt cgccgcatac actattctca   1620
gaatgacttg gttgagtcct gaatcgcccc atcatccagc cagaaagtga gggagccacg   1680
gttgatgaga gctttgttgt aggtggacca gttggtgatt ttgaactttt gctttgccac   1740
ggaacggtct gcgttgtcgg aagatgcgt gatctgatcc ttcaactcag caaaagttcg    1800
atttattcaa caaagccgcc gtcccgtcaa gtcagcgtaa tgctctgcca gtgttacaac   1860
caattaacca attctgatta gaaaaactca tcgagcatca aatgaaactg caatttattc   1920
atatcaggat tatcaatacc atattttga aaaagccgtt tctgtaatga aggagaaaac    1980
tcaccgagge agttccatag gatggcaaga tcctggtatc ggtctgcgat tccgactcgt   2040
ccaacatcaa tacaacctat taatttcccc tcgtcaaaaa taaggttatc aagtgagaaa   2100
tcaccatgag tgacgactga atccggtgag aatggcaaaa gcttatgcat ttctttccag   2160
acttgttcaa caggccagcc attacgctcg tcatcaaaat cactgcatca accaaaccgt   2220
tattcattcg tgattgcgcc tgagcgagac gaaatacgcg atcgctgtta aaaggacaat   2280
tacaaacagg aatcgaatgc aaccggcgca ggaacactgc cagcgcatca acaatatttt   2340
cacctgaatc aggatattct tctaatacct ggaatgctgt tttcccgggg atcgcagtgg   2400
tgagtaacca tgcatcatca ggagtacgga taaaatgctt gatggtcgga agaggcataa   2460
attccgtcag ccagtttagt ctgaccatct catctgtaac atcattggca acgctacctt   2520
tgccatgttt cagaaacaac tctggcgcat cgggcttccc atacaatcga tagattgtcg   2580
cacctgattg cccgacatta tcgcgagccc atttataccc atataaatca gcatccatgt   2640
tggaatttaa tcgcggcctc gagcaagacg tttcccgttg aatatggctc ataacacccc   2700
ttgtattact gtttatgtaa gcagacagtt ttattgttca tgatgatata tttttatctt   2760
gtgcaatgta acatcagaga ttttgagaca caacgtggct ttgttgaata atcgaactt    2820
ttgctgagtt gaaggatcag atcacgcatc ttcccgacaa cgcagaccgt tccgtggcaa   2880
agcaaaagtt caaaatcacc aactggtcca cctacaacaa agctctcatc aaccgtggct   2940
ccctcacttt ctggctggat gatggggcga ttcaggactc accagtcaca gaaaagcatc   3000
ttacggatgg catgacagta agagaattat gcagtgctgc cataaccatg agtgataaca   3060
ctgcggccaa cttacttctg acaacgatcg gaggaccgaa ggagctaacc gcttttttgc   3120
acaacatggg ggatcatgta actcgccttg atcgttggga accggagctg aatgaagcca   3180
```

```
taccaaacga cgagcgtgac accacgatgc ctgtagcaat ggcaacaacg ttgcgcaaac   3240
tattaactgg cgaactactt actctagctt cccggcaaca attaatagac tggatggagg   3300
cggataaagt tgcaggacca cttctgcgct cggcccttcc ggctggctgg tttattgctg   3360
ataaatctgg agccggtgag cgtgggtctc gcggtatcat tgcagcactg gggccagatg   3420
gtaagccctc ccgtatcgta gttatctaca cgacggggag tcaggcaact atggatgaac   3480
gaaatagaca gatcgctgag ataggtgcct cactgattaa gcattggtaa ctgtcagacc   3540
aagtttactc atatatactt tagattgatt taaaacttca tttttaattt aaaaggatct   3600
aggtgaagat cctttttgat aatctcatga ccaaaatccc ttaacgtgag ttttcgttcc   3660
actgagcgtc agaccccgta gaaaagatca aggatcttc ttgagatcct ttttttctgc   3720
gcgtaatctg ctgcttgcaa acaaaaaaac caccgctacc agcggtggtt tgtttgccgg   3780
atcaagagct accaactctt tttccgaagg taactggctt cagcagagcg cagataccaa   3840
atactgtcct tctagtgtag ccgtagttag gccaccactt caagaactct gtagcaccgc   3900
ctacatacct cgctctgcta atcctgttac cagtggctgc tgccagtggc gataagtcgt   3960
gtcttaccgg gttggactca agacgatagt taccggataa ggcgcagcgg tcgggctgaa   4020
cggggggttc gtgcacacag cccagcttgg agcgaacgac ctacaccgaa ctgagatacc   4080
tacagcgtga gctatgagaa agcgccacgc ttcccgaagg gagaaaggcg gacaggtatc   4140
cggtaagcgg cagggtcgga acaggagagc gcacgaggga gcttccaggg ggaaacgcct   4200
ggtatcttta tagtcctgtc gggtttcgcc acctctgact tgagcgtcga ttttgtgat   4260 gctcgtcagg ggggcggagc ctatggaaaa acgccagcaa cgcggccttt ttacggttcc   4320
tggccttttg ctggcctttt gctcacatgt tctttcctgc gttatcccct gattctgtgg   4380
ataaccgtat taccgccttt gagtgagctg ataccgctcg ccgcagccga acgaccgagc   4440
gcagcgagtc agtgagcgag gaagcggaag agcgcctgat gcggtatttt ctccttacgc   4500
atctgtgcgg tatttcacac cgcatatggt gcactctcag tacaatctgc tctgatgccg   4560
catagttaag ccagtataca ctccgctatc gctacgtgac tgggtcatgg ctgcgccccg   4620
acacccgcca cacccgctg acgcgccctg acgggcttgt ctgctcccgg catccgctta   4680
cagacaagct gtgaccgtct ccgggagctg catgtgtcag aggttttcac cgtcatcacc   4740
gaaacgcgcg aggcagcaga tcaattcgcg cgcgaaggcg aagcggcatg catttacgtt   4800
gacaccatcg aatggtgcaa acctttcgc ggtatggcat gatagcgccc ggaagagagt   4860
caattcaggg tggtgaatgt gaaaccagta acgttatacg atgtcgcaga gtatgccggt   4920
gtctcttatc agaccgtttc ccgcgtggtg aaccaggcca gccacgtttc tgcgaaaacg   4980
cgggaaaaag tggaagcggc gatggcggag ctgaattaca ttcccaaccg cgtggcacaa   5040
caactggcgg gcaaacagtc gttgctgatt ggcgttgcca cctccagtct ggccctgcac   5100
gcgccgtcgc aaattgtcgc ggcgattaaa tctcgcgccg atcaactggg tgccagcgtg   5160
gtggtgtcga tggtagaacg aagcggcgtc gaagcctgta aagcggcggt gcacaatctt   5220
ctcgcgcaac gcgtcagtgg gctgatcatt aactatccgc tggatgacca ggatgccatt   5280
gctgtggaag ctgcctgcac taatgttccg gcgttatttc ttgatgtctc tgaccagaca   5340
cccatcaaca gtattatttt ctcccatgaa gacggtacgc gactgggcgt ggagcatctg   5400
gtcgcattgg gtcaccagca aatcgcgctg ttagcgggcc cattaagttc tgtctcggcg   5460
cgtctgcgtc tggctggctg gcataaatat ctcactcgca atcaaattca gccgatagcg   5520
```

```
gaacgggaag cgactggag tgccatgtcc ggttttcaac aaaccatgca aatgctgaat    5580
gagggcatcg ttcccactgc gatgctggtt gccaacgatc agatggcgct gggcgcaatg    5640
cgcgccatta ccgagtccgg gctgcgcgtt ggtgcggata tctcggtagt gggatacgac    5700
gataccgaag acagctcatg ttatatcccg ccgtcaacca ccatcaaaca ggattttcgc    5760
ctgctggggc aaaccagcgt ggaccgcttg ctgcaactct ctcagggcca ggcggtgaag    5820
ggcaatcagc tgttgcccgt ctcactggtg aaaagaaaaa ccaccctggc gcccaatacg    5880
caaaccgcct ctccccgcgc gttggccgat tcattaatgc agctggcacg acaggtttcc    5940
cgactggaaa gcgggcagtg agcgcaacgc aattaatgtg agttagcgcg aattgatctg    6000
```

<210> SEQ ID NO 78
<211> LENGTH: 261
<212> TYPE: DNA
<213> ORGANISM: Artificial Sequence
<220> FEATURE:
<223> OTHER INFORMATION: Aspart-proinsulin
<400> SEQUENCE: 78

```
tttgtgaacc aacacctgtg cggctcacac ctggtggaag ctctctacct agtgtgcggg      60
gaacgaggct tcttctacac agacaagacc cgccggagg cagaggacct gcaggtgggg    120
caggtggagc tgggcggggg ccctggtgca ggcagcctgc agcccttggc cctggagggg    180
tccctgcaga agcgtggcat tgtgaacaa tgctgtacca gcatctgctc cctctaccag    240
ctggagaact actgcggcta g                                              261
```

<210> SEQ ID NO 79
<211> LENGTH: 6000
<212> TYPE: DNA
<213> ORGANISM: Artificial Sequence
<220> FEATURE:
<223> OTHER INFORMATION: pTrcHis2A(Kan) Vector with Lis-Pro-proinsulin
    insert <400> SEQUENCE: 79

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc    120
gcactcccgt tctggataat gttttttgcg ccgacatcat aacggttctg caaatattc    180 tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgatgca    420
tcatcatcat catcatggtg gccgctttgt gaaccaacac ctgtgcggct cacacctggt    480
ggaagctctc tacctagtgt gcggggaacg aggcttcttc tacacaaagc cgacccgccg    540
ggaggcagag gacctgcagg tggggcaggt ggagctgggc gggggccctg gtgcaggcag    600
cctgcagccc ttggccctgg aggggtccct gcagaagcgt ggcattgtgg aacaatgctg    660
taccagcatc tgctccctct accagctgga gaactactgc ggctaggaat tcgaagcttg    720
ggcccgaaca aaaactcatc tcagaagagg atctgaatag cgccgtcgac catcatcatc    780
atcatcattg agtttaaacg gtctccagct tggctgtttt ggcggatgag agaagatttt    840
cagcctgata cagattaaat cagaacgcag aagcggtctg ataaaacaga atttgcctgg    900
cggcagtagc gcggtggtcc cacctgaccc catgccgaac tcagaagtga aacgccgtag    960
```

```
cgccgatggt agtgtggggt ctccccatgc gagagtaggg aactgccagg catcaaataa    1020
aacgaaaggc tcagtcgaaa gactgggcct ttcgttttat ctgttgtttg tcggtgaacg    1080
ctctcctgag taggacaaat ccgccgggag cggatttgaa cgttgcgaag caacggcccg    1140
gagggtggcg ggcaggacgc ccgccataaa ctgccaggca tcaaattaag cagaaggcca    1200
tcctgacgga tggcctttt  gcgtttctac aaactctttt tgtttatttt tctaaataca    1260
ttcaaatatg tatccgctca tgagacaata accctgataa atgcttcaat aatattgaaa    1320
aaggaagagt atgagtattc aacatttccg tgtcgccctt attccttttt tgcggcatt     1380
ttgccttcct gtttttgctc acccagaaac gctggtgaaa gtaaaagatg ctgaagatca    1440
gttgggtgca cgagtgggtt acatcgaact ggatctcaac agcggtaaga tccttgagag    1500
ttttcgcccc gaagaacgtt ttccaatgat gagcactttt aaagttctgc tatgtggcgc    1560
ggtattatcc cgtgttgacg ccgggcaaga gcaactcggt cgccgcatac actattctca    1620
gaatgacttg gttgagtcct gaatcgcccc atcatccagc cagaaagtga gggagccacg    1680
gttgatgaga gctttgttgt aggtggacca gttggtgatt ttgaacttt  gctttgccac    1740
ggaacggtct gcgttgtcgg gaagatgcgt gatctgatcc ttcaactcag caaaagttcg    1800
atttattcaa caaagccgcc gtcccgtcaa gtcagcgtaa tgctctgcca gtgttacaac    1860
caattaacca attctgatta gaaaaactca tcgagcatca aatgaaactg caatttattc    1920
atatcaggat tatcaatacc atattttga  aaaagccgtt tctgtaatga aggagaaaac    1980
tcaccgaggc agttccatag gatggcaaga tcctggtatc ggtctgcgat tccgactcgt    2040
ccaacatcaa tacaacctat taatttcccc tcgtcaaaaa taaggttatc aagtgagaaa    2100
tcaccatgag tgacgactga atccggtgag aatggcaaaa gcttatgcat ttctttccag    2160
acttgttcaa caggccagcc attacgctcg tcatcaaaat cactgcatca accaaaccgt    2220
tattcattcg tgattgcgcc tgagcgagac gaaatacgcg atcgctgtta aaaggacaat    2280
tacaaacagg aatcgaatgc aaccggcgca ggaacactgc cagcgcatca acaatatttt    2340
cacctgaatc aggatattct tctaatacct ggaatgctgt tttcccgggg atcgcagtgg    2400
tgagtaacca tgcatcatca ggagtacgga taaaatgctt gatggtcgga agaggcataa    2460
attccgtcag ccagtttagt ctgaccatct catctgtaac atcattggca acgctacctt    2520
tgccatgttt cagaaacaac tctggcgcat cgggcttccc atacaatcga tagattgtcg    2580
cacctgattg cccgacatta tcgcgagccc atttatacccc atataaatca gcatccatgt    2640
tggaatttaa tcgcggcctc gagcaagacg tttcccgttg aatatggctc ataacacccc    2700
ttgtattact gtttatgtaa gcagacagtt ttattgttca tgatgatata tttttatctt    2760
gtgcaatgta acatcagaga ttttgagaca aacgtggct  ttgttgaata atcgaactt     2820
ttgctgagtt gaaggatcag atcacgcatc ttcccgacaa cgcagaccgt tccgtggcaa    2880
agcaaaagtt caaaatcacc aactggtcca cctacaacaa agctctcatc aaccgtggct    2940
ccctcacttt ctggctggat gatggggcga ttcaggactc accagtcaca gaaaagcatc    3000
ttacggatgg catgacagta agagaattat gcagtgctgc cataaccatg agtgataaca    3060
ctgcggccaa cttacttctg acaacgatcg gaggaccgaa ggagctaacc gcttttttgc    3120
acaacatggg ggatcatgta actcgccttg atcgttggga accggagctg aatgaagcca    3180
taccaaacga cgagcgtgac accacgatgc ctgtagcaat ggcaacaacg ttgcgcaaac    3240
tattaactgg cgaactactt actctagctt cccggcaaca attaatagac tggatggagg    3300
cggataaagt tgcaggacca cttctgcgct cggcccttcc ggctggctgg tttattgctg    3360
```

```
ataaatctgg agccggtgag cgtgggtctc gcggtatcat tgcagcactg gggccagatg    3420
gtaagccctc ccgtatcgta gttatctaca cgacggggag tcaggcaact atggatgaac    3480
gaaatagaca gatcgctgag ataggtgcct cactgattaa gcattggtaa ctgtcagacc    3540
aagtttactc atatatactt tagattgatt taaaacttca tttttaattt aaaaggatct    3600
aggtgaagat cctttttgat aatctcatga ccaaaatccc ttaacgtgag ttttcgttcc    3660
actgagcgtc agacccgta gaaaagatca aaggatcttc ttgagatcct ttttttctgc    3720
gcgtaatctg ctgcttgcaa acaaaaaaac caccgctacc agcggtggtt tgtttgccgg    3780
atcaagagct accaactctt tttccgaagg taactggctt cagcagagcg cagataccaa    3840
atactgtcct tctagtgtag ccgtagttag gccaccactt caagaactct gtagcaccgc    3900
ctacatacct cgctctgcta atcctgttac cagtggctgc tgccagtggc gataagtcgt    3960
gtcttaccgg gttggactca agacgatagt taccggataa ggcgcagcgg tcgggctgaa    4020
cggggggttc gtgcacacag cccagcttgg agcgaacgac ctacaccgaa ctgagatacc    4080
tacagcgtga gctatgagaa agcgccacgc ttcccgaagg gagaaaggcg gacaggtatc    4140
cggtaagcgg cagggtcgga acaggagagc gcacgaggga gcttccaggg ggaaacgcct    4200
ggtatcttta tagtcctgtc gggtttcgcc acctctgact tgagcgtcga ttttgtgat    4260
gctcgtcagg ggggcggagc ctatggaaaa acgccagcaa cgcggccttt ttacggttcc    4320
tggccttttg ctggcctttt gctcacatgt tctttcctgc gttatcccct gattctgtgg    4380
ataaccgtat taccgccttt gagtgagctg ataccgctcg ccgcagccga acgaccgagc    4440
gcagcgagtc agtgagcgag gaagcggaag agcgcctgat gcggtatttt ctccttacgc    4500
atctgtgcgg tatttcacac cgcatatggt gcactctcag tacaatctgc tctgatgccg    4560
catagttaag ccagtataca ctccgctatc gctacgtgac tgggtcatgg ctgcgccccg    4620
acacccgcca cacccgctg acgcgccctg acgggcttgt ctgctcccgg catccgctta    4680
cagacaagct gtgaccgtct ccgggagctg catgtgtcag aggttttcac cgtcatcacc    4740
gaaacgcgcg aggcagcaga tcaattcgcg cgcgaaggcg aagcggcatg catttacgtt    4800
gacaccatcg aatggtgcaa aacctttcgc ggtatggcat gatagcgccc ggaagagagt    4860
caattcaggg tggtgaatgt gaaaccagta acgttatacg atgtcgcaga gtatgccggt    4920
gtctcttatc agaccgtttc ccgcgtggtg aaccaggcca gccacgtttc tgcgaaaacg    4980
cgggaaaaag tggaagcggc gatggcggag ctgaattaca ttcccaaccg cgtggcacaa    5040
caactggcgc gcaaacagtc gttgctgatt ggcgttgcca cctccagtct ggccctgcac    5100
gcgccgtcgc aaattgtcgc ggcgattaaa tctcgcgccg atcaactggg tgccagcgtg    5160
gtggtgtcga tggtagaacg aagcggcgtc gaagcctgta aagcggcggt gcacaatctt    5220
ctcgcgcaac gcgtcagtgg gctgatcatt aactatccgc tggatgacca ggatgccatt    5280
gctgtggaag ctgcctgcac taatgttccg gcgttatttc ttgatgtctc tgaccagaca    5340
cccatcaaca gtattatttt ctcccatgaa gacggtacgc gactgggcgt ggagcatctg    5400
gtcgcattgg gtcaccagca aatcgcgctg ttagcgggcc cattaagttc tgtctcggcg    5460
cgtctgcgtc tggctggctg gcataaatat ctcactcgca atcaaattca gccgatagcg    5520
gaacgggaag gcgactggag tgccatgtcc ggttttcaac aaaccatgca aatgctgaat    5580
gagggcatcg ttcccactgc gatgctggtt gccaacgatc agatggcgct gggcgcaatg    5640
cgcgccatta ccgagtccgg gctgcgcgtt ggtgcggata tctcggtagt gggatacgac    5700
```

```
gataccgaag acagctcatg ttatatcccg ccgtcaacca ccatcaaaca ggattttcgc   5760
ctgctggggc aaaccagcgt ggaccgcttg ctgcaactct ctcagggcca ggcggtgaag   5820
ggcaatcagc tgttgcccgt ctcactggtg aaaagaaaaa ccaccctggc gcccaatacg   5880
caaaccgcct ctccccgcgc gttggccgat tcattaatgc agctggcacg acaggtttcc   5940
cgactggaaa gcgggcagtg agcgcaacgc aattaatgtg agttagcgcg aattgatctg   6000
```

<210> SEQ ID NO 80
<211> LENGTH: 261
<212> TYPE: PRT
<213> ORGANISM: Artificial Sequence
<220> FEATURE:
<223> OTHER INFORMATION: Lis-Pro proinsulin

<400> SEQUENCE: 80

```
Thr Thr Thr Gly Thr Gly Ala Ala Cys Cys Ala Ala Cys Ala Cys Cys
1               5                   10                  15

Thr Gly Thr Gly Cys Gly Gly Cys Thr Cys Ala Cys Ala Cys Cys Thr
            20                  25                  30

Gly Gly Thr Gly Gly Ala Ala Gly Cys Thr Cys Thr Cys Thr Ala Cys
        35                  40                  45

Cys Thr Ala Gly Thr Gly Thr Gly Cys Gly Gly Gly Gly Ala Ala Cys
    50                  55                  60

Gly Ala Gly Gly Cys Thr Thr Cys Thr Thr Cys Thr Ala Cys Ala Cys
65                  70                  75                  80

Ala Ala Ala Gly Cys Cys Gly Ala Cys Cys Gly Cys Cys Gly Gly Gly
                85                  90                  95

Gly Ala Gly Gly Cys Ala Gly Ala Gly Gly Ala Cys Cys Thr Gly Cys
            100                 105                 110

Ala Gly Gly Thr Gly Gly Gly Cys Ala Gly Gly Thr Gly Gly Ala
        115                 120                 125

Gly Cys Thr Gly Gly Gly Cys Gly Gly Gly Gly Gly Cys Cys Cys Thr
        130                 135                 140

Gly Gly Thr Gly Cys Ala Gly Gly Cys Ala Gly Cys Cys Thr Gly Cys
145                 150                 155                 160

Ala Gly Cys Cys Cys Thr Thr Gly Gly Cys Cys Cys Thr Gly Gly Ala
                165                 170                 175

Gly Gly Gly Gly Thr Cys Cys Cys Thr Gly Cys Ala Gly Ala Ala Gly
            180                 185                 190

Cys Gly Thr Gly Gly Cys Ala Thr Thr Gly Thr Gly Gly Ala Ala Cys
        195                 200                 205

Ala Ala Thr Gly Cys Thr Gly Thr Ala Cys Cys Ala Gly Cys Ala Thr
    210                 215                 220

Cys Thr Gly Cys Thr Cys Cys Cys Thr Cys Thr Ala Cys Cys Ala Gly
225                 230                 235                 240

Cys Thr Gly Gly Ala Gly Ala Ala Cys Thr Ala Cys Thr Gly Cys Gly
                245                 250                 255

Gly Cys Thr Ala Gly
            260
```

<210> SEQ ID NO 81
<211> LENGTH: 6000
<212> TYPE: DNA
<213> ORGANISM: Artificial Sequence
<220> FEATURE:
<223> OTHER INFORMATION: pTrcHis2a(Kan) vector with proinsulin insert

<400> SEQUENCE: 81

```
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg caaatattc    180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatgatgca   420
tcatcatcat catcatggtg gccgctttgt gaaccaacac ctgtgcggct cacacctggt   480
ggaagctctc tacctagtgt gcggggaacg aggcttcttc tacacaccga agacccgccg   540
ggaggcagag gacctgcagg tggggcaggt ggagctgggc gggggccctg gtgcaggcag   600
cctgcagccc ttggccctgg aggggtccct gcagaagcgt ggcattgtgg aacaatgctg   660
taccagcatc tgctccctct accagctgga gaactactgc ggctaggaat cgaagcttg    720
ggcccgaaca aaaactcatc tcagaagagg atctgaatag cgccgtcgac catcatcatc   780
atcatcattg agtttaaacg gtctccagct tggctgtttt ggcggatgag agaagatttt   840
cagcctgata cagattaaat cagaacgcag aagcggtctg ataaaacaga atttgcctgg   900
cggcagtagc gcggtggtcc cacctgaccc catgccgaac tcagaagtga aacgccgtag   960
cgccgatggt agtgtggggt ctccccatgc gagagtaggg aactgccagg catcaaataa  1020
aacgaaaggc tcagtcgaaa gactgggcct ttcgttttat ctgttgtttg tcggtgaacg  1080
ctctcctgag taggacaaat ccgccgggag cggatttgaa cgttgcgaag caacggcccg  1140
gagggtggcg gcaggacgc ccgccataaa ctgccaggca tcaaattaag cagaaggcca  1200
tcctgacgga tggccttttt gcgtttctac aaactctttt tgtttatttt tctaaataca  1260
ttcaaatatg tatccgctca tgagacaata accctgataa atgcttcaat aatattgaaa  1320
aaggaagagt atgagtattc aacatttccg tgtcgccctt attcccttt ttgcggcatt   1380
ttgccttcct gtttttgctc acccagaaac gctggtgaaa gtaaaagatg ctgaagatca  1440
gttgggtgca cgagtgggtt acatcgaact ggatctcaac agcggtaaga tccttgagag  1500
ttttcgcccc gaagaacgtt ttccaatgat gagcactttt aaagttctgc tatgtggcgc  1560
ggtattatcc cgtgttgacg ccgggcaaga gcaactcggt cgccgcatac actattctca  1620
gaatgacttg gttgagtcct gaatcgcccc atcatccagc cagaaagtga gggagccacg  1680
gttgatgaga gctttgttgt aggtggacca gttggtgatt ttgaacttt gctttgccac   1740
ggaacggtct gcgttgtcgg gaagatgcgt gatctgatcc ttcaactcag caaaagttcg  1800
atttattcaa caaagccgcc gtcccgtcaa gtcagcgtaa tgctctgcca gtgttacaac  1860
caattaaacca attctgatta gaaaaactca tcgagcatca aatgaaactg caatttattc  1920
atatcaggat tatcaatacc atattttga aaaagccgtt tctgtaatga aggagaaaac   1980
tcaccgaggc agttccatag gatggcaaga tcctggtatc ggtctgcgat tccgactcgt  2040
ccaacatcaa tacaacctat taatttcccc tcgtcaaaaa taaggttatc aagtgagaaa  2100
tcaccatgag tgacgactga atccggtgag aatggcaaaa gcttatgcat ttctttccag  2160
acttgttcaa caggccagcc attacgctcg tcatcaaaat cactgcatca accaaaccgt  2220
tattcattcg tgattgcgcc tgagcgagac gaaatacgcg atcgctgtta aaaggacaat  2280
tacaaacagg aatcgaatgc aaccggcgca ggaacactgc cagcgcatca acaatatttt  2340
```

-continued

```
cacctgaatc aggatattct tctaatacct ggaatgctgt tttcccgggg atcgcagtgg   2400
tgagtaacca tgcatcatca ggagtacgga taaaatgctt gatggtcgga agaggcataa   2460
attccgtcag ccagtttagt ctgaccatct catctgtaac atcattggca acgctacctt   2520
tgccatgttt cagaaacaac tctggcgcat cgggcttccc atacaatcga tagattgtcg   2580
cacctgattg cccgacatta tcgcgagccc atttataccc atataaatca gcatccatgt   2640
tggaatttaa tcgcggcctc gagcaagacg tttcccgttg aatatggctc ataacacccc   2700
ttgtattact gtttatgtaa gcagacagtt ttattgttca tgatgatata tttttatctt   2760
gtgcaatgta acatcagaga ttttgagaca caacgtggct tgttgaata aatcgaactt    2820 ttgctgagtt gaaggatcag atcacgcatc ttcccgacaa cgcagaccgt tccgtggcaa   2880
agcaaaagtt caaaatcacc aactggtcca cctacaacaa agctctcatc aaccgtggct   2940
ccctcacttt ctggctggat gatggggcga ttcaggactc accagtcaca gaaaagcatc   3000
ttacggatgg catgacagta agagaattat gcagtgctgc cataaccatg agtgataaca   3060
ctgcggccaa cttacttctg acaacgatcg gaggaccgaa ggagctaacc gcttttttgc   3120
acaacatggg ggatcatgta actcgccttg atcgttggga accggagctg aatgaagcca   3180
taccaaacga cgagcgtgac accacgatgc ctgtagcaat ggcaacaacg ttgcgcaaac   3240
tattaactgg cgaactactt actctagctt cccggcaaca attaatagac tggatggagg   3300
cggataaagt tgcaggacca cttctgcgct cggcccttcc ggctggctgg tttattgctg   3360
ataaatctgg agccggtgag cgtgggtctc gcggtatcat tgcagcactg ggccagatg    3420 gtaagccctc ccgtatcgta gttatctaca cgacggggag tcaggcaact atggatgaac   3480
gaaatagaca gatcgctgag ataggtgcct cactgattaa gcattggtaa ctgtcagacc   3540
aagtttactc atatatactt tagattgatt taaaacttca tttttaattt aaaaggatct   3600
aggtgaagat cctttttgat aatctcatga ccaaaatccc ttaacgtgag ttttcgttcc   3660
actgagcgtc agaccccgta gaaaagatca aggatcttc ttgagatcct ttttttctgc    3720
gcgtaatctg ctgcttgcaa acaaaaaaac caccgctacc agcggtggtt tgtttgccgg   3780
atcaagagct accaactctt tttccgaagg taactggctt cagcagagcg cagataccaa   3840
atactgtcct tctagtgtag ccgtagttag gccaccactt caagaactct gtagcaccgc   3900
ctacatacct cgctctgcta atcctgttac cagtggctgc tgccagtggc gataagtcgt   3960
gtcttaccgg gttggactca agacgatagt taccggataa ggcgcagcgg tcgggctgaa   4020
cggggggttc gtgcacacag cccagcttgg agcgaacgac ctacaccgaa ctgagatacc   4080
tacagcgtga gctatgagaa agcgccacgc ttcccgaagg gagaaaggcg gacaggtatc   4140
cggtaagcgg cagggtcgga acaggagagc gcacgaggga gcttccaggg ggaaacgcct   4200
ggtatcttta tagtcctgtc gggtttcgcc acctctgact tgagcgtcga ttttgtgat    4260 gctcgtcagg gggcggagc ctatggaaaa acgccagcaa cgcggccttt ttacggttcc    4320
tggccttttg ctggccttt gctcacatgt tctttcctgc gttatcccct gattctgtgg    4380
ataaccgtat taccgccttt gagtgagctg ataccgctcg ccgcagccga acgaccgagc   4440
gcagcgagtc agtgagcgag gaagcggaag agcgcctgat gcggtatttt ctccttacgc   4500
atctgtgcgg tatttcacac cgcatatggt gcactctcag tacaatctgc tctgatgccg   4560
catagttaag ccagtataca ctccgctatc gctacgtgac tgggtcatgg ctgcgccccg   4620
acacccgcca cacccgctg acgcgccctg acgggcttgt ctgctcccgg catccgctta   4680
```

| | |
|---|---:|
| cagacaagct gtgaccgtct ccgggagctg catgtgtcag aggttttcac cgtcatcacc | 4740 |
| gaaacgcgcg aggcagcaga tcaattcgcg cgcgaaggcg aagcggcatg catttacgtt | 4800 |
| gacaccatcg aatggtgcaa aacctttcgc ggtatggcat gatagcgccc ggaagagagt | 4860 |
| caattcaggt tggtgaatgt gaaaccagta acgttatacg atgtcgcaga gtatgccggt | 4920 |
| gtctcttatc agaccgtttc ccgcgtggtg aaccaggcca gccacgtttc tgcgaaaacg | 4980 |
| cgggaaaaag tggaagcggc gatggcggag ctgaattaca ttcccaaccg cgtggcacaa | 5040 |
| caactggcgg gcaaacagtc gttgctgatt ggcgttgcca cctccagtct ggccctgcac | 5100 |
| gcgccgtcgc aaattgtcgc ggcgattaaa tctcgcgccg atcaactggg tgccagcgtg | 5160 |
| gtggtgtcga tggtagaacg aagcggcgtc gaagcctgta aagcggcggt gcacaatctt | 5220 |
| ctcgcgcaac gcgtcagtgg gctgatcatt aactatccgc tggatgacca ggatgccatt | 5280 |
| gctgtggaag ctgcctgcac taatgttccg gcgttatttc ttgatgtctc tgaccagaca | 5340 |
| cccatcaaca gtattatttt ctcccatgaa gacggtacgc gactgggcgt ggagcatctg | 5400 |
| gtcgcattgg gtcaccagca atcgcgctg ttagcgggcc cattaagttc tgtctcggcg | 5460 |
| cgtctgcgtc tggctggctg gcataaatat ctcactcgca atcaaattca gccgatagcg | 5520 |
| gaacgggaag gcgactggag tgccatgtcc ggttttcaac aaaccatgca aatgctgaat | 5580 |
| gagggcatcg ttcccactgc gatgctggtt gccaacgatc agatggcgct gggcgcaatg | 5640 |
| cgcgccatta ccgagtccgg gctgcgcgtt ggtgcggata tctcggtagt gggatacgac | 5700 |
| gataccgaag acagctcatg ttatatcccg ccgtcaacca ccatcaaaca ggattttcgc | 5760 |
| ctgctgggc aaaccagcgt ggaccgcttg ctgcaactct ctcagggcca ggcggtgaag | 5820 |
| ggcaatcagc tgttgcccgt ctcactggtg aaaagaaaaa ccaccctggc gcccaatacg | 5880 |
| caaaccgcct ctccccgcgc gttggccgat tcattaatgc agctggcacg acaggtttcc | 5940 |
| cgactggaaa gcgggcagtg agcgcaacgc aattaatgtg agttagcgcg aattgatctg | 6000 |

<210> SEQ ID NO 82
<211> LENGTH: 294
<212> TYPE: DNA
<213> ORGANISM: Artificial Sequence
<220> FEATURE:
<223> OTHER INFORMATION: Human His-tagged proinsulin

<400> SEQUENCE: 82

| | |
|---|---:|
| atgatgcatc atcatcatca tcatggtggc cgctttgtga accaacacct gtgcggctca | 60 |
| cacctggtgg aagctctcta cctagtgtgc ggggaacgag gcttcttcta cacaccgaag | 120 |
| acccgccggg aggcagagga cctgcaggtg gggcaggtgg agctgggcgg gggccctggt | 180 |
| gcaggcagcc tgcagccctt ggccctggag gggtccctgc agaagcgtgg cattgtggaa | 240 |
| caatgctgta ccagcatctg ctccctctac cagctggaga actactgcgg ctag | 294 |

<210> SEQ ID NO 83
<211> LENGTH: 261
<212> TYPE: DNA
<213> ORGANISM: Artificial Sequence
<220> FEATURE:
<223> OTHER INFORMATION: Modified proinsulin

<400> SEQUENCE: 83

| | |
|---|---:|
| tttgtgaacc aacacctgtg cggctcacac ctggtggaag ctctctacct agtgtgcggg | 60 |
| gaacgaggct tcttctacac accgaagacc cgccggagg cagaggacct gcaggtgggg | 120 |
| caggtggagc tgggcggggg ccctggtgca ggcagcctgc agcccttggc cctggagggg | 180 |

```
tccctgcaga agcgtggcat tgtggaacaa tgctgtacca gcatctgctc cctctaccag    240
ctggagaact actgcggcta g                                              261
```

<210> SEQ ID NO 84
<211> LENGTH: 21
<212> TYPE: DNA
<213> ORGANISM: Artificial Sequence
<220> FEATURE:
<223> OTHER INFORMATION: Primer

<400> SEQUENCE: 84

```
gaggaataaa tcgaccggaa t                                              21
```

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85

```
aaaacagcca agctggagac                                                20
```

<210> SEQ ID NO 86
<211> LENGTH: 13
<212> TYPE: PRT
<213> ORGANISM: Homo sapiens

<400> SEQUENCE: 86

Gln Cys Cys Thr Ser Ile Cys Ser Leu Tyr Gln Leu Glu
1               5                   10

<210> SEQ ID NO 87
<211> LENGTH: 13
<212> TYPE: PRT
<213> ORGANISM: Homo sapiens

<400> SEQUENCE: 87

Phe Val Asn Gln His Leu Cys Gly Ser His Leu Val Glu
1               5                   10

<210> SEQ ID NO 88
<211> LENGTH: 4
<212> TYPE: PRT
<213> ORGANISM: Homo sapiens

<400> SEQUENCE: 88

Asn Tyr Cys Asn
1

<210> SEQ ID NO 89
<211> LENGTH: 8
<212> TYPE: PRT
<213> ORGANISM: Homo sapiens

<400> SEQUENCE: 89

Ala Leu Tyr Leu Val Cys Gly Glu
1               5

<210> SEQ ID NO 90
<211> LENGTH: 9
<212> TYPE: PRT
<213> ORGANISM: Homo sapiens

```
<400> SEQUENCE: 90

Arg Gly Phe Phe Tyr Thr Pro Lys Thr
1               5

<210> SEQ ID NO 91
<211> LENGTH: 4
<212> TYPE: PRT
<213> ORGANISM: Homo sapiens

<400> SEQUENCE: 91

Gly Ile Val Glu
1

<210> SEQ ID NO 92
<211> LENGTH: 86
<212> TYPE: PRT
<213> ORGANISM: Artificial Sequence
<220> FEATURE:
<223> OTHER INFORMATION: Modified proinsulin

<400> SEQUENCE: 92

Gly Ile Val Glu Gln Cys Cys Thr Ser Ile Cys Ser Leu Tyr Gln Leu
1               5                   10                  15

Glu Asn Tyr Cys Asn Arg Arg Glu Ala Glu Ala Leu Gln Val Gly Gln
            20                  25                  30

Val Glu Leu Gly Gly Gly Pro Gly Ala Gly Ser Leu Gln Pro Leu Ala
        35                  40                  45

Leu Glu Gly Ser Leu Gln Ala Arg Phe Val Asn Gln His Leu Cys Gly
    50                  55                  60

Ser His Leu Val Glu Ala Leu Tyr Leu Val Cys Gly Glu Arg Gly Phe
65                  70                  75                  80

Phe Tyr Thr Pro Lys Thr
                85

<210> SEQ ID NO 93
<211> LENGTH: 5
<212> TYPE: PRT
<213> ORGANISM: Artificial Sequence
<220> FEATURE:
<223> OTHER INFORMATION: N-terminal tag

<400> SEQUENCE: 93

Met His Gly Gly Arg
1               5
```